United States Patent
Tiller et al.

(10) Patent No.: US 11,472,880 B2
(45) Date of Patent: Oct. 18, 2022

(54) HUMANIZED ANTIBODIES FOR CD3

(71) Applicant: MORPHOSYS AG, Planegg (DE)

(72) Inventors: Thomas Tiller, Munich (DE); Steffen Runz, Heidelberg (DE); Julia Neugebauer, Munich (DE); Andreas Bültmann, Planegg (DE)

(73) Assignee: MORPHOSYS AG, Planegg (DE)

( * ) Notice: Subject to any disclaimer, the term of this patent is extended or adjusted under 35 U.S.C. 154(b) by 125 days.

(21) Appl. No.: 16/635,303

(22) PCT Filed: Aug. 13, 2018

(86) PCT No.: PCT/EP2018/071872
§ 371 (c)(1),
(2) Date: Jan. 30, 2020

(87) PCT Pub. No.: WO2019/034580
PCT Pub. Date: Feb. 21, 2019

(65) Prior Publication Data
US 2020/0377594 A1    Dec. 3, 2020

(30) Foreign Application Priority Data
Aug. 14, 2017    (EP) .................................. 17186128

(51) Int. Cl.
*C07K 16/28*    (2006.01)
*C07K 16/32*    (2006.01)
(52) U.S. Cl.
CPC .......... *C07K 16/2809* (2013.01); *C07K 16/32* (2013.01); *C07K 2317/24* (2013.01); *C07K 2317/31* (2013.01); *C07K 2317/55* (2013.01); *C07K 2317/622* (2013.01); *C07K 2317/71* (2013.01); *C07K 2317/73* (2013.01); *C07K 2317/92* (2013.01)
(58) Field of Classification Search
CPC ............ C07K 16/2809; C07K 2317/24; C07K 2317/31
USPC ..................................................... 424/133.1
See application file for complete search history.

(56) References Cited

U.S. PATENT DOCUMENTS

| | | | | |
|---|---|---|---|---|
| 2014/0302064 A1* | 10/2014 | Moore | ............... | C07K 16/2809 424/172.1 |
| 2014/0377270 A1* | 12/2014 | Moore | ............... | C07K 16/2803 424/136.1 |
| 2017/0157251 A1 | 6/2017 | Bonvini et al. | .. | A61K 39/39588 |

FOREIGN PATENT DOCUMENTS

| | | |
|---|---|---|
| WO | 2007/042261 | 4/2007 |
| WO | 2008/119566 | 10/2008 |
| WO | 2008/119567 | 10/2008 |
| WO | 2012/158818 | 11/2012 |
| WO | 2012/162067 | 11/2012 |
| WO | 2012/168199 | 12/2012 |
| WO | 2014/110601 | 7/2014 |
| WO | 2015/001085 | 1/2015 |
| WO | 2015/063339 | 5/2015 |
| WO | 2016/020444 | 2/2016 |
| WO | 2016/036937 | 3/2016 |
| WO | 2016/110576 | 7/2016 |
| WO | 2017/136659 | 8/2017 |

OTHER PUBLICATIONS

Abramowicz et al. "Release of Tumor Necrosis Factor, Interleukin-2, and Gamma-Interferon in Serum After Injection of OKT3 Monoclonal Antibody in Kidney Transplant Recipients" Transplantation 1989 47:606-608.
Alarcon et al. "The CD3-γ and CD3-δ subunits of the T cell antigen receptor can be expressed with distinct functional TCR/CD3 complexes" EMBO J. 1991 10:903-912.
Conrad et al. "TCR and CD3 Antibody Cross—Reactivity in 44 Species" Cytometry 2007 71A:925-33.
Ferran et al. "Cytokine-Related Syndrome Following Injection of Anti-CD 3 Monoclonal Antibody: Further Evidence for Transient In Vivo T Cell Activation" Eur. J. Immunol. 1990 20:509-515.
Hayward et al. "Failure of a pan-reactive anti-T cell antibody, OKT 3, to prevent graft versus host disease in severe combined immunodeficiency" J Pediatr. 1982 100(4):665-8.
Hirsch et al. "Effects of In Vivo Administration of Anti-CD3 Monoclonal Antibody on T Cell Function in Mice. II. In Vivo Activation of T Cells" J. Immunol. 1989 142:737-743.
Masharani, U.B. & Becker, J.B. "Teplizumab Therapy for Type I Diabetes" Expert Opin. Biol. Ther. 2010 10(3):459-465.
Pessano et al. "The T3/T cell receptor complex: antigenic distinction between the two 20-kd T3 (T3-δ and T3-θ) subunits" The EMBO J. 1985 4:337-344.
Römer et al. "Preculture of PBMCs at high cell density increases sensitivity of T-cell responses, revealing cytokine release by CD28 superagonist TGN1412" Blood 2011 118(26):6772-6781.
Salmeron et al. "A conformational epitope expressed upon association of CD3-epsilon with either CD3-delta or CD3-gamma is the main target for recognition by anti-CD3 monoclonal antibodies" J. Immunol. 1991 147:3047-52.
Yang et al. "A common pathway for T lymphocyte activation involving both the CD3-Ti complex and CD2 sheep erythrocyte receptor determinants" J. Immunol. 1986 137:1097-1100.

(Continued)

*Primary Examiner* — Lynn A Bristol
(74) *Attorney, Agent, or Firm* — Licata & Tyrrell P.C.

(57) ABSTRACT

The present disclosure provides humanized antibodies that specifically bind to CD3 with an optimized affinity and induce T cell-mediated killing of tumour related target antigen high expressing cells with high potency but have limited killing activity on target antigen low expressing cells. The present disclosure also provides bispecific antibodies comprising a first antigen-binding domain that specifically binds to human CD3 with optimized affinity and a second antigen-binding molecule that specifically binds a tumor-related antigen. The disclosure further relates to methods of generating such humanized antibodies and bispecific antibodies for biological, diagnostic, pharmaceutical and other uses.

15 Claims, 9 Drawing Sheets

Specification includes a Sequence Listing.

(56) References Cited

OTHER PUBLICATIONS

Yoshino et al. "Upgrading of Flow Cytometric Analysis for Absolute Counts, Cytokines and Other Antigenic Molecules of Cynomolgus Monkeys (*Macaca fascicularis*) by Using Anti-Human Cross-Reactive Antibodies" 2000 Exp. Anim 49:97-110.
International Search Report and Written Opinion in PCT/EP2018/071872 dated Dec. 11, 2018.
European Search Report for patent Application No. 17186128.9 dated Apr. 30, 2018.

* cited by examiner

| Kabat No. | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 31a | 31b | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| SP34_VH | SEQ ID NO:3 | E | V | Q | L | V | E | S | G | G | G | L | V | Q | P | K | G | S | L | K | L | S | C | A | A | S | G | F | T | F | N | T | | | Y | A | M | N | W | V | R | Q | A | P | G | K | G | L | E | W |
| mAb2: VH | SEQ ID NO:7 | E | V | Q | L | V | E | S | G | G | G | L | V | K | P | G | G | S | L | R | L | S | C | A | A | S | G | F | T | F | N | T | | | Y | A | M | N | W | V | R | Q | A | P | G | K | G | L | E | W |
| mAb3: VH | SEQ ID NO:9 | Q | V | Q | L | V | E | S | G | G | G | L | V | K | P | G | G | S | L | R | L | S | C | A | A | S | G | F | T | F | N | T | | | Y | A | M | N | W | I | R | Q | A | P | G | K | G | L | E | W |

HCDR1

| | 48 | 49 | 50 | 51 | 52 | 52a | 52b | 52c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | V | A | R | I | R | S | K | Y | N | N | N | Y | A | T | Y | Y | A | D | S | V | K | D | R | F | T | I | S | R | D | D | S | Q | S | I | L | Y | L | Q | M | N | N | L | K | T | E |
| | V | G | R | I | R | S | K | Y | N | N | N | Y | A | T | Y | Y | A | D | S | V | K | D | R | F | T | I | S | R | D | D | S | K | N | T | L | Y | L | Q | M | N | S | L | K | T | E |
| | V | S | R | I | R | S | K | Y | N | N | N | Y | A | T | Y | Y | A | D | S | V | K | D | R | F | T | I | S | R | D | N | A | K | N | S | L | Y | L | Q | M | N | S | L | R | A | E |

HCDR2

| | 86 | 87 | 88 | 89 | 90 | 91 | 92 | 93 | 94 | 95 | 96 | 97 | 98 | 99 | 100 | 100a | 100b | 100c | 100d | 100e | 100f | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|
| | D | T | A | M | Y | Y | C | V | R | H | G | N | F | G | N | S | Y | V | S | W | F | A | Y | W | G | Q | G | T | L | V | T | V | S | S |
| | D | T | A | V | Y | Y | C | V | R | T | H | G | N | F | G | N | S | Y | V | S | W | F | A | Y | W | G | Q | G | T | L | V | T | V | S | S |
| | D | T | A | V | Y | Y | C | V | R | H | G | N | F | G | N | S | Y | V | S | W | F | A | Y | W | G | Q | G | T | L | V | T | V | S | S |

HCDR3

Figure 3
A
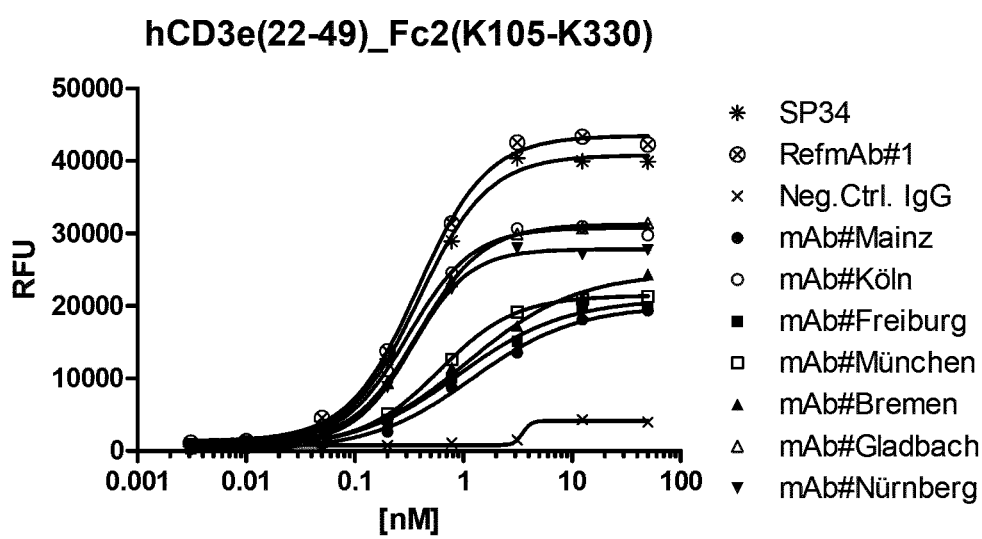
B
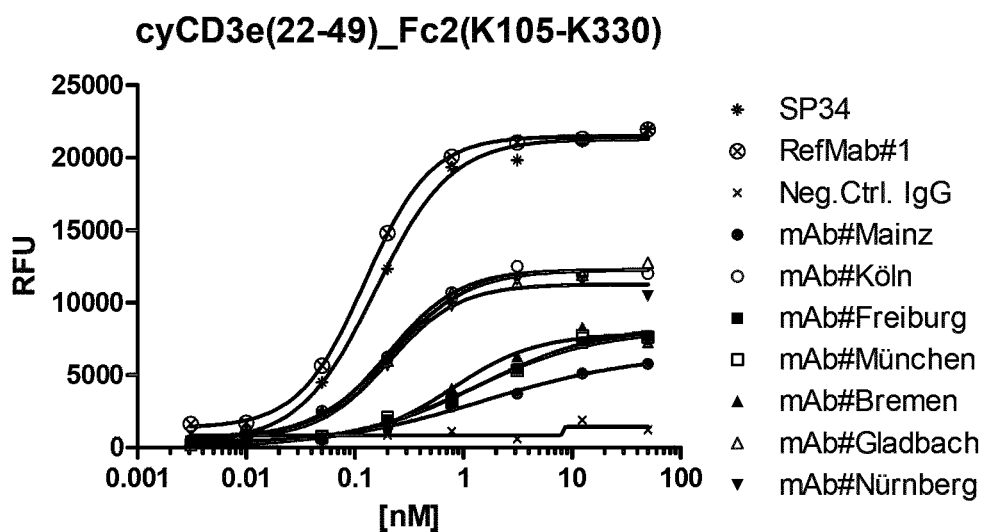

Figure 4
A
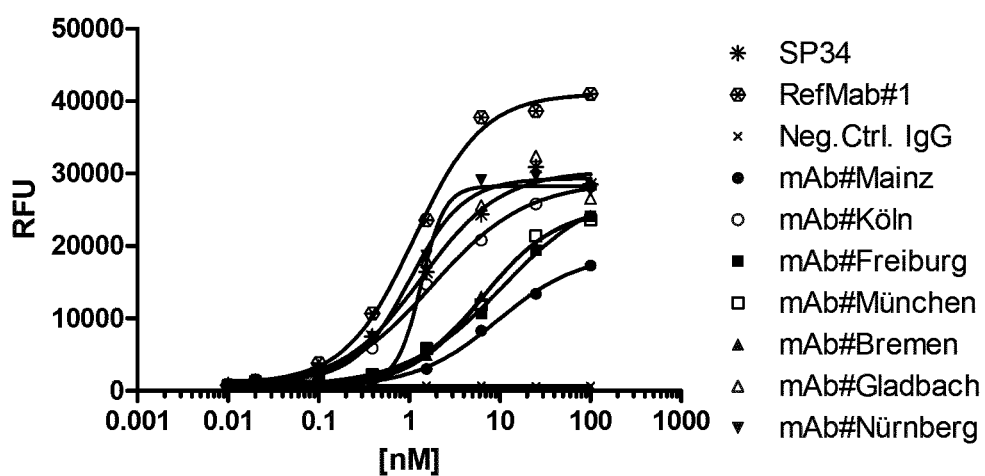
B
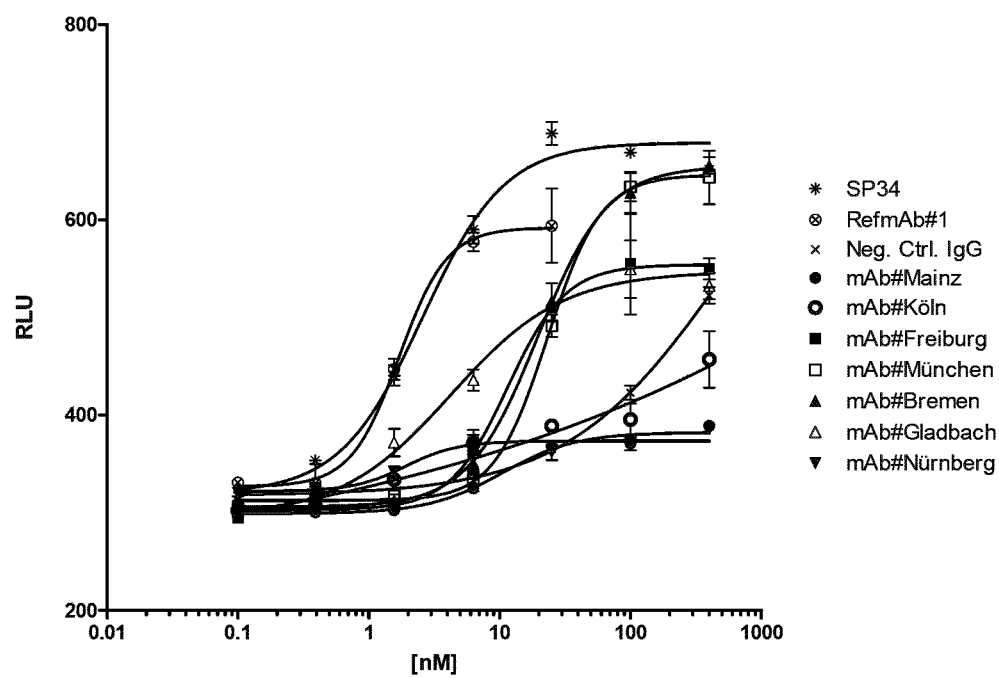

Figure 5
A
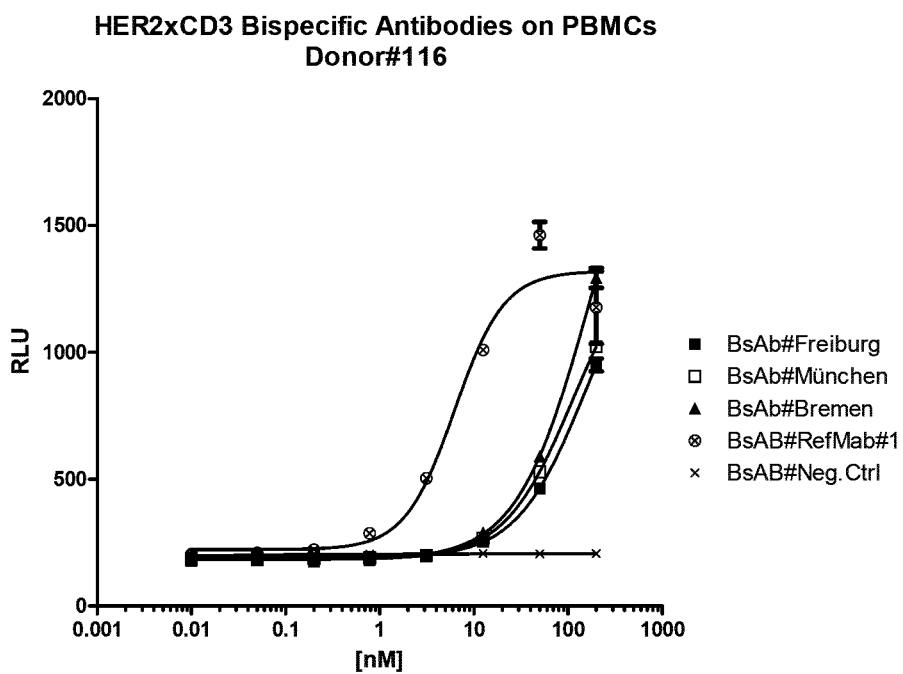
B
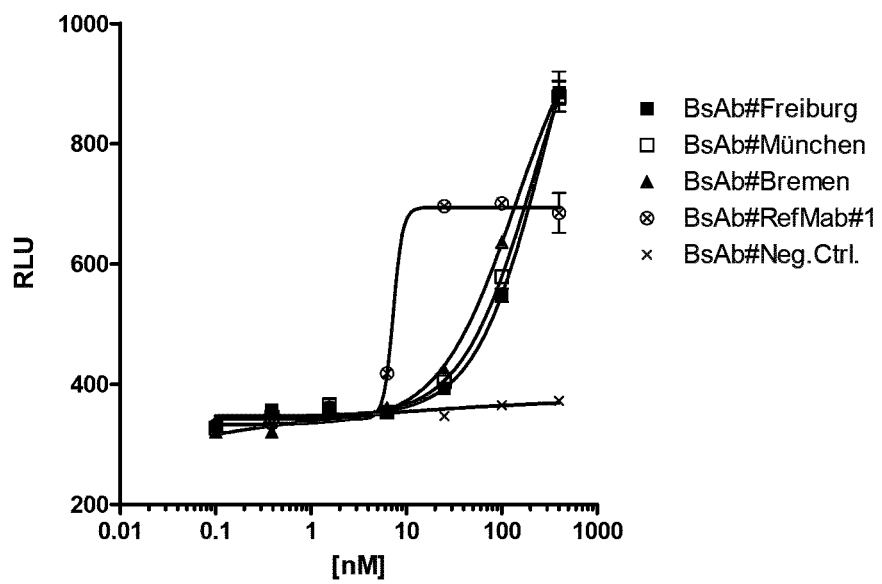

Figure 6
A
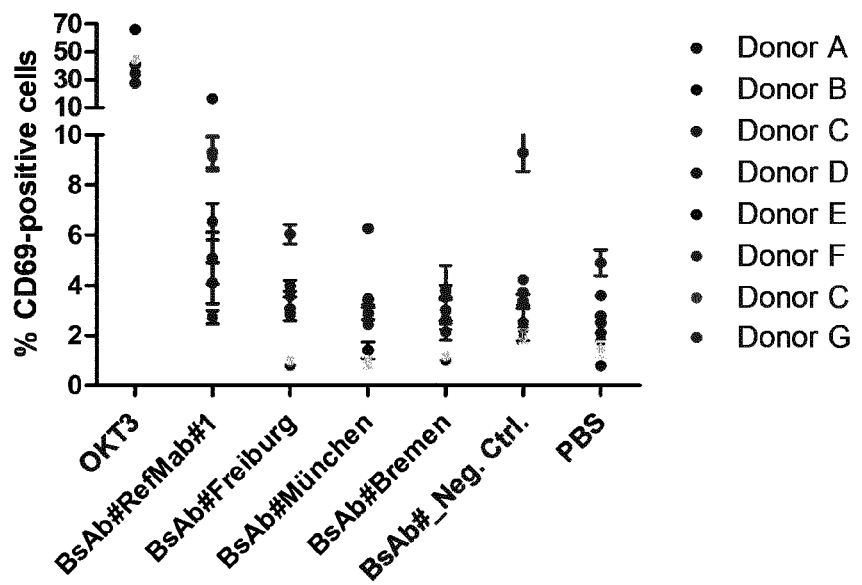
B
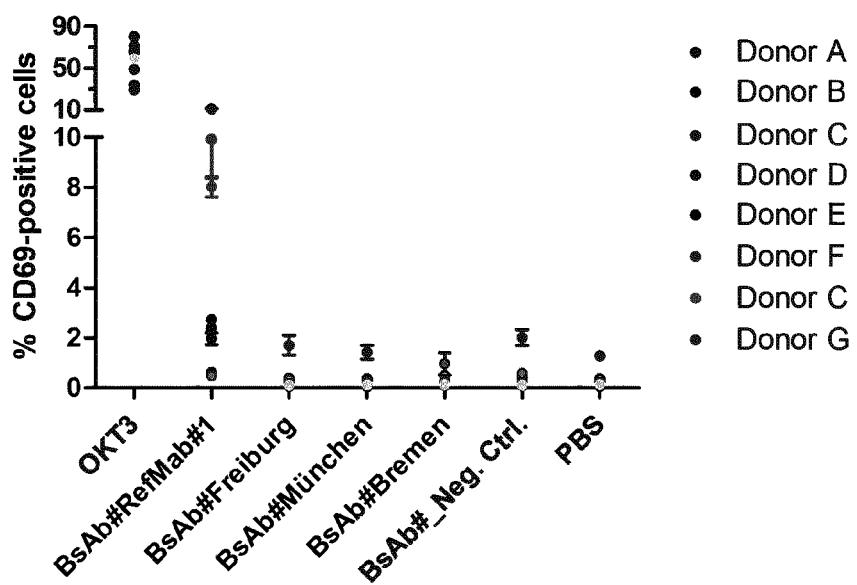

Figure 7
A
PBMC cytotoxicity assay with Her2$^{high}$ SKBR3 cells
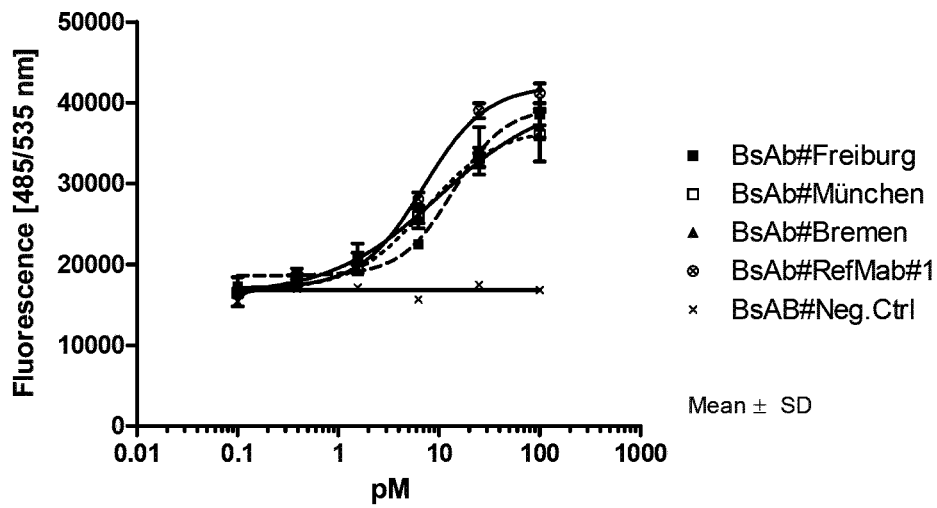
B
PBMC cytotoxicity assay with Her2$^{low}$ A498 cells
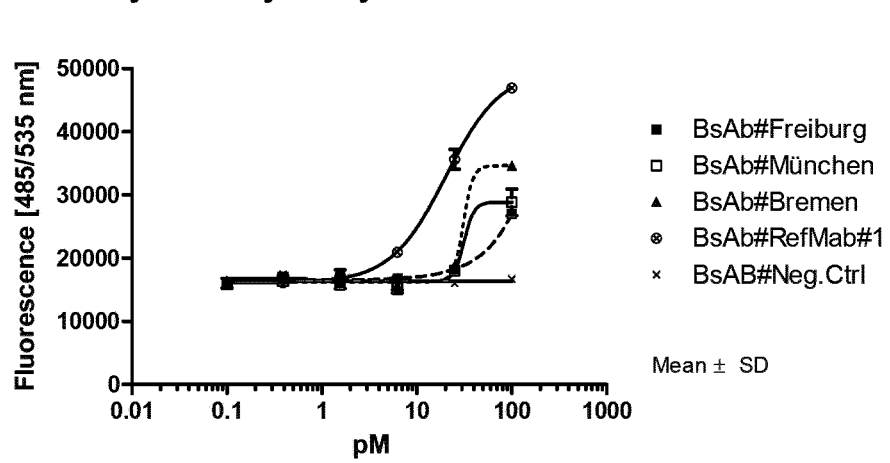
C
PBMC cytotoxicity assay with Her2$^{neg}$ MDA-MB468 cells
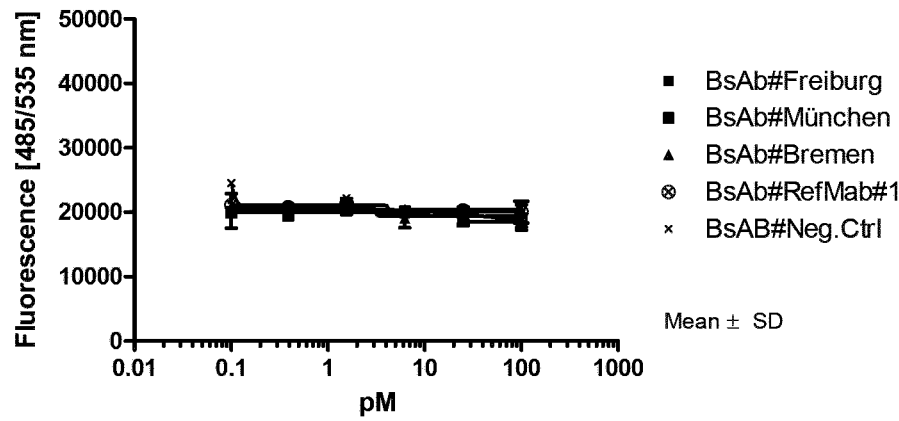

Figure 9
A
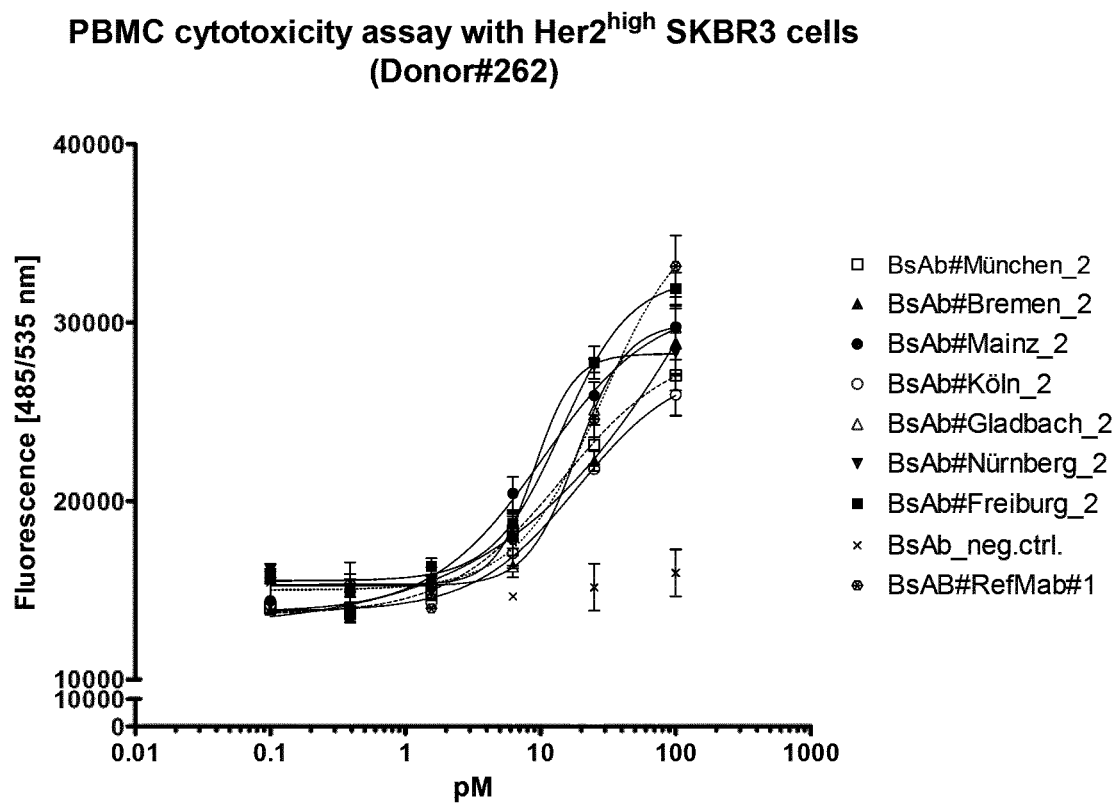
B
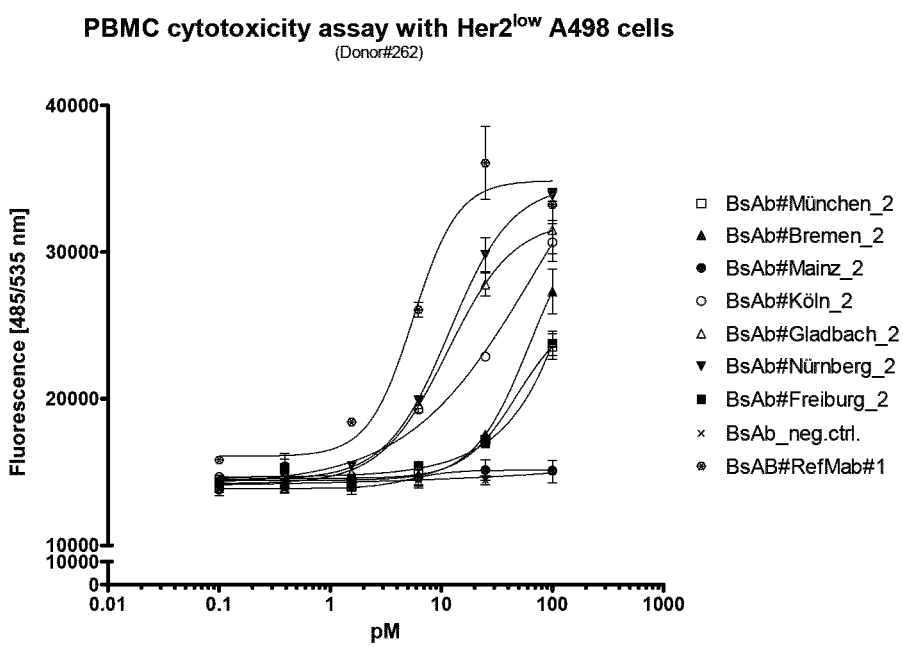

SEQUENCE LISTING

<160> NUMBER OF SEQ ID NOS: 157

<210> SEQ ID NO 1
<211> LENGTH: 104
<212> TYPE: PRT
<213> ORGANISM: Homo sapiens

<400> SEQUENCE: 1

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
                20                  25                  30

Ser Glu Ile Leu Trp Gln His Asn Asp Lys Asn Ile Gly Gly Asp Glu
            35                  40                  45

Asp Asp Lys Asn Ile Gly Ser Asp Glu Asp His Leu Ser Leu Lys Glu
        50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
                100

```
<210> SEQ ID NO 2
<211> LENGTH: 96
<212> TYPE: PRT
<213> ORGANISM: Macaca fascicularis

<400> SEQUENCE: 2

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
            20                  25                  30

Gly Ser Glu Ala Gln Trp Gln His Asn Gly Lys Asn Lys Glu Asp Ser
        35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                85                  90                  95

<210> SEQ ID NO 3
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 4
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30
```

```
Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Gly Gly Thr Lys Leu Thr Val Leu Gly Gln
                100                 105                 110
```

<210> SEQ ID NO 5
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser
        115                 120                 125
```

<210> SEQ ID NO 6
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

```
Gln Thr Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
                20                  25                  30

Asn Tyr Pro Asn Trp Val Gln Gln Lys Pro Gly Gln Ala Pro Arg Gly
            35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
```

```
                    85                  90                  95

Arg Trp Val Phe Gly Gly Gly Thr Lys Leu Thr Val Leu Gly Gln
            100                 105                 110

<210> SEQ ID NO 7
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 8
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
gaagtgcagc tggtggaatc tggcggcgga ctcgtgaagc ctggcggctc tctgagactg      60
agctgtgccg ccagcggctt caccttcaac acctacgcca tgaactgggt gcgccaggcc     120
cctggcaaag gcctggaatg ggtgggacgg atcagaagca agtacaacaa ttacgccacc     180
tactacgccg acagcgtgaa ggaccggttc accatcagcc gggacgacag caagaacacc     240
ctgtacctgc agatgaacag cctgaaaacc gaggacaccg ccgtgtacta ctgcaccacc     300
cacggcaact tcggcaacag ctatgtgtct tggtttgcct actggggcca gggcacccte     360 gtgacagtct cgagc                                                      375

<210> SEQ ID NO 9
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 10
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
caggtgcagc tggtggaatc tggcggcgga ctcgtgaagc ctggcggctc tctgagactg     60
agctgtgccg ccagcggctt caccttcaac acctacgcca tgaactggat ccggcaggcc    120
cctggcaagg gcctggaatg ggtgtcccgg atcagaagca gtacaacaa ttacgccacc     180 tactacgccg acagcgtgaa ggaccggttc accatcagcc gggacaacgc caagaacagc    240
ctgtacctgc agatgaactc cctgcgggcc gaggacaccg ccgtgtacta ttgtgtgcgg    300
cacggcaact cggcaacag ctatgtgtct tggtttgcct actggggcca gggcacc ctc    360 gtgacagtct cgagc                                                    375

<210> SEQ ID NO 11
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110

<210> SEQ ID NO 12
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
caggccgtgg ttacacaaga gcccagcctg acagttagcc ctggcggaac agtgaccctg     60
acctgcagat cttctacagg cgccgtgacc accagcaact acgccaattg ggtgcagcag    120
aagcctggac aggctcccag aggactgatc ggcggcacaa acaaaagagc cccttggaca    180
cccgccagat tcagcggatc actgctcgga ggaaaggccg cactgacaat cacaggtgcc    240
caggccgaag atgaggccga ttactattgc gccctgtggt acagcaacct gtgggtgttc    300
ggcggaggta ccaagctgac cgtgctgggc cag                                 333

<210> SEQ ID NO 13
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110

<210> SEQ ID NO 14
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
gagctggtgg tcacacaaga gcccagcctg acagtttctc ctggcggcac agtgaccctg     60
acctgcagat cttctacagg cgccgtgacc acctccaact acgccaattg ggtgcagcag    120
aagcctggac aggctcccag aggactgatc ggcggcacaa acaaaagagc ccctggcaca    180

```
ccagccagat tcagcggatc actgctcgga ggaaaggccg ctctgacact gtctggtgtc    240
cagcctgaag atgaggccga gtactactgc gccctgtggt acagcaatct gtgggtgttc    300
ggcggaggta ccaagctgac cgtgctgggc cag                                 333
```

<210> SEQ ID NO 15
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 15

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110
```

<210> SEQ ID NO 16
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 16

```
cagaccgtgg tcacacaaga gcccagcctg acagtttctc ctggcggcac agtgaccctg     60
acctgcagat cttctacagg cgccgtgacc accagcaact acgccaattg ggtgcagcag    120
aagcctggac aggctcccag aggactgatc ggcggcacaa acaaagagc ccctggcaca    180 ccagccagat tcagcggatc actgctcgga ggaaaggccg ctctgacact gcttggagca    240
cagcctgaag atgaggccga gtactactgc gccctgtggt acagcaatct gtgggtgttc    300
ggcggaggta ccaagctgac cgtgctgggc cag                                 333
```

<210> SEQ ID NO 17
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 17

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
```

```
            20                  25                  30
Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110

<210> SEQ ID NO 18
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa aatttctggc ccctggcaca     180
ccagccagat tctctggatc tctgctcggc ggaaaggccg ctctgacact gcttggagca     240
cagcctgaag atgaggccga gtactactgc gccctgtggt acagcaatct gtgggtgttc     300
ggcggaggta ccaagctgac cgtgctgggc cag                                  333

<210> SEQ ID NO 19
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110

<210> SEQ ID NO 20
<211> LENGTH: 333
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic polynucleotide"

<400> SEQUENCE: 20

```
cagaccgtgg tcacacaaga gcccagcctg acagtttctc ctggcggcac agtgaccctg    60
acctgcagat cttctacagg cgccgtgacc accagcaact acgccaattg ggtgcagcag   120
aagcctggac aggctcccag aggactgatc ggcggcacaa aatttctggc ccctggcaca   180
ccagccagat tctctggatc tctgctcggc ggaaaggccg ctctgacact gtctggtgtt   240
cagcctgagg acgaggccga gtactattgc gccctgtggt acagcaacct gtgggtgttc   300
ggcggaggta ccaagctgac cgtgctgggc cag                                333
```

<210> SEQ ID NO 21
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Gln Thr Val Val Thr Gln Glu Pro Ser Leu Thr Val Ser Pro Gly Gly
  1               5                  10                  15

Thr Val Thr Leu Thr Cys Arg Ser Ser Thr Gly Ala Val Thr Thr Ser
             20                  25                  30

Asn Tyr Ala Asn Trp Val Gln Gln Lys Pro Gly Gln Ala Pro Arg Gly
         35                  40                  45

Leu Ile Gly Gly Thr Asn Lys Arg Ala Pro Gly Thr Pro Ala Arg Phe
     50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gln
            100                 105                 110
```

<210> SEQ ID NO 22
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
cagaccgtgg tcacacaaga gcccagcctg acagtttctc ctggcggcac agtgaccctg    60
acctgcagat cttctacagg cgccgtgacc accagcaact acgccaattg ggtgcagcag   120
aagcctggac aggctcccag aggactgatc ggcggcacaa acaaaagagc cctggcaca   180
ccagccagat tcagcggatc actgctcgga ggaaaggccg ctctgacact gtctggtgtc   240
cagcctgaag atgaggccga gtactactgc gccctgtggt acagcaatct gtgggtgttc   300
ggcggaggta ccaagctgac cgtgctgggc cag                                333
```

<210> SEQ ID NO 23
<211> LENGTH: 5

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Thr Tyr Ala Met Asn
1               5

<210> SEQ ID NO 24
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Arg Ile Arg Ser Lys Tyr Asn Asn Tyr Ala Thr Tyr Tyr Ala Asp Ser
1               5                   10                  15

Val Lys Asp

<210> SEQ ID NO 25
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

His Gly Asn Phe Gly Asn Ser Tyr Val Ser Trp Phe Ala Tyr
1               5                   10

<210> SEQ ID NO 26
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Arg Ser Ser Thr Gly Ala Val Thr Thr Ser Asn Tyr Ala Asn
1               5                   10

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Thr Asn Lys Arg Ala Pro
1               5

<210> SEQ ID NO 28
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 28

Ala Leu Trp Tyr Ser Asn Leu Trp Val
1               5

<210> SEQ ID NO 29
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110

<210> SEQ ID NO 30
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

```
<210> SEQ ID NO 31
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
caggccgtgg ttacacaaga gcccagcctg acagttagcc ctggcggaac agtgaccctg      60
acctgcagat cttctacagg cgccgtgacc accagcaact acgccaattg ggtgcagcag     120
aagcctggac aggctcccag aggactgatc ggcggcacaa acaaaagagc cccttggaca     180
cccgccagat tcagcggatc actgctcgga ggaaaggccg cactgacaat cacaggtgcc     240
caggccgaag atgaggccga ttactattgc gccctgtggt acagcaacct gtgggtgttc     300
ggcggaggta ccaagctgac cgtgctgggc cag                                  333

<210> SEQ ID NO 32
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
caggtgcagc tggtggaatc tggcggcgga ctcgtgaagc ctggcggctc tctgagactg      60
agctgtgccg ccagcggctt caccttcaac acctacgcca tgaactggat ccggcaggcc     120
cctggcaagg gcctggaatg ggtgtcccgg atcagaagca gtacaacaa ttacgccacc      180 tactacgccg acagcgtgaa ggaccggttc accatcagcc gggacaacgc caagaacagc     240
ctgtacctgc agatgaactc cctgcgggcc gaggacaccg ccgtgtacta ttgtgtgcgg     300
cacggcaact cggcaacag ctatgtgtct tggtttgcct actggggcca gggcacccctc     360 gtgacagtct cgagc                                                      375

<210> SEQ ID NO 33
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
acctacgcca tg                                                          12

<210> SEQ ID NO 34
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
cggatcagaa gcaagtacaa caattacgcc acctactacg ccgacagcgt gaaggac         57
```

-continued

```
<210> SEQ ID NO 35
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
cacggcaact tcggcaacag ctatgtgtct tggtttgcct ac                           42

<210> SEQ ID NO 36
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
agatcttcta caggcgccgt gaccaccagc aactacgcca at                          42

<210> SEQ ID NO 37
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ggcacaaaca aaagagcccc t                                                  21

<210> SEQ ID NO 38
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gccctgtggt acagcaatct gtgggtg                                            27

<210> SEQ ID NO 39
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60
```

```
Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
            130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
            195                 200                 205

Val Ala Pro Thr Glu Cys Ser
            210                 215

<210> SEQ ID NO 40
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Asn Thr Tyr
             20                  25                  30

Ala Met Asn Trp Ile Arg Gln Ala Pro Gly Lys Gly Leu Glu Trp Val
             35                  40                  45

Ser Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
             85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
```

```
                195                 200                 205
Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 41
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
caggccgtgg ttacacaaga gcccagcctg acagttagcc ctggcggaac agtgaccctg      60
acctgcagat cttctacagg cgccgtgacc accagcaact acgccaattg ggtgcagcag     120
aagcctggac aggctcccag aggactgatc ggcggcacaa acaaaagagc cccttggaca     180
cccgccagat tcagcggatc actgctcgga ggaaaggccg cactgacaat cacaggtgcc     240
caggccgaag atgaggccga ttactattgc gccctgtggt acagcaacct gtgggtgttc     300
ggcggaggta ccaagctgac cgtgctgggc cagcccaaag ccgcccctag cgtgaccctg     360
ttccccccct cgagtgagga actccaggcc aacaaggcca cctcgtgtgt cctgatcagc     420
gacttctacc ctggcgccgt gaccgtggcc tggaaggccg atagcagccc tgtgaaggcc     480
ggcgtggaaa ccaccacccc cagcaagcag agcaacaaca aatacgccgc cagcagctac     540
```

```
ctgagcctga cccccgagca gtggaagtcc cacagatcct acagctgcca ggtcacacac      600
gagggcagca ccgtggaaaa gaccgtggcc cccaccgagt gcagc                      645
```

<210> SEQ ID NO 42
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42

```
caggtgcagc tggtggaatc tggcggcgga ctcgtgaagc ctggcggctc tctgagactg       60
agctgtgccg ccagcggctt caccttcaac acctacgcca tgaactggat ccggcaggcc      120
cctggcaagg gcctggaatg ggtgtcccgg atcagaagca agtacaacaa ttacgccacc      180
tactacgccg acagcgtgaa ggaccggttc accatcagcc gggacaacgc caagaacagc      240
ctgtacctgc agatgaactc cctgcgggcc gaggacaccg ccgtgtacta ttgtgtgcgg      300
cacggcaact tcggcaacag ctatgtgtct tggtttgcct actggggcca gggcacccTc      360
gtgacagtct cgagcgcgtc gaccaaaggc ccagcgtgt tccctctggc ccccagcagc       420
aagagcacct ctgggggaac agcccgccctg gctgcctgg tcaaggacta cttccccgag      480
cccgtgaccg tgtcctggaa ctctggcgcc ctgaccagcg gcgtgcacac ctttccagcc      540
gtgctccaga gcagcggcct gtacagcctg agcagcgtcg tgaccgtgcc cagcagcagc      600
ctgggcaccc agacctacat ctgcaacgtg aaccacaagc ccagcaacac aaaggtggac      660
aagcgggtgg aacccaagag ctgcgacaag acccacacct gtcccccctg ccctgcccct      720
gaactgctgg gaggccccctc cgtgttcctg ttccccccaa agcctaagga cacctgatg      780 atcagccgga cccccgaagt gacctgcgtg gtggtggacg tgtcccacga ggaccctgaa      840
gtgaagttta attggtacgt ggacggcgtg gaagtgcaca acgccaagac caagcccaga      900
gaggaacagt acaacagcac ctaccgggtg gtgtccgtgc tgaccgtgct gcaccaggac      960
tggctgaacg gcaaagagta caagtgcaag gtgtccaaca aggccctgcc tgccccatc     1020 gagaaaacca tcagcaaggc caaaggccag ccccgcgagc cccaggtgta cactgccc     1080 cctagccggg aagagatgac caagaaccag gtgtccctga cctgcctcgt gaaggcttc     1140 taccccagcg acattgccgt ggaatgggag agcaacggcc agcccgagaa caactacaag    1200 accaccccc ctgtgctgga cagcgacggc tcattcttcc tgtacagcaa gctgaccgtg    1260
gacaagagcc ggtggcagca gggcaacgtg ttcagctgct ccgtgatgca cgaggccctg    1320
cacaaccact acacccagaa gtccctgagc ctgagccccg gcaagtga                 1368
```

<210> SEQ ID NO 43
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

```
Ala Ser Pro Ala Ala Pro Ala Pro Ser Ala Gln Ala Val Val Thr Gln
1               5                   10                  15

Glu Pro Ser Leu Thr Val Ser Pro Gly Gly Thr Val Thr Leu Thr Cys
```

```
            20                  25                  30
Arg Ser Ser Thr Gly Ala Val Thr Thr Ser Asn Tyr Ala Asn Trp Val
        35                  40                  45
Gln Gln Lys Pro Gly Gln Ala Pro Arg Gly Leu Ile Gly Gly Thr Asn
    50                  55                  60
Lys Arg Ala Pro Trp Thr Pro Ala Arg Phe Ser Gly Ser Leu Leu Gly
65                  70                  75                  80
Gly Lys Ala Ala Leu Thr Ile Thr Gly Ala Gln Ala Glu Asp Glu Ala
                85                  90                  95
Asp Tyr Tyr Cys Ala Leu Trp Tyr Ser Asn Leu Trp Val Phe Gly Gly
            100                 105                 110
Gly Thr Lys Leu Thr Val Leu Gly Gln Ala Ser Pro Ala Ala Pro Ala
            115                 120                 125
Pro Ala Ser Pro Ala Ala Pro Ala Pro Ala Ser Gly Ser Gln Val Gln
        130                 135                 140
Leu Val Glu Ser Gly Gly Gly Leu Val Lys Pro Gly Gly Ser Leu Arg
145                 150                 155                 160
Leu Ser Cys Ala Ala Ser Gly Phe Thr Phe Asn Thr Tyr Ala Met Asn
                165                 170                 175
Trp Ile Arg Gln Ala Pro Gly Lys Gly Leu Glu Trp Val Ser Arg Ile
            180                 185                 190
Arg Ser Lys Tyr Asn Asn Tyr Ala Thr Tyr Tyr Ala Asp Ser Val Lys
        195                 200                 205
Asp Arg Phe Thr Ile Ser Arg Asp Asn Ala Lys Asn Ser Leu Tyr Leu
    210                 215                 220
Gln Met Asn Ser Leu Arg Ala Glu Asp Thr Ala Val Tyr Tyr Cys Val
225                 230                 235                 240
Arg His Gly Asn Phe Gly Asn Ser Tyr Val Ser Trp Phe Ala Tyr Trp
                245                 250                 255
Gly Gln Gly Thr Leu Val Thr Val Ser Ser
            260                 265
```

<210> SEQ ID NO 44
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

```
gcttctcctg ctgctcctgc tcctagcgct caggccgtgg ttacacaaga gcccagcctg      60
acagttagcc ctggcggaac agtgaccctg acctgcagat cttctacagg cgccgtgacc     120
accagcaact acgccaattg ggtgcagcag aagcctggac aggctcccag aggactgatc     180
ggcggcacaa acaaaagagc cccttggaca cccgccagat tcagcggatc actgctcgga     240
ggaaaggccg cactgacaat cacaggtgcc caggccgaag atgaggccga ttactattgc     300
gccctgtggt acagcaacct gtgggtgttc ggcggaggta ccaagctgac cgtgctgggc     360
caggcctctc ctgctgctcc tgctccagct tctccagccg ctccagctcc tgctagcgga     420
tctcaggtgc agctggtgga atctggcggc ggactcgtga agcctggcgg ctctctgaga     480
ctgagctgtg ccgccagcgg cttcaccttc aacacctacg ccatgaactg gatccggcag     540
gcccctggca agggcctgga atgggtgtcc cggatcagaa gcaagtacaa caattacgcc     600
```

```
acctactacg ccgacagcgt gaaggaccgg ttcaccatca gccgggacaa cgccaagaac    660
agcctgtacc tgcagatgaa ctccctgcgg gccgaggaca ccgccgtgta ctattgtgtg    720
cggcacggca acttcggcaa cagctatgtg tcttggtttg cctactgggg ccagggcacc    780
ctcgtgacag tctcgagc                                                  798
```

```
<210> SEQ ID NO 45
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110

<210> SEQ ID NO 46
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 47
```

<210> SEQ ID NO 47
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 47

```
gagctggtgg tcacacaaga gcccagcctg acagtttctc ctggcggcac agtgaccctg      60
acctgcagat cttctacagg cgccgtgacc acctccaact acgccaattg ggtgcagcag     120
aagcctggac aggctcccag aggactgatc ggcggcacaa acaaaagagc ccctggcaca     180
ccagccagat tcagcggatc actgctcgga ggaaaggccg ctctgacact gtctggtgtc     240
cagcctgaag atgaggccga gtactactgc gccctgtggt acagcaatct gtgggtgttc     300
ggcggaggta ccaagctgac cgtgctgggc cag                                  333
```

<210> SEQ ID NO 48
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
caggtgcagc tggtggaatc tggcggcgga ctcgtgaagc ctggcggctc tctgagactg      60
agctgtgccg ccagcggctt caccttcaac acctacgcca tgaactggat ccggcaggcc     120
cctggcaagg gcctggaatg ggtgtcccgg atcagaagca agtacaacaa ttacgccacc     180
tactacgccg acagcgtgaa ggaccggttc accatcagcc gggacaacgc caagaacagc     240
ctgtacctgc agatgaactc cctgcgggcc gaggacaccg ccgtgtacta ttgtgtgcgg     300
cacggcaact tcggcaacag ctatgtgtct tggtttgcct actggggcca gggcaccctc     360
gtgacagtct cgagc                                                       375
```

<210> SEQ ID NO 49
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Glu Leu Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
```

```
            100                 105                 110
Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 50
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240
```

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 51
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
gagctggtgg tcacacaaga gcccagcctg acagtttctc ctggcggcac agtgaccctg      60
acctgcagat cttctacagg cgccgtgacc acctccaact acgccaattg ggtgcagcag     120
aagcctggac aggctcccag aggactgatc ggcggcacaa acaaagagc ccctggcaca     180 ccagccagat tcagcggatc actgctcgga ggaaaggccg ctctgacact gtctggtgtc     240
cagcctgaag atgaggccga gtactactgc gccctgtggt acagcaatct gtgggtgttc     300
ggcggaggta ccaagctgac cgtgctgggc cagcccaaag ccgcccctag cgtgaccctg     360 ttcccccct cgagtgagga actccaggcc aacaaggcca ccctcgtgtg cctgatcagc     420
gacttctacc ctggcgccgt gaccgtggcc tggaaggccg atagcagccc tgtgaaggcc     480
ggcgtggaaa ccaccacccc cagcaagcag agcaacaaca atacgccgc cagcagctac     540 ctgagcctga cccccgagca gtggaagtcc cacagatcct acagctgcca ggtcacacac     600
gagggcagca ccgtggaaaa gaccgtggcc cccaccgagt gcagc                     645

<210> SEQ ID NO 52

<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

```
caggtgcagc tggtggaatc tgccggcgga ctcgtgaagc ctggcggctc tctgagactg      60
agctgtgccg ccagcggctt caccttcaac acctacgcca tgaactggat ccggcaggcc     120
cctggcaagg gcctggaatg ggtgtcccgg atcagaagca agtacaacaa ttacgccacc     180
tactacgccg acagcgtgaa ggaccggttc accatcagcc gggacaacgc caagaacagc     240
ctgtacctgc agatgaactc cctgcgggcc gaggacaccg ccgtgtacta ttgtgtgcgg     300
cacggcaact tcggcaacag ctatgtgtct tggtttgcct actggggcca gggcaccctc     360
gtgacagtct cgagcgcgtc gaccaaaggc cccagcgtgt tccctctggc ccccagcagc     420
aagagcacct ctgggggaac agccgccctg ggctgcctgg tcaaggacta cttcccccgag    480
cccgtgaccg tgtcctggaa ctctggcgcc ctgaccagcg gcgtgcacac ctttccagcc     540
gtgctccaga gcagcggcct gtacagcctg agcagcgtcg tgaccgtgcc cagcagcagc     600
ctgggcaccc agacctacat ctgcaacgtg aaccacaagc ccagcaacac aaaggtggac     660
aagcgggtgg aacccaagag ctgcgacaag acccacacct gtccccctg ccctgcccct      720
gaactgctgg gaggcccctc cgtgttcctg ttccccccaa agcctaagga caccctgatg     780
atcagccgga ccccgaagt gacctgcgtg gtggtggacg tgtcccacga ggaccctgaa     840
gtgaagttta attggtacgt ggacggcgtg gaagtgcaca acgccaagac caagcccaga     900
gaggaacagt acaacagcac ctaccgggtg gtgtccgtgc tgaccgtgct gcaccaggac     960
tggctgaacg gcaaagagta caagtgcaag gtgtccaaca aggccctgcc tgccccatc    1020
gagaaaacca tcagcaaggc caaaggccag ccccgcgagc cccaggtgta cactgccc    1080
cctagccggg aagagatgac caagaaccag gtgtccctga cctgcctcgt gaagggcttc    1140
taccccagcg acattgccgt ggaatgggag agcaacggcc agcccgagaa caactacaag    1200
accaccccc ctgtgctgga cagcgacggc tcattcttcc tgtacagcaa gctgaccgtg    1260
gacaagagcc ggtggcagca gggcaacgtg ttcagctgct ccgtgatgca cgaggccctg    1320
cacaaccact acacccagaa gtccctgagc ctgagccccg gcaagtga              1368
```

<210> SEQ ID NO 53
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Ala Ser Pro Ala Ala Pro Ala Pro Ser Ala Glu Leu Val Val Thr Gln
1               5                   10                  15

Glu Pro Ser Leu Thr Val Ser Pro Gly Gly Thr Val Thr Leu Thr Cys
            20                  25                  30

Arg Ser Ser Thr Gly Ala Val Thr Thr Ser Asn Tyr Ala Asn Trp Val
        35                  40                  45

Gln Gln Lys Pro Gly Gln Ala Pro Arg Gly Leu Ile Gly Gly Thr Asn
    50                  55                  60
```

Lys Arg Ala Pro Gly Thr Pro Ala Arg Phe Ser Gly Ser Leu Leu Gly
 65                  70                  75                  80

Gly Lys Ala Ala Leu Thr Leu Ser Gly Val Gln Pro Glu Asp Glu Ala
                 85                  90                  95

Glu Tyr Tyr Cys Ala Leu Trp Tyr Ser Asn Leu Trp Val Phe Gly Gly
            100                 105                 110

Gly Thr Lys Leu Thr Val Leu Gly Gln Ala Ser Pro Ala Ala Pro Ala
        115                 120                 125

Pro Ala Ser Pro Ala Ala Pro Ala Pro Ala Ser Gly Ser Gln Val Gln
130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Asn Thr Tyr Ala Met Asn
                165                 170                 175

Trp Ile Arg Gln Ala Pro Gly Lys Gly Leu Glu Trp Val Ser Arg Ile
            180                 185                 190

Arg Ser Lys Tyr Asn Asn Tyr Ala Thr Tyr Tyr Ala Asp Ser Val Lys
        195                 200                 205

Asp Arg Phe Thr Ile Ser Arg Asp Asn Ala Lys Asn Ser Leu Tyr Leu
210                 215                 220

Gln Met Asn Ser Leu Arg Ala Glu Asp Thr Ala Val Tyr Tyr Cys Val
225                 230                 235                 240

Arg His Gly Asn Phe Gly Asn Ser Tyr Val Ser Trp Phe Ala Tyr Trp
                245                 250                 255

Gly Gln Gly Thr Leu Val Thr Val Ser Ser
            260                 265

<210> SEQ ID NO 54
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
gcttctcctg ctgctcctgc tcctagcgct gagctggtgg tcacacaaga gcccagcctg      60
acagtttctc ctggcggcac agtgaccctg acctgcagat cttctacagg cgccgtgacc     120
acctccaact acgccaattg ggtgcagcag aagcctggac aggctcccag aggactgatc     180
ggcggcacaa acaaaagagc ccctggcaca ccagccagat cagcggatc actgctcgga      240 ggaaaggccg ctctgacact gtctggtgtc cagcctgaag atgaggccga gtactactgc     300
gccctgtggt acagcaatct gtgggtgttc ggcggaggta ccaagctgac cgtgctgggc     360
caggcctctc ctgctgctcc tgctccagct tctccagccg ctccagctcc tgctagcgga     420
tctcaggtgc agctggtgga atctggcggc ggactcgtga agcctggcgg ctctctgaga     480
ctgagctgtg ccgccagcgg cttcaccttc aacacctacg ccatgaactg gatccggcag     540
gcccctggca agggcctgga atgggtgtcc cggatcagaa gcaagtacaa caattacgcc     600
acctactacg ccgacagcgt gaaggaccgg ttcaccatca gccgggacaa cgccaagaac     660
agcctgtacc tgcagatgaa ctccctgcgg gccgaggaca ccgccgtgta ctattgtgtg     720
cggcacggca acttcggcaa cagctatgtg tcttggtttg cctactgggg ccagggcacc     780
ctcgtgacag tctcgagc                                                   798

<210> SEQ ID NO 55
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 55

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110
```

<210> SEQ ID NO 56
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 56

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 57
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 57

```
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa acaaaagagc ccctggcaca     180
ccagccagat tcagcggatc actgctcgga ggaaaggccg ctctgacact gcttggagca     240
cagcctgaag atgaggccga gtactactgc gccctgtggt acagcaatct gtgggtgttc     300
ggcggaggta ccaagctgac cgtgctgggc cag                                  333
```

<210> SEQ ID NO 58
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

```
gaagtgcagc tggtggaatc tggcggcgga ctcgtgaagc ctggcggctc tctgagactg      60
agctgtgccg ccagcggctt caccttcaac acctacgcca tgaactgggt cgccaggcc     120 cctggcaaag gcctggaatg ggtgggacgg atcagaagca gtacaacaa ttacgccacc     180 tactacgccg acagcgtgaa ggaccggttc accatcagcc gggacgacag caagaacacc     240
ctgtacctgc agatgaacag cctgaaaacc gaggacaccg ccgtgtacta ctgcaccacc     300
cacggcaact tcggcaacag ctatgtgtct tggtttgcct actggggcca gggcaccctc     360
gtgacagtct cgagc                                                      375
```

<210> SEQ ID NO 59
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

```
Gln Thr Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140
```

```
Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 60
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 61
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 61
cagaccgtgg tcacacaaga gcccagcctg acagtttctc ctggcggcac agtgaccctg        60
acctgcagat cttctacagg cgccgtgacc accagcaact acgccaattg ggtgcagcag       120
aagcctggac aggctcccag aggactgatc ggcggcacaa acaaaagagc ccctggcaca       180
ccagccagat tcagcggatc actgctcgga ggaaaggccg ctctgacact gcttggagca       240
cagcctgaag atgaggccga gtactactgc gccctgtggt acagcaatct gtgggtgttc       300
ggcggaggta ccaagctgac cgtgctgggc agcccaaaag ccgcccctag cgtgaccctg       360 ttcccccccct cgagtgagga actccaggcc aacaaggcca ccctcgtgtg cctgatcagc       420
gacttctacc ctggcgccgt gaccgtggcc tggaaggccg atagcagccc tgtgaaggcc       480
ggcgtggaaa ccaccacccc cagcaagcag agcaacaaca atacgccgc cagcagctac       540 ctgagcctga ccccgagca gtggaagtcc acagatcct acagctgcca ggtcacacac       600
gagggcagca ccgtggaaaa gaccgtggcc cccaccgagt gcagc                       645

<210> SEQ ID NO 62
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 62

```
gaagtgcagc tggtggaatc tggcggcgga ctcgtgaagc tggcggctc tctgagactg      60
agctgtgccg ccagcggctt caccttcaac acctacgcca tgaactgggt gcgccaggcc    120
cctggcaaag gcctggaatg ggtgggacgg atcagaagca agtacaacaa ttacgccacc    180
tactacgccg acagcgtgaa ggaccggttc accatcagcc gggacgacag caagaacacc    240
ctgtacctgc agatgaacag cctgaaaacc gaggacaccg ccgtgtacta ctgcaccacc    300
cacggcaact tcggcaacag ctatgtgtct tggtttgcct actggggcca gggcaccctc    360
gtgacagtct cgagcgcgtc gaccaaaggc cccagcgtgt tccctctggc cccagcagc    420
aagagcacct ctggcggaac agccgccctg gctgcctgg tcaaggacta cttccccgag    480
cccgtgaccg tgtcctggaa ctctggcgcc ctgaccagcg gcgtgcacac ctttccagcc    540
gtgctccaga gcagcggcct gtacagcctg agcagcgtcg tgaccgtgcc agcagcagc    600
ctgggcaccc agacctacat ctgcaacgtg aaccacaagc ccagcaacac aaaggtggac    660
aagcgggtgg aacccaagag ctgcgacaag acccacacct gtcccccctg ccctgcccct    720
gaactgctgg gaggccccc cgtgttcctg ttccccccaa agcctaagga caccctgatg    780
atcagccgga cccccgaagt gacctgcgtg gtggtggacg tgtcccacga ggaccctgaa    840
gtgaagttta attggtacgt ggacggcgtg gaagtgcaca acgccaagac caagcccaga    900
gaggaacagt acaacagcac ctaccgggtg gtgtccgtgc tgaccgtgct gcaccaggac    960
tggctgaacg gcaaagagta caagtgcaag gtgtccaaca aggccctgcc tgccccccatc   1020
gagaaaacca tcagcaaggc caaaggccag ccccgcgagc cccaggtgta cacactgccc    1080
cctagccggg aagagatgac caagaaccag gtgtccctga cctgcctcgt gaagggcttc    1140
taccccagcg acattgccgt ggaatgggag agcaacggcc agcccgagaa caactacaag    1200
accacccccc ctgtgctgga cagcgacggc tcattcttcc tgtacagcaa gctgaccgtg    1260
gacaagagcc ggtggcagca gggcaacgtg ttcagctgct ccgtgatgca cgaggccctg    1320
cacaaccact acacccagaa gtccctgagc ctgagccccg gcaag                    1365
```

<210> SEQ ID NO 63
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

```
Ala Ser Pro Ala Ala Pro Ala Pro Ser Ala Gln Thr Val Val Thr Gln
1               5                   10                  15

Glu Pro Ser Leu Thr Val Ser Pro Gly Gly Thr Val Thr Leu Thr Cys
            20                  25                  30

Arg Ser Ser Thr Gly Ala Val Thr Thr Ser Asn Tyr Ala Asn Trp Val
        35                  40                  45

Gln Gln Lys Pro Gly Gln Ala Pro Arg Gly Leu Ile Gly Gly Thr Asn
    50                  55                  60

Lys Arg Ala Pro Gly Thr Pro Ala Arg Phe Ser Gly Ser Leu Leu Gly
65                  70                  75                  80

Gly Lys Ala Ala Leu Thr Leu Leu Gly Ala Gln Pro Glu Asp Glu Ala
                85                  90                  95
```

Glu Tyr Tyr Cys Ala Leu Trp Tyr Ser Asn Leu Trp Val Phe Gly Gly
                100                 105                 110

Gly Thr Lys Leu Thr Val Leu Gly Gln Ala Ser Pro Ala Ala Pro Ala
        115                 120                 125

Pro Ala Ser Pro Ala Ala Pro Ala Pro Ala Ser Gly Ser Glu Val Gln
            130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Asn Thr Tyr Ala Met Asn
                165                 170                 175

Trp Val Arg Gln Ala Pro Gly Lys Gly Leu Glu Trp Val Gly Arg Ile
            180                 185                 190

Arg Ser Lys Tyr Asn Asn Tyr Ala Thr Tyr Tyr Ala Asp Ser Val Lys
        195                 200                 205

Asp Arg Phe Thr Ile Ser Arg Asp Asp Ser Lys Asn Thr Leu Tyr Leu
210                 215                 220

Gln Met Asn Ser Leu Lys Thr Glu Asp Thr Ala Val Tyr Tyr Cys Thr
225                 230                 235                 240

Thr His Gly Asn Phe Gly Asn Ser Tyr Val Ser Trp Phe Ala Tyr Trp
                245                 250                 255

Gly Gln Gly Thr Leu Val Thr Val Ser Ser
            260                 265

<210> SEQ ID NO 64
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
gcttctcctg ctgctcctgc tcctagcgct cagaccgtgg tcacacaaga gcccagcctg      60
acagtttctc ctggcggcac agtgaccctg acctgcagat cttctacagg cgccgtgacc     120
accagcaact acgccaattg ggtgcagcag aagcctggac aggctcccag aggactgatc     180
ggcggcacaa acaaaagagc ccctggcaca ccagccagat cagcggatc actgctcgga      240 ggaaaggccg ctctgacact gcttggagca cagcctgaag atgaggccga gtactactgc     300
gccctgtggt acagcaatct gtgggtgttc ggcggaggta ccaagctgac cgtgctgggc     360
caggcctctc ctgctgctcc tgctccagct tctccagccg ctccagctcc tgctagcgga     420
tctgaagtgc agctggtgga atctggcggc ggactcgtga agcctggcgg ctctctgaga     480
ctgagctgtg ccgccagcgg cttcaccttc aacacctacg ccatgaactg ggtgcgccag     540
gcccctggca aggcctgga atgggtggga cggatcagaa gcaagtacaa caattacgcc     600
acctactacg ccgacagcgt gaaggaccgg ttcaccatca gccggacga cagcaagaac     660 accctgtacc tgcagatgaa cagcctgaaa accgaggaca ccgccgtgta ctactgcacc     720
acccacggca acttcggcaa cagctatgtg tcttggtttg cctactgggg ccagggcacc     780
ctcgtgacag tctcgagc                                                   798

<210> SEQ ID NO 65
<211> LENGTH: 7
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 65

Gly Thr Lys Phe Leu Ala Pro
1               5

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
ggcacaaaat ttctggcccc t                                              21

<210> SEQ ID NO 67
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110

<210> SEQ ID NO 68
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60
```

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr His Gly Asn Phe Gly Asn Ser Tyr Val Ser Trp Phe
        100                 105                 110

Ala Tyr Trp Gly Gln Gly Thr Leu Val Thr Val Ser Ser
        115                 120                 125

<210> SEQ ID NO 69
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa aatttctggc ccctggcaca     180 ccagccgat tctctggatc tctgctcggc ggaaaggccg ctctgacact gcttggagca     240
cagcctgaag atgaggccga gtactactgc gccctgtggt acagcaatct gtgggtgttc     300
ggcggaggta ccaagctgac cgtgctgggc cag                                  333

<210> SEQ ID NO 70
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
gaagtgcagc tggtggaatc tggcggcgga ctcgtgaagc ctggcggctc tctgagactg      60
agctgtgccg ccagcggctt caccttcaac acctacgcca tgaactgggt gcgccaggcc     120
cctggcaaag cctggaatg ggtggacgg atcagaagca gtacaacaa ttacgccacc       180 tactacgccg acagcgtgaa ggaccggttc accatcagcc gggacgacag caagaacacc     240
ctgtacctgc agatgaacag cctgaaaacc gaggacaccg ccgtgtacta ctgcaccacc     300
cacggcaact tcggcaacag ctatgtgtct tggtttgcct actggggcca gggcaccctc     360
gtgacagtct cgagc                                                     375

<210> SEQ ID NO 71
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser

```
                20                  25                  30
Asn Tyr Ala Asn Trp Val Gln Gln Lys Pro Gly Gln Ala Pro Arg Gly
            35                  40                  45

Leu Ile Gly Gly Thr Lys Phe Leu Ala Pro Gly Thr Pro Ala Arg Phe
50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 72
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 73
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa aatttctggc ccctggcaca     180
ccagccgatt ctctggatc tctgctcggc ggaaaggccg ctctgacact gcttggagca     240
cagcctgaag atgaggccga gtactactgc gccctgtggt acagcaatct gtgggtgttc     300

| | |
|---|---|
| ggcggaggta ccaagctgac cgtgctgggc cagcccaaag ccgcccctag cgtgaccctg | 360 |
| ttccccccct cgagtgagga actccaggcc aacaaggcca ccctcgtgtg cctgatcagc | 420 |
| gacttctacc ctggcgccgt gaccgtggcc tggaaggccg atagcagccc tgtgaaggcc | 480 |
| ggcgtggaaa ccaccacccc cagcaagcag agcaacaaca aatacgccgc cagcagctac | 540 |
| ctgagcctga cccccgagca gtggaagtcc cacagatcct acagctgcca ggtcacacac | 600 |
| gagggcagca ccgtggaaaa gaccgtggcc cccaccgagt gcagc | 645 |

<210> SEQ ID NO 74
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 74

| | |
|---|---|
| gaagtgcagc tggtggaatc tggcggcgga ctcgtgaagc ctggcggctc tctgagactg | 60 |
| agctgtgccg ccagcggctt caccttcaac acctacgcca tgaactgggt gcgccaggcc | 120 |
| cctggcaaag gcctggaatg ggtgggacgg atcagaagca agtacaacaa ttacgccacc | 180 |
| tactacgccg acagcgtgaa ggaccggttc accatcagcc gggacgacag caagaacacc | 240 |
| ctgtacctgc agatgaacag cctgaaaacc gaggacaccg ccgtgtacta ctgcaccacc | 300 |
| cacggcaact cggcaacag ctatgtgtct tggtttgcct actggggcca gggcacccctc | 360 |
| gtgacagtct cgagcgcgtc gaccaaaggc cccagcgtgt tccctctggc ccccagcagc | 420 |
| aagagcacct ctggcggaac agccgccctg ggctgcctgg tcaaggacta cttccccgag | 480 |
| cccgtgaccg tgtcctggaa ctctggcgcc ctgaccagcg gcgtgcacac ctttccagcc | 540 |
| gtgctccaga gcagcggcct gtacagcctg agcagcgtcg tgaccgtgcc cagcagcagc | 600 |
| ctgggcaccc agacctacat ctgcaacgtg aaccacaagc cagcaacac aaaggtggac | 660 |
| aagcgggtgg aacccaagag ctgcgacaag acccacacct gtccccctg ccctgccct | 720 |
| gaactgctgg gaggccctc cgtgttcctg ttccccccaa agcctaagga caccctgatg | 780 |
| atcagccgga cccccgaagt gacctgcgtg gtggtggacg tgtcccacga ggaccctgaa | 840 |
| gtgaagttta attggtacgt ggacggcgtg gaagtgcaca acgccaagac caagcccaga | 900 |
| gaggaacagt acaacagcac ctaccgggtg gtgtccgtgc tgaccgtgct gcaccaggac | 960 |
| tggctgaacg gcaaagagta caagtgcaag gtgtccaaca aggccctgcc tgcccccatc | 1020 |
| gagaaaacca tcagcaaggc caaggccag ccccgcgagc ccaggtgta cacactgccc | 1080 |
| cctagccggg aagagatgac caagaaccag gtgtccctga cctgcctcgt gaagggcttc | 1140 |
| taccccagcg acattgccgt ggaatgggag agcaacggcc agcccgagaa caactacaag | 1200 |
| accaccccc ctgtgctgga cagcgacggc tcattcttcc tgtacagcaa gctgaccgtg | 1260 |
| gacaagagcc ggtggcagca gggcaacgtg ttcagctgct ccgtgatgca cgaggccctg | 1320 |
| cacaaccact acacccagaa gtccctgagc ctgagccccg gcaag | 1365 |

<210> SEQ ID NO 75
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 75

| | | | | | | | | | | | |
|---|---|---|---|---|---|---|---|---|---|---|---|
|Ala|Ser|Pro|Ala|Ala|Pro|Ala|Pro|Ser|Ala|Gln|Thr|Val|Val|Thr|Gln|
|1| | | |5| | | | |10| | | | |15| |

Glu Pro Ser Leu Thr Val Ser Pro Gly Gly Thr Val Thr Leu Thr Cys
           20               25               30

Arg Ser Ser Thr Gly Ala Val Thr Thr Ser Asn Tyr Ala Asn Trp Val
         35               40               45

Gln Gln Lys Pro Gly Gln Ala Pro Arg Gly Leu Ile Gly Gly Thr Lys
 50               55               60

Phe Leu Ala Pro Gly Thr Pro Ala Arg Phe Ser Gly Ser Leu Leu Gly
65              70               75               80

Gly Lys Ala Ala Leu Thr Leu Leu Gly Ala Gln Pro Glu Asp Glu Ala
               85               90               95

Glu Tyr Tyr Cys Ala Leu Trp Tyr Ser Asn Leu Trp Val Phe Gly Gly
          100              105              110

Gly Thr Lys Leu Thr Val Leu Gly Gln Ala Ser Pro Ala Ala Pro Ala
         115             120              125

Pro Ala Ser Pro Ala Ala Pro Ala Pro Ala Ser Gly Ser Glu Val Gln
   130               135              140

Leu Val Glu Ser Gly Gly Gly Leu Val Lys Pro Gly Gly Ser Leu Arg
145              150              155              160

Leu Ser Cys Ala Ala Ser Gly Phe Thr Phe Asn Thr Tyr Ala Met Asn
         165             170              175

Trp Val Arg Gln Ala Pro Gly Lys Gly Leu Glu Trp Val Gly Arg Ile
         180             185              190

Arg Ser Lys Tyr Asn Asn Tyr Ala Thr Tyr Tyr Ala Asp Ser Val Lys
         195             200              205

Asp Arg Phe Thr Ile Ser Arg Asp Asp Ser Lys Asn Thr Leu Tyr Leu
   210               215              220

Gln Met Asn Ser Leu Lys Thr Glu Asp Thr Ala Val Tyr Tyr Cys Thr
225              230              235              240

Thr His Gly Asn Phe Gly Asn Ser Tyr Val Ser Trp Phe Ala Tyr Trp
         245             250              255

Gly Gln Gly Thr Leu Val Thr Val Ser Ser
         260             265

<210> SEQ ID NO 76
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 76

```
gcttctcctg ctgctcctgc tcctagcgct cagaccgtgg tcacacaaga gcccagcctg      60
acagtttctc ctggcggcac agtgaccctg acctgcagat cttctacagg cgccgtgacc     120
accagcaact acgccaattg ggtgcagcag aagcctggac aggctcccag aggactgatc     180
ggcggcacaa aatttctggc ccctggcaca ccagccagat ctctggatc tctgctcggc      240 ggaaaggccg ctctgacact gcttggagca cagcctgaag atgaggccga gtactactgc     300
gccctgtggt acagcaatct gtgggtgttc ggcggaggta ccaagctgac cgtgctgggc     360
```

```
caggcctctc ctgctgctcc tgctccagct tctccagccg ctccagctcc tgctagcgga    420
tctgaagtgc agctggtgga atctggcggc ggactcgtga agcctggcgg ctctctgaga    480
ctgagctgtg ccgccagcgg cttcaccttc aacacctacg ccatgaactg ggtgcgccag    540
gcccctggca aaggcctgga atgggtggga cggatcagaa gcaagtacaa caattacgcc    600
acctactacg ccgacagcgt gaaggaccgg ttcaccatca gccgggacga cagcaagaac    660
accctgtacc tgcagatgaa cagcctgaaa accgaggaca ccgccgtgta ctactgcacc    720
acccacggca acttcggcaa cagctatgtg tcttggtttg cctactgggg ccagggcacc    780
ctcgtgacag tctcgagc                                                  798
```

```
<210> SEQ ID NO 77
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln
            100                 105                 110
```

```
<210> SEQ ID NO 78
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95
```

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 79
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag gggactgatc ggcggcacaa aatttctggc ccctggcaca     180
ccagccgatt tctctggatc tctgctcggc ggaaaggccg ctctgacact gtctggtgtt     240
cagcctgagg acgaggccga gtactattgc gccctgtggt acagcaacct gtgggtgttc     300
ggcggaggta ccaagctgac cgtgctgggc cag                                  333

<210> SEQ ID NO 80
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 80
gaagtgcagc tggtggaatc tggcggcgga ctcgtgaagc ctggcggctc tctgagactg      60
agctgtgccg ccagcggctt caccttcaac acctacgcca tgaactgggt gcgccaggcc     120
cctggcaaag gcctggaatg gtgggacgga tcagaagca agtacaacaa ttacgccacc     180
tactacgccg acagcgtgaa ggaccggttc accatcagcc gggacgacag caagaacacc     240
ctgtacctgc agatgaacag cctgaaaacc gaggacaccg ccgtgtacta ctgcaccacc     300
cacggcaact cggcaacag ctatgtgtct tggtttgcct actggggcca gggcacccctc     360 gtgacagtct cgagc                                                     375

<210> SEQ ID NO 81
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

```
Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 82
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Asn Thr Tyr
             20                  25                  30

Ala Met Asn Trp Val Arg Gln Ala Pro Gly Lys Gly Leu Glu Trp Val
         35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 83
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa aatttctggc ccctggcaca     180
ccagccagat ctctctggat cctgctcggc ggaaaggccg ctctgacact gtctggtgtt     240
cagcctgagg acgaggccga gtactattgc gccctgtggt acagcaacct gtgggtgttc     300
ggcggaggta ccaagctgac cgtgctgggc cagcccaaag ccgcccctag cgtgaccctg     360
ttccccccct cgagtgagga actccaggcc aacaaggcca ccctcgtgtg cctgatcagc     420
gacttctacc ctggcgccgt gaccgtggcc tggaaggcca tagcagccc tgtgaaggcc      480

| ggcgtggaaa ccaccacccc cagcaagcag agcaacaaca aatacgccgc cagcagctac | 540 |
| ctgagcctga cccccgagca gtggaagtcc acagatcct acagctgcca ggtcacacac | 600 |
| gagggcagca ccgtggaaaa gaccgtggcc cccaccgagt gcagc | 645 |

<210> SEQ ID NO 84
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 84

| gaagtgcagc tggtggaatc tggcggcgga ctcgtgaagc ctggcggctc tctgagactg | 60 |
| agctgtgccg ccagcggctt caccttcaac acctacgcca tgaactgggt gcgccaggcc | 120 |
| cctggcaaag gcctgaatg gtgggacgg atcagaagca agtacaacaa ttacgccacc | 180 |
| tactacgccg acagcgtgaa ggaccggttc accatcagcc gggacgacag caagaacacc | 240 |
| ctgtacctgc agatgaacag cctgaaaacc gaggacaccg ccgtgtacta ctgcaccacc | 300 |
| cacggcaact tcggcaacag ctatgtgtct tggtttgcct actggggcca gggcacccta | 360 |
| gtgacagtct cgagcgcgtc gaccaaaggc cccagcgtgt tccctctggc ccccagcagc | 420 |
| aagagcacct ctgggggaac agccgccctg ggctgcctgg tcaaggacta cttccccgag | 480 |
| cccgtgaccg tgtcctggaa ctctggcgcc ctgaccagcg gcgtgcacac ctttccagcc | 540 |
| gtgctccaga gcagcggcct gtacagcctg agcagcgtcg tgaccgtgcc cagcagcagc | 600 |
| ctgggcaccc agacctacat ctgcaacgtg aaccacaagc ccagcaacac aaaggtggac | 660 |
| aagcgggtgg aacccaagag ctgcgacaag acccacacct gtcccccctg ccctgcccct | 720 |
| gaactgctgg gaggcccctc cgtgttcctg ttccccccaa agcctaagga caccctgatg | 780 |
| atcagccgga cccccgaagt gacctgcgtg gtggtggacg tgtcccacga ggaccctgaa | 840 |
| gtgaagttta attggtacgt ggacggcgtg gaagtgcaca acgccaagac caagcccaga | 900 |
| gaggaacagt acaacagcac ctaccgggtg gtgtccgtgc tgaccgtgct gcaccaggac | 960 |
| tggctgaacg gcaaagagta caagtgcaag gtgtccaaca aggccctgcc tgcccccatc | 1020 |
| gagaaaacca tcagcaaggc caaaggccag ccccgcgagc cccaggtgta cactgccc | 1080 |
| cctagccggg aagagatgac caagaaccag gtgtccctga cctgcctcgt gaagggcttc | 1140 |
| taccccagcg acattgccgt ggaatgggag agcaacggcc agcccgagaa caactacaag | 1200 |
| accaccccc ctgtgctgga cagcgacggc tcattcttcc tgtacagcaa gctgaccgtg | 1260 |
| gacaagagcc ggtggcagca gggcaacgtg ttcagctgct ccgtgatgca cgaggccctg | 1320 |
| cacaaccact acacccagaa gtccctgagc ctgagccccg gcaag | 1365 |

<210> SEQ ID NO 85
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 85

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gln Ala Pro Arg Gly
        35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
65                   70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gln
            100                 105                 110

<210> SEQ ID NO 86
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asn Ala Lys Asn Ser
65                   70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 87
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa aatttctggc ccctggcaca     180
ccagccagat ctctctggatc tctgctcggc ggaaaggccg ctctgacact gtctggtgtt     240
cagcctgagg acgaggccga gtactattgc gccctgtggt acagcaacct gtgggtgttc     300
ggcggaggta ccaagctgac cgtgctgggc cag                                  333

<210> SEQ ID NO 88
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 88

```
caggtgcagc tggtggaatc tggcggcgga ctcgtgaagc tggcggctc tctgagactg      60 agctgtgccg ccagcggctt caccttcaac acctacgcca tgaactggat ccggcaggcc     120
cctggcaagg gcctggaatg ggtgtcccgg atcagaagca agtacaacaa ttacgccacc     180
tactacgccg acagcgtgaa ggaccggttc accatcagcc gggacaacgc caagaacagc     240
ctgtacctgc agatgaactc cctgcgggcc gaggacaccg ccgtgtacta ttgtgtgcgg     300
cacggcaact tcggcaacag ctatgtgtct tggtttgcct actggggcca gggcacactc     360
gtgacagtct cgagc                                                     375
```

<210> SEQ ID NO 89
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 89

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 90
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
```

|   |   |   |   |   | 355 |   |   |   |   | 360 |   |   |   |   | 365 |   |
|---|---|---|---|---|---|---|---|---|---|---|---|---|---|---|---|---|

Asn Gln Val Ser Leu Thr Cys Leu Val Lys Gly Phe Tyr Pro Ser Asp
    370                            375                        380

Ile Ala Val Glu Trp Glu Ser Asn Gly Gln Pro Glu Asn Asn Tyr Lys
385                        390                      395                        400

Thr Thr Pro Pro Val Leu Asp Ser Asp Gly Ser Phe Phe Leu Tyr Ser
                    405                      410                        415

Lys Leu Thr Val Asp Lys Ser Arg Trp Gln Gln Gly Asn Val Phe Ser
            420                      425                      430

Cys Ser Val Met His Glu Ala Leu His Asn His Tyr Thr Gln Lys Ser
                435                    440                      445

Leu Ser Leu Ser Pro Gly Lys
  450                        455

<210> SEQ ID NO 91
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91

| | | | | | |
|---|---|---|---|---|---|
| cagaccgtgg | tcacacaaga | gcccagcctg | acagtttctc | ctggcggcac | agtgaccctg | 60 |
| acctgcagat | cttctacagg | cgccgtgacc | accagcaact | acgccaattg | ggtgcagcag | 120 |
| aagcctggac | aggctcccag | aggactgatc | ggcggcacaa | aatttctggc | ccctggcaca | 180 |
| ccagccagat | ctctctggatc | tctgctcggc | ggaaaggccg | ctctgacact | gtctggtgtt | 240 |
| cagcctgagg | acgaggccga | gtactattgc | gccctgtggt | acagcaacct | gtgggtgttc | 300 |
| ggcggaggta | ccaagctgac | cgtgctgggc | agcccaaag | ccgcccctag | cgtgaccctg | 360 |
| ttcccccccct | cgagtgagga | actccaggcc | aacaaggcca | ccctcgtgtg | cctgatcagc | 420 |
| gacttctacc | tggcgccgt | gaccgtggcc | tggaaggccg | atagcagccc | tgtgaaggcc | 480 |
| ggcgtggaaa | ccaccacccc | cagcaagcag | agcaacaaca | aatacgccgc | cagcagctac | 540 |
| ctgagcctga | ccccccagca | gtggaagtcc | cacagatcct | acagctgcca | ggtcacacac | 600 |
| gagggcagca | ccgtggaaaa | gaccgtggcc | cccaccgagt | gcagc | | 645 |

<210> SEQ ID NO 92
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 92

| | | | | | |
|---|---|---|---|---|---|
| caggtgcagc | tggtggaatc | tggcggcgga | ctcgtgaagc | ctggcggctc | tctgagactg | 60 |
| agctgtgccg | ccagcggctt | caccttcaac | acctacgcca | tgaactggat | ccggcaggcc | 120 |
| cctggcaagg | gcctggaatg | ggtgtcccgg | atcagaagca | agtacaacaa | ttacgccacc | 180 |
| tactacgccg | acagcgtgaa | ggaccggttc | accatcagcc | gggacaacgc | caagaacagc | 240 |
| ctgtacctgc | agatgaactc | cctgcgggcc | gaggacaccg | ccgtgtacta | ttgtgtgcgg | 300 |
| cacggcaact | cggcaacag | ctatgtgtct | tggtttgcct | actggggcca | gggcacccctc | 360 |
| gtgacagtct | cgagcgcgtc | gaccaaaggc | cccagcgtgt | tccctctggc | ccccagcagc | 420 |

```
aagagcacct ctggcggaac agccgccctg ggctgcctgg tcaaggacta cttccccgag    480
cccgtgaccg tgtcctggaa ctctggcgcc ctgaccagcg gcgtgcacac ctttccagcc    540
gtgctccaga gcagcggcct gtacagcctg agcagcgtcg tgaccgtgcc cagcagcagc    600
ctgggcaccc agacctacat ctgcaacgtg aaccacaagc ccagcaacac aaaggtggac    660
aagcgggtgg aacccaagag ctgcgacaag acccacacct gtccccctg ccctgcccct     720 gaactgctgg gaggcccctc cgtgttcctg ttccccccaa agcctaagga cacctgatg    780 atcagccgga ccccgaagt gacctgcgtg gtggtggacg tgtcccacga ggaccctgaa    840
gtgaagttta attggtacgt ggacggcgtg gaagtgcaca acgccaagac caagcccaga    900
gaggaacagt acaacagcac ctaccggtg gtgtccgtgc tgaccgtgct gcaccaggac    960
tggctgaacg gcaaagagta caagtgcaag gtgtccaaca aggccctgcc tgcccccatc   1020
gagaaaacca tcagcaaggc caaggccag ccccgcgagc cccaggtgta cacactgccc   1080
cctagccggg aagagatgac caagaaccag gtgtccctga cctgcctcgt gaagggcttc   1140
taccccagcg acattgccgt ggaatgggag agcaacggcc agcccgagaa caactacaag   1200
accacccccc ctgtgctgga cagcgacggc tcattcttcc tgtacagcaa gctgaccgtg   1260
gacaagagcc ggtggcagca gggcaacgtg ttcagctgct ccgtgatgca cgaggccctg   1320
cacaaccact acacccagaa gtccctgagc ctgagccccg gcaagtga               1368

<210> SEQ ID NO 93
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Ala Ser Pro Ala Ala Pro Ala Pro Ser Ala Gln Thr Val Val Thr Gln
1               5                   10                  15

Glu Pro Ser Leu Thr Val Ser Pro Gly Gly Thr Val Thr Leu Thr Cys
            20                  25                  30

Arg Ser Ser Thr Gly Ala Val Thr Thr Ser Asn Tyr Ala Asn Trp Val
        35                  40                  45

Gln Gln Lys Pro Gly Gln Ala Pro Arg Gly Leu Ile Gly Gly Thr Lys
    50                  55                  60

Phe Leu Ala Pro Gly Thr Pro Ala Arg Phe Ser Gly Ser Leu Leu Gly
65                  70                  75                  80

Gly Lys Ala Ala Leu Thr Leu Ser Gly Val Gln Pro Glu Asp Glu Ala
                85                  90                  95

Glu Tyr Tyr Cys Ala Leu Trp Tyr Ser Asn Leu Trp Val Phe Gly Gly
            100                 105                 110

Gly Thr Lys Leu Thr Val Leu Gly Gln Ala Ser Pro Ala Ala Pro Ala
        115                 120                 125

Pro Ala Ser Pro Ala Ala Pro Ala Pro Ala Ser Gly Ser Gln Val Gln
    130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Asn Thr Tyr Ala Met Asn
                165                 170                 175

Trp Ile Arg Gln Ala Pro Gly Lys Gly Leu Glu Trp Val Ser Arg Ile
```

```
                    180                 185                 190
Arg Ser Lys Tyr Asn Asn Tyr Ala Thr Tyr Tyr Ala Asp Ser Val Lys
                195                 200                 205

Asp Arg Phe Thr Ile Ser Arg Asp Asn Ala Lys Asn Ser Leu Tyr Leu
        210                 215                 220

Gln Met Asn Ser Leu Arg Ala Glu Asp Thr Ala Val Tyr Tyr Cys Val
225                 230                 235                 240

Arg His Gly Asn Phe Gly Asn Ser Tyr Val Ser Trp Phe Ala Tyr Trp
                245                 250                 255

Gly Gln Gly Thr Leu Val Thr Val Ser Ser
            260                 265

<210> SEQ ID NO 94
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94
gcttctcctg ctgctcctgc tcctagcgct cagaccgtgg tcacacaaga gcccagcctg      60
acagtttctc ctggcggcac agtgaccctg acctgcagat cttctacagg cgccgtgacc     120
accagcaact acgccaattg ggtgcagcag aagcctggac aggctcccag aggactgatc     180
ggcggcacaa aatttctggc ccctggcaca ccagccagat tctctggatc tctgctcggc     240
ggaaaggccg ctctgacact gtctggtgtt cagcctgagg acgaggccga gtactattgc     300
gccctgtggt acagcaacct gtgggtgttc ggcggaggta ccaagctgac cgtgctgggc     360
caggcctctc ctgctgctcc tgctccagct tctccagccg ctccagctcc tgctagcgga     420
tctcaggtgc agctggtgga atctggcggc ggactcgtga agcctggcgg ctctctgaga     480
ctgagctgtg ccgccagcgg cttcaccttc aacacctacg ccatgaactg gatccggcag     540
gccccctggc agggcctgga atgggtgtcc cggatcagaa gcaagtacaa caattacgcc     600
acctactacg ccgacagcgt gaaggaccgg ttcaccatca gccgggacaa cgccaagaac     660
agcctgtacc tgcagatgaa ctccctgcgg gccgaggaca ccgccgtgta ctattgtgtg     720
cggcacggca acttcggcaa cagctatgtg tcttggtttg cctactgggg ccagggcacc     780
ctcgtgacag tctcgagc                                                   798

<210> SEQ ID NO 95
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
```

```
                50                  55                  60
Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gln
            100                 105                 110

<210> SEQ ID NO 96
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Asn Thr Tyr
             20                  25                  30

Ala Met Asn Trp Ile Arg Gln Ala Pro Gly Lys Gly Leu Glu Trp Val
         35                  40                  45

Ser Arg Ile Arg Ser Lys Tyr Asn Asn Tyr Ala Thr Tyr Tyr Ala Asp
     50                  55                  60

Ser Val Lys Asp Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 97
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa acaaagagc ccctggcaca      180 ccagccagat tcagcggatc actgctcgga ggaaaggccg ctctgacact gtctggtgtc     240
cagcctgaag atgaggccga gtactactgc gccctgtggt acagcaatct gtgggtgttc     300
ggcggaggta ccaagctgac cgtgctgggc cag                                  333

<210> SEQ ID NO 98
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 98

```
caggtgcagc tggtggaatc tggcggcgga ctcgtgaagc tggcggctc tctgagactg    60
agctgtgccg ccagcggctt caccttcaac acctacgcca tgaactggat ccggcaggcc   120
cctggcaagg gcctggaatg ggtgtcccgg atcagaagca agtacaacaa ttacgccacc   180
tactacgccg acagcgtgaa ggaccggttc accatcagcc gggacaacgc caagaacagc   240
ctgtacctgc agatgaactc cctgcgggcc gaggacaccg ccgtgtacta ttgtgtgcgg   300
cacggcaact tcggcaacag ctatgtgtct tggtttgcct actggggcca gggcaccctc   360
gtgacagtct cgagc                                                   375
```

<210> SEQ ID NO 99
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 99

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 100
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 100

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400
```

```
Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
    450                 455
```

<210> SEQ ID NO 101
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101

| | | |
|---|---|---|
| cagaccgtgg tcacacaaga gcccagcctg acagtttctc ctggcggcac agtgaccctg | 60 |
| acctgcagat cttctacagg cgccgtgacc accagcaact acgccaattg ggtgcagcag | 120 |
| aagcctggac aggctcccag aggactgatc ggcggcacaa acaaaagagc ccctggcaca | 180 |
| ccagccagat tcagcggatc actgctcgga ggaaaggccg ctctgacact gtctggtgtc | 240 |
| cagcctgaag atgaggccga gtactactgc gccctgtggt acagcaatct gtgggtgttc | 300 |
| ggcggaggta ccaagctgac cgtgctgggc cagcccaaag ccgcccctag cgtgaccctg | 360 |
| ttcccccccct cgagtgagga actccaggcc aacaaggcca ccctcgtgtg cctgatcagc | 420 |
| gacttctacc ctggcgccgt gaccgtggcc tggaaggccg atagcagccc tgtgaaggcc | 480 |
| ggcgtggaaa ccaccacccc cagcaagcag agcaacaaca atacgccgc cagcagctac | 540 |
| ctgagcctga cccccgagca gtggaagtcc acagatcct acagctgcca ggtcacacac | 600 |
| gagggcagca ccgtggaaaa gaccgtggcc cccaccgagt gcagc | 645 |

<210> SEQ ID NO 102
<211> LENGTH: 1368
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 102

| | | |
|---|---|---|
| caggtgcagc tggtggaatc tggcggcgga ctcgtgaagc ctggcggctc tctgagactg | 60 |
| agctgtgccg ccagcggctt caccttcaac acctacgcca tgaactggat ccggcaggcc | 120 |
| cctggcaagg gcctggaatg ggtgtcccgg atcagaagca gtacaacaa ttacgccacc | 180 |
| tactacgccg acagcgtgaa ggaccggttc accatcagcc gggacaacgc caagaacagc | 240 |
| ctgtacctgc agatgaactc cctgcgggcc gaggacaccg ccgtgtacta ttgtgtgcgg | 300 |
| cacggcaact tcggcaacag ctatgtgtct tggtttgcct actggggcca gggcacccct | 360 |
| gtgacagtct cgagcgcgtc gaccaaaggc ccagcgtgt tccctctggc ccccagcagc | 420 |
| aagagcacct ctggcggaac agccgccctg ggctgcctgg tcaaggacta cttccccgag | 480 |
| cccgtgaccg tgtcctggaa ctctggcgcc ctgaccagcg gcgtgcacac ctttccagcc | 540 |
| gtgctccaga gcagcggcct gtacagcctg agcagcgtcg tgaccgtgcc cagcagcagc | 600 |

```
ctgggcaccc agacctacat ctgcaacgtg aaccacaagc ccagcaacac aaaggtggac    660
aagcgggtgg aacccaagag ctgcgacaag acccacacct gtccccctg ccctgccct     720 gaactgctgg gaggcccctc cgtgttcctg ttccccccaa agcctaagga caccctgatg    780
atcagccgga ccccgaagt gacctgcgtg gtggtggacg tgtcccacga ggaccctgaa     840
gtgaagttta attggtacgt ggacggcgtg gaagtgcaca acgccaagac caagcccaga    900
gaggaacagt acaacagcac ctaccgggtg gtgtccgtgc tgaccgtgct gcaccaggac    960
tggctgaacg gcaaagagta caagtgcaag gtgtccaaca aggccctgcc tgcccccatc   1020
gagaaaacca tcagcaaggc caaggccag ccccgcgagc cccaggtgta cacactgccc    1080
cctagccggg aagagatgac caagaaccag gtgtccctga cctgcctcgt gaagggcttc   1140
tacccccagc gacattgccgt ggaatgggag agcaacggcc agcccgagaa caactacaag   1200 accaccccc ctgtgctgga cagcgacggc tcattcttcc tgtacagcaa gctgaccgtg    1260
gacaagagcc ggtggcagca gggcaacgtg ttcagctgct ccgtgatgca cgaggccctg   1320
cacaaccact acacccagaa gtccctgagc ctgagccccg gcaagtga               1368
```

<210> SEQ ID NO 103
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

```
Ala Ser Pro Ala Ala Pro Ala Pro Ser Ala Gln Thr Val Val Thr Gln
1               5                   10                  15

Glu Pro Ser Leu Thr Val Ser Pro Gly Gly Thr Val Thr Leu Thr Cys
            20                  25                  30

Arg Ser Ser Thr Gly Ala Val Thr Thr Ser Asn Tyr Ala Asn Trp Val
        35                  40                  45

Gln Gln Lys Pro Gly Gln Ala Pro Arg Gly Leu Ile Gly Gly Thr Asn
    50                  55                  60

Lys Arg Ala Pro Gly Thr Pro Ala Arg Phe Ser Gly Ser Leu Leu Gly
65                  70                  75                  80

Gly Lys Ala Ala Leu Thr Leu Ser Gly Val Gln Pro Glu Asp Glu Ala
                85                  90                  95

Glu Tyr Tyr Cys Ala Leu Trp Tyr Ser Asn Leu Trp Val Phe Gly Gly
            100                 105                 110

Gly Thr Lys Leu Thr Val Leu Gly Gln Ala Ser Pro Ala Ala Pro Ala
        115                 120                 125

Pro Ala Ser Pro Ala Ala Pro Ala Pro Ser Gly Ser Gln Val Gln
    130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Asn Thr Tyr Ala Met Asn
                165                 170                 175

Trp Ile Arg Gln Ala Pro Gly Lys Gly Leu Glu Trp Val Ser Arg Ile
            180                 185                 190

Arg Ser Lys Tyr Asn Asn Tyr Ala Thr Tyr Tyr Ala Asp Ser Val Lys
        195                 200                 205

Asp Arg Phe Thr Ile Ser Arg Asp Asn Ala Lys Asn Ser Leu Tyr Leu
    210                 215                 220
```

Gln Met Asn Ser Leu Arg Ala Glu Asp Thr Ala Val Tyr Tyr Cys Val
225                 230                 235                 240

Arg His Gly Asn Phe Gly Asn Ser Tyr Val Ser Trp Phe Ala Tyr Trp
                245                 250                 255

Gly Gln Gly Thr Leu Val Thr Val Ser Ser
            260                 265

<210> SEQ ID NO 104
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 104
gcttctcctg ctgctcctgc tcctagcgct cagaccgtgg tcacacaaga gcccagcctg      60
acagtttctc ctggcggcac agtgaccctg acctgcagat cttctacagg cgccgtgacc     120
accagcaact acgccaattg ggtgcagcag aagcctggac aggctcccag aggactgatc     180
ggcggcacaa acaaaagagc ccctggcaca ccagccagat tcagcggatc actgctcgga     240
ggaaaggccg ctctgacact gtctggtgtc cagcctgaag atgaggccga gtactactgc     300
gccctgtggt acagcaatct gtgggtgttc ggcggaggta ccaagctgac cgtgctgggc     360
caggcctctc ctgctgctcc tgctccagct tctccagccg ctccagctcc tgctagcgga     420
tctcaggtgc agctggtgga atctggcggc ggactcgtga agcctggcgg ctctctgaga     480
ctgagctgtg ccgccagcgg cttcaccttc aacacctacg ccatgaactg gatccggcag     540
gcccctggca agggcctgga atgggtgtcc cggatcagaa gcaagtacaa caattacgcc     600
acctactacg ccgacagcgt gaaggaccgg ttcaccatca gccgggacaa cgccaagaac     660
agcctgtacc tgcagatgaa ctccctgcgg gccgaggaca ccgccgtgta ctattgtgtg     720
cggcacggca acttcggcaa cagctatgtg tcttggtttg cctactgggg ccagggcacc     780
ctcgtgacag tctcgagc                                                  798

<210> SEQ ID NO 105
<211> LENGTH: 716
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

-continued

```
Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ala Ser Pro Ala Ala Pro Ala Pro Ser Ala Gln Ala Val Val
    450                 455                 460

Thr Gln Glu Pro Ser Leu Thr Val Ser Pro Gly Gly Thr Val Thr Leu
465                 470                 475                 480

Thr Cys Arg Ser Ser Thr Gly Ala Val Thr Thr Ser Asn Tyr Ala Asn
                485                 490                 495

Trp Val Gln Gln Lys Pro Gly Gln Ala Pro Arg Gly Leu Ile Gly Gly
            500                 505                 510
```

| | | | | | | | | | | | |
|---|---|---|---|---|---|---|---|---|---|---|---|
|Thr|Asn|Lys|Arg|Ala|Pro|Trp|Thr|Pro|Ala|Arg|Phe|Ser|Gly|Ser|Leu|
| |  |515| |   | |520|   | |   | |525|   |   |   |    |

Thr Asn Lys Arg Ala Pro Trp Thr Pro Ala Arg Phe Ser Gly Ser Leu
                515                 520                 525

Leu Gly Gly Lys Ala Ala Leu Thr Ile Thr Gly Ala Gln Ala Glu Asp
            530                 535                 540

Glu Ala Asp Tyr Tyr Cys Ala Leu Trp Tyr Ser Asn Leu Trp Val Phe
545                 550                 555                 560

Gly Gly Gly Thr Lys Leu Thr Val Leu Gly Gln Ala Ser Pro Ala Ala
                565                 570                 575

Pro Ala Pro Ala Ser Pro Ala Ala Pro Ala Ser Gly Ser Gln
            580                 585                 590

Val Gln Leu Val Glu Ser Gly Gly Leu Val Lys Pro Gly Gly Ser
            595                 600                 605

Leu Arg Leu Ser Cys Ala Ala Ser Gly Phe Thr Phe Asn Thr Tyr Ala
            610                 615                 620

Met Asn Trp Ile Arg Gln Ala Pro Gly Lys Gly Leu Glu Trp Val Ser
625                 630                 635                 640

Arg Ile Arg Ser Lys Tyr Asn Asn Tyr Ala Thr Tyr Tyr Ala Asp Ser
                645                 650                 655

Val Lys Asp Arg Phe Thr Ile Ser Arg Asp Asn Ala Lys Asn Ser Leu
            660                 665                 670

Tyr Leu Gln Met Asn Ser Leu Arg Ala Glu Asp Thr Ala Val Tyr Tyr
            675                 680                 685

Cys Val Arg His Gly Asn Phe Gly Asn Ser Tyr Val Ser Trp Phe Ala
            690                 695                 700

Tyr Trp Gly Gln Gly Thr Leu Val Thr Val Ser Ser
705                 710                 715

<210> SEQ ID NO 106
<211> LENGTH: 2148
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
caggtgcaat tggtggagtc tggcggagga ctggtgcagc ctgggggcag cctgagactg    60
agctgcgccg ccagcggctt caacatcaag gacacctaca tccactgggt gcgccaggct   120
ccaggcaagg gactggaatg ggtggcccgg atctacccca ccaacggcta caccagatac   180
gccgacagcg tgaagggccg gttcaccatc agcgccgaca ccagcaagaa caccgcctac   240
ctgcagatga acagcctgcg ggccgaggac accgccgtgt actactgcag cagatggggc   300
ggagatggct tctacgccat ggactactgg ggccagggca ccctggtgac cgtctcgagc   360
gcgtcgacca aggccccag cgtgttccct ctggccccca gcagcaagag cacctctggc   420
ggaacagccg ccctgggctg cctggtcaag gactacttcc ccgagcccgt gaccgtgtcc   480
tggaactctg gcgccctgac cagcggcgtg cacaccttc agccgtgct ccagagcagc   540 ggcctgtaca gcctgagcag cgtcgtgacc gtgcccagca gcagcctggg cacccagacc   600
tacatctgca acgtgaacca caagcccagc aacacaaagg tggacaagcg gtggaaccc   660 aagagctgcg acaagaccca cacctgtccc cctgccctg cccctgaagc ggagggagcc   720
ccctccgtgt tcctgttccc cccaaagcct aaggacaccc tgatgatcag ccggacccc   780 gaagtgacct gcgtggtggt ggacgtgtcc cacgaggacc ctgaagtgaa gtttaattgg   840

```
tacgtggacg gcgtggaagt gcacaacgcc aagaccaagc ccagagagga acagtacaac   900
agcacctacc gggtggtgtc cgtgctgacc gtgctgcacc aggactggct gaacggcaaa   960
gagtacaagt gcaaggtgtc caacaaggcc ctgccttcct ccatcgagaa aaccatcagc  1020
aaggccaaag ccagccccg cgagcccag gtgtacacac tgcccctag ccgggaagag   1080 atgaccaaga accaggtgtc cctgacctgc ctcgtgaagg gcttctaccc cagcgacatt  1140
gccgtggaat gggagagcaa cggccagccc gagaacaact acaagaccac ccccctgtg  1200 ctggacagcg acggctcatt cttcctgtac agcaagctga ccgtggacaa gagccggtgg  1260
cagcagggca acgtgttcag ctgctccgtg atgcacgagg ccctgcacaa ccactacacc  1320
cagaagtccc tgagcctgag ccccggcaag gcttctcctg ctgctcctgc tcctagcgct  1380
caggccgtgg ttacacaaga gcccagcctg acagttagcc ctggcggaac agtgaccctg  1440
acctgcagat cttctacagg cgccgtgacc accagcaact acgccaattg ggtgcagcag  1500
aagcctggac aggctcccag aggactgatc ggcggcacaa acaaaagagc cccttggaca  1560
cccgccagat tcagcggatc actgctcgga ggaaaggccg cactgacaat cacaggtgcc  1620
caggccgaag atgaggccga ttactattgc gccctgtggt acagcaacct gtgggtgttc  1680
ggcggaggta ccaagctgac cgtgctgggc caggcctctc ctgctgctcc tgctccagct  1740
tctccagccg ctccagctcc tgctagcgga tctcaggtgc agctggtgga atctggcggc  1800
ggactcgtga agcctggcgg ctctctgaga ctgagctgtg ccgccagcgg cttcaccttc  1860
aacacctacg ccatgaactg gatccggcag gcccctggca agggcctgga atgggtgtcc  1920
cggatcagaa gcaagtacaa caattacgcc acctactacg ccgacagcgt gaaggaccgg  1980
ttcaccatca gccgggacaa cgccaagaac agcctgtacc tgcagatgaa ctccctgcgg  2040
gccgaggaca ccgccgtgta ctattgtgtg cggcacggca acttcggcaa cagctatgtg  2100
tcttggtttg cctactgggg ccagggcacc ctcgtgacag tctcgagc              2148
```

<210> SEQ ID NO 107
<211> LENGTH: 716
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 107

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ala Ser Pro Ala Ala Pro Ala Pro Ser Ala Glu Leu Val Val
    450                 455                 460

Thr Gln Glu Pro Ser Leu Thr Val Ser Pro Gly Gly Thr Val Thr Leu
465                 470                 475                 480

Thr Cys Arg Ser Ser Thr Gly Ala Val Thr Thr Ser Asn Tyr Ala Asn
                485                 490                 495

Trp Val Gln Gln Lys Pro Gly Gln Ala Pro Arg Gly Leu Ile Gly Gly
            500                 505                 510

Thr Asn Lys Arg Ala Pro Gly Thr Pro Ala Arg Phe Ser Gly Ser Leu
        515                 520                 525

Leu Gly Gly Lys Ala Ala Leu Thr Leu Ser Gly Val Gln Pro Glu Asp
    530                 535                 540
```

Glu Ala Glu Tyr Tyr Cys Ala Leu Trp Tyr Ser Asn Leu Trp Val Phe
545                 550                 555                 560

Gly Gly Gly Thr Lys Leu Thr Val Leu Gly Gln Ala Ser Pro Ala Ala
                565                 570                 575

Pro Ala Pro Ala Ser Pro Ala Ala Pro Ala Pro Ala Ser Gly Ser Gln
                580                 585                 590

Val Gln Leu Val Glu Ser Gly Gly Gly Leu Val Lys Pro Gly Gly Ser
                595                 600                 605

Leu Arg Leu Ser Cys Ala Ala Ser Gly Phe Thr Phe Asn Thr Tyr Ala
610                 615                 620

Met Asn Trp Ile Arg Gln Ala Pro Gly Lys Gly Leu Glu Trp Val Ser
625                 630                 635                 640

Arg Ile Arg Ser Lys Tyr Asn Asn Tyr Ala Thr Tyr Tyr Ala Asp Ser
                645                 650                 655

Val Lys Asp Arg Phe Thr Ile Ser Arg Asp Asn Ala Lys Asn Ser Leu
                660                 665                 670

Tyr Leu Gln Met Asn Ser Leu Arg Ala Glu Asp Thr Ala Val Tyr Tyr
                675                 680                 685

Cys Val Arg His Gly Asn Phe Gly Asn Ser Tyr Val Ser Trp Phe Ala
690                 695                 700

Tyr Trp Gly Gln Gly Thr Leu Val Thr Val Ser Ser
705                 710                 715

<210> SEQ ID NO 108
<211> LENGTH: 2148
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108
caggtgcaat tggtggagtc tggcggagga ctggtgcagc ctgggggcag cctgagactg      60
agctgcgccg ccagcggctt caacatcaag gacacctaca tccactgggt gcgccaggct     120
ccaggcaagg gactggaatg ggtggcccgg atctacccca ccaacggcta caccagatac     180
gccgacagcg tgaagggccg gttcaccatc agcgccgaca ccagcaagaa caccgcctac     240
ctgcagatga cagcctgcgg ggccgaggac accgccgtgt actactgcag cagatggggc     300
ggagatggct tctacgccat ggactactgg ggccagggca ccctggtgac cgtctcgagc     360
gcgtcgacca aggcccccag cgtgttccct ctggccccca gcagcaagag cacctctggc     420
ggaacagccg ccctgggctg cctggtcaag gactacttcc ccgagcccgt gaccgtgtcc     480
tggaactctg gcgccctgac cagcggcgtg cacaccttc cagccgtgct ccagagcagc     540
ggcctgtaca gcctgagcag cgtcgtgacc gtgcccagca gcagcctggg cacccagacc     600
tacatctgca acgtgaacca caagcccagc aacacaaagg tggacaagcg ggtggaaccc     660
aagagctgcg acaagaccca cacctgtccc cctgccctg ccctgaagc ggagggagcc     720 ccctccgtgt tcctgttccc cccaaagcct aaggacaccc tgatgatcag ccggaccccc     780
gaagtgacct gcgtggtggt ggacgtgtcc cacgaggacc ctgaagtgaa gtttaattgg     840
tacgtggacg gcgtggaagt gcacaacgcc aagaccaagc cagagagga acagtacaac     900 agcacctacc gggtggtgtc cgtgctgacc gtgctgcacc aggactggct gaacggcaaa     960
gagtacaagt gcaaggtgtc caacaaggcc ctgcctcct ccatcgagaa aaccatcagc    1020

```
aaggccaaag gccagccccg cgagcccag gtgtacacac tgccccctag ccgggaagag    1080
atgaccaaga accaggtgtc cctgacctgc ctcgtgaagg gcttctaccc cagcgacatt   1140
gccgtggaat gggagagcaa cggccagccc gagaacaact acaagaccac ccccctgtg    1200
ctggacagcg acggctcatt cttcctgtac agcaagctga ccgtggacaa gagccggtgg   1260
cagcagggca acgtgttcag ctgctccgtg atgcacgagg ccctgcacaa ccactacacc   1320
cagaagtccc tgagcctgag ccccggcaag gcttctcctg ctgctcctgc tcctagcgct   1380
gagctggtgg tcacacaaga gcccagcctg acagtttctc ctggcggcac agtgaccctg   1440
acctgcagat cttctacagg cgccgtgacc acctccaact acgccaattg ggtgcagcag   1500
aagcctggac aggctcccag aggactgatc ggcggcacaa acaaaagagc ccctggcaca   1560
ccagccagat tcagcggatc actgctcgga ggaaaggccg ctctgacact gtctggtgtc   1620
cagcctgaag atgaggccga gtactactgc gccctgtggt acagcaatct gtgggtgttc   1680
ggcggaggta ccaagctgac cgtgctgggc caggcctctc ctgctgctcc tgctccagct   1740
tctccagccg ctccagctcc tgctagcgga tctcaggtgc agctggtgga atctggcggc   1800
ggactcgtga agcctggcgg ctctctgaga ctgagctgtg ccgccagcgg cttcaccttc   1860
aacacctacg ccatgaactg gatccggcag gcccctggca agggcctgga atgggtgtcc   1920
cggatcagaa gcaagtacaa caattacgcc acctactacg ccgacagcgt gaaggaccgg   1980
ttcaccatca gccgggacaa cgccaagaac agcctgtacc tgcagatgaa ctccctgcgg   2040
gccgaggaca ccgccgtgta ctattgtgtg cggcacggca acttcggcaa cagctatgtg   2100
tcttggtttg cctactgggg ccagggcacc ctcgtgacag tctcgagc                2148
```

<210> SEQ ID NO 109
<211> LENGTH: 716
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Ala Ser Pro Ala Ala Pro Ala Pro Ser Ala Gln Thr Val Val
450                 455                 460

Thr Gln Glu Pro Ser Leu Thr Val Ser Pro Gly Gly Thr Val Thr Leu
465                 470                 475                 480

Thr Cys Arg Ser Ser Thr Gly Ala Val Thr Thr Ser Asn Tyr Ala Asn
            485                 490                 495

Trp Val Gln Gln Lys Pro Gly Gln Ala Pro Arg Gly Leu Ile Gly Gly
            500                 505                 510

Thr Asn Lys Arg Ala Pro Gly Thr Pro Ala Arg Phe Ser Gly Ser Leu
            515                 520                 525

Leu Gly Gly Lys Ala Ala Leu Thr Leu Leu Gly Ala Gln Pro Glu Asp
            530                 535                 540

Glu Ala Glu Tyr Tyr Cys Ala Leu Trp Tyr Ser Asn Leu Trp Val Phe
545                 550                 555                 560

Gly Gly Gly Thr Lys Leu Thr Val Leu Gly Gln Ala Ser Pro Ala Ala
            565                 570                 575

Pro Ala Pro Ala Ser Pro Ala Ala Pro Ala Ser Gly Ser Glu
            580                 585                 590

Val Gln Leu Val Glu Ser Gly Gly Gly Leu Val Lys Pro Gly Gly Ser
            595                 600                 605

Leu Arg Leu Ser Cys Ala Ala Ser Gly Phe Thr Phe Asn Thr Tyr Ala
            610                 615                 620

Met Asn Trp Val Arg Gln Ala Pro Gly Lys Gly Leu Glu Trp Val Gly
625                 630                 635                 640

Arg Ile Arg Ser Lys Tyr Asn Asn Tyr Ala Thr Tyr Tyr Ala Asp Ser
                645                 650                 655

Val Lys Asp Arg Phe Thr Ile Ser Arg Asp Asp Ser Lys Asn Thr Leu
            660                 665                 670

Tyr Leu Gln Met Asn Ser Leu Lys Thr Glu Asp Thr Ala Val Tyr Tyr
            675                 680                 685

Cys Thr Thr His Gly Asn Phe Gly Asn Ser Tyr Val Ser Trp Phe Ala
            690                 695                 700

Tyr Trp Gly Gln Gly Thr Leu Val Thr Val Ser Ser
705                 710                 715

<210> SEQ ID NO 110
<211> LENGTH: 2148
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110

```
caggtgcaat tggtggagtc tggcggagga ctggtgcagc ctgggggcag cctgagactg      60
agctgcgccg ccagcggctt caacatcaag gacacctaca tccactgggt gcgccaggct     120
ccaggcaagg gactggaatg ggtggcccgg atctacccca ccaacggcta caccagatac     180
gccgacagcg tgaagggccg gttcaccatc agcgccgaca ccagcaagaa caccgcctac     240
ctgcagatga acagcctgcg ggccgaggac accgccgtgt actactgcag cagatggggc     300
ggagatggct tctacgccat ggactactgg ggccagggca ccctggtgac cgtctcgagc     360
gcgtcgacca aaggcccag cgtgttccct ctggccccca gcagcaagag cacctctggc     420
ggaacagccg ccctgggctg cctggtcaag gactacttcc ccgagcccgt gaccgtgtcc     480
tggaactctg gcgccctgac cagcggcgtg cacaccttt cagccgtgct ccagagcagc     540
ggcctgtaca gcctgagcag cgtcgtgacc gtgcccagca gcagcctggg cacccagacc     600
tacatctgca acgtgaacca caagcccagc aacacaaagg tggacaagcg ggtggaaccc     660
aagagctgcg acaagaccca cacctgtccc cctgccctg ccctgaagc ggagggagcc     720
ccctccgtgt tcctgttccc cccaaagcct aaggacaccc tgatgatcag ccggaccccc     780
gaagtgacct gcgtggtggt ggacgtgtcc cacgaggacc ctgaagtgaa gtttaattgg     840
tacgtggacg gcgtggaagt gcacaacgcc aagaccaagc ccagagagga cagtacaac     900
agcacctacc gggtggtgtc cgtgctgacc gtgctgcacc aggactggct gaacggcaaa     960
gagtacaagt gcaaggtgtc caacaaggcc ctgcctccc ccatcgagaa accatcagc    1020
aaggccaaag gccagccccg cgagccccag gtgtacacac tgccccctag ccgggaagag    1080
atgaccaaga accaggtgtc cctgacctgc ctcgtgaagg gcttctaccc cagcgacatt    1140
gccgtggaat gggagagcaa cggccagccc gagaacaact acaagaccac ccccctgtg    1200
```

-continued

```
ctggacagcg acggctcatt cttcctgtac agcaagctga ccgtggacaa gagccggtgg    1260
cagcagggca acgtgttcag ctgctccgtg atgcacgagg ccctgcacaa ccactacacc    1320
cagaagtccc tgagcctgag ccccggcaag gcttctcctg ctgctcctgc tcctagcgct    1380
cagaccgtgg tcacacaaga gcccagcctg acagtttctc ctggcggcac agtgaccctg    1440
acctgcagat cttctacagg cgccgtgacc accagcaact acgccaattg ggtgcagcag    1500
aagcctggac aggctcccag aggactgatc ggcggcacaa acaaaagagc ccctggcaca    1560
ccagccagat tcagcggatc actgctcgga ggaaaggccg ctctgacact gcttggagca    1620
cagcctgaag atgaggccga gtactactgc gccctgtggt acagcaatct gtgggtgttc    1680
ggcggaggta ccaagctgac cgtgctgggc caggcctctc ctgctgctcc tgctccagct    1740
tctccagccg ctccagctcc tgctagcgga tctgaagtgc agctggtgga atctggcggc    1800
ggactcgtga agcctggcgg ctctctgaga ctgagctgtg ccgccagcgg cttcaccttc    1860
aacacctacg ccatgaactg ggtgcgccag gcccctggca aaggcctgga atgggtggga    1920
cggatcagaa gcaagtacaa caattacgcc acctactacg ccgacagcgt gaaggaccgg    1980
ttcaccatca gccgggacga cagcaagaac accctgtacc tgcagatgaa cagcctgaaa    2040
accgaggaca ccgccgtgta ctactgcacc acccacggca acttcggcaa cagctatgtg    2100
tcttggtttg cctactgggg ccagggcacc ctcgtgacag tctcgagc                  2148
```

<210> SEQ ID NO 111  
<211> LENGTH: 716  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 111

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ala Ser Pro Ala Ala Pro Ala Pro Ser Ala Gln Thr Val Val
    450                 455                 460

Thr Gln Glu Pro Ser Leu Thr Val Ser Pro Gly Gly Thr Val Thr Leu
465                 470                 475                 480

Thr Cys Arg Ser Ser Thr Gly Ala Val Thr Thr Ser Asn Tyr Ala Asn
                485                 490                 495

Trp Val Gln Gln Lys Pro Gly Gln Ala Pro Arg Gly Leu Ile Gly Gly
            500                 505                 510

Thr Lys Phe Leu Ala Pro Gly Thr Pro Ala Arg Phe Ser Gly Ser Leu
        515                 520                 525

Leu Gly Gly Lys Ala Ala Leu Thr Leu Leu Gly Ala Gln Pro Glu Asp
    530                 535                 540

Glu Ala Glu Tyr Tyr Cys Ala Leu Trp Tyr Ser Asn Leu Trp Val Phe
545                 550                 555                 560

Gly Gly Gly Thr Lys Leu Thr Val Leu Gly Gln Ala Ser Pro Ala Ala
                565                 570                 575

Pro Ala Pro Ala Ser Pro Ala Ala Pro Ala Pro Ala Ser Gly Ser Glu
            580                 585                 590

Val Gln Leu Val Glu Ser Gly Gly Gly Leu Val Lys Pro Gly Gly Ser
        595                 600                 605
```

| Leu | Arg | Leu | Ser | Cys | Ala | Ala | Ser | Gly | Phe | Thr | Phe | Asn | Thr | Tyr | Ala |
|---|---|---|---|---|---|---|---|---|---|---|---|---|---|---|---|
| | 610 | | | | 615 | | | | | 620 | | | | | |

| Met | Asn | Trp | Val | Arg | Gln | Ala | Pro | Gly | Lys | Gly | Leu | Glu | Trp | Val | Gly |
|---|---|---|---|---|---|---|---|---|---|---|---|---|---|---|---|
| 625 | | | | | 630 | | | | | 635 | | | | | 640 |

| Arg | Ile | Arg | Ser | Lys | Tyr | Asn | Asn | Tyr | Ala | Thr | Tyr | Tyr | Ala | Asp | Ser |
|---|---|---|---|---|---|---|---|---|---|---|---|---|---|---|---|
| | | | | 645 | | | | | 650 | | | | | 655 | |

| Val | Lys | Asp | Arg | Phe | Thr | Ile | Ser | Arg | Asp | Asp | Ser | Lys | Asn | Thr | Leu |
|---|---|---|---|---|---|---|---|---|---|---|---|---|---|---|---|
| | | | 660 | | | | | 665 | | | | | 670 | | |

| Tyr | Leu | Gln | Met | Asn | Ser | Leu | Lys | Thr | Glu | Asp | Thr | Ala | Val | Tyr | Tyr |
|---|---|---|---|---|---|---|---|---|---|---|---|---|---|---|---|
| | | | 675 | | | | | 680 | | | | | 685 | | |

| Cys | Thr | Thr | His | Gly | Asn | Phe | Gly | Asn | Ser | Tyr | Val | Ser | Trp | Phe | Ala |
|---|---|---|---|---|---|---|---|---|---|---|---|---|---|---|---|
| | 690 | | | | | 695 | | | | | 700 | | | | |

| Tyr | Trp | Gly | Gln | Gly | Thr | Leu | Val | Thr | Val | Ser | Ser |
|---|---|---|---|---|---|---|---|---|---|---|---|
| 705 | | | | | 710 | | | | | 715 | |

<210> SEQ ID NO 112
<211> LENGTH: 2148
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 112

| | | | | | |
|---|---|---|---|---|---|
| caggtgcaat | tggtggagtc | tgcggagga | ctggtgcagc | ctgggggcag | cctgagactg | 60 |
| agctgcgccg | ccagcggctt | caacatcaag | gacacctaca | tccactgggt | gcgccaggct | 120 |
| ccaggcaagg | gactggaatg | ggtggcccgg | atctacccca | ccaacggcta | caccagatac | 180 |
| gccgacagcg | tgaagggccg | gttcaccatc | agcgccgaca | ccagcaagaa | caccgcctac | 240 |
| ctgcagatga | acagcctgcg | ggccgaggac | accgccgtgt | actactgcag | cagatggggc | 300 |
| ggagatggct | tctacgccat | ggactactgg | ggccagggca | ccctggtgac | cgtctcgagc | 360 |
| gcgtcgacca | aaggccccag | cgtgttccct | ctggcccca | gcagcaagag | cacctctggc | 420 |
| ggaacagccg | ccctgggctg | cctggtcaag | gactacttcc | ccgagcccgt | gaccgtgtcc | 480 |
| tggaactctg | gcgccctgac | cagcggcgtg | cacaccttc | agccgtgct | ccagagcagc | 540 |
| ggcctgtaca | gcctgagcag | cgtcgtgacc | gtgcccagca | gcagcctggg | cacccagacc | 600 |
| tacatctgca | acgtgaacca | caagcccagc | aacacaaagg | tggacaagcg | ggtggaaccc | 660 |
| aagagctgcg | acaagaccca | cacctgtccc | ccctgccctg | ccctgaagc | ggagggagcc | 720 |
| ccctccgtgt | tcctgttccc | cccaaagcct | aaggacaccc | tgatgatcag | ccggaccccc | 780 |
| gaagtgacct | gcgtggtggt | ggacgtgtcc | cacgaggacc | ctgaagtgaa | gtttaattgg | 840 |
| tacgtggacg | gcgtggaagt | gcacaacgcc | aagaccaagc | ccagagagga | acagtacaac | 900 |
| agcacctacc | gggtggtgtc | cgtgctgacc | gtgctgcacc | aggactggct | gaacggcaaa | 960 |
| gagtacaagt | gcaaggtgtc | caacaaggcc | ctgcctcct | ccatcgagaa | aaccatcagc | 1020 |
| aaggccaaag | gccagccccg | cgagccccag | gtgtacacac | tgcccctag | ccgggaagag | 1080 |
| atgaccaaga | accaggtgtc | cctgacctgc | ctcgtgaagg | gcttctaccc | cagcgacatt | 1140 |
| gccgtggaat | gggagagcaa | cggccagccc | gagaacaact | acaagaccac | cccccctgtg | 1200 |
| ctggacagcg | acggctcatt | cttcctgtac | agcaagctga | ccgtggacaa | gagccggtgg | 1260 |
| cagcagggca | acgtgttcag | ctgctccgtg | atgcacgagg | ccctgcacaa | ccactacacc | 1320 |
| cagaagtccc | tgagcctgag | ccccggcaag | gcttctcctg | ctgctcctgc | tcctagcgct | 1380 |

```
cagaccgtgg tcacacaaga gcccagcctg acagtttctc ctggcggcac agtgaccctg    1440
acctgcagat cttctacagg cgccgtgacc accagcaact acgccaattg ggtgcagcag    1500
aagcctggac aggctcccag aggactgatc ggcggcacaa aatttctggc ccctggcaca    1560
ccagccagat tctctggatc tctgctcggc ggaaaggccg ctctgacact gcttggagca    1620
cagcctgaag atgaggccga gtactactgc gccctgtggt acagcaatct gtgggtgttc    1680
ggcggaggta ccaagctgac cgtgctgggc caggcctctc ctgctgctcc tgctccagct    1740
tctccagccg ctccagctcc tgctagcgga tctgaagtgc agctggtgga atctggcggc    1800
ggactcgtga agcctggcgg ctctctgaga ctgagctgtg ccgccagcgg cttcaccttc    1860
aacacctacg ccatgaactg ggtgcgccag gcccctggca aaggcctgga atgggtggga    1920
cggatcagaa gcaagtacaa caattacgcc acctactacg ccgacagcgt gaaggaccgg    1980
ttcaccatca gccgggacga cagcaagaac accctgtacc tgcagatgaa cagcctgaaa    2040
accgaggaca ccgccgtgta ctactgcacc acccacggca acttcggcaa cagctatgtg    2100
tcttggtttg cctactgggg ccagggcacc ctcgtgacag tctcgagc                 2148
```

<210> SEQ ID NO 113
<211> LENGTH: 716
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

```
Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ala Ser Pro Ala Ala Pro Ala Pro Ser Ala Gln Thr Val Val
    450                 455                 460

Thr Gln Glu Pro Ser Leu Thr Val Ser Pro Gly Gly Thr Val Thr Leu
465                 470                 475                 480

Thr Cys Arg Ser Ser Thr Gly Ala Val Thr Thr Ser Asn Tyr Ala Asn
                485                 490                 495

Trp Val Gln Gln Lys Pro Gly Gln Ala Pro Arg Gly Leu Ile Gly Gly
            500                 505                 510

Thr Lys Phe Leu Ala Pro Gly Thr Pro Ala Arg Phe Ser Gly Ser Leu
        515                 520                 525

Leu Gly Gly Lys Ala Ala Leu Thr Leu Ser Gly Val Gln Pro Glu Asp
    530                 535                 540

Glu Ala Glu Tyr Tyr Cys Ala Leu Trp Tyr Ser Asn Leu Trp Val Phe
545                 550                 555                 560

Gly Gly Gly Thr Lys Leu Thr Val Leu Gly Gln Ala Ser Pro Ala Ala
                565                 570                 575

Pro Ala Pro Ala Ser Pro Ala Ala Pro Ala Pro Ser Ala Gly Ser Glu
            580                 585                 590

Val Gln Leu Val Glu Ser Gly Gly Gly Leu Val Lys Pro Gly Gly Ser
        595                 600                 605

Leu Arg Leu Ser Cys Ala Ala Ser Gly Phe Thr Phe Asn Thr Tyr Ala
    610                 615                 620

Met Asn Trp Val Arg Gln Ala Pro Gly Lys Gly Leu Glu Trp Val Gly
625                 630                 635                 640
```

```
Arg Ile Arg Ser Lys Tyr Asn Asn Tyr Ala Thr Tyr Tyr Ala Asp Ser
                645                 650                 655

Val Lys Asp Arg Phe Thr Ile Ser Arg Asp Asp Ser Lys Asn Thr Leu
        660                 665                 670

Tyr Leu Gln Met Asn Ser Leu Lys Thr Glu Asp Thr Ala Val Tyr Tyr
    675                 680                 685

Cys Thr Thr His Gly Asn Phe Gly Asn Ser Tyr Val Ser Trp Phe Ala
690                 695                 700

Tyr Trp Gly Gln Gly Thr Leu Val Thr Val Ser Ser
705                 710                 715
```

<210> SEQ ID NO 114
<211> LENGTH: 2148
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114

```
caggtgcaat tggtggagtc tggcggagga ctggtgcagc ctgggggcag cctgagactg    60
agctgcgccg ccagcggctt caacatcaag gacacctaca tccactgggt gcgccaggct   120
ccaggcaagg gactggaatg ggtggcccgg atctacccca ccaacggcta caccagatac   180
gccgacagcg tgaagggccg gttcaccatc agcgccgaca ccagcaagaa caccgcctac   240
ctgcagatga acagcctgcg ggccgaggac accgccgtgt actactgcag cagatggggc   300
ggagatggct tctacgccat ggactactgg ggccagggca cctgtgtgac cgtctcgagc   360
gcgtcgacca aggcccccag cgtgttccct ctggccccca gcagcaagag cacctctggc   420
ggaacagccg ccctgggctg cctggtcaag gactacttcc ccgagcccgt gaccgtgtcc   480
tggaactctg gcgccctgac cagcggcgtg cacaccttte agcccgtgct ccagagcagc   540
ggcctgtaca gcctgagcag cgtcgtgacc gtgcccagca gcagcctggg cacccagacc   600
tacatctgca acgtgaacca caagcccagc aacacaaagg tggacaagcg ggtggaaccc   660
aagagctgcg acaagaccca cacctgtccc cctgccctg  cctgaagc ggagggagcc   720 ccctccgtgt tcctgttccc cccaaagcct aaggacaccc tgatgatcag ccggaccccc   780
gaagtgacct gcgtggtggt ggacgtgtcc cacgaggacc ctgaagtgaa gtttaattgg   840
tacgtggacg gcgtggaagt gcacaacgcc aagaccaagc ccagagagga acagtacaac   900
agcacctacc gggtggtgtc cgtgctgacc gtgctgcacc aggactggct gaacggcaaa   960
gagtacaagt gcaaggtgtc caacaaggcc ctgccttcct ccatcgagaa aaccatcagc  1020
aaggccaaag gccagccccg cgagccccag gtgtacacac tgccccctag ccgggaagag  1080
atgaccaaga accaggtgtc cctgacctgc ctcgtgaagg gcttctaccc cagcgacatt  1140
gccgtggaat gggagagcaa cggccagccc gagaacaact acaagaccac ccccctgtg   1200 ctggacagcg acggctcatt cttcctgtac agcaagctga ccgtggacaa gagccggtgg  1260
cagcagggca acgtgttcag ctgctccgtg atgcacgagg ccctgcacaa ccactacacc  1320
cagaagtccc tgagcctgag ccccggcaag gcttctcctg ctgctcctgc tcctagcgct  1380
cagaccgtgg tcacacaaga gcccagcctg acagtttctc ctggcggcac agtgaccctg  1440
acctgcagat cttctacagg cgccgtgacc accagcaact acgccaattg ggtgcagcag  1500
aagcctggac aggctcccag aggactgatc ggcggcacaa aatttctggc ccctggcaca  1560
```

```
ccagccagat tctctggatc tctgctcggc ggaaaggccg ctctgacact gtctggtgtt    1620
cagcctgagg acgaggccga gtactattgc gccctgtggt acagcaacct gtgggtgttc    1680
ggcggaggta ccaagctgac cgtgctgggc caggcctctc ctgctgctcc tgctccagct    1740
tctccagccg ctccagctcc tgctagcgga tctgaagtgc agctggtgga atctggcggc    1800
ggactcgtga agcctggcgg ctctctgaga ctgagctgtg ccgccagcgg cttcaccttc    1860
aacacctacg ccatgaactg ggtgcgccag gcccctggca aaggcctgga atgggtggga    1920
cggatcagaa gcaagtacaa caattacgcc acctactacg ccgacagcgt gaaggaccgg    1980
ttcaccatca gccgggacga cagcaagaac accctgtacc tgcagatgaa cagcctgaaa    2040
accgaggaca ccgccgtgta ctactgcacc acccacggca acttcggcaa cagctatgtg    2100
tcttggtttg cctactgggg ccagggcacc ctcgtgacag tctcgagc                 2148
```

<210> SEQ ID NO 115
<211> LENGTH: 716
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 115

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys Ala Ser Pro Ala Ala Pro Ala Pro Ser Ala Gln Thr Val Val
        450                 455                 460

Thr Gln Glu Pro Ser Leu Thr Val Ser Pro Gly Gly Thr Val Thr Leu
465                 470                 475                 480

Thr Cys Arg Ser Ser Thr Gly Ala Val Thr Thr Ser Asn Tyr Ala Asn
                485                 490                 495

Trp Val Gln Gln Lys Pro Gly Gln Ala Pro Arg Gly Leu Ile Gly Gly
        500                 505                 510

Thr Lys Phe Leu Ala Pro Gly Thr Pro Ala Arg Phe Ser Gly Ser Leu
        515                 520                 525

Leu Gly Gly Lys Ala Ala Leu Thr Leu Ser Gly Val Gln Pro Glu Asp
530                 535                 540

Glu Ala Glu Tyr Tyr Cys Ala Leu Trp Tyr Ser Asn Leu Trp Val Phe
545                 550                 555                 560

Gly Gly Gly Thr Lys Leu Thr Val Leu Gly Gln Ala Ser Pro Ala Ala
                565                 570                 575

Pro Ala Pro Ala Ser Pro Ala Ala Pro Ala Pro Ala Ser Gly Ser Gln
        580                 585                 590

Val Gln Leu Val Glu Ser Gly Gly Gly Leu Val Lys Pro Gly Gly Ser
        595                 600                 605

Leu Arg Leu Ser Cys Ala Ala Ser Gly Phe Thr Phe Asn Thr Tyr Ala
        610                 615                 620

Met Asn Trp Ile Arg Gln Ala Pro Gly Lys Gly Leu Glu Trp Val Ser
625                 630                 635                 640

Arg Ile Arg Ser Lys Tyr Asn Asn Tyr Ala Thr Tyr Tyr Ala Asp Ser
                645                 650                 655

Val Lys Asp Arg Phe Thr Ile Ser Arg Asp Asn Ala Lys Asn Ser Leu
        660                 665                 670
```

```
Tyr Leu Gln Met Asn Ser Leu Arg Ala Glu Asp Thr Ala Val Tyr Tyr
            675                 680                 685

Cys Val Arg His Gly Asn Phe Gly Asn Ser Tyr Val Ser Trp Phe Ala
        690                 695                 700

Tyr Trp Gly Gln Gly Thr Leu Val Thr Val Ser Ser
705                 710                 715

<210> SEQ ID NO 116
<211> LENGTH: 2148
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116
caggtgcaat tggtggagtc tggcggagga ctggtgcagc ctgggggcag cctgagactg     60
agctgcgccg ccagcggctt caacatcaag gacacctaca tccactgggt gcgccaggct    120
ccaggcaagg gactggaatg gtggcccgg atctacccca ccaacggcta caccagatac    180
gccgacagcg tgaagggccg gttcaccatc agcgccgaca ccagcaagaa cacggcctac    240
ctgcagatga acagcctgcg ggccgaggac accgccgtgt actactgcag cagatggggc    300
ggagatggct ctacgccat ggactactgg ggccagggca ccctggtgac cgtctcgagc    360
gcgtcgacca aaggcccag cgtgttccct ctggccccca gcagcaagag cacctctggc    420
ggaacagccg ccctgggctg cctggtcaag gactacttcc ccgagcccgt gaccgtgtcc    480
tggaactctg gcgccctgac cagcggcgtg cacacctttc cagccgtgct ccagagcagc    540
ggcctgtaca gcctgagcag cgtcgtgacc gtgcccagca gcagcctggg cacccagacc    600
tacatctgca acgtgaacca caagcccagc aacacaaagg tggacaagcg ggtggaaccc    660
aagagctgcg acaagaccca cacctgtccc cctgccctg ccctgaagc ggagggagcc    720 ccctccgtgt tcctgttccc cccaaagcct aaggacaccc tgatgatcag ccggacccc    780 gaagtgacct gcgtggtggt ggacgtgtcc cacgaggacc ctgaagtgaa gtttaattgg    840
tacgtggacg gcgtggaagt gcacaacgcc aagaccaagc ccagagagga cagtacaac    900 agcacctacc gggtggtgtc cgtgctgacc gtgctgcacc aggactggct gaacggcaaa    960
gagtacaagt gcaaggtgtc caacaaggcc ctgccttcct ccatcgagaa aaccatcagc   1020
aaggccaaag gccagccccg cgagcccag gtgtacacac tgcccctag ccgggaagag   1080 atgaccaaga accaggtgtc cctgacctgc ctcgtgaagg gcttctaccc cagcgacatt   1140
gccgtggaat gggagagcaa cggccagccc gagaacaact acaagaccac ccccctgtg   1200 ctggacagcg acggctcatt cttcctgtac agcaagctga ccgtggacaa gagccggtgg   1260
cagcagggca acgtgttcag ctgctccgtg atgcacgagg ccctgcacaa ccactacacc   1320
cagaagtccc tgagcctgag ccccggcaag gcttctcctg ctgctcctgc tcctagcgct   1380
cagaccgtgg tcacacaaga gccagcctg acagtttctc ctggcggcac agtgaccctg   1440
acctgcagat cttctacagg cgccgtgacc accagcaact acgccaattg ggtgcagcag   1500
aagcctggac aggctcccag aggactgatc ggcggcacaa aatttctggc ccctggcaca   1560
ccagccagat ctctggatc tctgctcggc ggaaaggccg ctctgacact gtctggtgtt   1620
cagcctgagg acgaggccga gtactattgc gccctgtggt acagcaacct gtgggtgttc   1680
ggcggaggta ccaagctgac cgtgctgggc caggcctctc ctgctgctcc tgctccagct   1740
```

```
tctccagccg ctccagctcc tgctagcgga tctcaggtgc agctggtgga atctggcggc  1800
ggactcgtga agcctggcgg ctctctgaga ctgagctgtg ccgccagcgg cttcaccttc  1860
aacacctacg ccatgaactg gatccggcag gcccctggca agggcctgga atgggtgtcc  1920
cggatcagaa gcaagtacaa caattacgcc acctactacg ccgacagcgt gaaggaccgg  1980
ttcaccatca gccgggacaa cgccaagaac agcctgtacc tgcagatgaa ctccctgcgg  2040
gccgaggaca ccgccgtgta ctattgtgtg cggcacggca cttcggcaa cagctatgtg  2100 tcttggtttg cctactgggg ccagggcacc ctcgtgacag tctcgagc  2148
```

<210> SEQ ID NO 117
<211> LENGTH: 716
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Glu Gly Ala
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ala Ser Pro Ala Ala Pro Ala Pro Ser Ala Gln Thr Val Val
    450                 455                 460

Thr Gln Glu Pro Ser Leu Thr Val Ser Pro Gly Gly Thr Val Thr Leu
465                 470                 475                 480

Thr Cys Arg Ser Ser Thr Gly Ala Val Thr Thr Ser Asn Tyr Ala Asn
                485                 490                 495

Trp Val Gln Gln Lys Pro Gly Gln Ala Pro Arg Gly Leu Ile Gly Gly
            500                 505                 510

Thr Asn Lys Arg Ala Pro Gly Thr Pro Ala Arg Phe Ser Gly Ser Leu
        515                 520                 525

Leu Gly Gly Lys Ala Ala Leu Thr Leu Ser Gly Val Gln Pro Glu Asp
    530                 535                 540

Glu Ala Glu Tyr Tyr Cys Ala Leu Trp Tyr Ser Asn Leu Trp Val Phe
545                 550                 555                 560

Gly Gly Gly Thr Lys Leu Thr Val Leu Gly Gln Ala Ser Pro Ala Ala
                565                 570                 575

Pro Ala Pro Ala Ser Pro Ala Ala Pro Ala Pro Ala Ser Gly Ser Gln
            580                 585                 590

Val Gln Leu Val Glu Ser Gly Gly Leu Val Lys Pro Gly Gly Ser
        595                 600                 605

Leu Arg Leu Ser Cys Ala Ala Ser Gly Phe Thr Phe Asn Thr Tyr Ala
    610                 615                 620

Met Asn Trp Ile Arg Gln Ala Pro Gly Lys Gly Leu Glu Trp Val Ser
625                 630                 635                 640

Arg Ile Arg Ser Lys Tyr Asn Asn Tyr Ala Thr Tyr Tyr Ala Asp Ser
                645                 650                 655

Val Lys Asp Arg Phe Thr Ile Ser Arg Asp Asn Ala Lys Asn Ser Leu
            660                 665                 670

Tyr Leu Gln Met Asn Ser Leu Arg Ala Glu Asp Thr Ala Val Tyr Tyr
        675                 680                 685

Cys Val Arg His Gly Asn Phe Gly Asn Ser Tyr Val Ser Trp Phe Ala
    690                 695                 700
```

Tyr Trp Gly Gln Gly Thr Leu Val Thr Val Ser Ser
705                 710                 715

<210> SEQ ID NO 118
<211> LENGTH: 2148
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118

| | | | | |
|---|---|---|---|---|
| caggtgcaat | tggtggagtc | tggcggagga | ctggtgcagc | ctgggggcag | cctgagactg | 60 |
| agctgcgccg | ccagcggctt | caacatcaag | gacacctaca | tccactgggt | gcgccaggct | 120 |
| ccaggcaagg | gactggaatg | ggtggcccgg | atctacccca | ccaacggcta | caccagatac | 180 |
| gccgacagcg | tgaagggccg | gttcaccatc | agcgccgaca | ccagcaagaa | caccgcctac | 240 |
| ctgcagatga | acagcctgcg | ggccgaggac | accgccgtgt | actactgcag | cagatggggc | 300 |
| ggagatggct | tctacgccat | ggactactgg | ggccagggca | ccctggtgac | cgtctcgagc | 360 |
| gcgtcgacca | aggccccag | cgtgttccct | ctggccccca | gcagcaagag | cacctctggc | 420 |
| ggaacagccg | ccctgggctg | cctggtcaag | gactacttcc | ccgagcccgt | gaccgtgtcc | 480 |
| tggaactctg | gcgccctgac | cagcggcgtg | cacacctttc | cagccgtgct | ccagagcagc | 540 |
| ggcctgtaca | gcctgagcag | cgtcgtgacc | gtgcccagca | gcagcctggg | cacccagacc | 600 |
| tacatctgca | acgtgaacca | caagcccagc | aacacaaagg | tggacaagcg | ggtggaaccc | 660 |
| aagagctgcg | acaagaccca | cacctgtccc | ccctgccctg | cccctgaagc | ggagggagcc | 720 |
| ccctccgtgt | tcctgttccc | cccaaagcct | aaggacaccc | tgatgatcag | ccggaccccc | 780 |
| gaagtgacct | gcgtggtggt | ggacgtgtcc | cacgaggacc | ctgaagtgaa | gtttaattgg | 840 |
| tacgtggacg | gcgtggaagt | gcacaacgcc | aagaccaagc | cagagagga | acagtacaac | 900 |
| agcacctacc | gggtggtgtc | cgtgctgacc | gtgctgcacc | aggactggct | gaacggcaaa | 960 |
| gagtacaagt | gcaaggtgtc | caacaaggcc | ctgcccttcct | ccatcgagaa | aaccatcagc | 1020 |
| aaggccaaag | gccagccccg | cgagccccag | gtgtacacac | tgcccccctag | ccgggaagag | 1080 |
| atgaccaaga | accaggtgtc | cctgacctgc | ctcgtgaagg | gcttctaccc | cagcgacatt | 1140 |
| gccgtggaat | gggagagcaa | cggccagccc | gagaacaact | acaagaccac | cccccctgtg | 1200 |
| ctggacagcg | acggctcatt | cttcctgtac | agcaagctga | ccgtggacaa | gagccggtgg | 1260 |
| cagcagggca | acgtgttcag | ctgctccgtg | atgcacgagg | ccctgcacaa | ccactacacc | 1320 |
| cagaagtccc | tgagcctgag | ccccggcaag | gcttctcctg | ctgctcctgc | tcctagcgct | 1380 |
| cagaccgtgg | tcacacaaga | gcccagcctg | acagtttctc | ctggcggcac | agtgaccctg | 1440 |
| acctgcagat | cttctacagg | cgccgtgacc | accagcaact | acgccaattg | ggtgcagcag | 1500 |
| aagcctggac | aggctcccag | aggactgatc | ggcggcacaa | acaaaagagc | ccctggcaca | 1560 |
| ccagccagat | tcagcggatc | actgctcgga | ggaaaggccg | ctctgacact | gtctggtgtc | 1620 |
| cagcctgaag | atgaggccga | gtactactgc | gccctgtggt | acagcaatct | gtgggtgttc | 1680 |
| ggcggaggta | ccaagctgac | cgtgctgggc | caggcctctc | ctgctgctcc | tgctccagct | 1740 |
| tctccagccg | ctccagctcc | tgctagcgga | tctcaggtgc | agctggtgga | atctggcggc | 1800 |
| ggactcgtga | agcctggcgg | ctctctgaga | ctgagctgtg | ccgccagcgg | cttcaccttc | 1860 |
| aacacctacg | ccatgaactg | gatccggcag | gcccctggca | agggcctgga | atgggtgtcc | 1920 |

```
cggatcagaa gcaagtacaa caattacgcc acctactacg ccgacagcgt gaaggaccgg    1980
ttcaccatca gccgggacaa cgccaagaac agcctgtacc tgcagatgaa ctccctgcgg    2040
gccgaggaca ccgccgtgta ctattgtgtg cggcacggca acttcggcaa cagctatgtg    2100
tcttggtttg cctactgggg ccagggcacc ctcgtgacag tctcgagc                 2148
```

<210> SEQ ID NO 119
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 119

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 120
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120

```
gatatccaga tgacccagag ccccagcagc ctgagcgcca gcgtgggcga cagagtgacc    60
atcacctgcc gggccagcca ggacgtgaac accgccgtgg cctggtatca gcagaagccc    120
ggcaaggccc ccaagctgct gatctacagc gccagcttcc tgtacagcgg cgtgcccagc    180
```

```
cggttcagcg gcagcagaag cggcaccgac ttcaccctga ccatcagctc cctgcagccc    240
gaggacttcg ccacctacta ctgccagcag cactacacca ccccccccac cttcggccag    300
ggtaccaaag tggaaatcaa gcggaccgtg ccgctccct ccgtgttcat cttcccaccc    360
agcgacgagc agctgaagtc cggcacagcc agcgtcgtgt gcctgctgaa caacttctac    420
ccccgcgagg ccaaagtgca gtggaaggtg gacaacgccc tccagagcgg caacagccag    480
gaaagcgtca ccgagcagga cagcaaggac tccacctaca gcctgagcag caccctgacc    540
ctgagcaagg ccgactacga gaagcacaag gtgtacgcct gcgaagtgac ccaccagggc    600
ctgtccagcc ccgtgaccaa gagcttcaac cggggcgagt gt                      642
```

<210> SEQ ID NO 121
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

-continued

```
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ser Ser Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys Ala Ser Pro Ala Ala Pro Ala Pro Ser
    450                 455                 460
Ala Asp Ile Gln Met Thr Gln Ser Pro Ser Ser Leu Ser Ala Ser Val
465                 470                 475                 480
Gly Asp Arg Val Thr Ile Thr Cys Arg Ala Ser Gln Asp Val Asn Thr
                485                 490                 495
Ala Val Ala Trp Tyr Gln Gln Lys Pro Gly Lys Ala Pro Lys Leu Leu
            500                 505                 510
Ile Tyr Ser Ala Ser Phe Leu Tyr Ser Gly Val Pro Ser Arg Phe Ser
        515                 520                 525
Gly Ser Arg Ser Gly Thr Asp Phe Thr Leu Thr Ile Ser Ser Leu Gln
    530                 535                 540
Pro Glu Asp Phe Ala Thr Tyr Tyr Cys Gln Gln His Tyr Thr Thr Pro
545                 550                 555                 560
Pro Thr Phe Gly Gln Gly Thr Lys Val Glu Ile Lys Arg Thr Ala Ser
                565                 570                 575
Pro Ala Ala Pro Ala Pro Ala Ser Pro Ala Ala Pro Ala Pro Ala Ser
            580                 585                 590
Gly Ser Gln Val Gln Leu Val Glu Ser Gly Gly Gly Leu Val Gln Pro
        595                 600                 605
Gly Gly Ser Leu Arg Leu Ser Cys Ala Ala Ser Gly Phe Asn Ile Lys
    610                 615                 620
Asp Thr Tyr Ile His Trp Val Arg Gln Ala Pro Gly Lys Gly Leu Glu
625                 630                 635                 640
Trp Val Ala Arg Ile Tyr Pro Thr Asn Gly Tyr Thr Arg Tyr Ala Asp
                645                 650                 655
Ser Val Lys Gly Arg Phe Thr Ile Ser Ala Asp Thr Ser Lys Asn Thr
            660                 665                 670
Ala Tyr Leu Gln Met Asn Ser Leu Arg Ala Glu Asp Thr Ala Val Tyr
        675                 680                 685
```

Tyr Cys Ser Arg Trp Gly Gly Asp Gly Phe Tyr Ala Met Asp Tyr Trp
    690                 695                 700

Gly Gln Gly Thr Leu Val Thr Val Ser Ser
705                 710

<210> SEQ ID NO 122
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122
gaagtgcagc tggtggaatc tggcggcgga ctcgtgaagc ctggcggctc tctgagactg    60
agctgtgccg ccagcggctt caccttcaac acctacgcca tgaactgggt gcgccaggcc    120
cctggcaaag gcctggaatg ggtgggacgg atcagaagca agtacaacaa ttacgccacc    180
tactacgccg acagcgtgaa ggaccggttc accatcagcc gggacgacag caagaacacc    240
ctgtacctgc agatgaacag cctgaaaacc gaggacaccg ccgtgtacta ctgcaccacc    300
cacggcaact tcggcaacag ctatgtgtct tggtttgcct actggggcca gggcaccctc    360
gtgacagtct cgagcgcgtc gaccaaaggc cccagcgtgt tccctctggc ccccagcagc    420
aagagcacct ctgggggaac agccgccctg ggctgcctgg tcaaggacta cttccccgag    480
cccgtgaccg tgtcctggaa ctctggcgcc ctgaccagcg gcgtgcacac ctttccagcc    540
gtgctccaga gcagcggcct gtacagcctg agcagcgtcg tgaccgtgcc cagcagcagc    600
ctgggcaccc agacctacat ctgcaacgtg aaccacaagc ccagcaacac aaaggtggac    660
aagcgggtgg aacccaagag ctgcgacaag acccacacct gtccccctg ccctgcccct    720 gaagcggagg agccccctc cgtgttcctg ttccccccaa agcctaagga caccctgatg    780
atcagccgga ccccgaagt gacctgcgtg gtggtggacg tgtcccacga ggaccctgaa    840
gtgaagttta attggtacgt ggacggcgtg gaagtgcaca acgccaagac caagcccaga    900
gaggaacagt acaacagcac ctaccgggtg gtgtccgtgc tgaccgtgct gcaccaggac    960
tggctgaacg gcaaagagta caagtgcaag gtgtccaaca aggccctgcc ttcctccatc   1020
gagaaaacca tcagcaaggc caagggccag ccccgcgagc cccaggtgta cactctgccc   1080
cctagccggg aagagatgac caagaaccag gtgtccctga cctgcctcgt gaagggcttc   1140
taccccagcg acattgccgt ggaatgggag agcaacggcc agcccgagaa caactacaag   1200
accacccccc ctgtgctgga cagcgacggc tcattcttcc tgtacagcaa gctgaccgtg   1260
gacaagagcc ggtggcagca gggcaacgtg ttcagctgct ccgtgatgca cgaggccctg   1320
cacaaccact acacccagaa gtccctgagc ctgagccccg gcaaggcttc tcctgctgct   1380
cctgctccta cgctgacat ccagatgacc cagagcccta gcagcctgag cgccagcgtg   1440
ggcgacagag tgaccatcac ctgtagagcc agcaggacg tgaacaccgc cgtggcctgg   1500
tatcagcaga agcctggcaa ggcccccaag ctgctgatct acagcgccag cttcctgtac   1560
agcggcgtgc ccagcagatt cagcggcagc agatccggca ccgacttcac cctgaccatc   1620
agcagcctgc agcccgagga cttcgccacc tactactgcc agcagcacta caccacccc   1680 cccacatttg gccagggcac caaggtggaa atcaagcgga cagcctctcc tgccgcccct   1740
gctcctgctt ctcctgctgc tccagctcca gccagcggat ctcaggtgca gctggtggaa   1800
tctggcggcg gactggtgca gcctggcgga tctctgagac tgagctgtgc cgccagcggc   1860
ttcaacatca aggacaccta catccactgg gtgcgccagg cccctggaaa gggactggaa   1920
tgggtggcca gaatctaccc caccaacggc tacaccagat acgccgacag cgtgaagggc   1980
cggttcacca tcagcgccga caccagcaag aataccgcct acctgcagat gaacagcctg   2040
agagccgagg ataccgccgt gtactactgc tccagatggg gaggcgacgg cttctacgcc   2100
atggactatt ggggccaggg aaccctcgtg accgtgtcct ct                     2142

<210> SEQ ID NO 123
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 124
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124
cagaccgtgg tcacacaaga gcccagcctg acagtttctc ctggcggcac agtgaccctg   60

| | | |
|---|---|---|
| acctgcagat cttctacagg cgccgtgacc accagcaact acgccaattg ggtgcagcag | 120 | |
| aagcctggac aggctcccag aggactgatc ggcggcacaa aatttctggc ccctggcaca | 180 | |
| ccagccagat tctctggatc tctgctcggc ggaaaggccg ctctgacact gcttggagca | 240 | |
| cagcctgaag atgaggccga gtactactgc gccctgtggt acagcaatct gtgggtgttc | 300 | |
| ggcggaggta ccaagctgac cgtgctgggc cagcccaaag ccgcccctag cgtgaccctg | 360 | |
| ttcccccccct cgagtgagga actccaggcc aacaaggcca ccctcgtgtg cctgatcagc | 420 | |
| gacttctacc ctggcgccgt gaccgtggcc tggaaggccg atagcagccc tgtgaaggcc | 480 | |
| ggcgtggaaa ccaccacccc cagcaagcag agcaacaaca aatacgccgc cagcagctac | 540 | |
| ctgagcctga cccccgagca gtggaagtcc cacagatcct acagctgcca ggtcacacac | 600 | |
| gagggcagca ccgtggaaaa gaccgtggcc cccaccgagt gcagc | 645 | |

<210> SEQ ID NO 125
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

```
Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
            435                 440                 445

Leu Ser Leu Ser Pro Gly Lys Ala Ser Pro Ala Pro Ala Pro Ser
450                 455                 460

Ala Asp Ile Gln Met Thr Gln Ser Pro Ser Ser Leu Ser Ala Ser Val
465                 470                 475                 480

Gly Asp Arg Val Thr Ile Thr Cys Arg Ala Ser Gln Asp Val Asn Thr
            485                 490                 495

Ala Val Ala Trp Tyr Gln Gln Lys Pro Gly Lys Ala Pro Lys Leu Leu
        500                 505                 510

Ile Tyr Ser Ala Ser Phe Leu Tyr Ser Gly Val Pro Ser Arg Phe Ser
            515                 520                 525

Gly Ser Arg Ser Gly Thr Asp Phe Thr Leu Thr Ile Ser Ser Leu Gln
    530                 535                 540

Pro Glu Asp Phe Ala Thr Tyr Tyr Cys Gln Gln His Tyr Thr Thr Pro
545                 550                 555                 560

Pro Thr Phe Gly Gln Gly Thr Lys Val Glu Ile Lys Arg Thr Ala Ser
            565                 570                 575

Pro Ala Ala Pro Ala Pro Ala Ser Pro Ala Ala Pro Ala Pro Ala Ser
        580                 585                 590

Gly Ser Gln Val Gln Leu Val Glu Ser Gly Gly Leu Val Gln Pro
    595                 600                 605

Gly Gly Ser Leu Arg Leu Ser Cys Ala Ala Ser Gly Phe Asn Ile Lys
    610                 615                 620

Asp Thr Tyr Ile His Trp Val Arg Gln Ala Pro Gly Lys Gly Leu Glu
625                 630                 635                 640

Trp Val Ala Arg Ile Tyr Pro Thr Asn Gly Tyr Thr Arg Tyr Ala Asp
                645                 650                 655

Ser Val Lys Gly Arg Phe Thr Ile Ser Ala Asp Thr Ser Lys Asn Thr
            660                 665                 670
```

```
Ala Tyr Leu Gln Met Asn Ser Leu Arg Ala Glu Asp Thr Ala Val Tyr
            675                 680                 685
Tyr Cys Ser Arg Trp Gly Gly Asp Gly Phe Tyr Ala Met Asp Tyr Trp
        690                 695                 700
Gly Gln Gly Thr Leu Val Thr Val Ser Ser
705                 710

<210> SEQ ID NO 126
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126
gaagtgcagc tggtggaatc tggcggcgga ctcgtgaagc ctggcggctc tctgagactg      60
agctgtgccg ccagcggctt caccttcaac acctacgcca tgaactgggt gcgccaggcc     120
cctggcaaag gcctggaatg ggtgggacgg atcagaagca agtacaacaa ttacgccacc     180
tactacgccg acagcgtgaa ggaccggttc accatcagcc gggacgacag caagaacacc     240
ctgtacctgc agatgaacag cctgaaaacc gaggacaccg ccgtgtacta ctgcaccacc     300
cacggcaact tcggcaacag ctatgtgtct tggtttgcct actggggcca gggcacccte     360 gtgacagtct cgagcgcgtc gaccaaaggc ccagcgtgt ccctctggc cccagcagc       420 aagagcacct ctggcggaac agccgccctg ggctgcctgg tcaaggacta cttccccgag     480
cccgtgaccg tgtcctggaa ctctggcgcc ctgaccagcg gcgtgcacac ctttccagcc     540
gtgctccaga gcagcggcct gtacagcctg agcagcgtcg tgaccgtgcc agcagcagc     600 ctgggcaccc agacctacat ctgcaacgtg aaccacaagc ccagcaacac aaaggtggac     660
aagcgggtgg aacccaagag ctgcgacaag acccacacct gtccccctg ccctgccct      720 gaagcggagg gagcccctc cgtgttcctg ttccccccaa agcctaagga caccctgatg     780
atcagccgga ccccgaagt gacctgcgtg gtggtggacg tgtcccacga ggaccctgaa     840
gtgaagttta attggtacgt ggacggcgtg gaagtgcaca acgccaagac caagcccaga     900
gaggaacagt acaacagcac ctaccgggtg gtgtccgtgc tgaccgtgct gcaccaggac     960
tggctgaacg gcaaagagta caagtgcaag gtgtccaaca aggccctgcc ttcctccatc    1020
gagaaaacca tcagcaaggc caaggccag ccccgcgagc cccaggtgta cacactgccc     1080
cctagccggg aagagatgac caagaaccag gtgtccctga cctgcctcgt gaagggcttc    1140
taccccagcg acattgccgt ggaatgggag agcaacggcc agcccgagaa caactacaag    1200 accaccccc ctgtgctgga cagcgacggc tcattcttcc tgtacagcaa gctgaccgtg    1260
gacaagagcc ggtggcagca gggcaacgtg ttcagctgct ccgtgatgca cgaggccctg    1320
cacaaccact acacccagaa gtccctgagc ctgagcccg gcaaggcttc tcctgctgct    1380
cctgctccta gcgctgacat ccagatgacc cagagcccta gcagcctgag cgccagcgtg    1440
ggcgacagag tgaccatcac ctgtagagcc agccaggacg tgaacaccgc cgtggcctgg    1500
tatcagcaga gcctggcaa ggcccccaag ctgctgatct acagcgccag cttcctgtac    1560
agcggcgtgc ccagcagatt cagcggcagc agatccggca ccgacttcac cctgaccatc    1620
agcagcctgc agcccgagga cttcgccacc tactactgcc agcagcacta ccacccccc    1680 cccacatttg gccagggcac caaggtggaa atcaagcgga cagcctctcc tgccgcccct    1740
```

-continued

```
gctcctgctt ctcctgctgc tccagctcca gccagcggat ctcaggtgca gctggtggaa   1800
tctggcggcg gactggtgca gcctggcgga tctctgagac tgagctgtgc cgccagcggc   1860
ttcaacatca aggacaccta catccactgg gtgcgccagg cccctggaaa gggactggaa   1920
tgggtggcca gaatctaccc caccaacggc tacaccagat acgccgacag cgtgaagggc   1980
cggttcacca tcagcgccga caccagcaag aataccgcct acctgcagat gaacagcctg   2040
agagccgagg ataccgccgt gtactactgc tccagatggg gaggcgacgg cttctacgcc   2100
atggactatt ggggccaggg aaccctcgtg accgtgtcct ct                      2142
```

<210> SEQ ID NO 127
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 128
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 128

```
cagaccgtgg tcacacaaga gcccagcctg acagtttctc ctggcggcac agtgaccctg    60
acctgcagat cttctacagg cgccgtgacc accagcaact acgccaattg ggtgcagcag   120
aagcctggac aggctcccag aggactgatc ggcggcacaa aatttctggc ccctggcaca   180
ccagccagat tctctggatc tctgctcggc ggaaaggccg ctctgacact gtctggtgtt   240
cagcctgagg acgaggccga gtactattgc gccctgtggt acagcaacct gtgggtgttc   300
ggcggaggta ccaagctgac cgtgctgggc cagcccaaag ccgcccctag cgtgaccctg   360
ttccccccct cgagtgagga actccaggcc aacaaggcca ccctcgtgtg cctgatcagc   420
gacttctacc ctggcgccgt gaccgtggcc tggaaggccg atagcagccc tgtgaaggcc   480
ggcgtggaaa ccaccacccc cagcaagcag agcaacaaca atacgccgc cagcagctac   540 ctgagcctga cccccgagca gtggaagtcc cacagatcct acagctgcca ggtcacacac   600
gagggcagca ccgtggaaaa gaccgtggcc cccaccgagt gcagc               645
```

<210> SEQ ID NO 129
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 129

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240
```

```
Glu Ala Glu Gly Ala Pro Ser Val Phe Leu Phe Pro Lys Pro Lys
                    245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys Ala Ser Pro Ala Ala Pro Ala Pro Ser
        450                 455                 460

Ala Asp Ile Gln Met Thr Gln Ser Pro Ser Ser Leu Ser Ala Ser Val
465                 470                 475                 480

Gly Asp Arg Val Thr Ile Thr Cys Arg Ala Ser Gln Asp Val Asn Thr
                485                 490                 495

Ala Val Ala Trp Tyr Gln Gln Lys Pro Gly Lys Ala Pro Lys Leu Leu
            500                 505                 510

Ile Tyr Ser Ala Ser Phe Leu Tyr Ser Gly Val Pro Ser Arg Phe Ser
        515                 520                 525

Gly Ser Arg Ser Gly Thr Asp Phe Thr Leu Thr Ile Ser Ser Leu Gln
    530                 535                 540

Pro Glu Asp Phe Ala Thr Tyr Tyr Cys Gln Gln His Tyr Thr Thr Pro
545                 550                 555                 560

Pro Thr Phe Gly Gln Gly Thr Lys Val Glu Ile Lys Arg Thr Ala Ser
                565                 570                 575

Pro Ala Ala Pro Ala Pro Ala Ser Pro Ala Ala Pro Ala Pro Ala Ser
            580                 585                 590

Gly Ser Gln Val Gln Leu Val Glu Ser Gly Gly Gly Leu Val Gln Pro
        595                 600                 605

Gly Gly Ser Leu Arg Leu Ser Cys Ala Ala Ser Gly Phe Asn Ile Lys
    610                 615                 620

Asp Thr Tyr Ile His Trp Val Arg Gln Ala Pro Gly Lys Gly Leu Glu
625                 630                 635                 640

Trp Val Ala Arg Ile Tyr Pro Thr Asn Gly Tyr Thr Arg Tyr Ala Asp
                645                 650                 655
```

```
Ser Val Lys Gly Arg Phe Thr Ile Ser Ala Asp Thr Ser Lys Asn Thr
            660                 665                 670

Ala Tyr Leu Gln Met Asn Ser Leu Arg Ala Glu Asp Thr Ala Val Tyr
        675                 680                 685

Tyr Cys Ser Arg Trp Gly Gly Asp Gly Phe Tyr Ala Met Asp Tyr Trp
    690                 695                 700

Gly Gln Gly Thr Leu Val Thr Val Ser Ser
705             710

<210> SEQ ID NO 130
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
caggtgcagc tggtggaatc tggcggcgga ctcgtgaagc tggcggctc tctgagactg      60 agctgtgccg ccagcggctt caccttcaac acctacgcca tgaactggat ccggcaggcc    120
cctggcaagg gcctggaatg ggtgtcccgg atcagaagca agtacaacaa ttacgccacc    180
tactacgccg acagcgtgaa ggaccggttc accatcagcc gggacaacgc caagaacagc    240
ctgtacctgc agatgaactc cctgcgggcc gaggacaccg ccgtgtacta ttgtgtgcgg    300
cacggcaact tcggcaacag ctatgtgtct tggtttgcct actggggcca gggcaccctc    360
gtgacagtct cgagcgcgtc gaccaaaggc cccagcgtgt tcctctggc cccagcagc     420 aagagcacct ctggcggaac agccgccctg gctgcctgg tcaaggacta cttccccgag    480
cccgtgaccg tgtcctggaa ctctggcgcc ctgaccagcg gcgtgcacac ctttccagcc    540
gtgctccaga gcagcggcct gtacagcctg agcagcgtcg tgaccgtgcc cagcagcagc    600
ctgggcaccc agacctacat ctgcaacgtg aaccacaagc ccagcaacac aaaggtggac    660
aagcgggtgg aacccaagag ctgcgacaag acccacacct gtccccctg ccctgcccct    720 gaagcggagg agccccctc cgtgttcctg ttccccccaa agcctaagga caccctgatg    780
atcagccgga ccccgaagt gacctgcgtg gtggtggacg tgtcccacga ggaccctgaa    840
gtgaagttta attggtacgt ggacggcgtg gaagtgcaca acgccaagac caagccagag    900
gaggaacagt acaacagcac ctaccgggtg gtgtccgtgc tgaccgtgct gcaccaggac    960
tggctgaacg gcaaagagta caagtgcaag gtgtccaaca aggccctgcc ttcctccatc   1020
gagaaaacca tcagcaaggc caaaggccag ccccgcgagc cccaggtgta cactctgccc   1080
cctagccggg aagagatgac caagaaccag gtgtccctga cctgcctcgt gaagggcttc   1140
taccccagcg acattgccgt ggaatgggag agcaacggcc agcccgagaa caactacaag   1200
accacccccc ctgtgctgga cagcgacggc tcattcttcc tgtacagcaa gctgaccgtg   1260
gacaagagcc ggtggcagca gggcaacgtg ttcagctgct ccgtgatgca cgaggccctg   1320
cacaaccact acacccagaa gtccctgagc ctgagccccg gcaaggcttc tcctgctgct   1380
cctgctccta gcgctgacat ccagatgacc cagagcccta gcagcctgag cgccagcgtg   1440
ggcgacagag tgaccatcac ctgtagagcc agccaggacg tgaacaccgc cgtggcctgg   1500
tatcagcaga agcctggcaa ggcccccaag ctgctgatct acagcgccag cttcctgtac   1560
agcggcgtgc ccagcagatt cagcggcagc agatccggca ccgacttcac cctgaccatc   1620
agcagcctgc agcccgagga cttcgccacc tactactgcc agcagcacta caccacccc    1680
```

| | |
|---|---|
| cccacatttg gccagggcac caaggtggaa atcaagcgga cagcctctcc tgccgcccct | 1740 |
| gctcctgctt ctcctgctgc tccagctcca gccagcggat ctcaggtgca gctggtggaa | 1800 |
| tctggcggcg gactggtgca gcctggcgga tctctgagac tgagctgtgc cgccagcggc | 1860 |
| ttcaacatca aggacaccta catccactgg gtgcgccagg cccctggaaa gggactggaa | 1920 |
| tgggtggcca gaatctaccc caccaacggc tacaccagat acgccgacag cgtgaagggc | 1980 |
| cggttcacca tcagcgccga caccagcaag aataccgcct acctgcagat gaacagcctg | 2040 |
| agagccgagg ataccgccgt gtactactgc tccagatggg aggcgacgg cttctacgcc | 2100 |
| atggactatt ggggccaggg aaccctcgtg accgtgtcct ct | 2142 |

<210> SEQ ID NO 131
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 131

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 132
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 132

```
caggccgtgg ttacacaaga gcccagcctg acagttagcc ctggcggaac agtgaccctg      60
acctgcagat cttctacagg cgccgtgacc accagcaact acgccaattg ggtgcagcag     120
aagcctggac aggctcccag aggactgatc ggcggcacaa acaaaagagc cccttggaca     180
cccgccagat tcagcggatc actgctcgga ggaaaggccg cactgacaat acacaggtgcc    240
caggccgaag atgaggccga ttactattgc gccctgtggt acagcaacct gtgggtgttc     300
ggcggaggta ccaagctgac cgtgctgggc cagcccaaag ccgcccctag cgtgaccctg     360
ttcccccccct cgagtgagga actccaggcc aacaaggcca ccctcgtgtg cctgatcagc    420
gacttctacc ctggcgccgt gaccgtggcc tggaaggccg atagcagccc tgtgaaggcc     480
ggcgtggaaa ccaccacccc cagcaagcag agcaacaaca atacgccgc cagcagctac      540
ctgagcctga cccccgagca gtggaagtcc cacagatcct acagctgcca ggtcacacac     600
gagggcagca ccgtggaaaa gaccgtggcc cccaccgagt gcagc                     645
```

<210> SEQ ID NO 133
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220
```

```
Pro Lys Ser Cys Asp Lys Thr His Thr Cys Pro Cys Pro Ala Pro
225                 230                 235                 240

Glu Ala Glu Gly Ala Pro Ser Val Phe Leu Phe Pro Pro Lys Pro Lys
            245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys Ala Ser Pro Ala Ala Pro Ala Pro Ser
450                 455                 460

Ala Asp Ile Gln Met Thr Gln Ser Pro Ser Ser Leu Ser Ala Ser Val
465                 470                 475                 480

Gly Asp Arg Val Thr Ile Thr Cys Arg Ala Ser Gln Asp Val Asn Thr
            485                 490                 495

Ala Val Ala Trp Tyr Gln Gln Lys Pro Gly Lys Ala Pro Lys Leu Leu
            500                 505                 510

Ile Tyr Ser Ala Ser Phe Leu Tyr Ser Gly Val Pro Ser Arg Phe Ser
            515                 520                 525

Gly Ser Arg Ser Gly Thr Asp Phe Thr Leu Thr Ile Ser Ser Leu Gln
            530                 535                 540

Pro Glu Asp Phe Ala Thr Tyr Tyr Cys Gln Gln His Tyr Thr Thr Pro
545                 550                 555                 560

Pro Thr Phe Gly Gln Gly Thr Lys Val Glu Ile Lys Arg Thr Ala Ser
            565                 570                 575

Pro Ala Ala Pro Ala Pro Ala Ser Pro Ala Ala Pro Ala Pro Ala Ser
            580                 585                 590

Gly Ser Gln Val Gln Leu Val Glu Ser Gly Gly Gly Leu Val Gln Pro
            595                 600                 605

Gly Gly Ser Leu Arg Leu Ser Cys Ala Ala Ser Gly Phe Asn Ile Lys
            610                 615                 620

Asp Thr Tyr Ile His Trp Val Arg Gln Ala Pro Gly Lys Gly Leu Glu
625                 630                 635                 640
```

```
Trp Val Ala Arg Ile Tyr Pro Thr Asn Gly Tyr Thr Arg Tyr Ala Asp
                645                 650                 655

Ser Val Lys Gly Arg Phe Thr Ile Ser Ala Asp Thr Ser Lys Asn Thr
            660                 665                 670

Ala Tyr Leu Gln Met Asn Ser Leu Arg Ala Glu Asp Thr Ala Val Tyr
        675                 680                 685

Tyr Cys Ser Arg Trp Gly Gly Asp Gly Phe Tyr Ala Met Asp Tyr Trp
    690                 695                 700

Gly Gln Gly Thr Leu Val Thr Val Ser Ser
705                 710
```

```
<210> SEQ ID NO 134
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134
caggtgcagc tggtggaatc tggcggcgga ctcgtgaagc ctggcggctc tctgagactg      60
agctgtgccg ccagcggctt caccttcaac acctacgcca tgaactggat ccggcaggcc     120
cctggcaagg gcctggaatg ggtgtcccgg atcagaagca agtacaacaa ttacgccacc     180
tactacgccg acagcgtgaa ggaccggttc accatcagcc gggacaacgc caagaacagc     240
ctgtacctgc agatgaactc cctgcgggcc gaggacaccg ccgtgtacta ttgtgtgcgg     300
cacggcaact tcggcaacag ctatgtgtct tggtttgcct actggggcca gggcacccct     360
gtgacagtct cgagcgcgtc gaccaaaggc cccagcgtgt tccctctggc ccccagcagc     420
aagagcacct ctggcggaac agccgccctg ggctgcctgg tcaaggacta cttccccgag     480
cccgtgaccg tgtcctggaa ctctggcgcc ctgaccagcg gcgtgcacac ctttccagcc     540
gtgctccaga gcagcggcct gtacagcctg agcagcgtcg tgaccgtgcc cagcagcagc     600
ctgggcaccc agacctacat ctgcaacgtg aaccacaagc ccagcaacac aaaggtggac     660
aagcgggtgg aacccaagag ctgcgacaag acccacacct gtccccctg ccctgcccct     720 gaagcggagg gagcccccct cgtgttcctg ttcccccaa agcctaagga caccctgatg     780
atcagccgga cccccgaagt gacctgcgtg gtggtggacg tgtcccacga ggaccctgaa     840
gtgaagttta attggtacgt ggacggcgtg gaagtgcaca acgccaagac caagcccaga     900
gaggaacagt acaacagcac ctaccgggtg gtgtccgtgc tgaccgtgct gcaccaggac     960
tggctgaacg gcaaagagta caagtgcaag gtgtccaaca aggccctgcc ttcctccatc    1020
gagaaaacca tcagcaaggc caaggccag ccccgcgagc cccaggtgta cactgccc     1080 cctagccggg aagagatgac caagaaccag gtgtccctga cctgcctcgt gaagggcttc    1140
taccccagcg acattgccgt ggaatgggag agcaacggcc agcccgagaa caactacaag    1200
accacccccc ctgtgctgga cagcgacggc tcattcttcc tgtacagcaa gctgaccgtg    1260
gacaagagcc ggtggcagca gggcaacgtg ttcagctgct ccgtgatgca cgaggccctg    1320
cacaaccact acacccagaa gtccctgagc ctgagccccg gcaaggcttc tcctgctgct    1380
cctgctccta gcgctgacat ccagatgacc cagagcccta gcagcctgag cgccagcgtg    1440
ggcgacagag tgaccatcac ctgtagagcc agccaggacg tgaacaccgc cgtggcctgg    1500
tatcagcaga agcctggcaa ggcccccaag ctgctgatct acagcgccag cttcctgtac    1560
```

```
agcggcgtgc ccagcagatt cagcggcagc agatccggca ccgacttcac cctgaccatc    1620
agcagcctgc agcccgagga cttcgccacc tactactgcc agcagcacta caccacccccc    1680 cccacatttg gccagggcac caaggtggaa atcaagcgga cagcctctcc tgccgcccct    1740
gctcctgctt ctcctgctgc tccagctcca gccagcggat ctcaggtgca gctggtggaa    1800
tctggcggcg gactggtgca gcctggcgga tctctgagac tgagctgtgc cgccagcggc    1860
ttcaacatca aggacaccta catccactgg gtgcgccagg ccctggaaa gggactggaa      1920 tgggtggcca gaatctaccc caccaacggc tacaccgat acgccacag cgtgaagggc      1980 cggttcacca tcagcgccga caccagcaag aataccgcct acctgcagat gaacagcctg    2040
agagccgagg ataccgccgt gtactactgc tccagatggg gaggcgacgg cttctacgcc    2100
atggactatt ggggccaggg aaccctcgtg accgtgtcct ct                       2142
```

<210> SEQ ID NO 135
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 135

```
Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 136
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 136

```
gagctggtgg tcacacaaga gcccagcctg acagtttctc ctggcggcac agtgaccctg    60
acctgcagat cttctacagg cgccgtgacc acctccaact acgccaattg ggtgcagcag   120
aagcctggac aggctcccag aggactgatc ggcggcacaa acaaaagagc ccctggcaca   180
ccagccagat tcagcggatc actgctcgga ggaaaggccg ctctgacact gtctggtgtc   240
cagcctgaag atgaggccga gtactactgc gccctgtggt acagcaatct gtgggtgttc   300
ggcggaggta ccaagctgac cgtgctgggc cagcccaaag ccgcccctag cgtgaccctg   360
ttccccccct cgagtgagga actccaggcc aacaaggcca ccctcgtgtg cctgatcagc   420
gacttctacc ctggcgccgt gaccgtggcc tggaaggccg atagcagccc tgtgaaggcc   480
ggcgtggaaa ccaccacccc cagcaagcag agcaacaaca atacgccgc cagcagctac   540 ctgagcctga cccccgagca gtggaagtcc cacagatcct acagctgcca ggtcacacac   600
gagggcagca ccgtggaaaa gaccgtggcc cccaccgagt gcagc              645
```

<210> SEQ ID NO 137
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 137

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

```
Asn Val Asn His Lys Pro Ser Asn Thr Lys Val Asp Lys Arg Val Glu
    210                 215                 220
Pro Lys Ser Cys Asp Lys Thr His Thr Cys Pro Pro Cys Pro Ala Pro
225                 230                 235                 240
Glu Ala Glu Gly Ala Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ser Ser Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys Ala Ser Pro Ala Ala Pro Ala Pro Ser
    450                 455                 460
Ala Asp Ile Gln Met Thr Gln Ser Pro Ser Ser Leu Ser Ala Ser Val
465                 470                 475                 480
Gly Asp Arg Val Thr Ile Thr Cys Arg Ala Ser Gln Asp Val Asn Thr
                485                 490                 495
Ala Val Ala Trp Tyr Gln Gln Lys Pro Gly Lys Ala Pro Lys Leu Leu
            500                 505                 510
Ile Tyr Ser Ala Ser Phe Leu Tyr Ser Gly Val Pro Ser Arg Phe Ser
        515                 520                 525
Gly Ser Arg Ser Gly Thr Asp Phe Thr Leu Thr Ile Ser Ser Leu Gln
    530                 535                 540
Pro Glu Asp Phe Ala Thr Tyr Tyr Cys Gln Gln His Tyr Thr Thr Pro
545                 550                 555                 560
Pro Thr Phe Gly Gln Gly Thr Lys Val Glu Ile Lys Arg Thr Ala Ser
                565                 570                 575
Pro Ala Ala Pro Ala Pro Ala Ser Pro Ala Ala Pro Ala Pro Ala Ser
            580                 585                 590
Gly Ser Gln Val Gln Leu Val Glu Ser Gly Gly Leu Val Gln Pro
        595                 600                 605
Gly Gly Ser Leu Arg Leu Ser Cys Ala Ala Ser Gly Phe Asn Ile Lys
    610                 615                 620
```

Asp Thr Tyr Ile His Trp Val Arg Gln Ala Pro Gly Lys Gly Leu Glu
625                 630                 635                 640

Trp Val Ala Arg Ile Tyr Pro Thr Asn Gly Tyr Thr Arg Tyr Ala Asp
            645                 650                 655

Ser Val Lys Gly Arg Phe Thr Ile Ser Ala Asp Thr Ser Lys Asn Thr
        660                 665                 670

Ala Tyr Leu Gln Met Asn Ser Leu Arg Ala Glu Asp Thr Ala Val Tyr
    675                 680                 685

Tyr Cys Ser Arg Trp Gly Gly Asp Gly Phe Tyr Ala Met Asp Tyr Trp
690                 695                 700

Gly Gln Gly Thr Leu Val Thr Val Ser Ser
705                 710

<210> SEQ ID NO 138
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 138
caggtgcagc tggtggaatc tggcggcgga ctcgtgaagc ctggcggctc tctgagactg      60
agctgtgccg ccagcggctt caccttcaac acctacgcca tgaactggat ccggcaggcc     120
cctggcaagg gcctggaatg ggtgtcccgg atcagaagca gtacaacaa ttacgccacc      180 tactacgccg acagcgtgaa ggaccggttc accatcagcc gggacaacgc caagaacagc     240
ctgtacctgc agatgaactc cctgcgggcc gaggacaccg ccgtgtacta ttgtgtgcgg     300
cacggcaact cggcaacag ctatgtgtct tggtttgcct actggggcca gggcacccctc    360 gtgacagtct cgagcgcgtc gaccaaaggc ccagcgtgt tccctctggc ccccagcagc     420
aagagcacct ctgggggaac agccgccctg ggctgcctgg tcaaggacta cttccccgag    480
cccgtgaccg tgtcctggaa ctctggcgcc ctgaccagcg gcgtgcacac ctttccagcc    540
gtgctccaga gcagcggcct gtacagcctg agcagcgtcg tgaccgtgcc cagcagcagc    600
ctgggcaccc agacctacat ctgcaacgtg aaccacaagc ccagcaacac aaaggtggac    660
aagcgggtgg aacccaagag ctgcgacaag acccacacct gtccccctg ccctgcccct     720 gaagcggagg gagccccctc cgtgttcctg ttccccccaa agcctaagga caccctgatg    780
atcagccgga cccccgaagt gacctgcgtg gtggtggacg tgtcccacga ggaccctgaa    840
gtgaagttta attggtacgt ggacggcgtg gaagtgcaca acgccaagac caagcccaga    900
gaggaacagt acaacagcac ctaccgggtg gtgtccgtgc tgaccgtgct gcaccaggac    960
tggctgaacg gcaaagagta caagtgcaag gtgtccaaca aggccctgcc ttcctccatc   1020
gagaaaacca tcagcaaggc caaggccag ccccgcgagc cccaggtgta cactgccc      1080 cctagccggg aagagatgac caagaaccag gtgtccctga cctgcctcgt gaagggcttc   1140
taccccagcg acattgccgt ggaatgggag agcaacggcc agcccgagaa caactacaag   1200
accacccccc ctgtgctgga cagcgacggc tcattcttcc tgtacagcaa gctgaccgtg   1260
gacaagagcc ggtggcagca gggcaacgtg ttcagctgct ccgtgatgca cgaggccctg   1320
cacaaccact acacccagaa gtccctgagc ctgagccccg gcaaggcttc tcctgctgct   1380
cctgctccta gcgctgacat ccagatgacc cagagcccta gcagcctgag cgccagcgtg   1440
ggcgacagag tgaccatcac ctgtagagcc agccaggacg tgaacaccgc cgtggcctgg   1500

```
tatcagcaga agcctggcaa ggcccccaag ctgctgatct acagcgccag cttcctgtac    1560
agcggcgtgc ccagcagatt cagcggcagc agatccggca ccgacttcac cctgaccatc    1620
agcagcctgc agcccgagga cttcgccacc tactactgcc agcagcacta caccacccc     1680 cccacatttg gccagggcac caaggtggaa atcaagcgga cagcctctcc tgccgccct     1740 gctcctgctt ctcctgctgc tccagctcca gccagcggat ctcaggtgca gctggtggaa    1800
tctggcggcg actggtgca gcctggcgga tctctgagac tgagctgtgc cgccagcggc    1860
ttcaacatca aggacaccta catccactgg gtgcgccagg cccctggaaa gggactggaa    1920
tgggtggcca gaatctaccc caccaacggc tacaccagat acgccgacag cgtgaagggc    1980
cggttcacca tcagcgccga caccagcaag aataccgcct acctgcagat gaacagcctg    2040
agagccgagg ataccgccgt gtactactgc tccagatggg gaggcgacgg cttctacgcc    2100
atggactatt ggggccaggg aaccctcgtg accgtgtcct ct                       2142
```

<210> SEQ ID NO 139
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 139

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 140

<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 140

```
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa aatttctggc ccctggcaca     180
ccagccagat tctctggatc tctgctcggc ggaaaggccg ctctgacact gtctggtgtt     240
cagcctgagg acgaggccga gtactattgc gccctgtggt acagcaacct gtgggtgttc     300
ggcggaggta ccaagctgac cgtgctgggc cagcccaaag ccgcccctag cgtgaccctg     360
ttccccccct cgagtgagga actccaggcc aacaaggcca ccctcgtgtg cctgatcagc     420
gacttctacc ctggcgccgt gaccgtggcc tggaaggcca tagcagccc tgtgaaggcc      480
ggcgtggaaa ccaccacccc cagcaagcag agcaacaaca atacgccgc cagcagctac      540
ctgagcctga cccccgagca gtggaagtcc cacagatcct acagctgcca ggtcacacac     600
gagggcagca ccgtggaaaa gaccgtggcc cccaccgagt gcagc                     645
```

<210> SEQ ID NO 141
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 141

```
Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Asn Thr Tyr
            20                  25                  30

Ala Met Asn Trp Ile Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

```
Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys Ala Ser Pro Ala Ala Pro Ala Pro Ser
        450                 455                 460

Ala Asp Ile Gln Met Thr Gln Ser Pro Ser Ser Leu Ser Ala Ser Val
465                 470                 475                 480

Gly Asp Arg Val Thr Ile Thr Cys Arg Ala Ser Gln Asp Val Asn Thr
                485                 490                 495

Ala Val Ala Trp Tyr Gln Gln Lys Pro Gly Lys Ala Pro Lys Leu Leu
                500                 505                 510

Ile Tyr Ser Ala Ser Phe Leu Tyr Ser Gly Val Pro Ser Arg Phe Ser
            515                 520                 525

Gly Ser Arg Ser Gly Thr Asp Phe Thr Leu Thr Ile Ser Ser Leu Gln
        530                 535                 540

Pro Glu Asp Phe Ala Thr Tyr Tyr Cys Gln Gln His Tyr Thr Thr Pro
545                 550                 555                 560

Pro Thr Phe Gly Gln Gly Thr Lys Val Glu Ile Lys Arg Thr Ala Ser
                565                 570                 575

Pro Ala Ala Pro Ala Pro Ala Ser Pro Ala Ala Pro Ala Pro Ala Ser
                580                 585                 590

Gly Ser Gln Val Gln Leu Val Glu Ser Gly Gly Gly Leu Val Gln Pro
            595                 600                 605
```

```
Gly Gly Ser Leu Arg Leu Ser Cys Ala Ala Ser Gly Phe Asn Ile Lys
    610                 615                 620

Asp Thr Tyr Ile His Trp Val Arg Gln Ala Pro Gly Lys Gly Leu Glu
625                 630                 635                 640

Trp Val Ala Arg Ile Tyr Pro Thr Asn Gly Tyr Thr Arg Tyr Ala Asp
                645                 650                 655

Ser Val Lys Gly Arg Phe Thr Ile Ser Ala Asp Thr Ser Lys Asn Thr
            660                 665                 670

Ala Tyr Leu Gln Met Asn Ser Leu Arg Ala Glu Asp Thr Ala Val Tyr
        675                 680                 685

Tyr Cys Ser Arg Trp Gly Gly Asp Gly Phe Tyr Ala Met Asp Tyr Trp
    690                 695                 700

Gly Gln Gly Thr Leu Val Thr Val Ser Ser
705                 710

<210> SEQ ID NO 142
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 142
caggtgcagc tggtggaatc tggcggcgga ctcgtgaagc ctggcggctc tctgagactg      60
agctgtgccg ccagcggctt caccttcaac acctacgcca tgaactggat ccggcaggcc     120
cctggcaagg gcctggaatg ggtgtcccgg atcagaagca agtacaacaa ttacgccacc     180
tactacgccg acagcgtgaa ggaccggttc accatcagcc gggacaacgc caagaacagc     240
ctgtacctgc agatgaactc cctgcgggcc gaggacaccg ccgtgtacta ttgtgtgcgg     300
cacggcaact tcggcaacag ctatgtgtct tggtttgcct actggggcca gggcacccta     360
gtgacagtct cgagcgcgtc gaccaaaggc ccagcgtgt tccctctggc cccagcagc      420 aagagcacct tggcggaac agccgccctg gctgcctgg tcaaggacta cttccccgag      480
cccgtgaccg tgtcctggaa ctctggcgcc ctgaccagc gcgtgcacac ctttccagcc     540
gtgctccaga gcagcggcct gtacagcctg agcagcgtcg tgaccgtgcc cagcagcagc     600
ctgggcaccc agacctacat ctgcaacgtg aaccacaagc ccagcaacac aaaggtggac     660
aagcgggtgg aacccaagag ctgcgacaag acccacacct gtccccctg ccctgcccct     720 gaagcggagg gagccccctc cgtgttcctg ttccccccaa agcctaagga caccctgatg     780
atcagccgga cccccgaagt gacctgcgtg gtggtggacg tgtcccacga ggaccctgaa     840
gtgaagttta attggtacgt ggacggcgtg gaagtgcaca acgccaagac caagcccaga     900
gaggaacagt acaacagcac ctaccgggtg gtgtccgtgc tgaccgtgct gcaccaggac     960
tggctgaacg gcaaagagta caagtgcaag gtgtccaaca aggccctgcc ttcctccatc    1020
gagaaaacca tcagcaaggc caaaggccag ccccgcgagc cccaggtgta cactctgccc    1080
cctagccggg aagagatgac caagaaccag gtgtccctga cctgcctcgt gaagggcttc    1140
taccccagcg acattgccgt ggaatgggag agcaacggcc agcccgagaa caactacaag    1200 accaccccc ctgtgctgga cagcgacggc tcattcttcc tgtacagcaa gctgaccgtg    1260
gacaagagcc ggtggcagca gggcaacgtg ttcagctgct ccgtgatgca cgaggccctg    1320
cacaaccact acacccagaa gtccctgagc ctgagccccg gcaaggcttc tcctgctgct    1380
```

```
cctgctccta gcgctgacat ccagatgacc cagagccctc gcagcctgag cgccagcgtg    1440
ggcgacagag tgaccatcac ctgtagagcc agccaggacg tgaacaccgc cgtggcctgg    1500
tatcagcaga agcctggcaa ggcccccaag ctgctgatct acagcgccag cttcctgtac    1560
agcggcgtgc ccagcagatt cagcggcagc agatccggca ccgacttcac cctgaccatc    1620
agcagcctgc agcccgagga cttcgccacc tactactgcc agcagcacta caccccccc    1680 cccacatttg gccagggcac caaggtggaa atcaagcgga cagcctctcc tgccgcccct    1740
gctcctgctt ctcctgctgc tccagctcca gccagcggat ctcaggtgca gctggtggaa    1800
tctggcggcg gactggtgca gcctggcgga tctctgagac tgagctgtgc cgccagcggc    1860
ttcaacatca aggacaccta catccactgg gtgcgccagg cccctggaaa gggactggaa    1920
tgggtggcca gaatctaccc caccaacggc tacaccagat acgccgacag cgtgaagggc    1980
cggttcacca tcagcgccga caccagcaag aataccgcct acctgcagat gaacagcctg    2040
agagccgagg ataccgccgt gtactactgc tccagatggg gaggcgacgg cttctacgcc    2100
atggactatt ggggccaggg aaccctcgtg accgtgtcct ct                       2142
```

<210> SEQ ID NO 143
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 144
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144

```
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa acaaaagagc ccctggcaca     180
ccagccagat tcagcggatc actgctcgga ggaaaggccg ctctgacact gtctggtgtc     240
cagcctgaag atgaggccga gtactactgc gccctgtggt acagcaatct gtgggtgttc     300
ggcggaggta ccaagctgac cgtgctgggc cagcccaaag ccgcccctag cgtgaccctg     360
ttcccccct cgagtgagga actccaggcc aacaaggcca ccctcgtgtg cctgatcagc     420
gacttctacc ctggcgccgt gaccgtggcc tggaaggccg atagcagccc tgtgaaggcc     480
ggcgtggaaa ccaccacccc cagcaagcag agcaacaaca atacgccgc cagcagctac     540
ctgagcctga cccccgagca gtggaagtcc acagatcct acagctgcca ggtcacacac     600
gagggcagca ccgtggaaaa gaccgtggcc cccaccgagt gcagc                    645
```

<210> SEQ ID NO 145
<211> LENGTH: 714
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 145

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Ala Ser Pro Ala Ala Pro Ala Pro Ser
    450                 455                 460

Ala Asp Ile Gln Met Thr Gln Ser Pro Ser Ser Leu Ser Ala Ser Val
465                 470                 475                 480

Gly Asp Arg Val Thr Ile Thr Cys Arg Ala Ser Gln Asp Val Asn Thr
                485                 490                 495

Ala Val Ala Trp Tyr Gln Gln Lys Pro Gly Lys Ala Pro Lys Leu Leu
            500                 505                 510

Ile Tyr Ser Ala Ser Phe Leu Tyr Ser Gly Val Pro Ser Arg Phe Ser
        515                 520                 525

Gly Ser Arg Ser Gly Thr Asp Phe Thr Leu Thr Ile Ser Ser Leu Gln
    530                 535                 540

Pro Glu Asp Phe Ala Thr Tyr Tyr Cys Gln Gln His Tyr Thr Thr Pro
545                 550                 555                 560

Pro Thr Phe Gly Gln Gly Thr Lys Val Glu Ile Lys Arg Thr Ala Ser
                565                 570                 575

Pro Ala Ala Pro Ala Pro Ala Ser Pro Ala Ala Pro Ala Pro Ala Ser
            580                 585                 590
```

Gly Ser Gln Val Gln Leu Val Glu Ser Gly Gly Gly Leu Val Gln Pro
            595                 600                 605

Gly Gly Ser Leu Arg Leu Ser Cys Ala Ala Ser Gly Phe Asn Ile Lys
        610                 615                 620

Asp Thr Tyr Ile His Trp Val Arg Gln Ala Pro Gly Lys Gly Leu Glu
625                 630                 635                 640

Trp Val Ala Arg Ile Tyr Pro Thr Asn Gly Tyr Thr Arg Tyr Ala Asp
                645                 650                 655

Ser Val Lys Gly Arg Phe Thr Ile Ser Ala Asp Thr Ser Lys Asn Thr
            660                 665                 670

Ala Tyr Leu Gln Met Asn Ser Leu Arg Ala Glu Asp Thr Ala Val Tyr
        675                 680                 685

Tyr Cys Ser Arg Trp Gly Gly Asp Gly Phe Tyr Ala Met Asp Tyr Trp
690                 695                 700

Gly Gln Gly Thr Leu Val Thr Val Ser Ser
705                 710

<210> SEQ ID NO 146
<211> LENGTH: 2142
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 146

| | |
|---|---:|
| gaagtgcagc tggtggaatc tggcggcgga ctcgtgaagc tggcggctc tctgagactg | 60 |
| agctgtgccg ccagcggctt caccttcaac acctacgcca tgaactgggt gcgccaggcc | 120 |
| cctggcaaag gcctggaatg ggtgggacgg atcagaagca agtacaacaa ttacgccacc | 180 |
| tactacgccg acagcgtgaa ggaccggttc accatcagcc gggacgacag caagaacacc | 240 |
| ctgtacctgc agatgaacag cctgaaaacc gaggacaccg ccgtgtacta ctgcaccacc | 300 |
| cacggcaact cggcaacag ctatgtgtct tggtttgcct actggggcca gggcacccc | 360 |
| gtgacagtct cgagcgcgtc gaccaaaggc cccagcgtgt tccctctggc ccccagcagc | 420 |
| aagagcacct ctggcggaac agccgccctg ggctgcctgg tcaaggacta cttccccgag | 480 |
| cccgtgaccg tgtcctggaa ctctggcgcc ctgaccagcg gcgtgcacac ctttccagcc | 540 |
| gtgctccaga gcagcggcct gtacagcctg agcagcgtcg tgaccgtgcc agcagcagc | 600 |
| ctgggcaccc agacctacat ctgcaacgtg aaccacaagc ccagcaacac aaaggtggac | 660 |
| aagcgggtgg aacccaagag ctgcgacaag acccacacct gtcccccctg ccctgcccct | 720 |
| gaagcggagg agccccctc cgtgttcctg ttccccccaa agcctaagga cacctgatg | 780 |
| atcagccgga ccccgaagt gacctgcgtg gtggtggacg tgtcccacga ggaccctgaa | 840 |
| gtgaagttta attggtacgt ggacggcgtg gaagtgcaca acgccaagac caagcccaga | 900 |
| gaggaacagt acaacagcac ctaccgggtg gtgtccgtgc tgaccgtgct gcaccaggac | 960 |
| tggctgaacg gcaaagagta caagtgcaag gtgtccaaca aggccctgcc ttcctccatc | 1020 |
| gagaaaacca tcagcaaggc caaggccag ccccgcgagc cccaggtgta cactgccc | 1080 |
| cctagccggg aagagatgac caagaaccag gtgtccctga cctgcctcgt gaagggcttc | 1140 |
| taccccagcg acattgccgt ggaatgggag agcaacggcc agcccgagaa caactacaag | 1200 |
| accacccccc ctgtgctgga cagcgacggc tcattcttcc tgtacagcaa gctgaccgtg | 1260 |
| gacaagagcc ggtggcagca gggcaacgtg ttcagctgct ccgtgatgca cgaggccctg | 1320 |

```
cacaaccact acacccagaa gtccctgagc ctgagccccg gcaaggcttc tcctgctgct    1380
cctgctccta gcgctgacat ccagatgacc cagagcccta gcagcctgag cgccagcgtg    1440
ggcgacagag tgaccatcac ctgtagagcc agccaggacg tgaacaccgc cgtggcctgg    1500
tatcagcaga agcctggcaa ggcccccaag ctgctgatct acagcgccag cttcctgtac    1560
agcggcgtgc ccagcagatt cagcggcagc agatccggca ccgacttcac cctgaccatc    1620
agcagcctgc agcccgagga cttcgccacc tactactgcc agcagcacta caccaccccc    1680
cccacatttg gccagggcac caaggtggaa atcaagcgga cagcctctcc tgccgcccct    1740
gctcctgctt ctcctgctgc tccagctcca gccagcggat ctcaggtgca gctggtggaa    1800
tctggcggcg gactggtgca gcctggcgga tctctgagac tgagctgtgc cgccagcggc    1860
ttcaacatca aggacaccta catccactgg gtgcgccagg cccctggaaa gggactggaa    1920
tgggtggcca gaatctaccc caccaacggc tacaccagat acgccgacag cgtgaagggc    1980
cggttcacca tcagcgccga caccagcaag aataccgcct acctgcagat gaacagcctg    2040
agagccgagg ataccgccgt gtactactgc tccagatggg gaggcgacgg cttctacgcc    2100
atggactatt ggggccaggg aaccctcgtg accgtgtcct ct                        2142
```

<210> SEQ ID NO 147
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Leu Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 148
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 148

```
cagaccgtgg tcacacaaga gcccagcctg acagtttctc ctggcggcac agtgaccctg      60
acctgcagat cttctacagg cgccgtgacc accagcaact acgccaattg ggtgcagcag     120
aagcctggac aggctcccag aggactgatc ggcggcacaa acaaaagagc ccctggcaca     180
ccagccagat tcagcggatc actgctcgga ggaaaggccg ctctgacact gcttggagca     240
cagcctgaag atgaggccga gtactactgc gccctgtggt acagcaatct gtgggtgttc     300
ggcggaggta ccaagctgac cgtgctgggc cagcccaaag ccgcccctag cgtgaccctg     360
ttccccccct cgagtgagga actccaggcc aacaaggcca ccctcgtgtg cctgatcagc     420
gacttctacc ctggcgccgt gaccgtggcc tggaaggccg atagcagccc tgtgaaggcc     480
ggcgtggaaa ccaccacccc cagcaagcag agcaacaaca aatacgccgc cagcagctac     540
ctgagcctga cccccgagca gtggaagtcc cacagatcct acagctgcca ggtcacacac     600
gagggcagca ccgtggaaaa gaccgtggcc cccaccgagt gcagc                     645
```

<210> SEQ ID NO 149
<211> LENGTH: 256
<212> TYPE: PRT
<213> ORGANISM: Homo sapiens

<400> SEQUENCE: 149

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Asp Ile Lys Thr
            20                  25                  30

His Thr Cys Pro Pro Cys Pro Ala Pro Glu Leu Leu Gly Gly Pro Ser
        35                  40                  45

Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
145                 150                 155                 160

Pro Pro Ser Arg Glu Glu Met Thr Lys Asn Gln Val Ser Leu Thr Cys
                165                 170                 175

```
Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Val Leu Asp
            195                 200                 205

Ser Asp Gly Ser Phe Phe Leu Tyr Ser Lys Leu Thr Val Asp Lys Ser
        210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255

<210> SEQ ID NO 150
<211> LENGTH: 256
<212> TYPE: PRT
<213> ORGANISM: Macaca fascicularis

<400> SEQUENCE: 150

Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Asp Ile Lys Thr
            20                  25                  30

His Thr Cys Pro Pro Cys Pro Ala Pro Glu Leu Leu Gly Gly Pro Ser
        35                  40                  45

Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Val Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
145                 150                 155                 160

Pro Pro Ser Arg Glu Glu Met Thr Lys Asn Gln Val Ser Leu Thr Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Val Leu Asp
            195                 200                 205

Ser Asp Gly Ser Phe Phe Leu Tyr Ser Lys Leu Thr Val Asp Lys Ser
        210                 215                 220

Arg Trp Gln Gln Gly Asn Val Phe Ser Cys Ser Val Met His Glu Ala
225                 230                 235                 240

Leu His Asn His Tyr Thr Gln Lys Ser Leu Ser Leu Ser Pro Gly Lys
                245                 250                 255

<210> SEQ ID NO 151
<211> LENGTH: 261
<212> TYPE: PRT
<213> ORGANISM: Homo sapiens

<400> SEQUENCE: 151
```

Gln Asp Gly Asn Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Asp Ile Asp Tyr Lys Asp Asp Asp Lys Ile Glu Gly Arg Met
            100                 105                 110

Asp Lys Val Phe Gly Arg Cys Glu Leu Ala Ala Ala Met Lys Arg His
            115                 120                 125

Gly Leu Asp Asn Tyr Arg Gly Tyr Ser Leu Gly Asn Trp Val Cys Ala
        130                 135                 140

Ala Lys Phe Glu Ser Asn Phe Asn Thr Gln Ala Thr Asn Arg Asn Thr
145                 150                 155                 160

Asp Gly Ser Thr Asp Tyr Gly Ile Leu Gln Ile Asn Ser Arg Trp Trp
                165                 170                 175

Cys Asn Asp Gly Arg Thr Pro Gly Ser Arg Asn Leu Cys Asn Ile Pro
            180                 185                 190

Cys Ser Ala Leu Leu Ser Ser Asp Ile Thr Ala Ser Val Asn Cys Ala
            195                 200                 205

Lys Lys Ile Val Ser Asp Gly Asn Gly Met Asn Ala Trp Val Ala Trp
    210                 215                 220

Arg Asn Arg Cys Lys Gly Thr Asp Val Gln Ala Trp Ile Arg Gly Cys
225                 230                 235                 240

Arg Leu Val Asn Ser Arg Gly Leu Asn Asp Ile Phe Glu Ala Gln Lys
                245                 250                 255

Ile Glu Trp His Glu
            260

<210> SEQ ID NO 152
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
                    85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 153
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 154
<211> LENGTH: 207
<212> TYPE: PRT
<213> ORGANISM: Homo sapiens

<400> SEQUENCE: 154

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160
```

-continued

Pro Val Thr Arg Gly Ala Gly Ala Gly Arg Gln Arg Gly Gln Asn
                165                 170                 175

Lys Glu Arg Pro Pro Val Pro Asn Pro Asp Tyr Glu Pro Ile Arg
        180                 185                 190

Lys Gly Gln Arg Asp Leu Tyr Ser Gly Leu Asn Gln Arg Arg Ile
    195                 200                 205

<210> SEQ ID NO 155
<211> LENGTH: 198
<212> TYPE: PRT
<213> ORGANISM: Macaca fascicularis

<400> SEQUENCE: 155

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Leu Val Tyr Tyr Trp Ser Lys
    130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
        195

<210> SEQ ID NO 156
<211> LENGTH: 266
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Ala Ser Pro Ala Ala Pro Ala Pro Ser Ala Gln Thr Val Val Thr Gln
1               5                   10                  15

Glu Pro Ser Leu Thr Val Ser Pro Gly Gly Thr Val Thr Leu Thr Cys
            20                  25                  30

Arg Ser Ser Thr Gly Ala Val Thr Thr Ser Asn Tyr Ala Asn Trp Val
        35                  40                  45

Gln Gln Lys Pro Gly Gln Ala Pro Arg Gly Leu Ile Gly Gly Thr Lys
    50                  55                  60

```
Phe Leu Ala Pro Gly Thr Pro Ala Arg Phe Ser Gly Ser Leu Leu Gly
 65                  70                  75                  80

Gly Lys Ala Ala Leu Thr Leu Ser Gly Val Gln Pro Glu Asp Glu Ala
                 85                  90                  95

Glu Tyr Tyr Cys Ala Leu Trp Tyr Ser Asn Leu Trp Val Phe Gly Gly
            100                 105                 110

Gly Thr Lys Leu Thr Val Leu Gly Gln Ala Ser Pro Ala Ala Pro Ala
        115                 120                 125

Pro Ala Ser Pro Ala Ala Pro Ala Pro Ala Ser Gly Ser Glu Val Gln
    130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Asn Thr Tyr Ala Met Asn
                165                 170                 175

Trp Val Arg Gln Ala Pro Gly Lys Gly Leu Glu Trp Val Gly Arg Ile
            180                 185                 190

Arg Ser Lys Tyr Asn Asn Tyr Ala Thr Tyr Tyr Ala Asp Ser Val Lys
        195                 200                 205

Asp Arg Phe Thr Ile Ser Arg Asp Asp Ser Lys Asn Thr Leu Tyr Leu
    210                 215                 220

Gln Met Asn Ser Leu Lys Thr Glu Asp Thr Ala Val Tyr Tyr Cys Thr
225                 230                 235                 240

Thr His Gly Asn Phe Gly Asn Ser Tyr Val Ser Trp Phe Ala Tyr Trp
                245                 250                 255

Gly Gln Gly Thr Leu Val Thr Val Ser Ser
            260                 265

<210> SEQ ID NO 157
<211> LENGTH: 798
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157
gcttctcctg ctgctcctgc tcctagcgct cagaccgtgg tcacacaaga gcccagcctg      60
acagtttctc ctggcggcac agtgaccctg acctgcagat cttctacagg cgccgtgacc     120
accagcaact acgccaattg ggtgcagcag aagcctggac aggctcccag aggactgatc     180
ggcggcacaa aatttctggc ccctggcaca ccagccagat ctctggatc tctgctcggc      240 ggaaaggccg ctctgacact gtctggtgtt cagcctgagg acgaggccga gtactattgc     300
gccctgtggt acagcaacct gtgggtgttc ggcggaggta ccaagctgac cgtgctgggc     360
caggcctctc ctgctgctcc tgctccagct tctccagccg ctccagctcc tgctagcgga     420
tctgaagtgc agctggtgga atctggcggc ggactcgtga agcctggcgg ctctctgaga     480
ctgagctgtg ccgccagcgg cttcaccttc aacacctacg ccatgaactg ggtgcgccag     540
gcccctggca aggcctgga atgggtggga cggatcagaa gcaagtacaa caattacgcc     600
acctactacg ccgacagcgt gaaggaccgg ttcaccatca gccgggacga cagcaagaac     660
```

```
accctgtacc tgcagatgaa cagcctgaaa accgaggaca ccgccgtgta ctactgcacc    720
acccacggca acttcggcaa cagctatgtg tcttggtttg cctactgggg ccagggcacc    780
ctcgtgacag tctcgagc                                                  798
```

HUMANIZED ANTIBODIES FOR CD3

This patent application is the National Stage of International Application No. PCT/EP2018/071872 filed Aug. 13, 2018, which claims the benefit of priority from EP 17186128.9 filed Aug. 14, 2017, each of which is incorporated herein by reference in its entirety.

FIELD OF THE INVENTION

The present disclosure relates to humanized antibodies and antibody fragments which interact with the human epsilon chain of CD3. The present disclosure also provides bispecific antibodies comprising such humanized antibodies. The disclosure also relates to nucleic acids, vectors and host cells capable of expressing such antibodies, pharmaceutical compositions comprising said antibodies and uses of said antibodies and pharmaceutical compositions for the treatment of specific diseases.

BACKGROUND

CD3 is a homodimeric or heterodimeric antigen expressed on T cells in association with the T cell receptor complex (TCR) and is required for T cell activation. CD3 is formed by the dimeric association of two of four different chains: epsilon, zeta, delta and gamma. The CD3 dimeric arrangements include gamma/epsilon, delta/epsilon and zeta/zeta.

Antibodies against CD3 have been shown to cluster CD3 on T cells, thereby causing T cell activation in a manner similar to the engagement of the TCR by peptide-loaded MHC molecules. Thus, CD3 specific antibodies have been proposed for therapies involving the activation of T cells.

In addition, bispecific antibodies that co-engage CD3 and a tumor antigen target have been generated to redirect T cells to attack and lyse targeted tumor cells. Examples include the BITE and DART formats, which monovalently engage CD3 and a tumor antigen but also IgG like formats, such as BEAT antibodies, where one binding arm binds to the tumor antigen and the second arm binds to CD3 on T-cells.

While the CD3 targeting approach has shown considerable promise, a common side effect of such therapies is the associated production of cytokines, often leading to toxic cytokine release syndrome causing pyrexia, nausea, vomiting, chills, tachycardia and hypotension. This syndrome is believed to reflect anti-CD3 mediated cross-linking of the TCR/CD3 complex on the T cell surface and the resultant release of cytokines (e.g., tumor necrosis factor alpha (TNFα), interferon-γ, interleukins IL-2, IL-3, IL-4, IL-6, IL-10 and granulocyte-macrophage colony-stimulating factor (Masharani, U. B. et al. (2010) "Teplizumab Therapy For Type I Diabetes" Expert Opin. Biol. Ther. 10(3):459-465; Abramowicz, D. et al. (1989) "Release Of Tumor Necrosis Factor, Interleukin-2, And Gamma-Inteferon In Serum After Injection Of OKT3 Monoclonal Antibody In Kidney Transplant Recipients" Transplantation 47:606-608; Ferran, C. et al. (1990) "Cytokine-Related Syndrome Following Injection Of Anti-CD 3 Monoclonal Antibody: Further Evidence For Transient In Vivo T Cell Activation" Eur. J. Immunol. 20:509-515; Hirsch, R. et al. (12989) "Effects OF In Vivo Administration Of Anti-CD3 Monoclonal Antibody On T Cell Function In Mice. II. In Vivo Activation Of T Cells" J. Immunol. 142:737-743). Because the CD3 specific binding domain of the bispecific antibody engages all T cells, the high cytokine-producing CD4 T cell subset is recruited. Moreover, the CD4 T cell subset includes regulatory T cells, whose recruitment and expansion can potentially lead to immune suppression and have a negative impact on long-term tumor suppression.

One way to minimize cytokine production while retaining T cell activation and subsequent target cell depletion is the reduction of the affinity of the CD3 specific binding domain while retaining the affinity of the tumor antigen specific binding domain.

Moreover, bispecific antibodies comprising CD3 specific binding domains with reduced affinity towards CD3 may have limited capability to mediate redirected T cell cytotoxic killing of target antigen low expressing cells such as present on healthy tissue but high potency in depleting target antigen high expressing cancer cells.

It should be further noted that formats such as BITE and DART do not contain Fc domains and therefore show very short serum half-lives in patients. As such, CD3 specific antibodies having reduced side effects while maintaining efficacy and desirable pharmacokinetic (PK) are advantageous in particular when employed in a bispecific therapy.

Consequently, there exists a need for alternative bispecific antigen-binding molecules having controlled cytotoxicity and better PK properties. Such cancer therapies would be quite useful in therapeutic settings.

An antibody specific for human CD3 with cross reactivity to non-human primate CD3 is the mouse monoclonal antibody SP34 (Yoshino N. et al., Exp. Anim 49:97-110, 2000; Conrad M L. et al., Cytometry 71A:925-33, 2007), which binds specifically to human CD3 in denatured form and in native form (Pressano, S. The EMBO J. 4:337-344, 1985; Alarcon, B. EMBO J. 10:903-912, 1991). SP34 also binds to CD3 epsilon singly transfected COS cells as well as CD3epsilon/gamma or CD3ε/8 double transfectants (Salmeron A. et al., J. Immunol. 147:3047-52, 1991). SP34 recognizes an N-terminal 1-27 amino acid residue polypeptide fragment of the extracellular domain of CD3 epsilon. Because of its cross reactivity to non-human primate CD3, humanized variants of SP34 can be used both for preclinical evaluation of safety, activity and/or pharmacokinetic profile of these in primates and—in the identical form—as drugs in humans. SP34 activate T cells when being cross-linked (Yang et al., J. Immunol. 137:1097-1100, 1986). Because of its murine origin, SP34 induces an immunogenic reaction in humans, which limits its effectiveness and also can cause dangerous allergic reactions. Accordingly, any immunogenic uncontrollable reaction directed to this murine antibody bears a significant safety risk for humans. Accordingly, one aspect of the present invention relates to humanized SP34 antibodies having reduced immunogenicity in humans.

SP34 has been subjected to a large number of humanization approaches to generate antibody variants suited for use in human and monkey. Such antibodies have been described in WO 2007/042261 (MICROMET AG), WO 2008/119567 (MICROMET AG), WO 2012/158818 (FABION PHARMACEUTICALS, INC), WO2012/162067 (MACROGENICS, INC.), WO 2016/020444 (AFFIMED GMBH); WO 2015/001085 (GENMAB A/S), WO 2014/110601 (XENCOR, INC.), WO 2015/063339 (GLENMARK PHARMACEUTICALS S.A.), WO 2016/036937 (JANSSEN PHARMACEUTICA NV), US2017/0157251 (MacroGenics, Inc.), WO2017/136659 (THE CALIFORNIA INSTITUTE FOR BIOMEDICAL RESEARCH).

One significant drawback associated with humanisation is that it often results in a significant reduction in the binding affinity of the resulting humanized antibody over that exhibited by the non-humanised donor antibody. Other relevant drawbacks associated with humanization are reduction of productivity and stability. The humanized SP34 binding domains describe in the art were designed to exhibit an equivalent or even better binding affinity towards human and cynomolgus CD3 when compared to the parental antibody SP34 and/or to preserve its productivity and stability. This is typically achieved by an iterative process of back-mutating human residues with the amino acids at the same position in the donor antibody. The back mutation process can result in further non-human amino acid residues being reintroduced into the humanised antibody and as such, the risk for induction of an immunogenic reaction in humans is increased again. Such immunogenic reaction can result in the restoration of an unwanted bivalent or multivalent CD3 binding for antibody formats employing only monovalent CD3 binding.

In addition, by retaining or even improving the binding affinity of SP34, bispecific antibody constructs comprising such "high affinity" binding domains reveal a T cell mediated killing of target antigen low expressing cells (such as present on healthy tissue) similar or comparable to the killing of target antigen high expressing cells rendering such constructs less favourable in terms of inducing potential side effects.

Finally, most of the described humanized SP34 binding domains in the art are used in antibody formats employing monovalent binding to CD3 in order to prevent transient activation of T cells caused by cross-linking of CD3 molecules through bivalent binding to CD3. However, bispecific antibody constructs with monovalent binding to CD3 comprising humanized SP34 binding domains described in the art still revealed an undesired activation of T cells in the absence of target antigen expressing cells in vitro, as shown by the induction of the expression of the T cell activation marker CD69. Even more, such in vitro assays are usually not carried out under high PBMC density pre-culture conditions as suggested by Römer and colleagues (Römer et al., BLOOD, 22 Dec. 2011, VOLUME 118, NUMBER 26, PAGE 6772-6781) and as sucg might underestimate the risk of triggering a cytokine release syndrome in human patients.

Accordingly, the present disclosure provides novel humanized antibodies and antibody fragments specific for CD3, which are superior to the humanized antibodies described in the art. In particular, the humanized antibodies of the present disclosure display weaker binding affinities to human and non-human primate CD3 when compared to the parental murine antibody SP34 resulting in the reduced activation of T cells and associated release of inflammatory cytokines. Moreover, bispecific antibodies comprising the humanized SP34 binding domains of the present disclosure have limited capability to mediate redirected T cell killing of target antigen low expressing cells such as present on healthy tissue. Together with their low immunogenicity risk in humans, the antibodies of the present disclosure combine favorable functional and safety properties never observed before. These features makes the antibodies and antibody fragments of the present disclosure highly desirable for therapeutic use.

SUMMARY OF THE DISCLOSURE

In one aspect, the present disclosure provides humanized antibodies and antigen-binding fragments that specifically bind to human CD3.

In another aspect, the humanized antibodies or antibody fragments according to the present disclosure are used for targeting T cells expressing CD3 (CD3 expressing T cells) and stimulating T cell activation, e.g., under circumstances where T cell-mediated killing is beneficial or desirable. The CD3 specific antibodies or antibody fragments of the present disclosure or antigen-binding fragments may be used in bispecific formats that direct CD3 mediated T cell activation to specific cell types such as tumor cells. The disclosure also relates to methods of reducing or eliminating tumor burden and controlling the toxic side effects that may be associated with tumor immunotherapy.

In another aspect, the present disclosure provides humanized CD3 antibodies or antibody fragments, which specifically bind to CD3 with an optimized affinity compared to the murine antibody SP34 with $K_D$ values typically in the double digit nanomolar range as determined in an in vitro affinity binding assay.

In another aspect, the present disclosure relates to humanized antibodies or antibody fragments specifically binding to human and non-human CD3, and in particular to such antibodies or antibody fragments that are cross-reactive with CD3 epsilon of a non-human primate such as cynomolgus monkey.

Consequently, the disclosed humanized antibodies are superior to the CD3 specific antibodies described in the prior art in terms of safety and pharmacokinetic (PK) properties and provide well suited and promising compounds for the treatment of humans suffering particular from diseases such like cancer.

Accordingly, in another aspect, the present disclosure provides humanized antibodies or antibody fragments comprising CD3 specific binding domains that are "optimized affinity" binding domains to CD3 as measured using for instance a Biacore® (scientific, electrical, optical and measuring apparatus and instruments) assay. In particular, the present disclosure provides antibodies comprising humanized CD3 specific binding domains that have an "optimized affinity" CD3 epsilon binding when compared to the murine antibody SP34.

In another aspect, the present disclosure provides bispecific antibodies comprising humanized CD3 specific binding domains that have an "optimized affinity" CD3 epsilon binding when compared to the murine antibody SP34 and consequently display a weaker potency in killing target antigen low expressing cells but an equivalent, similar or comparable potency in killing target antigen high expressing cancer cells. As such, the bispecific antibodies of the present disclosure may not mediate redirected T cell cytotoxicity (RTCC) killing of target antigens expressed on healthy tissue.

In another aspect, the present disclosure also comprises full length IgGs for improving the pharmacokinetics (PK) and potentially lowering the immunogenicity of the molecules.

In an embodiment, the present disclosure provides an antibody or antibody fragment specific for cluster of differentiation 3 (CD3), wherein said antibody or antibody fragment specifically binds to human CD3 and to non-human primate CD3, wherein said antibody or antibody fragment comprises a) the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or b) the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, the present disclosure provides an antibody or antibody fragment specific for CD3, wherein said antibody or antibody fragment specifically binds to human CD3 and cynomolgus monkey CD3.

In an embodiment, the present disclosure provides an antibody or antibody fragment specific for CD3, wherein said antibody or antibody fragment specifically binds to human CD3 epsilon and cynomolgus monkey CD3 epsilon.

In embodiments, the present disclosure provides an antibody or antibody fragment specific for CD3, wherein said antibody or antibody fragment is a humanized or chimeric antibody or antibody fragment thereof.

In further embodiments, the present disclosure provides an antibody or antibody fragment specific for CD3, wherein said antibody or antibody fragment comprises
  a) a variable light chain selected from the group consisting of SEQ ID NO: 11, SEQ ID NO: 13, SEQ ID NO: 15, SEQ ID NO: 17, SEQ ID NO: 19 and SEQ ID NO: 21 and
  b) a variable heavy chain selected from the group consisting of SEQ ID NO: 7 and SEQ ID NO: 9.

In further embodiments, the present disclosure provides an antibody or antibody fragment specific for CD3, wherein the variable heavy chain and variable light chain are selected from the group consisting of:
the variable heavy chain having SEQ ID NO: 7 and the variable light chain having SEQ ID NO: 11;
the variable heavy chain having SEQ ID NO: 7 and the variable light chain having SEQ ID NO: 13;
the variable heavy chain having SEQ ID NO: 7 and the variable light chain having SEQ ID NO: 15;
the variable heavy chain having SEQ ID NO: 7 and the variable light chain having SEQ ID NO: 17;
the variable heavy chain having SEQ ID NO: 7 and the variable light chain having SEQ ID NO: 19;
the variable heavy chain having SEQ ID NO: 7 and the variable light chain having SEQ ID NO: 21;
the variable heavy chain having SEQ ID NO: 9 and the variable light chain having SEQ ID NO: 11;
the variable heavy chain having SEQ ID NO: 9 and the variable light chain having SEQ ID NO: 13;
the variable heavy chain having SEQ ID NO: 9 and the variable light chain having SEQ ID NO: 15;
the variable heavy chain having SEQ ID NO: 9 and the variable light chain having SEQ ID NO: 17;
the variable heavy chain having SEQ ID NO: 9 and the variable light chain having SEQ ID NO: 19 and
the variable heavy chain having SEQ ID NO: 9 and the variable light chain having SEQ ID NO: 21.

In further embodiments, the present disclosure provides an antibody or antibody fragment specific for CD3, wherein the variable heavy chain and variable light chain are selected from the group consisting of:
  the variable heavy chain domain having SEQ ID NO: 7 and the variable light chain having SEQ ID NO: 15;
  the variable heavy chain domain having SEQ ID NO: 7 and the variable light chain having SEQ ID NO: 17 and
  the variable heavy chain domain having SEQ ID NO: 7 and the variable light chain having SEQ ID NO: 19.

In certain embodiments of the present disclosure, the antibody or antibody fragment comprises the variable heavy chain having SEQ ID NO: 7 and the variable light chain having SEQ ID NO: 17.

In certain embodiments of the present disclosure, said antibody or antibody fragment specific for CD3 is an isolated antibody or antibody fragment.

In certain embodiments of the present disclosure, said antibody or antibody fragment specific for CD3 is a recombinant antibody or antibody fragment.

In another embodiment of the present disclosure the antibody or antibody fragment is a monoclonal antibody or antibody fragment.

In certain embodiments of the present disclosure, said antibody or antibody fragment specific for CD3 is a full-length IgG.

In certain embodiments of the present disclosure, said antibody or antibody fragment specific for CD3 is a full-length IgG of an isotype selected from the group consisting of IgG1, IgG2, IgG3, and IgG4.

In further embodiments, the present disclosure provides an antibody or antibody fragment specific for CD3, wherein the full-length IgG comprises an Fc region that has reduced effector function relative to that of a wild type Fc-receptor.

In further embodiments, the present disclosure provides an antibody or antibody fragment specific for CD3, wherein said antibody comprises a Fc region, wherein in at least 5 amino acids in the positions corresponding to positions L234, L235, D237, N330, P331 in a human IgG1 heavy chain, are mutated to A, E, A, S, and S, respectively.

In further embodiments, the present disclosure provides an antibody or antibody fragment specific for CD3, wherein said antibody fragment is a Fab fragment.

In further embodiments, the present disclosure provides an antibody or antibody fragment specific for CD3, wherein the antibody is a single chain antibody.

In an aspect, the present disclosure provides a bispecific antibody comprising a first antigen binding domain of an antibody or antibody fragment specific for CD3 according to the present disclosure, and a second antigen binding domain which binds a different target antigen than said first antigen binding domain.

In an embodiment, the present disclosure provides a bispecific antibody, wherein said second binding domain specifically binds a cell surface target antigen.

In an embodiment, the present disclosure provides a bispecific antibody, wherein said cell surface target antigen is a tumor antigen.

In an embodiment, the present disclosure provides a bispecific antibody, wherein said bispecific antibody comprises a Fc region modified according to the present disclosure.

In an aspect, the present disclosure provides a bispecific antibody, wherein said bispecific antibody comprises an Fc region that has reduced effector function relative to that of a wild type Fc-receptor.

In an aspect, the present disclosure provides a bispecific antibody, wherein said bispecific antibody comprises an Fc region, wherein in at least 5 amino acids in the positions corresponding to positions L234, L235, D237, N330, P331 in a human IgG1 heavy chain, are mutated to A, E, A, S, and S, respectively.

In certain aspects, the present disclosure provides a nucleic acid composition comprising a nucleic acid sequence or a plurality of nucleic acid sequences encoding the antibody or antibody fragment according to any one of the preceding claims.

In certain aspects, the present disclosure provides a vector composition comprising a vector or a plurality of vectors comprising the nucleic acid sequence or plurality of nucleic acid sequences according to the present disclosure.

In yet another aspect, the present disclosure provides a host cell comprising the vector composition according to the present disclosure.

In an embodiment, said host cell is mammalian cell.

In an embodiment, said host cell is prokaryotic cell.

In further embodiments, the present disclosure provides an antibody or antibody fragment specific for CD3 for use in the treatment of a subject in need thereof.

In further embodiments, the present disclosure provides an antibody or antibody fragment specific for CD3 for use as a medicament.

In further embodiments, the present disclosure provides a pharmaceutical composition comprising the antibody or antibody fragment according to the present disclosure and a pharmaceutically acceptable carrier or excipient.

There is utility in the claimed antibodies or antibody fragments. Furthermore, there is utility in the claimed method to generate such antibodies or fragments.

Utilization of the claimed antibodies or antibody fragments is to target T cells expressing CD3, and for stimulating T cell activation, e.g., under circumstances where T cell-mediated killing is beneficial or desirable. In particular the claimed antibodies or antibody fragments are for therapeutic use, such as the treatment of cancer.

BRIEF DESCRIPTION OF THE DRAWINGS

FIG. 1: Amino acid sequence alignments of the variable light chain of the murine antibody SP34 and 6 generated humanized VL variants thereof.

FIG. 2: Amino acid sequence alignments of the variable heavy chain of the murine antibody SP34 and 2 generated humanized VH variants thereof.

FIG. 3: ELISA binding of 7 mammalian produced IgGs comprising humanized variable heavy and light chains of SP34 according to the present disclosure. FIG. 3A depicts binding to human CD3 epsilon and FIG. 3B binding to cynomolgus monkey CD3 epsilon in comparison to control IgG SP34 and RefmAb #1.

FIG. 4: Cell binding of 7 mammalian produced IgGs comprising humanized variable heavy and light chains of SP34 according to the present disclosure. FIG. 4A shows binding as a function of antibody concentration as determined on CD3 positive Jurkat cells by flow cytometry. As positive controls, SP34 IgG (m/h chimera) and RefmAb #1 were included. FIG. 4B depicts the same as FIG. 4A with the difference that binding on cynomolgus derived PBMCs is shown.

FIG. 5: Cell binding of 3 HER2-IgG×CD3-scFv bispecific antibodies comprising humanized variable heavy and light chains of SP34 according to the present disclosure in comparison to positive control BsAb #RefMab #1 and negative control bsAbs #neg.control. FIG. 5A depicts binding to human PBMCs derived from one donor as a function of antibody concentration as determined by flow cytometry. FIG. 5B depicts binding to cynomolgus derived PBMCs.

FIG. 6: T-cell activation assay for 3 HER2-IgG×CD3-scFv bispecific antibodies comprising humanized variable heavy and light chains of SP34 according to the present disclosure. Activation of T-cells is determined by evaluation of CD69 expression on CD4 positive T-cells (FIG. 6B) or CD8 positive T-cells (FIG. 6A) as assessed by flow cytometry. FIG. 6A is a graph showing the percentage of CD69+ activated CD8+ T cells derived from 7 different donors as a function of antibody concentration. FIG. 6B is a graph showing the percentage of CD69+ activated CD4+ T cells derived from 7 different donors as a function of antibody concentration.

FIG. 7: Cytotoxicity assay for 3 HER2-IgG×CD3-scFv bispecific antibodies comprising humanized variable heavy and light chains of SP34 according to the present disclosure on HER2 high expressing SKBR3 cells, HER2 low expressing A498 cells and HER2 negative cell line MDA-MB-468 in presence of human derived PBMCs. Cytotoxic activity of PBMCs is assessed by measuring incorporated CellTox-Green™ (Real-Time Cell Death Assay with Multiplexing Compatibility) fluorescence. FIG. 7A is a graph showing the relative fluorescence of HER2 high expressing SKBR3 cells as a function of antibody concentration. FIG. 7B indicates the same as FIG. 7A but with results obtained from HER2 low expressing A498 cells. FIG. 7C indicates the same as FIG. 7A but with results obtained from HER2 negative MDA-MB-468 cells.

FIG. 8 is a graph indicating the concentration of released Interferon-gamma from T-cells derived from one donor as a function of antibody concentration. As positive control BsAb #RefMAb #1 was included.

FIG. 9: Cytotoxicity assay for 7 CD3-IgG×HER2-scFv bispecific antibodies comprising humanized variable heavy and light chains of SP34 according to the present disclosure tested on HER2 high expressing SKBR3 cells (FIG. 9A) and HER2 low expressing A498 cells (FIG. 9B). Cytotoxic activity of PBMCs is assessed by measuring incorporated CellToxGreen™ fluorescence.

DETAILED DESCRIPTION OF THE DISCLOSURE

Definitions

Figure 8:
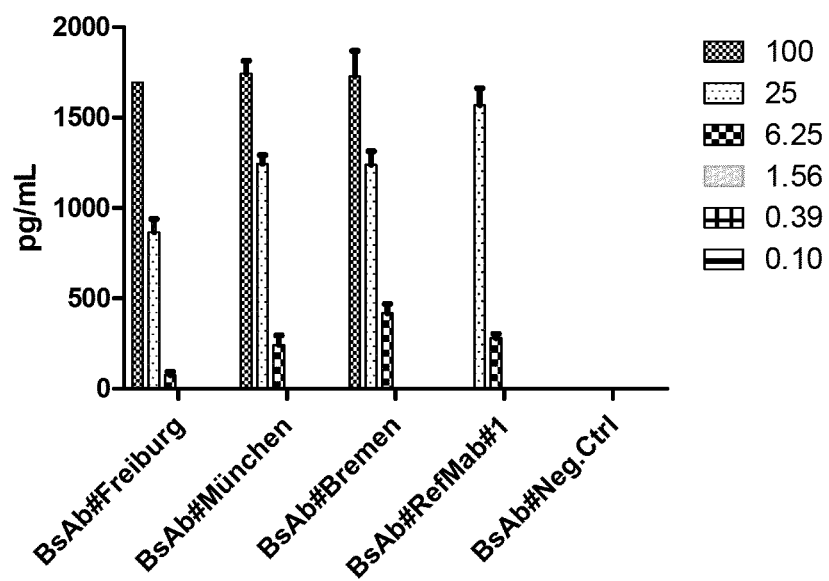
FIG. 8: Cytotoxicity assay for 3 HER2-IgG×CD3-scFv bispecific antibodies comprising humanized variable heavy and light chains of SP34 according to the present disclosure in the presence of HER2 high expressing SKBR3 cells. Cytotoxic activity is assessed by measuring release of Interferon-gamma from T-cells using the commercially available Human IFN-gamma Duo SET ELISA purchased form R&D Systems.

The term "CD3" refers to an antigen which is expressed on T cells as part of the multi-molecular T cell receptor (TCR) and which consists of a homodimer or heterodimer formed from the association of two of four receptor chains: CD3-epsilon, CD3-delta, CD3-zeta, and CD3-gamma.

Human CD3 Epsilon has the Amino Acid Sequence of UniProt P07766

(SEQ ID NO: 154)
MQSGTHWRVLGLCLLSVGVWGQDGNEEMGGITQTPYKVSISGTTVILTC

PQYPGSEILWQHNDKNIGGDEDDKNIGSDEDHLSLKEFSELEQSGYYVC

YPRGSKPEDANFYLYLRARVCENCMEMDVMSVATIVIVDICITGGLLLL

VYYWSKNRKAKAKPVTRGAGAGGRQRGQNKERPPPVPNPDYEPIRKGQR

DLYSGLNQRRI

The extracellular domain of human CD3 epsilon without the signal sequence comprises amino acid residues 23-126 and has the amino acid sequence of as set forth in SEQ ID NO: 1 of TABLE 1.

Cynomolgus CD3 Epsilon has the Amino Acid Sequence of UniProt Q95L15

(SEQ ID NO: 155)
MQSGTRWRVLGLCLLSIGVWGQDGNEEMGSITQTPYQVSISGTTVILTC

SQHLGSEAQWQHNGKNKEDSGDRLFLPEFSEMEQSGYYVCYPRGSNPED

ASHHLYLKARVCENCMEMDVMAVATIVIVDICITLGLLLLVYYWSKNRK

AKAKPVTRGAGAGGRQRGQNKERPPPVPNPDYEPIRKGQQDLYSGLNQR

RI

The extracellular domain of cynomolgus monkey CD3 epsilon without the signal sequence comprises amino acid residues 22-117 and has the amino acid sequence of as set forth in SEQ ID NO: 2 of TABLE 1.

The term "antibody" as used herein refers to a protein comprising at least two heavy (H) chains and two light (L) chains inter-connected by disulfide bonds which interacts with an antigen. Each heavy chain is comprised of a heavy chain variable region or domain (abbreviated herein as VH) and a heavy chain constant region. The heavy chain constant region is comprised of three domains, CH1, CH2 and CH3. Each light chain is comprised of a light chain variable region or domain (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology.

The phrase "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8:1057-1062; and U.S. Pat. No. 5,641,870).

A "human antibody" or "human antibody fragment", as used herein, includes antibodies and antibody fragments having variable regions in which both the framework and CDR regions are derived from sequences of human origin. Furthermore, if the antibody contains a constant region, the constant region also is derived from such sequences. Human origin includes, e.g., human germline sequences, or mutated versions of human germline sequences or antibody containing consensus framework sequences derived from human framework sequences analysis, for example, as described in Knappik et al., (2000) J Mol Biol 296:57-86). Thereby said human antibody can be obtained from technology platforms which comprise antibodies derived from human germline genes either generated by PCR-amplification of VHA/L repertoire isolated from B-cells or are generated synthetically. Technology platforms include library based approaches comprising human immunoglobulin genes displayed on phage, ribosome or yeast. Respective display technologies are standard in the scientific community. Furthermore immunization of a transgenic mouse carrying human immunoglobulin repertoire is another approach to generate human antibodies against an antigen of interest. Antibodies or fragments thereof selected from an antibody library based on the MorphoSys HuCAL® concept (Knappik et al., (2000) J Mol Biol 296:57-86) are considered as fully human.

A "humanized antibody" or "humanized antibody fragment" is defined herein as an antibody or antibody fragment which has constant antibody regions derived from sequences of human origin and the variable antibody regions or parts thereof or only the CDRs are derived from another species. For example a humanized antibody can be CDR-grafted, wherein the CDRs of the variable domain are from a non-human origin, while one or more frameworks of the variable domain are of human origin and the constant domain (if any) is of human origin.

The term "chimeric antibody" or "chimeric antibody fragment" is defined herein as an antibody molecule which has constant antibody regions derived from, or corresponding to, sequences found in one species and variable antibody regions derived from another species. Preferably, the constant antibody regions are derived from, or corresponding to, sequences found in humans, and the variable antibody regions (e.g. VH, VL, CDR or FR regions) are derived from sequences found in a non-human animal, e.g. a mouse, rat, rabbit or hamster.

The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948.

The term "isolated" refers to a compound, which can be e.g. an antibody or antibody fragment, that is substantially free of other antibodies or antibody fragments having different antigenic specificities. Thus, in some aspects, antibodies provided are isolated antibodies which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "recombinant antibody", as used herein, includes all antibodies that are prepared, expressed, created or segregated by means not existing in nature. For example antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences or antibodies isolated from an animal (e.g., a mouse) that is transgenic or transchromosomal for human immunoglobulin genes or a hybridoma prepared therefrom. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody.

As used herein, the term "monoclonal antibody" refers to an antibody that is derived from a single clone, including any eukaryotic, prokaryotic, or phage clone, and not the method by which it is produced. Monoclonal antibodies as disclosed herein may be made by the hybridoma method as described in Kohler et al.; Nature, 256:495 (1975) or may be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Other exemplary methods of producing other monoclonal antibodies are provided in the Examples herein.

As used herein, an antibody "binds specifically to", "specifically binds to", is "specific to/for" or "specifically recognizes" an antigen if such antibody is able to discriminate between such antigen and one or more reference antigen(s), since binding specificity is not an absolute, but a relative property. For example, a standard ELISA assay can be carried out. The scoring may be carried out by standard color development (e.g. secondary antibody with horseradish peroxide and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like.

As used herein, "an antibody that binds to CD3" or an "anti-CD3 antibody" or "antibody specific for CD3" includes antibodies and antibody fragments that specifically recognize one or more CD3 subunit (e.g., epsilon, delta, gamma or zeta), as well as antibodies and antibody fragments that specifically recognize a dimeric complex of two CD3 subunits (e.g., gamma/epsilon, delta/epsilon, and zeta/zeta CD3 dimers). The antibodies and antibody fragments of the present disclosure may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the term "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity.

The term "$K_D$", as used herein, refers to the dissociation constant, which is obtained from the ratio of $K_d$ to $K_a$ (i.e. $K_d/K_a$) and is expressed as a molar concentration (M). $K_D$ values for antigen binding moieties like e.g. monoclonal antibodies can be determined using methods well established in the art. Methods for determining the $K_D$ of an antigen binding moiety like e.g. a monoclonal antibody are SET (soluble equilibrium titration) or surface plasmon resonance using a biosensor system such as a Biacore® system. In the present disclosure an antibody specific to the CD3 epsilon polypeptide typically has a dissociation rate constant ($K_D$) ($k_{off}/k_{on}$) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than $10^{-10}$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower.

The term "epitope" includes any proteinacious region which is specifically recognized by an antibody or fragment thereof or a T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

"Binds the same epitope as" means the ability of an antibody, antibody fragment or other antigen-binding moiety to bind to a specific antigen and binding to the same epitope as the exemplified antibody when using the same epitope mapping technique for comparing the antibodies. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two-dimensional nuclear magnetic resonance.

Compositions of the present disclosure may be used for therapeutic or prophylactic applications. The present disclosure, therefore, includes a pharmaceutical composition containing an antibody (or functional antibody fragment) as disclosed herein and a pharmaceutically acceptable carrier or excipient therefor. In a related aspect, the present disclosure provides a method for treating cancer or an inflammatory disorder. Such method contains the steps of administering to a subject in need thereof an effective amount of the pharmaceutical composition that contains an antibody (or functional antibody fragment) as described or contemplated herein.

The present disclosure provides therapeutic methods comprising the administration of a therapeutically effective amount of a humanized CD3 specific antibody or antibody fragment as disclosed to a subject in need of such treatment. A "therapeutically effective amount" or "effective amount", as used herein, refers to the amount of an anti-CD3 antibody necessary to elicit the desired biological response. In accordance with the disclosure, the therapeutic effective amount is the amount of a CD3 specific antibody or antibody fragment necessary to treat and/or prevent a disease.

"Species", as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably the subject is a primate, most preferably a human.

The "non-chimpanzee primate" species may be understood within the meaning of the disclosure to be a lemur, a tarsier, a gibbon, a marmoset (belonging to New World Monkeys of the family Cebidae) or an Old-World Monkey (belonging to the superfamily Cercopithecoidea).

As used herein, an "Old-World Monkey" comprises any monkey falling in the superfamily Cercopithecoidea, itself subdivided into the families: the Cercopithecinae, which are mainly African but include the diverse genus of macaques which are Asian and North African; and the Colobinae, which include most of the Asian genera but also the African colobus monkeys.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et at., Sequences of Proteins of Immunological Interest, Fifth Edition, NIH Publication 9 1-3242, Bethesda Md. (1991), vols. 1-3.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

The terms "cancer" and "cancerous" refer to or describe the physiological condition in mammals that is typically characterized by unregulated cell growth.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of a compound, for example, an CD3 specific antibody of the disclosure or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this disclosure, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater.

By "increase" is meant the ability to cause an overall increase, for example, of 20% or greater, of 50% or greater, or of 75%, 85%, 90%, 95%, or greater.

The term "$EC_{50}$", as used herein, refers to the concentration of an antibody or an antibody fragment which induces a response in an assays half way between the baseline and maximum. It therefore represents the antibody concentration at which 50% of the maximal effect is observed.

The term "$IC_{50}$", as used herein, refers to the concentration of an inhibitor (e.g. an antibody or antibody fragment) that inhibits a response in an assay half way between the maximal response and the baseline. It represents the antibody concentration that reduces a given response by 50%.

The terms "inhibition" or "inhibit" or "reduction" or "reduce" or "neutralization" or "neutralize" refer to a decrease or cessation of any phenotypic characteristic (such as binding, a biological activity or function) or to the decrease or cessation in the incidence, degree, or likelihood of that characteristic. The "inhibition", "reduction" or "neutralization" needs not to be complete as long as it is detectable using an appropriate assay. In some embodiments, by "reduce" or "inhibit" is meant the ability to cause a decrease of 20% or greater. In another embodiment, by "reduce" or "inhibit" is meant the ability to cause a decrease of 50% or greater. In yet another embodiment, by "reduce" or "inhibit" is meant the ability to cause an overall decrease of 75%, 85%, 90%, 95%, or greater.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts PILR, e.g., in the fluid phase or colloidal phase, but also situations where the agonist or antagonist does not contact the cell or the receptor.

Bispecific Antigen-Binding Molecules

The CD3 specific antibodies or antibody fragments of the present disclosure can be linked to or co-expressed with another functional molecule, e.g., another peptide or protein. For example, an antibody or antibody fragment thereof can be functionally linked (e.g., by chemical coupling, genetic fusion, noncovalent association or otherwise) to one or more other molecular entities, such as another antibody or antibody fragment to produce a bispecific antibody with a second binding specificity.

The antibodies of the present disclosure may be monospecific or bispecific antibodies. A bispecific antibody may be specific for different epitopes of one target antigen or may contain antigen-binding domains specific for more than one target antigen. See, e.g., Tutt et al., 1991, J. Immunol. 147:60-69; Kufer et al., 2004, Trends Biotechnol. 22:238-244.

Use of the expression "anti-CD3 antibody" or "CD3 specific antibody" herein is intended to include both monospecific CD3 specific antibodies as well as bispecific antibodies. Bispecific antibodies according to the present disclosure were designed using an IgG-scFv format comprising a monoclonal IgG1 binding moiety and a scFv binding moiety, with the N-terminus of each scFv VL domain fused to the C-terminal end of each IgG heavy chain via a peptide linker. Both Fabs arms of the IgG may bind to the cell surface target antigen while the scFv is specific for CD3 (both scFv are identical and display the same specificity for CD3). Alternatively, bispecific antibodies can be generated, wherein the two scFv molecules were specific for cell surface target antigen and the Fab arms of the IgG1 portion are specific for CD3.

The CD3 specific binding domains of the CD3 specific antibodies or antibody fragments of the present disclosure can comprise any of the heavy or light chain variable regions or CDR amino acid sequences as set forth in Tables 3-5 as disclosed herein.

In the context of bispecific antibodies according to the present disclosure, the cell surface target antigen can be a cancer-associated antigen. Non-limiting examples of cancer related antigens include, e.g., an antigen that is expressed on the surface of a tumor.

Any bispecific antibody format or technology may be used to make the bispecific antigen-binding molecules of the present disclosure. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule.

Specific exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab.sup.2 bispecific formats (see, e.g., Klein et al. 2012, mAbs 4:6, 1-11, and references cited therein, for a review of the foregoing formats).

EMBODIMENTS

Humanized antibodies or antibody fragment specific for CD3 according the present disclosure are listed in Table 5-7.

In an embodiment, the present disclosure refers to an monoclonal antibody or antibody fragment specific for CD3 comprising the variable heavy chain (VH) and the variable light chain (VL) of any one of the antibodies disclosed in Table 5. In an embodiment, the present disclosure refers to an monoclonal antibody or antibody fragment specific for CD3 comprising the heavy chain (HC) and the light chain (LC) of any one of the antibodies disclosed in Tables 5-7. In an embodiment, the present disclosure refers to a monoclonal antibody or antibody fragment specific for CD3 comprising 6 CDRs defined by Kabat of any one of the antibodies disclosed in Tables 5. In an embodiment, the present disclosure refers to a monoclonal antibody or antibody fragment specific for CD3 comprising 6 CDRs of any one of the antibodies disclosed in Table 5.

In an embodiment, the present disclosure provides an antibody or antibody fragment specific for cluster of differentiation 3 (CD3), wherein said antibody or antibody fragment specifically binds to human CD3 and to non-human primate CD3, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, the present disclosure provides an antibody or antibody fragment specific for CD3, wherein said antibody or antibody fragment specifically binds to human CD3 epsilon and to non-human primate CD3 epsilon, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, the present disclosure provides an antibody or antibody fragment specific for CD3, wherein said antibody or antibody fragment specifically binds to human CD3 and to non-human primate CD3, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28

In an embodiment, the present disclosure provides an antibody or antibody fragment specific for CD3, wherein said antibody or antibody fragment specifically binds to human CD3 and to non-human primate CD3, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, the present disclosure provides an antibody or antibody fragment specific for cluster of differentiation 3 (CD3), wherein said antibody or antibody fragment specifically binds to human CD3 and to non-human primate CD3, wherein said antibody or antibody fragment comprises the HCDR1 region comprising the amino acid sequence of SEQ ID NO: 23, the HCDR2 region comprising the amino acid sequence of SEQ ID NO: 24, the HCDR3 region comprising the amino acid sequence of SEQ ID NO: 25, the LCDR1 region comprising the amino acid sequence of SEQ ID NO: 26, the LCDR2 region comprising the amino acid sequence of SEQ ID NO: 27 and the LCDR3 region comprising the amino acid sequence of SEQ ID NO: 28 or the HCDR1 region comprising the amino acid sequence of SEQ ID NO: 23, the HCDR2 region comprising the amino acid sequence of SEQ ID NO: 24, the HCDR3 region comprising the amino acid sequence of SEQ ID NO: 25, the LCDR1 region comprising the amino acid sequence of SEQ ID NO: 26, the LCDR2 region comprising the amino acid sequence of SEQ ID NO: 65 and the LCDR3 region comprising the amino acid sequence of SEQ ID NO: 28.

In one embodiment of the present disclosure, the antibody or antibody fragment specific for CD3 according to the present disclosure is a humanized, chimeric or synthetic antibody or antibody fragment.

In an embodiment, the antibody or antibody fragment according to the present disclosure is an isolated antibody or antibody fragment. In an embodiment, the antibody or antibody fragment according to the present disclosure is a recombinant antibody or antibody fragment. In another embodiment of the present disclosure the antibody or antibody fragment is a monoclonal antibody or antibody fragment. In an embodiment, said antibody or antibody fragment is a humanized monoclonal human antibody or antibody fragment.

In an embodiment, the antibody of the present disclosure is a full-length IgG. In an embodiment, the antibody of the present disclosure is a full-length IgG of an isotype selected from the group consisting of IgG1, IgG2, IgG3, and IgG4. In another embodiment the antibody is of the IgG1 isotype. In an embodiment, the antibody is of the human IgG1 isotype.

In an embodiment, the antibody of the present disclosure comprises a Fc region that has reduced effector function relative to that of a wild type Fc-receptor. In an embodiment, the antibody of the present disclosure comprises a Fc region, wherein in at least 5 amino acids in the positions corresponding to positions L234, L235, D237, N330, P331 in a human IgG1 heavy chain, are mutated to A, E, A, S, and S, respectively.

In one embodiment, the antibody fragment is selected from the group consisting of a Fab, a Fab', a Fv, a scFv. In an embodiment, the antibody or antibody fragment of the present disclosure is a Fab fragment. In an embodiment, the antibody or antibody fragment of the present disclosure is a single chain antibody.

In an embodiment of the present disclosure, the antibody or antibody fragment specifically binds to human CD3 and cynomolgus CD3. In a further embodiment, the antibody or antibody fragment according to the present disclosure specifically binds to human CD3 epsilon and cynomolgus CD3 epsilon.

In an embodiment, the antibody or antibody fragment according to the present disclosure is a humanized or chimeric antibody or antibody fragment thereof.

In an embodiment, the present disclosure provides an antibody or antibody fragment specific for CD3, wherein said antibody or antibody fragment specifically binds to human CD3 and to non-human primate CD3, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 30 and a light chain variable region having SEQ ID NO: 29 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 46 and a light chain variable region having SEQ ID NO: 45 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 56 and a light chain variable region having SEQ ID NO: 55 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 68 and a light chain variable region having SEQ ID NO: 67 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 78 and a light chain variable region having SEQ ID NO: 77 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 86 and a light chain variable region having SEQ ID NO: 85 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 96 and a light chain variable region having SEQ ID NO: 95.

In an embodiment, the present disclosure provides an antibody or antibody fragment specific for CD3, wherein said antibody or antibody fragment specifically binds to human CD3 and to non-human primate CD3, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 9 and a light chain variable region having SEQ ID NO: 11 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 9 and a light chain variable region having SEQ ID NO: 13 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 7 and a light chain variable region having SEQ ID NO: 15 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 7 and a light chain variable region having SEQ ID NO: 17 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 7 and a light chain variable region having SEQ ID NO: 19 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 9 and a light chain variable region having SEQ ID NO: 19 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises the heavy chain variable region having SEQ ID NO: 9 and a light chain variable region having SEQ ID NO: 21

In an embodiment, the present disclosure provides an antibody or antibody fragment specific for CD3, wherein said antibody or antibody fragment specifically binds to human CD3 and to non-human primate CD3, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 68 and a light chain variable region having SEQ ID NO: 67.

In an embodiment, the present disclosure provides an antibody or antibody fragment specific for CD3, wherein said antibody or antibody fragment specifically binds to human CD3 and to non-human primate CD3, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28, and further comprises the heavy chain variable region having SEQ ID NO: 7 and a light chain variable region having SEQ ID NO: 17.

In further embodiments, the present disclosure provides an antibody or antibody fragment specific for CD3, wherein said antibody or antibody fragment comprises
a) a variable light chain selected from the group consisting of SEQ ID NO: 11, SEQ ID NO: 13, SEQ ID NO: 15, SEQ ID NO: 17, SEQ ID NO: 19 and SEQ ID NO: 21
and
b) a variable heavy chain selected from the group consisting of SEQ ID NO: 7 and SEQ ID NO: 9.

In an embodiment, the present disclosure refers to an antibody or antibody fragment specific for CD3, wherein said antibody or antibody fragment comprises
a) the variable heavy chain of SEQ ID NO: 9 and the variable light chain of SEQ ID NO: 11 or
b) the variable heavy chain of SEQ ID NO: 9 and the variable light chain of SEQ ID NO: 13 or
c) the variable heavy chain of SEQ ID NO: 7 and the variable light chain of SEQ ID NO: 15 or
d) the variable heavy chain of SEQ ID NO: 7 and the variable light chain of SEQ ID NO: 17 or
e) the variable heavy chain of SEQ ID NO: 7 and the variable light chain of SEQ ID NO: 19 or
f) the variable heavy chain of SEQ ID NO: 9 and the variable light chain of SEQ ID NO: 19 or
g) the variable heavy chain of SEQ ID NO: 9 and the variable light chain of SEQ ID NO: 21 or
a variable heavy chain and a variable light chain that has at least 60%, at least 70%, at least 80%, at least 90% or at least 95% identity to the variable heavy chain of SEQ ID NO: 17, 28, 39 or 50 and to the variable light chain of SEQ ID NO: 18, 29, 40 or 51.

In further embodiments, the present disclosure provides an antibody or antibody fragment specific for CD3, wherein the variable heavy chain consists of SEQ ID NO: 7 and the variable light chain consist of SEQ ID NO: 11.

In further embodiments, the present disclosure provides an antibody or antibody fragment specific for CD3, wherein the variable heavy chain consists of SEQ ID NO: 7 and the variable light chain consist of SEQ ID NO: 13.

In further embodiments, the present disclosure provides an antibody or antibody fragment specific for CD3, wherein the variable heavy chain consists of SEQ ID NO: 7 and the variable light chain consist of SEQ ID NO: 15.

In further embodiments, the present disclosure provides an antibody or antibody fragment specific for CD3, wherein the variable heavy chain consists of SEQ ID NO: 7 and the variable light chain consist of SEQ ID NO 17.

In further embodiments, the present disclosure provides an antibody or antibody fragment specific for CD3, wherein the variable heavy chain consists of SEQ ID NO: 7 and the variable light chain consist of SEQ ID NO: 19.

In further embodiments, the present disclosure provides an antibody or antibody fragment specific for CD3, wherein the variable heavy chain consists of SEQ ID NO: 7 and the variable light chain consist of SEQ ID NO: 21.

In further embodiments, the present disclosure provides an antibody or antibody fragment specific for CD3, wherein the variable heavy chain consists of SEQ ID NO: 9 and the variable light chain consist of SEQ ID NO: 11.

In further embodiments, the present disclosure provides an antibody or antibody fragment specific for CD3, wherein the variable heavy chain consists of SEQ ID NO: 9 and the variable light chain consist of SEQ ID NO: 13.

In further embodiments, the present disclosure provides an antibody or antibody fragment specific for CD3, wherein the variable heavy chain consists of SEQ ID NO: 9 and the variable light chain consist of SEQ ID NO: 15.

In further embodiments, the present disclosure provides an antibody or antibody fragment specific for CD3, wherein the variable heavy chain consists of SEQ ID NO: 9 and the variable light chain consist of SEQ ID NO: 17.

In further embodiments, the present disclosure provides an antibody or antibody fragment specific for CD3, wherein the variable heavy chain consists of SEQ ID NO: 9 and the variable light chain consist of SEQ ID NO: 19.

In further embodiments, the present disclosure provides an antibody or antibody fragment specific for CD3, wherein the variable heavy chain consists of SEQ ID NO: 9 and the variable light chain consist of SEQ ID NO: 21.

In further embodiments, the present disclosure provides an antibody or antibody fragment specific for CD3, wherein the variable heavy chain and variable light chain are selected from the group consisting of:
the variable heavy chain domain having SEQ ID NO: 7 and the variable light chain having SEQ ID NO: 15;
the variable heavy chain domain having SEQ ID NO: 7 and the variable light chain having SEQ ID NO: 17 and
the variable heavy chain domain having SEQ ID NO: 7 and the variable light chain having SEQ ID NO: 19.

In an embodiment, the present disclosure provides an antibody or antibody fragment specific for CD3, wherein the variable heavy chain comprises SEQ ID NO: 7 and the variable light chain comprises SEQ ID NO 17 or a sequence having at least 60%, at least 70%, at least 80%, at least 90%, or at least 95% identity with these sequences but which retains the same activity as the said antibody or antibody fragment.

In an embodiment, the present disclosure provides an antibody or antibody fragment specific for CD3, wherein the variable heavy chain comprises SEQ ID NO: 7 and the variable light chain comprises SEQ ID NO 17.

Bispecific Antibodies

In an embodiment, the present disclosure provides a bispecific antibody comprising a first antigen binding domain specific for CD3 and a second binding domain which binds a different target than said first antigen binding region, wherein said first binding domain specific for CD3 comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, the present disclosure provides a bispecific antibody comprising a first antigen binding domain specific for CD3 and a second binding domain, wherein said second binding domain specifically binds a cell surface target antigen and wherein said binding domain specific for CD3 comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, the bispecific antibody of the present disclosure binds to CD3 located on an immune effector cell and a cell surface target antigen that is expressed on a target cell other than the immune effector cell, wherein the bispecific antibody comprises an binding domain specific for CD3 comprising the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, the cell surface target antigen is a tumor antigen. In an embodiment, said immune effector cell is a cytotoxic T-lymphocytes.

In an embodiment, the present disclosure provides a bispecific antibody comprising a first antigen binding domain specific for CD3 and a second binding domain, wherein said second binding domain specifically binds a cell surface target antigen and wherein said bispecific antibody comprises a modified Fc region wherein in at least 5 amino acids in the positions corresponding to positions L234, L235, D237, N330, P331 in a human IgG1 heavy chain, are mutated to A, E, A, S, and S, respectively.

In an embodiment, the present disclosure provides a bispecific antibody comprising a first antigen binding domain specific for CD3 and a second binding domain, wherein said second binding domain specifically binds a cell surface target antigen and wherein said bispecific antibody comprises a modified Fc region wherein in at least 5 amino acids in the positions corresponding to positions L234, L235, D237, N330, P331 in a human IgG1 heavy chain, are mutated to A, E, A, S, and S, respectively and wherein said binding domain specific for CD3 comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In further embodiment, said bispecific antibody according to the present comprises a first antigen binding domain, wherein said first antigen binding domain comprises an antibody or antibody fragment specific for CD3, wherein said antibody or antibody fragment comprises
  a) the variable heavy chain of SEQ ID NO: 9 and the variable light chain of SEQ ID NO: 11 or
  b) the variable heavy chain of SEQ ID NO: 9 and the variable light chain of SEQ ID NO: 13 or
  c) the variable heavy chain of SEQ ID NO: 7 and the variable light chain of SEQ ID NO: 15 or
  d) the variable heavy chain of SEQ ID NO: 7 and the variable light chain of SEQ ID NO: 17 or
  e) the variable heavy chain of SEQ ID NO: 7 and the variable light chain of SEQ ID NO: 19 or
  f) the variable heavy chain of SEQ ID NO: 9 and the variable light chain of SEQ ID NO: 19 or
  g) the variable heavy chain of SEQ ID NO: 9 and the variable light chain of SEQ ID NO: 21 or
a variable heavy chain and a variable light chain that has at least 60%, at least 70%, at least 80%, at least 90% or at least 95% identity to the variable heavy chain of SEQ ID NO: 17, 28, 39 or 50 and to the variable light chain of SEQ ID NO: 18, 29, 40 or 51.

In further embodiment, said bispecific antibody according to the present comprises a first antigen binding domain, wherein said first antigen binding domain comprises an antibody or antibody fragment specific for CD3, wherein said antibody or antibody fragment comprises the variable heavy chain of SEQ ID NO: 7 and the variable light chain of SEQ ID NO: 17 or a variable heavy chain and a variable light chain that has at least 60%, at least 70%, at least 80%, at least 90% or at least 95% identity to the variable heavy chain of SEQ ID NO: 7 and to the variable light chain of SEQ ID NO: 17.

In an embodiment, the present disclosure provides a nucleic acid sequence or a plurality of nucleic acid sequences encoding an antibody or antibody fragment according to the present disclosure which specifically binds to CD3.

In an embodiment, the present disclosure provides a nucleic acid composition comprising a nucleic acid sequence or a plurality of nucleic acid sequences encoding the antibody or antibody fragment specific for CD3 according to the present disclosure, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In another embodiment, the present disclosure refers to an isolated nucleic acid or a plurality of nucleic acid sequences encoding a heavy chain sequence and/or light chain sequence of an antibody or antibody fragment specific for CD3, the nucleic acid comprising a) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 37 and the LCDR3 region of SEQ ID NO: 38,
or
b) the HCDR1 region of SEQ ID NO: 33, the HCDR2 region of SEQ ID NO: 34, the HCDR3 region of SEQ ID NO: 35, the LCDR1 region of SEQ ID NO: 36, the LCDR2 region of SEQ ID NO: 66 and the LCDR3 region of SEQ ID NO: 38, In another embodiment, the present disclosure refers to an isolated nucleic acid or a plurality of nucleic acid sequences encoding a heavy chain sequence and/or light chain sequence of an antibody or antibody fragment specific for CD3, the nucleic acid comprising
a) the HCDR1 region comprising the nucleic acid sequence of SEQ ID NO: 33, the HCDR2 region comprising the nucleic acid sequence of SEQ ID NO: 34, the HCDR3 region comprising the nucleic acid sequence of SEQ ID NO: 35, the LCDR1 region comprising the nucleic acid sequence of SEQ ID NO: 36, the LCDR2 region comprising the nucleic acid sequence of SEQ ID NO: 37 and the LCDR3 region comprising the nucleic acid sequence of SEQ ID NO: 38,
or
b) the HCDR1 region comprising the nucleic acid sequence of SEQ ID NO: 33, the HCDR2 region comprising the nucleic acid sequence of SEQ ID NO: 34, the HCDR3 region comprising the nucleic acid sequence of SEQ ID NO: 35, the LCDR1 region comprising the nucleic acid sequence of SEQ ID NO: 36, the LCDR2 region comprising the nucleic acid sequence of SEQ ID NO: 66 and the LCDR3 region comprising the nucleic acid sequence of SEQ ID NO: 38, In an embodiment, the present disclosure refers to a nucleic acid sequence or a plurality of nucleic acid sequences encoding an antibody or antibody fragment specific for CD3, wherein the nucleic acid sequence or plurality of nucleic acid sequences comprises the VH of SEQ ID NO: 70 and/or the VL of SEQ ID NO: 69, or the VH and/or the VL that has at least 60%, at least 70%, at least 80%, at least 90% or at least 95% identity to the VH of SEQ ID NO: 70 and the VL of SEQ ID NO: 69.

In an embodiment, the present disclosure refers to a nucleic acid sequence or a plurality of nucleic acid sequences encoding an antibody or antibody fragment specific for CD3, wherein the nucleic acid sequence or plurality of nucleic acid sequences comprises the VH of SEQ ID NO: 8 and/or the VL of SEQ ID NO: 18, or the VH and/or the VL that has at least 60%, at least 70%, at least 80%, at least 90% or at least 95% identity to the VH of SEQ ID NO: 8 and the VL of SEQ ID NO: 18.

In an embodiment, the present disclosure provides a vector composition comprising a vector or a plurality of vectors comprising the nucleic acid sequence or plurality of nucleic acid sequences encoding an antibody or antibody fragment as disclosed in TABLE 5-7.

In an embodiment, the present disclosure refers to a vector composition comprising a vector or a plurality of vectors comprising a nucleic acid sequence or plurality of nucleic acid sequences disclosed in Tables 3-7. In an embodiment, the present disclosure provides a vector comprising a nucleic acid encoding an antibody or antibody fragment specific for CD3 according to the present disclosure. In an embodiment, the present disclosure provides a vector comprising a nucleic acid disclosed in Tables 3-7. In an embodiment, the present disclosure provides a vector comprising a nucleic acid encoding an antibody or antibody fragment disclosed in Tables 3-7. In one embodiment, the present disclosure refers to a host cell comprising a vector composition comprising a vector or a plurality of vectors comprising the nucleic acid sequence or plurality of nucleic acid sequences encoding an antibody or antibody fragment as disclosed in Tables 5-7.

In an embodiment, the present disclosure provides a host cell comprising a vector comprising a nucleic acid encoding an antibody or antibody fragment specific for CD3 according to the present disclosure. In an embodiment, the present disclosure provides a host cell comprising a nucleic acid encoding an antibody or antibody fragment specific for CD3 of the present disclosure. In another embodiment, the present disclosure provides an isolated host cell comprising a vector comprising a nucleic acid disclosed in Tables 3-7. In an embodiment, the host cell of the present disclosure is a mammalian cell. In an embodiment, the host cell of the present disclosure is a prokaryotic cell.

In certain embodiments of the present disclosure, additional amino acid residues, polypeptides or moieties are added to the antibody or antibody fragment of the present disclosure, for example to aid in the expression or purification or to increase the stability of the antibody or antibody fragment of the present disclosure.

In an embodiment, the present disclosure provides an antibody or antibody fragment specific for CD3 for use in the treatment of a subject in need thereof, wherein said antibody or antibody fragment comprises the
HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28
or
the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, said antibody or antibody fragment specific for CD3 comprises a variable heavy chain of SEQ ID NO: 7 and the variable light chain of SEQ ID NO 17 or a sequence having at least 60%, at least 70%, at least 80%, at least 90%, or at least 95% identity with these sequences but which retains the same activity as the said antibody or antibody fragment.

In an embodiment, said antibody or antibody fragment specific for CD3 comprises a variable heavy chain of SEQ ID NO: 7 and the variable light chain of SEQ ID NO 17.

In an embodiment, the present disclosure provides an antibody or antibody fragment specific for CD3 for use as a medicament, wherein said antibody or antibody fragment comprises the
HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28
or
the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, said antibody or antibody fragment specific for CD3 comprises a variable heavy chain of SEQ ID NO: 7 and the variable light chain of SEQ ID NO 17.

In an embodiment, the present disclosure provides an antibody or antibody fragment specific for CD3 for use in treating or delaying progression of a cell proliferative disorder or an autoimmune disorder in a subject in need thereof.

In an embodiment, the present disclosure provides an antibody or antibody fragment specific for CD3 for use in treating or delaying progression of a cell proliferative disorder or an autoimmune disorder in a subject in need thereof, wherein said antibody or antibody fragment comprises the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In an embodiment, said antibody or antibody fragment specific for CD3 comprises a variable heavy chain of SEQ ID NO: 7 and the variable light chain of SEQ ID NO 17.

In an embodiment, the present disclosure provides an antibody or antibody fragment specific for CD3 for use in enhancing immune function in a subject having a cell proliferative disorder or an autoimmune disorder.

In an embodiment, the present disclosure provides an antibody or antibody fragment specific for CD3 for use in enhancing immune function in a subject having a cell proliferative disorder wherein the cell proliferative disorder is a cancer.

In an embodiment, the cancer is selected from the group consisting of esophageal cancer, stomach cancer, small intestine cancer, large intestine cancer, colorectal cancer, breast cancer, non-small cell lung cancer, non-Hodgkin's lymphoma (NHL), B cell lymphoma, B cell leukemia, multiple myeloma, renal cancer, prostate cancer, liver cancer, head and neck cancer, melanoma, ovarian cancer, mesothelioma, glioblastoma, germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenstrom macroglobulinemia, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma.

In another embodiment, the autoimmune disorder is selected from the group consisting of rheumatoid arthritis, juvenile rheumatoid arthritis, systemic lupus erythematosus (SUE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, Neuromyelitis Optica (NMO) and IgG neuropathy.

The present disclosure also provides methods for treating a subject suffering from a disorder, such as cancer, by administering to said subject an effective amount of an antibody or antibody according to the present disclosure. Preferably said subject is a human.

In an embodiment, said antibody or antibody fragment specific for CD3 comprises a variable heavy chain of SEQ ID NO: 7 and the variable light chain of SEQ ID NO 17.

In an embodiment, the present disclosure provides a pharmaceutical composition comprising an antibody or antibody fragment as disclosed in Tables 5-7 and a pharmaceutically acceptable carrier or excipient. In an embodiment, said antibody or antibody fragment specific for CD3 comprises a variable heavy chain of SEQ ID NO: 7 and the variable light chain of SEQ ID NO 17.

The present disclosure also provides methods for treating a subject suffering from a disorder, such as cancer or an autoimmune disorder, by administering to said subject an effective amount of an antibody or antibody fragment as disclosed in Table 5-7. In an embodiment, said antibody or antibody fragment specific for CD3 comprises a variable heavy chain of SEQ ID NO: 7 and the variable light chain of SEQ ID NO 17.

Preferably said subject is a human.

In certain embodiments, the present disclosure provides an antibody or antibody fragment which specifically binds to human or cynomolgus CD3 epsilon with an $EC_{50}$ concentration of greater than 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM as determined in an ELISA assay.

In an embodiment, said antibody or antibody fragment specifically binds to human CD3 epsilon with an $EC_{50}$ of concentration of greater 500 pM. In an embodiment, said antibody or antibody fragment specifically binds to cynomolgus CD3 epsilon with an $EC_{50}$ of concentration of greater 1 nM as determined in an ELISA assay.

In an embodiment, said antibody or antibody fragment specifically binds to human CD3 epsilon with an $EC_{50}$ of concentration of greater 500 pM and to cynomolgus CD3 epsilon with an $EC_{50}$ concentration of greater 1 nM as determined in an ELISA assay.

In alternative aspects said antibody or antibody fragment specifically binds to human or cynomolgus CD3 epsilon with an $EC_{50}$ of concentration of greater 100 pM, 200 pM, 300 pM, 400 pM, 500 pM, 600 pM, 700 pM, 800 pM, 900 pM, 1 nM or 2 nM as determined in an ELISA assay. In a preferred embodiment, said antibody or antibody fragment specifically binds to human or cynomolgus CD3 epsilon with an $EC_{50}$ of concentration of greater 500 pM as determined in an ELISA assay.

In one aspect said antibody or antibody fragment specifically binds to human or cynomolgus CD3 epsilon with an $EC_{50}$ of concentration of greater 100 pm as determined in an ELISA assay.

In an embodiment, the present disclosure provides an antibody or antibody fragment which specifically binds to human or cynomolgus CD3 epsilon with an $EC_{50}$ concentration which is higher compared to the $EC_{50}$ concentration of any one of reference antibodies RefMAb #1 or SP34 as determined in an ELISA assay.

In certain embodiments, the present disclosure provides an antibody or antibody fragment which specifically binds to human or cynomolgus CD3 epsilon with an $EC_{50}$ concentration which is at least 0.5 fold or higher, 1 fold or higher, 1.5 fold or higher, 2 fold or higher, 3 fold or higher, 4 fold or higher, 5 fold or higher, 6 fold or higher, 7 fold or higher, 8 fold or higher, 9 fold or higher, 10 fold or higher, 20 fold or higher, 50 fold or higher, 100 fold or higher as the $EC_{50}$ concentration of any one of reference antibodies RefMAb #1 or SP34 as determined in an ELISA assay.

In certain embodiments, the present disclosure provides an antibody or antibody fragment which specifically binds to recombinant human or cynomolgus CD3 epsilon with an $EC_{50}$ concentration of greater than 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM as determined in an ELISA assay.

In alternative aspects said antibody or antibody fragment specifically binds to recombinant human or cynomolgus CD3 epsilon with an $EC_{50}$ of concentration of greater 100 pM, 200 pM, 300 pM, 400 pM, 500 pM, 600 pM, 700 pM, 800 pM, 900 pM, 1 nM or 2 nM as determined in an ELISA assay.

In one aspect said antibody or antibody fragment specifically binds to recombinant human or cynomolgus CD3 epsilon with an $EC_{50}$ of concentration of greater 100 pm as determined in an ELISA assay.

In certain embodiments, the present disclosure provides an antibody or antibody fragment which specifically binds to recombinant human or cynomolgus CD3 epsilon with an $EC_{50}$ concentration which is at least 0.5 fold or higher, 1 fold or higher, 1.5 fold or higher, 2 fold or higher, 3 fold or higher, 4 fold or higher, 5 fold or higher, 10 fold or higher, 20 fold or higher, 50 fold or higher, 100 fold or higher as the $EC_{50}$ concentration of any one of reference antibodies RefMAb #1 or SP34 as determined in an ELISA assay.

In an embodiment, said antibody or antibody fragment specific for CD3 comprises
a) the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28
or
b) the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In a further embodiment, said antibody or antibody fragment specific for CD3, comprises
a) the variable heavy chain of SEQ ID NO: 9 and the variable light chain of SEQ ID NO: 11 or
b) the variable heavy chain of SEQ ID NO: 9 and the variable light chain of SEQ ID NO: 13 or
c) the variable heavy chain of SEQ ID NO: 7 and the variable light chain of SEQ ID NO: 15 or
d) the variable heavy chain of SEQ ID NO: 7 and the variable light chain of SEQ ID NO: 17 or
e) the variable heavy chain of SEQ ID NO: 7 and the variable light chain of SEQ ID NO: 19 or
f) the variable heavy chain of SEQ ID NO: 9 and the variable light chain of SEQ ID NO: 19 or
g) the variable heavy chain of SEQ ID NO: 9 and the variable light chain of SEQ ID NO: 21.

In an embodiment, said antibody or antibody fragment specific for CD3, comprises the variable heavy chain of SEQ ID NO: 7 and the variable light chain of SEQ ID NO: 17.

In some embodiments, said human CD3 epsilon is hCD3 epsilon 22-49/Fc. In some embodiments, said cynomolgus CD3 epsilon is cyCD3 epsilon 22-49/Fc. In embodiments, said $EC_{50}$ concentration is determined by an ELISA assay as described herein in Example 4 using soluble CD3 epsilon/Fc.

In certain embodiments, the present disclosure provides an antibody or antibody fragment which specifically binds to CD3 expressed on cells with an $EC_{50}$ concentration of greater than 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM as determined in an FACS assay.

In alternative aspects, said antibody or antibody fragment which specifically binds to CD3 expressed on cells with an $EC_{50}$ of concentration of greater 0.5 nM, 1 nM, 2.5 nM, 5 nM, 10 nM or 20 nM or 100 nM as determined in a FACS assay.

In one aspect said antibody or antibody fragment specifically binds to CD3 expressed on cells with an $EC_{50}$ of concentration of greater 0.9 nM as determined in an FACS assay.

In one aspect said antibody or antibody fragment specifically binds to CD3 expressed on cells with an $EC_{50}$ of concentration of greater 40 nM as determined in an FACS assay.

In certain aspect said CD3 is human CD3. In other aspect said CD3 is cynomolgus CD3. In other aspects said cell is an immune cell. In an embodiment, said cells is a Jurkat cells. In embodiments, said $EC_{50}$ concentration is determined by an FACS assay as described herein in Example 5 or Example 9 using Jurkat cells.

In certain embodiment, the present disclosure provides an antibody or antibody fragment which specifically binds to CD3 expressed on cells with an $EC_{50}$ concentration which is higher as the $EC_{50}$ concentration of any one of the control antibodies RefMab #1, BsAB #RefMab #1 or SP34 as determined in a FACS assay.

In certain embodiments the present disclosure provides an antibody or antibody fragment which specifically binds to CD3 expressed on cells with an $EC_{50}$ concentration which is at least 0.4 fold or higher, 1 fold or higher, 2 fold or higher, 3 fold or higher, 4 fold or higher, 5 fold or higher, 10 fold or higher, 20 fold or higher, 50 fold or higher, 100 fold or higher as the $EC_{50}$ concentration of any one of the control antibodies RefMab #1, BsAB #RefMab #1 or SP34 as determined in a FACS assay.

In a further embodiment, said antibody or antibody fragment specific for CD3, comprises
a) the variable heavy chain of SEQ ID NO: 9 and the variable light chain of SEQ ID NO: 11 or b) the variable heavy chain of SEQ ID NO: 9 and the variable light chain of SEQ ID NO: 13 or
c) the variable heavy chain of SEQ ID NO: 7 and the variable light chain of SEQ ID NO: 15 or
d) the variable heavy chain of SEQ ID NO: 7 and the variable light chain of SEQ ID NO: 17 or
e) the variable heavy chain of SEQ ID NO: 7 and the variable light chain of SEQ ID NO: 19 or
f) the variable heavy chain of SEQ ID NO: 9 and the variable light chain of SEQ ID NO: 19 or
g) the variable heavy chain of SEQ ID NO: 9 and the variable light chain of SEQ ID NO: 21.

In an embodiment, said antibody or antibody fragment specific for CD3, comprises the variable heavy chain of SEQ ID NO: 7 and the variable light chain of SEQ ID NO: 17. In certain embodiments, said CD3 is human CD3. In certain embodiments, said CD3 is human CD3 epsilon. In embodiments, said $EC_{50}$ concentration is determined by an FACS assay as described herein in Example 5 using Jurkat cells.

In some embodiments, the present disclosure provides an antibody or antibody fragment which specifically binds to CD3 with a $K_D$ of 1 nM or higher, 10 nM or higher, 20 nM or higher, 30 nM or higher, 40 nM or higher, 50 nM or higher, 60 nM or higher, 70 nM or higher, 80 nM or higher, 90 nM or higher, 100 nM or higher, 250 nM or higher, 500 nM or higher.

In certain embodiments, the present disclosure provides an antibody or antibody fragment which specifically binds to CD3 with a $K_D$ of 1 nM or higher. In certain embodiments, the present disclosure provides an antibody or antibody fragment which specifically binds to CD3 with a $K_D$ of 50 nM or higher.

In certain embodiments, the present disclosure provides an antibody or antibody fragment which specifically binds to CD3 with a $K_D$ which is higher when compared to the $K_D$ of any one of the control antibodies RefMab #1, BsAB #RefMab #1 or SP34.

In certain embodiments, the present disclosure provides an antibody or antibody fragment which specifically binds to CD3 with a $K_D$ which is at least 0 fold or higher, 1 fold or higher, 2 fold or higher, 3 fold or higher, 4 fold or higher, 5 fold or higher, 10 fold or higher, 20 fold or higher, 30 fold or higher, 40 fold or higher, 50 fold or higher, 100 fold or higher of any one of the control antibodies RefMab #1, BsAB #RefMab #1 or SP34.

In some embodiments, the $K_D$ is determined by Biacore®. In some embodiments, said $K_D$ is determined by Biacore® as described herein in Example 6 or Example 14. In some embodiments, the human CD3 is human CD3 epsilon. In some embodiments, the human CD3 is hCD epsilon 22-49 Fc. In some embodiments, the human CD3 is hCD3e(22-118)_F-chLys_avi.

In certain embodiments, said antibody or antibody fragment specific for CD3 is an antibody or antibody fragment as disclosed in Tables 5-7.

In certain embodiments, said antibody or antibody fragment specific for CD3, comprises
a) the variable heavy chain of SEQ ID NO: 9 and the variable light chain of SEQ ID NO: 11 or
b) the variable heavy chain of SEQ ID NO: 9 and the variable light chain of SEQ ID NO: 13 or
c) the variable heavy chain of SEQ ID NO: 7 and the variable light chain of SEQ ID NO: 15 or
d) the variable heavy chain of SEQ ID NO: 7 and the variable light chain of SEQ ID NO: 17 or
e) the variable heavy chain of SEQ ID NO: 7 and the variable light chain of SEQ ID NO: 19 or
f) the variable heavy chain of SEQ ID NO: 9 and the variable light chain of SEQ ID NO: 19 or
g) the variable heavy chain of SEQ ID NO: 9 and the variable light chain of SEQ ID NO: 21.

In one embodiment, said antibody or antibody fragment specific for CD3, comprises the variable heavy chain of SEQ ID NO: 7 and the variable light chain of SEQ ID NO: 17.

In certain embodiments, the present disclosure provides an antibody or antibody fragment which specifically binds to CD3 expressed on immune effector cells and does not activate T-cells.

In certain embodiments, the present disclosure provides an antibody or antibody fragment which specifically binds to CD3 expressed on immune effector cells and does not activate T-cells in the absence of a cell surface target antigen expressing cell. In certain embodiments, said antibody or antibody fragment binds bivalently to CD3 expressed on immune effector cells. In certain embodiments, said antibody or antibody fragment binds bivalently to CD3 expressed on immune effector cells.

In certain aspects of the disclosure, the activation of T-cells can be determined by the method as described herein in Example 11.

In certain embodiments, the present disclosure provides an antibody or antibody fragment which specifically binds to CD3 expressed on immune effector cells and does not induce upregulation of CD69 expression on CD4 positive and/or CD8 positive T cells In certain embodiments, the present disclosure provides an antibody or antibody fragment which specifically binds to CD3 expressed on immune effector cells and does not induce upregulation of CD69 expression on CD4 positive and CD8 positive T cells in the absence of a cell surface target antigen expressing cell. In certain embodiments, the present disclosure provides an antibody or antibody fragment which specifically binds to CD3 expressed on immune effector cells and does not induce upregulation of CD69 expression on CD4 positive T cells in the absence of a cell surface target antigen expressing cell. In certain embodiments, the present disclosure provides an antibody or antibody fragment which specifically binds to CD3 expressed on immune effector cells and does not induce upregulation of CD69 expression on CD8 positive T cells in the absence of a cell surface target antigen expressing cell. In certain embodiments, said antibody or antibody fragment binds bivalently to CD3 expressed said immune effector cells In certain embodiments, said antibody or antibody fragment binds monovalently to CD3 expressed on said immune effector cells In certain embodiments, the present disclosure provides an antibody or antibody fragment which specifically binds to CD3 expressed on immune effector cells and induces lower extent of upregulation of CD69 expression on CD4 positive and/or CD8 positive T cells in the absence of a cell surface target antigen expressing cell when compared to any one of the control antibodies RefMab #1, BsAB #RefMab #1 or SP34. In certain embodiments, said antibody or antibody fragment binds bivalently and/or monovalently to CD3 expressed on said immune effector cells In certain embodiments, the present disclosure provides an antibody or antibody fragment which specifically binds to CD3 expressed on immune effector cells and induces upregulation of CD69 expression in a lower number of CD4 positive and/or CD8 positive T cells in the absence of a cell surface target antigen expressing cell when compared to any one of the control antibodies RefMab #1, BsAB #RefMab #1 or SP34. In certain embodiments, said antibody or antibody fragment binds bivalently and/or monovalently to CD3 expressed on said immune effector cells In certain aspects of the disclosure, the upregulation of CD69 expression can be determined by the method as described herein in Example 11.

In certain embodiments, said antibody is a bispecific antibody. In certain embodiments, said bispecific antibody binds bivalently and/or monovalently to CD3 expressed on immune effector cells In certain embodiments, said bispecific antibody binds bivalently to CD3 expressed on immune effector cells In certain embodiments, the present disclosure provides a bispecific antibody comprising an antibody or antibody fragment which specifically binds to CD3 expressed on immune effector cells and wherein the bispecific antibody does not activate T-cells in the absence of a target antigen expressing cells. In certain embodiments, said antibody or antibody fragment binds bivalently and/or monovalently to CD3 expressed on immune effector cells In certain embodiments, said antibody or antibody fragment binds bivalently to CD3 expressed on immune effector cells.

In certain embodiments, the present disclosure provides a bispecific antibody comprising an antibody or antibody fragment which specifically binds to CD3 expressed on immune effector cells and wherein the bispecific antibody does not induce upregulation of CD69 expression on CD4 positive and CD8 positive T cells in the absence of a target antigen expressing cell. In certain embodiments, the present disclosure provides a bispecific antibody comprising an antibody or antibody fragment, which specifically binds to CD3 expressed on immune effector cells and wherein the bispecific antibody does not induce upregulation of CD69 expression on CD4 positive and/or CD8 positive T cells in the absence of a target antigen expressing cell.

In certain embodiments, the present disclosure provides a bispecific antibody which specifically binds to CD3 expressed on immune effector cells and induces lower extent of upregulation of CD69 expression on CD4 positive and/or CD8 positive T cells in the absence of a cell surface target antigen expressing cell when compared to any one of the control antibodies RefMab #1, BsAB #RefMab #1 or SP34. In certain embodiments, said antibody or antibody fragment binds bivalently or monovalently to CD3 expressed on immune effector cells In certain embodiments, said antibody or antibody fragment binds bivalently to CD3 expressed on immune effector cells In certain embodiments, the present disclosure provides a bispecific antibody which specifically binds to CD3 expressed on immune effector cells and induces upregulation of CD69 expression in a lower number of CD4 positive and/or CD8 positive T cells in the absence of a cell surface target antigen expressing cell when compared to any one of the control antibodies RefMab #1, BsAB #RefMab #1 or SP34. In certain embodiments, said antibody or antibody fragment binds bivalently and/or monovalently to CD3 expressed on said immune effector cells In certain embodiments, said bispecific antibody is a bispecific antibody as disclosed in TABLE 6 and TABLE 7.

In certain embodiments, said antibody or antibody fragment specific for CD3 is an antibody or antibody fragment as disclosed in Tables 5-7, In certain embodiments, said antibody or antibody fragment specific for CD3, comprises
  a) the variable heavy chain of SEQ ID NO: 9 and the variable light chain of SEQ ID NO: 11 or
  b) the variable heavy chain of SEQ ID NO: 9 and the variable light chain of SEQ ID NO: 13 or
  c) the variable heavy chain of SEQ ID NO: 7 and the variable light chain of SEQ ID NO: 15 or
  d) the variable heavy chain of SEQ ID NO: 7 and the variable light chain of SEQ ID NO: 17 or
  e) the variable heavy chain of SEQ ID NO: 7 and the variable light chain of SEQ ID NO: 19 or
  f) the variable heavy chain of SEQ ID NO: 9 and the variable light chain of SEQ ID NO: 19 or
  g) the variable heavy chain of SEQ ID NO: 9 and the variable light chain of SEQ ID NO: 21.

In one embodiment, said antibody or antibody fragment specific for CD3, comprises the variable heavy chain of SEQ ID NO: 7 and the variable light chain of SEQ ID NO: 17.

In certain aspects of the disclosure, the upregulation of CD69 expression can be determined by the method as described herein in Example 11.

In certain embodiments, the present disclosure provides a bispecific antibody comprising an antibody or antibody fragment which specifically binds to CD3 expressed on immune effector cells and wherein said bispecific antibody induces human T cell proliferation in the presence of a cell surface target antigen expressing cell.

In certain embodiments, the present disclosure provides a bispecific antibody comprising an antibody or antibody fragment which specifically binds to CD3 expressed on immune effector cells wherein the bispecific antibody mediates target cell killing of target antigen high expressing cells.

In certain embodiments, the present disclosure provides a bispecific antibody comprising a first antigen binding domain, wherein said first antigen binding domain specifically binds to CD3 expressed on immune effector cells and a second antigen binding domain, wherein said second antigen binding domain binds a cell surface target antigen, wherein said bispecific antibody mediates target cell killing, wherein the target cell killing of target antigen low expressing cells is significant (at least 2 fold) weaker when compared to the target cell killing of target antigen high expressing cells.

In certain embodiments, said target cell killing of target antigen low expressing cells is at least 1.5 fold weaker, at least 2 fold weaker, at least 3 fold weaker, at least 5 fold weaker when compared to the target cell killing mediated by BsAB #RefMab #1 or to a bispecific antibody comprising the CD3 specific antigen binding domains of SP34.

In certain embodiments, the present disclosure provides a bispecific antibody comprising an antibody or antibody fragment which specifically binds to CD3 expressed on immune effector cells wherein the bispecific antibody mediates target cell killing of target antigen high expressing cells similar to BsAB #RefMab #1 or a bispecific antibody comprising the CD3 specific antigen binding domains of SP34 but which mediates a significant weaker target cell killing of target antigen low expressing cells compared to BsAB #RefMab #1 or to a bispecific antibody comprising the CD3 specific antigen binding domains of SP34.

In certain aspects, target cell killing can be determined by the method as described herein in Example 12.

In certain embodiments, the present disclosure provides a bispecific antibody comprising an antibody or antibody fragment which specifically binds to CD3 expressed on immune effector cells and wherein the bispecific antibody mediates killing of target antigen low expressing cells with an $IC_{50}$ concentration which is at least 100 fold or lower, 50 fold or lower, 40 fold or lower, 30 fold or lower, 20 fold or lower, 10 fold or lower, 5 fold or lower, 4 fold or lower, 3 fold or lower, 2 fold or lower, 1 fold lower as the $IC_{50}$ concentration of any one of control antibodies RefMab #1, BsAB #RefMab #1 or SP34 as determined in Example 12 or Example 13.

In certain embodiments, the present disclosure provides a bispecific antibody comprising an antibody or antibody fragment which specifically binds to CD3 expressed on immune effector cells and wherein the bispecific antibody mediates killing of target antigen low expressing cells with an $IC_{50}$ concentration which is at least 1 fold higher, 2 fold higher, 3 fold higher, 4 fold higher, 5 fold or higher, 10 fold or higher, 15 fold higher, 20 fold higher, 30 fold higher, 40 fold higher, 50 fold higher, or 100 fold higher as the $IC_{50}$ concentration of any one of control antibodies RefMab #1, BsAB #RefMab #1 or SP34 as determined in Example 12 or Example 13.

In certain embodiments, the present disclosure provides a bispecific antibody comprising an antibody or antibody fragment which specifically binds to CD3 expressed on immune effector cells, wherein said bispecific antibody induces interferon gamma release by T-cells in the presence target high expressing cells but not in the presence of target low expressing cells.

In certain embodiments, the present disclosure provides a bispecific antibody comprising an antibody or antibody fragment which specifically binds to CD3 expressed on immune effector cells and wherein the bispecific antibody induces interferon gamma release by T-cells in the presence of target antigen low expressing cells with an $IC_{50}$ concentration which is at least 100 fold or lower, 50 fold or lower, 40 fold or lower, 30 fold or lower, 20 fold or lower, 10 fold or lower, 5 fold or lower, 4 fold or lower, 3 fold or lower, 2 fold or lower, 1 fold lower as the $IC_{50}$ concentration of any one of control antibodies RefMab #1, BsAB #RefMab #1 or SP34 as determined in Example 12.

In another embodiment said bispecific antibody comprises an antibody or antibody fragment which specifically binds to CD3 expressed on immune effector cells comprising the the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28 or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 65 and the LCDR3 region of SEQ ID NO: 28.

In certain embodiments, said bispecific antibody is a bispecific antibody as disclosed in TABLE 6 and 7.

In other embodiments, said bispecific antibody comprises an antibody or antibody fragment which specifically binds to CD3 expressed on immune effector cells comprising a variable heavy chain selected from the group of SEQ ID NO: 7 and SEQ ID NO: 9 and a variable light chain selected from the group of SEQ ID NO: 11, SEQ ID NO: 13, SEQ ID NO: 15, SEQ ID NO: 17, SEQ ID NO: 19, SEQ ID NO: 21 or a variable heavy chain and a variable light chain that has at least 60%, at least 70%, at least 80%, at least 90% or at least 95% identity to the variable heavy chain of SEQ ID NO: 7 and 9 and to the variable light chain of SEQ ID NO: 11, 13, 15, 17, 19, 21.

In an embodiment the disclosed antibody or antibody fragment is specific for human CD3 epsilon encoded by the amino acid sequence of SEQ ID NO: 1. In one embodiment the disclosed antibody or antibody fragment is specific for a polypeptide comprising the amino acid sequence of SEQ ID NO: 1. In a further embodiment said monoclonal antibody or antibody fragment is a monoclonal antibody or antibody fragment specific for a polypeptide consisting of the amino acid sequence of SEQ ID NO: 1.

In an embodiment, the antibody or antibody fragment of the present disclosure is cross-reactive to cynomolgus monkey CD3. In one embodiments, the antibody or antibody fragment according to the present disclosure is specific for cynomolgus monkey CD3. In an embodiment, the antibody or antibody fragment according to the present disclosure is specific for human and cynomolgus monkey CD3. In one embodiment, the disclosure refers to an isolated antibody or antibody fragment specific for CD3, wherein said antibody or antibody fragment binds to human CD3 and to cynomolgus monkey CD3. In an embodiment, the present disclosure refers to an humanized antibody or antibody fragment specific for CD3, wherein said antibody or antibody fragment binds to human CD3 and to cynomolgus CD3. In an embodiment, said CD3 is CD3 epsilon.

In one embodiment the disclosed antibody or antibody fragment specific for CD3 epsilon is a monoclonal antibody or antibody fragment. In one embodiment the disclosed antibody or antibody fragment specific for CD3 epsilon is a humanized or chimeric antibody. In certain embodiments, said antibody or antibody fragment specific for CD3 epsilon is an isolated antibody or antibody fragment. In another embodiment said antibody or antibody fragment is a recombinant antibody or antibody fragment. In a further embodiment said antibody or antibody fragment is a recombinant human antibody or antibody fragment. In a further embodiment said recombinant human antibody or antibody fragment is an isolated recombinant human antibody or antibody fragment. In a further embodiment said recombinant human antibody or antibody fragment or isolated recombinant human antibody or antibody fragment is monoclonal.

In one embodiment, the present disclosure refers to an antibody or antibody fragment comprising 6 CDRs defined by Kabat of any of the antibodies in Table 5. In another aspect, the disclosure pertains to an isolated monoclonal antibody or fragment thereof comprising 6 CDRs defined by Kabat of each of the antibodies in Table 5.

In one embodiment, the disclosure pertains to an isolated monoclonal antibody or fragment comprising a VH and a VL of any of the antibodies in Table 5.

In another embodiment, the disclosure pertains to an isolated monoclonal antibody or fragment comprising a heavy chain and a light chain of any of the antibodies in Table 5.

In another embodiment, the disclosure pertains to a scFv antibody having an amino acid sequence as disclosed in Table 5.

In another embodiment, the disclosure pertains to a scFv antibody having a nucleotide sequence as disclosed in Table 5.

In another embodiment, the disclosure refers to a nucleic acid encoding an antibody or antibody fragment thereof wherein the nucleic acid comprises a VH and a VL of any of the antibodies in Table 5.

In another embodiment, the disclosure refers to a nucleic acid encoding an antibody or fragment thereof wherein the nucleic acid comprises a heavy chain and a light chain of any of the antibodies in Table 5.

In another embodiment, the disclosure refers to a nucleic acid encoding a scFv antibody wherein the scFv comprises a nucleic acid comprising a sequence as disclosed in Table 5.

In another embodiment, the disclosure refers to a method of producing an isolated monoclonal antibody or fragment thereof of any of the antibodies in Table 5.

Methods and techniques for identifying CDRs within heavy chain variable regions and light chain variable region amino acid sequences are well known in the art and can be used to identify CDRs within the specified within heavy chain variable regions and light chain variable region amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

The coding sequences for the heavy and light chains of the antibody or antibody fragment of the present disclosure can be recombinant DNA molecules, which are introduced into expression vectors by operatively linking the DNA to the necessary expression control regions (e.g. regulatory regions) required for gene expression The skilled man will realize that the polynucleotides encoding the heavy or light chain can be cloned into different vectors or in the same vector. In a preferred embodiment, said polynucleotides are cloned in the same vector. The vectors can be introduced into the appropriate host cells such as prokaryotic (e.g., bacterial) or eukaryotic (e.g., yeast or mammalian) cells by methods well known in the art (see e.g., "Current Protocol in Molecular Biology", Ausubel et al. (eds.), Greene Publishing Assoc. and John Wiley Interscience, New York, 1989 and 1992). Numerous cloning vectors are known to those of skill in the art, and the selection of an appropriate cloning vector is a matter of choice. The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. Upon expression in host cells, the antibody or antibody fragment of the present disclosure is obtained.

These steps can be achieved in different ways, as will be known by the person skilled in the art. In general, such steps typically include transforming or transfecting a suitable host cell with a nucleic acid or vector or an infectious particle which encodes the Fab molecule. Further, such steps typically include culturing said host cells under conditions suitable for the proliferation (multiplication, growth) of said host cells and a culturing step under conditions suitable for the production (expression, synthesis) of the encoded antibody or antibody fragments. The culturing of host cells under conditions suitable for proliferation or expression is typically accomplished in the presence of media comprising components suitable for cell growth or induction of expression. In particular embodiments, the methods for the production of antibody or antibody fragments of the present disclosure further comprise the step of isolating the produced antibody or antibody fragments from the host cells or medium. Depending on the expression system and host selected, the antibody or antibody fragment of the present disclosure are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

The antibody or antibody fragment of the present disclosure can then be purified by a number of techniques as known to the person skilled in the art. It should be noted that Fabs of the disclosure are not naturally occurring proteins. Typically, the antibody or antibody fragment of the present disclosure is recombinant, synthetic or semi-synthetic amino acid sequence, polypeptide or protein.

The present disclosure also provides recombinant expression vectors capable of expressing a polypeptide comprising a heavy or light chain variable region of an antibody or antibody fragment specific for CD3 according to the present disclosure. For example, the present disclosure includes recombinant expression vectors comprising any of the nucleic acid molecules mentioned in Table 5-7, i.e., nucleic acid molecules encoding any of the VH, VL, and/or CDR sequences as set forth in Table 5.

Also included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

The present disclosure includes antibodies or antibody fragments specific for CD3 having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the disclosure provides a pharmaceutical composition comprising a humanized antibody or fragment which specifically binds to CD3 and a pharmaceutically acceptable carrier.

In a related aspect, the disclosure features a composition which is a combination of an antibody or antibody fragment which specifically binds to CD3 and a second therapeutic agent. In one embodiment, the second therapeutic agent is any agent that is advantageously combined with an antibody which specifically binds to CD3. Exemplary agents that may be advantageously combined with an antibody or antibody fragment of the present disclosure include, without limitation, other agents that bind and/or activate CD3 signaling (including other antibodies or antigen-binding fragments thereof, etc.) and/or agents which do not directly bind CD3 but nonetheless activate or stimulate immune cell activation. Additional combination therapies and co-formulations involving the CD3 specific antibodies of the present disclosure are disclosed elsewhere herein.

In yet another aspect, the disclosure provides therapeutic methods for stimulating T cell activation using an antibody or antibody fragment which specifically binds to CD3, wherein the therapeutic methods comprise administering a therapeutically effective amount of a pharmaceutical composition comprising an antibody or antibody fragment according to the present disclosure to a subject in need thereof.

The disorder treated is any disease or condition which is improved, ameliorated, inhibited or prevented by stimulation of CD3 activity or signaling.

In some aspects, the antibody or antibody fragment of the present disclosure which can be for use as a medicament.

In an embodiment, the present disclosure refers to an antibody or antibody fragments according to the present disclosure for use in medicine. In an embodiment, the present disclosure refers to an antibody or antibody fragment according to the present disclosure for use in the preparation of a medicament.

In some embodiments, the antibody or antibody fragment of the present disclosure can be for use in treating or delaying progression of a cell proliferative disorder or an autoimmune disorder in a subject in need thereof.

In some embodiments, the antibody or antibody fragment of the present disclosure can used in enhancing immune function in a subject having a cell proliferative disorder or an autoimmune disorder.

In some aspects, the present disclosure provides the use of an antibody or antibody fragment as disclosed herein for the manufacture of a medicament for treating or delaying progression of a cell proliferative disorder or an autoimmune disorder.

In some aspects, the present disclosure provides the use of an antibody or antibody fragment as discloses herein for the manufacture of a medicament for enhancing immune function in a subject having a cell proliferative disorder or an autoimmune disorder In certain aspects, the present disclosure provides the use of an antibody or antibody fragment as disclosed herein for the manufacture of a medicament.

In certain aspect, the disclosure provides a method of treating a subject in need thereof with an antibody or antibody fragment as disclosed herein.

A further aspect of the disclosure provides a method of treating or delaying the progression of a cell proliferative disorder or an autoimmune disorder in a subject in need thereof, the method comprising administering to the subject an effective amount any one of the antibody or antibody fragment as disclosed herein.

A further aspect of the disclosure provides a method of enhancing immune function in a subject having a cell proliferative disorder or an autoimmune disorder, the method comprising administering to the subject any one of the antibody or antibody fragment as disclosed herein.

In some embodiments, bispecific antibody of the present disclosure binds to a) a CD3 molecule expressed on an immune effector cell and b) a second molecule located on a target cell other than the immune effector cell. In some embodiments, said bispecific antibody activates the immune effector cell following binding to (a) and (b). In some embodiments, the activated immune effector cell is capable of exerting a cytotoxic effect and/or an apoptotic effect on the target cell.

In some embodiments, the antibody or antibody fragment according to the present disclosure is administered to the subject in a dosage of 0.01 mg/kg to 10 mg/kg. In some embodiments, the antibody or antibody fragment according to the present disclosure is administered to the subject in a dosage of 0.1 mg/kg to 10 mg/kg. In some embodiments, the antibody or antibody fragment is administered to the subject in a dosage of 1 mg/kg.

In some embodiments, the antibody or antibody fragment according to the present disclosure is administered subcutaneously, intravenously, intramuscularly, topically, orally, transdermally, intraperitoneally, intraorbitally, by implantation, by inhalation, intrathecally, intraventricularly, or intranasally. In some embodiments, the antibody or antibody fragment according to the present disclosure is administered subcutaneously. In some embodiments, the antibody specific for CD3 is administered intravenously.

The compositions of the present disclosure are preferably pharmaceutical compositions comprising an antibody or antibody fragment specific for CD3 as disclosed herein and a pharmaceutically acceptable carrier, diluent or excipient, for the treatment of an autoimmune disorders or cancer. Such carriers, diluents and excipients are well known in the art, and the skilled artisan will find a formulation and a route of administration best suited to treat a subject with the antibodies or antibody fragments specific for CD3 of the present disclosure.

TABLE 1

Amino acid sequences of the extracellular domain of human and cynomolgus CD3 epsilon without signal sequences.

| Target protein | SEQ ID NO: | [aa] |
|---|---|---|
| Mature human CD3e (23-126) | SEQ ID NO: 1 | DGNEEMGGITQTPYKVSISGTTVI LTCPQYPGSEILWQHNDKNIGGDE DDKNIGSDEDHLSLKEFSELEQSG YYVCYPRGSKPEDANFYLYLRARV CENCMEMD |
| Mature cynomolgus CD3e (22-117) | SEQ ID NO: 2 | QDGNEEMGSITQTPYQVSISGTTV ILTCSQHLGSEAQWQHNGKNKEDS GDRLFLPEFSEMEQSGYYVCYPRG SNPEDASHHLYLKARVCENCMEMD |
| Human CD3e (22-49)-Fc2 (K105-K330) | SEQ ID NO: 149 | QDGNEEMGGITQTPYKVSISGTTV ILTCDIKTHTCPPCPAPELLGGPS VFLFPPKPKDTLMISRTPEVTCVV VDVSHEDPEVKFNWYVDGVEVHNA KTKPREEQYNSTYRVVSVLTVLHQ DWLNGKEYKCKVSNKALPAPIEKT ISKAKGQPREPQVYTLPPSREEMT KNQVSLTCLVKGFYPSDIAVEWES NGQPENNYKTTPPVLDSDGSFFLY SKLTVDKSRWQQGNVFSCSVMHEA LHNHYTQKSLSLSPGK |
| Cyno CD3e (22-49-Fc2 (K105-K330) | SEQ ID NO: 150 | QDGNEEMGSITQTPYQVSISGTTV ILTCDIKTHTCPPCPAPELLGGPS VFLFPPKPKDTLMISRTPEVTCVV VDVSHEDPEVKFNWYVDGVEVHNA KTKPREEQYNSTYRVVSVLTVLHQ DWLNGKEYKCKVSNKALPAPIEKT ISKAKGQPREPQVYTLPPSREEMT KNQVSLTCLVKGFYPSDIAVEWES NGQPENNYKTTPPVLDSDGSFFLY SKLTVDKSRWQQGNVFSCSVMHEA LHNHYTQKSLSLSPGK |
| Human CD3e (22-118) Flag_chLys_avi | SEQ ID NO: 151 | QDGNEEMGGITQTPYKVSISGTTV ILTCPQYPGSEILWQHNDKNIGGD EDDKNIGSDEDHLSLKEFSELEQS GYYVCYPRGSKPEDANFYLYLRAR VDIDYKDDDDKIEGRMDKVFGRCE LAAAMKRHGLDNYRGYSLGNWVCA AKFESNFNTQATNRNTDGSTDYGI LQINSRWWCNDGRTPGSRNLCNIP CSALLSSDITASVNCAKKIVSDGN GMNAWVAWRNRCKGTDVQAWIRGC RLVNSRGLNDIFEAQKIEWHE |

TABLE 2

Amino acid sequences of the VH and VL of SP34 and RefMab#1

| Antibody | Chain | SEQ ID NO: | [aa] |
|---|---|---|---|
| SP34_VH | VH | SEQ ID NO: 3 | EVQLVESGGGLVQPKGSLKLSCAASGFTFNTYAMNWVRQAPGKGLEWVARIRSKYNNYATYYADSVKDRFTISRDDSQSILYLQMNNLKTEDTAMYYCVRHGNFGNSYVSWFAYWGQGTLVTVSS |
| SP34_VL | VL | SEQ ID NO: 4 | QAVVTQESALTTSPGETVTLCRSSTGAVTTSNYANWVQEKPDHLFTGLIGGTNKRAPGVPARFSGSLIGDKAALTITGAQTEDEAIYFCALWYSNLWVFGGGTKLTVLGQ |
| RefmAb#01_VH | VH | SEQ ID NO: 5 | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS |
| RefmAb#1_VL | VL | SEQ ID NO: 6 | QTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGQ |
| RefmAb_2_VH | VH | SEQ ID NO: 152 | QVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS |
| RefmAb_2_VL | VL | SEQ ID NO: 153 | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRT |

TABLE 3

Humanized variable heavy chain (VH) amino acid and nucleotide sequences of SP34

| Construct | Chain | SEQ ID NO: | [aa]/[nt] |
|---|---|---|---|
| mAb#2_VH | VH | SEQ ID NO: 7 | EVQLVESGGGLVKPGGSLRLSCAASGFTFNTYAMNWVRQAPGKGLEWVGRIRSKYNNYATYYADSVKDRFTISRDDSKNTLYLQMNSLKTEDTAVYYCTTHGNFGNSYVSWFAYWGQGTLVTVSS |
| mAb#2_VH (DNA) | VH | SEQ ID NO: 8 | gaagtgcagctggtggaatctgcggcggactcgtgaagcctggcggctctctgagactgagctgtgccgccagcggcttcaccttcacacctacgccatgaactgggtgcgccaggcccctggcaagggcctggaatgggtgggacggatcagaagcaagtacaacaattacgccacctactacgccgacagcgtgaaggaccggttcaccatcagccgggacgacagcaagaacaccctgtacctgcagatgaacagcctgaaaaccgaggacaccgccgtgtactactgcaccacccacggcaacttcggcaacagctatgtgtct |

TABLE 3-continued

Humanized variable heavy chain (VH) amino acid and nucleotide sequences of SP34

| Construct | Chain | SEQ ID NO: | [aa]/[nt] |
|---|---|---|---|
| | | | tggtttgcctactggggccaggcaccctcgtgacagtctcgagc |
| mAb#3_VH | VH | SEQ ID NO: 9 | QVQLVESGGGLVKPGGSLRLSCAASGFTFNTYAMNWIRQAPGKGLEWVSRIRSKYNNYATYYADSVKDRFTISRDNAKNSLYLQMNSLRAEDTAVYYCVRHGNFGNSYVSWFAYWGQGTLVTVSS |
| mAb#3_VH (DNA) | VH | SEQ ID NO: 10 | caggtgcagctggtggaatctgcggcggactcgtgaagcctggcggctctctgagactgagctgtgccgccagcggcttcaccttcacacctacgccatgaactggatccggcaggcccctggcaagggcctggaatgggtgtcccggatcagaagcaagtacaacaattacgccacctactacgccgacagcgtgaaggaccggttcaccatcagccgggacaacgccaagaacagcctgtacctgcagatgaactccctgcgggccgaggacaccgccgtgtactattgtgtgcggcacggcaacttcggcaacagctatgtgtctggtttgcctactggggccaggcaccctcgtgacagtctcgagc |

TABLE 4

Humanized VL amino acid sequences of SP34

| Construct | Chain | SEQ ID NO: | [aa]/[nt] |
|---|---|---|---|
| mAb#4_VL | VL | SEQ ID NO: 11 | QAVVTQEPSLTVSPGGTVTLTCRSSTGAVTTSNYANWVQQKPGQAPRGLIGGTNKRAPWTPARFSGSLLGGKAALTITGAQAEDEADYYCALWYSNLWVFGGGTKLTVLGQ |
| mAb#4_VL (DNA) | VL | SEQ ID NO: 12 | caggccgtggttacacaagagcccagcctgacagttagccctggcggaacagtgaccctgacctgcagatcttctacaggcgccgtgaccaccaacaactacgccaattgggtgcagcagaagcctggacaggctcccagaggactgatcggcggcacaaacaaaagagccccttggacacccgccagatcagcggatcactgctcggaggaaaggccgcactgacaatcacaggtgcccaggccgaagatgaggccgattactattgcgccctgtggtacagcaacctgtgggtgttcggcgaggtaccaagctgaccgtgctgggccag |
| mAb#5_VL | VL | SEQ ID NO: 13 | ELVVTQEPSLTVSPGGTVTLTCRSSTGAVTTSNYANWVQQKPGQAPRGLIGGINKRAPGTPARFSGSLLGGKAALTLSGVQPEDEAEYYCALWYSNLWVFGGGTKLTVLGQ |

TABLE 4-continued

Humanized VL amino acid sequences of SP34

| Construct | Chain | SEQ ID NO: | [aa]/[nt] |
|---|---|---|---|
| mAb#5_VL (DNA) | VL | SEQ ID NO: 14 | gagctggtggtcacacaag agcccagcctgacagtttc tcctggcggcacagtgacc ctgacctgcagatcttcta caggcgccgtgaccacctc caactacgccaattgggtg cagcagaagcctggacagg ctcccagaggactgatcgg cggcacaaacaaaagagcc cctggcacaccagccagat tcagcggatcactgctcgg aggaaaggccgctctgaca ctgtctggtgtccagcctg aagatgaggccgagtacta ctgcgccctgtggtacagc aatctgtgggtgttcggcg gaggtaccaagctgaccgt gctgggccag |
| mAb#6_VL | VL | SEQ ID NO: 15 | QTVVTQEPSLTVSPGGTVT LTCRSSTGAVTTSNYANWV QQKPGQAPRGLIGGINKRA PGTPARFSGSLLGKAALT LLGAQPEDEAEYYCALWYS NLWVFGGGTKLTVLGQ |
| mAb#6_VL (DNA) | VL | SEQ ID NO: 16 | cagaccgtggtcacacaag agcccagcctgacagtttc tcctggcggcacagtgacc ctgacctgcagatcttcta caggcgccgtgaccaccag caactacgccaattgggtg cagcagaagcctggacagg ctcccagaggactgatcgg cggcacaaacaaaagagcc cctggcacaccagccagat tcagcggatcactgctcgg aggaaaggccgctctgaca ctgcttggagcacagcctg aagatgaggccgagtacta ctgcgccctgtggtacagc aatctgtgggtgttcggcg gaggtaccaagctgaccgt gctgggccag |
| mAb#7_VL | VL | SEQ ID NO: 17 | QTVVTQEPSLTVSPGGTVT LTCRSSTGAVTTSNYANWV QQKPGQAPRGLIGGTKFLA PGTPARFSGSLLGKAALT LLGAQPEDEAEYYCALWYS NLWVFGGGTKLTVLGQ |
| mAb#7_VL (DNA) | VL | SEQ ID NO: 18 | cagaccgtggtcacacaag agcccagcctgacagtttc tcctggcggcacagtgacc ctgacctgcagatcttcta caggcgccgtgaccaccag caactacgccaattgggtg cagcagaagcctggacagg ctcccagaggactgatcgg cggcacaaaattctggcc cctggcacaccagccagat tctctggatctctgctcgg cggaaaggccgctctgaca ctgcttggagcacagcctg aagatgaggccgagtacta ctgcgccctgtggtacagc aatctgtgggtgttcggcg gaggtaccaagctgaccgt gctgggccag |
| mAb#8_VL | VL | SEQ ID NO: 19 | QTVVTQEPSLTVSPGGTVT LTCRSSTGAVTTSNYANWV QQKPGQAPRGLIGGTKFLA PGTPARFSGSLLGKAALT LSGVQPEDEAEYYCALWYS NLWVFGGGTKLTVLGQ |
| mAb#8_VL (DNA) | VL | SEQ ID NO: 20 | cagaccgtggtcacacaag agcccagcctgacagtttc tcctggcggcacagtgacc ctgacctgcagatcttcta caggcgccgtgaccaccag caactacgccaattgggtg cagcagaagcctggacagg ctcccagaggactgatcgg cggcacaaaattctggcc cctggcacaccagccagat tctctggatctctgctcgg cggaaaggccgctctgaca ctgtctggtgttcagcctg aggacgaggccgagtacta ttgcgccctgtggtacagc aacctgtgggtgttcggcg gaggtaccaagctgaccgt gctgggccag |
| mAb#9_VL | VL | SEQ ID NO: 21 | QTVVTQEPSLTVSPGGTVT LTCRSSTGAVTTSNYANWV QQKPGQAPRGLIGGTNKRA PGTPARFSGSLLGKAALT LSGVQPEDEAEYYCALWYS NLWVFGGGTKLTVLGQ |
| mAb#9_VL (DNA) | VL | SEQ ID NO: 22 | cagaccgtggtcacacaag agcccagcctgacagtttc tcctggcggcacagtgacc ctgacctgcagatcttcta caggcgccgtgaccaccag caactacgccaattgggtg cagcagaagcctggacagg ctcccagaggactgatcgg cggcacaaacaaaagagcc cctggcacaccagccagat tcagcggatcactgctcgg aggaaaggccgctctgaca ctgtctggtgtccagcctg aagatgaggccgagtacta ctgcgccctgtggtacagc aatctgtgggtgttcggcg gaggtaccaagctgaccgt gctgggccag |

TABLE 14

Concordance table of the antibody names and the SEQ ID NO identifiers used in Table 3 and Table 5 for the humanized variable heavy chains of the present disclosure

| Antibody | VH according Table 3 | VH SEQ ID NO Protein according Table 3 | VH SEQ ID NO Protein according Table 5 | VH SEQ ID NO DNA according Table 3 | VH SEQ ID NO DNA according Table 5 |
|---|---|---|---|---|---|
| Mainz | mAb#3_VH | 9 | 30 | 10 | 32 |
| Köln | mab#3_VH | 9 | 46 | 10 | 48 |
| Freiburg | mAb#2_VH | 7 | 56 | 8 | 58 |
| München | mAb#2_VH | 7 | 68 | 8 | 70 |
| Bremen | mAb#2_VH | 7 | 78 | 8 | 80 |
| Gladbach | mAb#3_VH | 9 | 86 | 10 | 88 |
| Nürnberg | mAb#3_VH | 9 | 96 | 10 | 98 |

TABLE 15

Concordance table of the antibody names and the SEQ ID NO identifiers used in Table 4 and Table 5 for the humanized variable light chains of the present disclosure

| Antibody | VL according Table 4 | VL SEQ ID NO Protein according Table 4 | VL SEQ ID NO Protein according Table 5 | VL SEQ ID NO DNA according Table 4 | VL SEQ ID NO DNA according Table 5 |
|---|---|---|---|---|---|
| Mainz | mAb#4_VL | 11 | 29 | 12 | 31 |
| Köln | mAb#5_VL | 13 | 45 | 14 | 47 |
| Freiburg | mAb#6_VL | 15 | 55 | 16 | 57 |
| München | mAb#7_VL | 17 | 67 | 18 | 69 |
| Bremen | mAb#8_VL | 19 | 77 | 20 | 79 |
| Gladbach | mAb#8_VL | 19 | 85 | 20 | 87 |
| Nürnberg | mAb#9_VL | 21 | 95 | 22 | 97 |

TABLE 5

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| Mainz | HCDR1 (Kabat) | SEQ ID NO: 23 | TYAMN |
| | HCDR2 (Kabat) | SEQ ID NO: 24 | RIRSKYNNYATYYADSVKD |
| | HCDR3 (Kabat) | SEQ ID NO: 25 | HGNFGNSYVSWFAY |
| | LCDR1 (Kabat) | SEQ ID NO: 26 | RSSTGAVTTSNYAN |
| | LCDR2 (Kabat) | SEQ ID NO: 27 | GTNKRAP |
| | LCDR3 (Kabat) | SEQ ID NO: 28 | ALWYSNLWV |
| | VL | SEQ ID NO: 29 SEQ ID NO: 11 | QAVVTQEPSLTVSPGGTVTLTCRSST GAVTTSNYANWVQQKPGQAPRGLIG GTNKRAPWTPARFSGSLLGGKAALTI TGAQAEDEADYYCALWYSNLWVFG GGTKLTVLGQ |
| | VH | SEQ ID NO: 30 SEQ ID NO: 9 | QVQLVESGGGLVKPGGSLRLSCAAS GFTFNTYAMNWIRQAPGKGLEWVSR IRSKYNNYATYYADSVKDRFTISRDN AKNSLYLQMNSLRAEDTAVYYCVRH GNFGNSYVSWFAYWGQGTLVTVSS |
| | VL (DNA) | SEQ ID NO: 31 SEQ ID NO: 12 | caggccgtggttacacaagagcccagcctgacag ttagccctggcggaacagtgaccctgacctgcaga tcttctacaggcgccgtgaccaccagcaactacgc caattgggtgcagcagaagcctggacaggctcc agaggactgatcggcggcacaaacaaaagagcc ccttggacacccgccagattcagcggatcactgctc ggaggaaaggccgcactgacaatcacaggtgcc caggccgaagatgaggccgattactattgcgccct gtggtacagcaacctgtgggtgttcggcggaggta ccaagctgaccgtgctgggccag |
| | VH (DNA) | SEQ ID NO: 32 SEQ ID NO: 10 | caggtgcagctggtggaatctggcggcggactcgt gaagcctggcggctctctgagactgagctgtgccg ccagcggcttcaccttcaacacctacgccatgaact ggatccggcaggcccctggcaagggcctggaatg ggtgtcccggatcagaagcaagtacaacaattacg ccacctactacgccgacagcgtgaaggaccggtt caccatcagccgggacaacgccaagaacagcctg tacctgcagatgaactccctgcgggccgaggacac cgccgtgtactattgtgtgcggcacggcaacttcgg caacagctatgtgtcttggtttgcctactggggccag ggcaccctcgtgacagtctcgagc |
| | HCDR1 (Kabat) (DNA) | SEQ ID NO: 33 | acctacgccatg |
| | HCDR2 (Kabat) (DNA) | SEQ ID NO: 34 | cggatcagaagcaagtacaacaattacgccacct actacgccgacagcgtgaaggac |
| | HCDR3 (Kabat) (DNA) | SEQ ID NO: 35 | cacggcaacttcggcaacagctatgtgtcttggtttg cctac |
| | LCDR1 (Kabat) (DNA) | SEQ ID NO: 36 | agatcttctacaggcgccgtgaccaccagcaacta cgccaat |
| | LCDR2 (Kabat) (DNA) | SEQ ID NO: 37 | ggcacaaacaaaagagcccct |
| | LCDR3 (Kabat) (DNA) | SEQ ID NO: 38 | gccctgtggtacagcaatctgtgggtg |
| | Light chain (VL + CL) | SEQ ID NO: 39 | QAVVTQEPSLTVSPGGTVTLTCRSST GAVTTSNYANWVQQKPGQAPRGLIG GTNKRAPWTPARFSGSLLGGKAALTI TGAQAEDEADYYCALWYSNLWVFG |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | GGTKLTVLGQPKAAPSVTLFPPSSEE LQANKATLVCLISDFYPGAVTVAWKA DSSPVKAGVETTTPSKQSNNKYAAS SYLSLTPEQWKSHRSYSCQVTHEGS TVEKTVAPTECS |
| | Heavy chain (IgG1) | SEQ ID NO: 40 | QVQLVESGGGLVKPGGSLRLSCAAS GFTFNTYAMNWIRQAPGKGLEWVSR IRSKYNNYATYYADSVKDRFTISRDN AKNSLYLQMNSLRAEDTAVYYCVRH GNFGNSYVSWFAYWGQGTLVTVSS ASTKGPSVFPLAPSSKSTSGGTAALG CLVKDYFPEPVTVSWNSGALTSGVH TFPAVLQSSGLYSLSSVVTVPSSSLG TQTYICNVNHKPSNTKVDKRVEPKSC DKTHTCPPCPAPELLGGPSVFLFPPK PKDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQV YTLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGK |
| | Light chain (VL + CL) (DNA) | SEQ ID NO: 41 | caggccgtggttacacaagagcccagcctgacag ttagccctggcggaacagtgaccctgacctgcaga tcttctacaggcgccgtgaccaccagcaactacgc caattgggtgcagcagaagcctggacaggctcc agaggactgatcggcggcacaaacaaaagagcc ccttggacacccgccagattcagcggatcactgctc ggaggaaaggccgcactgacaatcacaggtgcc caggccgaagatgaggccgattactattgcgccct gtggtacagcaacctgtgggtgttcggcggaggta ccaagctgaccgtgctgggccagcccaaagccgc ccctagcgtgaccctgttccccccctcgagtgagga actccaggccaacaaggccaccctcgtgtgcctga tcagcgacttctaccctggcgccgtgaccgtggcct ggaaggccgatagcagccctgtgaaggccggcgt ggaaaccaccacccccagcaagcagagcaaca acaaatacgccgccagcagctacctgagcctgac ccccgagcagtggaagtcccacagatcctacagct gccaggtcacacacgagggcagcaccgtggaaa agaccgtggcccccaccgagtgcagc |
| | Heavy chain (IgG1, DNA) | SEQ ID NO: 42 | caggtgcagctggtggaatctggcggcggactcgt gaagcctggcggctctctgagactgagctgtgccg ccagcggcttcaccttcaacacctacgccatgaact ggatccggcaggcccctggcaagggcctggaatg ggtgtcccggatcagaagcaagtacaacaattacg ccacctactacgccgacagcgtgaaggaccggttc accatcagccgggacaacgccaagaacagcctg tacctgcagatgaactccctgcgggccgaggacac cgccgtgtactattgtgtgcggcacggcaacttcgg caacagctatgtgtcttggtttgcctactggggccag ggcaccctcgtgacagtctcgagcgcgtcgaccaa aggccccagcgtgttccctctggccccagcagca agagcacctctggcggaacagccgccctgggctg cctggtcaaggactacttccccgagcccgtgaccgt gtcctggaactctggcgccctgaccagcggcgtgc acacctttccagccgtgctccagagcagcggcctgt acagcctgagcagcgtcgtgaccgtgcccagcag cagcctgggcacccagacctacatctgcaacgtga accacaagcccagcaacacaaaggtggacaag cgggtggaacccaagagctgcgacaagacccac acctgtcccccctgccctgcccctgaactgctggga ggcccctcgtgttcctgttccccccaaagcctaag gacaccctgatgatcagccggacccccgaagtga cctgcgtggtggtggacgtgtcccacgaggaccct gaagtgaagtttaattggtacgtggacggcgtggaa gtgcacaacgccaagaccaagccccagagagga acagtacaacagcacctacggggtggtgtccgtgc tgaccgtgctgcaccaggactggctgaacggcaa agagtacaagtgcaaggtgtccaacaaggccctg cctgccccatcgagaaaaccatcagcaaggcca |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | aaggccagccccgcgagccccaggtgtacacact gcccctagccgggaagagatgaccaagaacca ggtgtccctgacctgcctcgtgaagggcttctaccc agcgacattgccgtggaatgggagagcaacggcc agcccgagaacaactacaagaccaccccccctgt gctggacagcgacggctcattcttcctgtacagcaa gctgaccgtggacaagagccggtggcagcaggg caacgtgttcagctgctccgtgatgcacgaggccct gcacaaccactacacccagaagtccctgagcctg agccccggcaagtga |
| | scFv (VL-linker-VH) | SEQ ID NO: 43 | ASPAAPAPSAQAVVTQEPSLTVSPG GTVTLTCRSSTGAVTTSNYANWVQQ KPGQAPRGLIGGTNKRAPWTPARFS GSLLGGKAALTITGAQAEDEADYYCA LWYSNLWVFGGGTKLTVLGQASPAA PAPASPAAPAPASGSQVQLVESGGG LVKPGGSLRLSCAASGFTFNTYAMN WIRQAPGKGLEWVSRIRSKYNNYAT YYADSVKDRFTISRDNAKNSLYLQMN SLRAEDTAVYYCVRHGNFGNSYVSW FAYWGQGTLVTVSS |
| | scFv (VL-linker-VH) (DNA) | SEQ ID NO: 44 | gcttctcctgctgctcctgctcctagcgctcaggccgt ggttacacaagagcccagcctgacagttagccctg gcggaacagtgaccctgacctgcagatcttctaca ggcgccgtgaccaccagcaactacgccaattgggt gcagcagaagcctggacaggctcccagaggact gatcggcggcacaaacaaaagagccccttggac acccgccagattcagcggatcactgctcggagga aaggccgcactgacaatcacaggtgcccaggcc gaagatgaggccgattactattgcgccctgtggtac agcaacctgtgggtgttcggcggaggtaccaagct gaccgtgctgggccaggcctctcctgctgctcctgct ccagcttctccagccgctccagctcctgctagcgga tctcaggtgcagctggtggaatctggcggcggactc gtgaagcctggcggctctctgagactgagctgtgcc gccagcggcttcaccttcaacacctacgccatgaa ctggatccggcaggcccctggcaagggcctggaa tgggtgtcccggatcagaagcaagtacaacaatta cgccacctactacgccgacagcgtgaaggaccgg ttcaccatcagccgggacaacgccaagaacagcc tgtacctgcagatgaactccctgcgggccgaggac accgccgtgtactattgtgtgcggcacggcaacttc ggcaacagctatgtgtcttggtttgcctactggggcc agggcaccctcgtgacagtctcgagc |
| Köln | HCDR1 (Kabat) | SEQ ID NO: 23 | TYAMN |
| | HCDR2 (Kabat) | SEQ ID NO: 24 | RIRSKYNNYATYYADSVKD |
| | HCDR3 (Kabat) | SEQ ID NO: 25 | HGNFGNSYVSWFAY |
| | LCDR1 (Kabat) | SEQ ID NO: 26 | RSSTGAVTTSNYAN |
| | LCDR2 (Kabat) | SEQ ID NO: 27 | GTNKRAP |
| | LCDR3 (Kabat) | SEQ ID NO: 28 | ALWYSNLWV |
| | VL | SEQ ID NO: 45 SEQ ID NO: 13 | ELVVTQEPSLTVSPGGTVTLTCRSST GAVTTSNYANWVQQKPGQAPRGLIG GTNKRAPGTPARFSGSLLGGKAALTL SGVQPEDEAEYYCALWYSNLWVFG GGTKLTVLGQ |
| | VH | SEQ ID NO: 46 SEQ ID NO: 9 | QVQLVESGGGLVKPGGSLRLSCAAS GFTFNTYAMNWIRQAPGKGLEWVSR IRSKYNNYATYYADSVKDRFTISRDN AKNSLYLQMNSLRAEDTAVYYCVRH GNFGNSYVSWFAYWGQGTLVTVSS |
| | VL (DNA) | SEQ ID NO: 47 SEQ ID NO: 14 | gagctggtggtcacacaagagcccagcctgacag tttctcctggcggcacagtgaccctgacctgcagatc ttctacaggcgccgtgaccacctccaactacgcca attgggtgcagcagaagcctggacaggctcccag aggactgatcggcggcacaaacaaaagagcccc tggcacaccagccagattcagcggatcactgctcg gaggaaaggccgctctgacactgtctggtgtccag cctgaagatgaggccgagtactactgcgccctgtg gtacagcaatctgtgggtgttcggcggaggtacca agctgaccgtgctgggccag |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | VH (DNA) | SEQ ID NO: 48 SEQ ID NO: 10 | caggtgcagctggtggaatctggcggcggactcgt gaagcctggcggctctctgagactgagctgtgccg ccagcggcttcaccttcaacacctacgccatgaact ggatccggcaggcccctggcaagggcctggaatg ggtgtcccggatcagaagcaagtacaacaattacg ccacctactacgccgacagcgtgaaggaccggttc accatcagccgggacaacgccaagaacagcctg tacctgcagatgaactccctgcgggccgaggacac cgccgtgtactattgtgtgcggcacggcaacttcgg caacagctatgtgtcttggtttgcctactggggccag ggcaccctcgtgacagtctcgagc |
| | HCDR1 (Kabat) (DNA) | SEQ ID NO: 33 | acctacgccatg |
| | HCDR2 (Kabat) (DNA) | SEQ ID NO: 34 | cggatcagaagcaagtacaacaattacgccacct actacgccgacagcgtgaaggac |
| | HCDR3 (Kabat) (DNA) | SEQ ID NO: 35 | cacggcaacttcggcaacagctatgtgtcttggtttg cctac |
| | LCDR1 (Kabat) (DNA) | SEQ ID NO: 36 | agatcttctacaggcgccgtgaccaccagcaacta cgccaat |
| | LCDR2 (Kaba) (DNA) | SEQ ID NO: 37 | ggcacaaacaaaagagcccct |
| | LCDR3 (Kabat) (DNA) | SEQ ID NO: 38 | gccctgtggtacagcaatctgtgggtg |
| | Light chain (VL + CL) | SEQ ID NO: 49 | ELVVTQEPSLTVSPGGTVTLTCRSST GAVTTSNYANWVQQKPGQAPRGLIG GINKRAPGTPARFSGSLLGGKAALTL SGVQPEDEAEYYCALWYSNLWVFG GGTKLTVLGQPKAAPSVTLFPPSSEE LQANKATLVCLISDFYPGAVTVAWKA DSSPVKAGVETTTPSKQSNNKYAAS SYLSLTPEQWKSHRSYSCQVTHEGS TVEKTVAPTECS |
| | Heavy chain (IgG1) | SEQ ID NO: 50 | QVQLVESGGGLVKPGGSLRLSCAAS GFTFNTYAMNWIRQAPGKGLEWVSR IRSKYNNYATYYADSVKDRFTISRDN AKNSLYLQMNSLRAEDTAVYYCVRH GNFGNSYVSWFAYWGQGTLVTVSS ASTKGPSVFPLAPSSKSTSGGTAALG CLVKDYFPEPVTVSWNSGALTSGVH TFPAVLQSSGLYSLSSVVTVPSSSLG TQTYICNVNHKPSNTKVDKRVEPKSC DKTHTCPPCPAPELLGGPSVFLFPPK PKDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQV YTLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGK |
| | Light chain (DNA) | SEQ ID NO: 51 | gagctggtggtcacacaagagcccagcctgacag tttctcctggcggcacagtgaccctgacctgcagatc ttctacaggcgccgtgaccaccagcaactacgcca attgggtgcagcagaagcctggacaggctcccag aggactgatcggcggcacaaacaaaagagcccc tggcacaccagccagattcagcggatcactgctcg gaggaaaggccgctctgacactgtctggtgtccag cctgaagatgaggccgagtactactgcgccctgtg gtacagcaatctgtgggtgttcggcggaggtacca agctgaccgtgctgggccagcccaaagccgccc tagcgtgacccttgttccccccctcgagtgaggaact ccaggccaacaaggccaccctcgtgtgcctgatca gcgacttctaccctggcgccgtgaccgtggcctgga aggccgatagcagccctgtgaaggccggcgtgga aaccaccaccccagcaagcagagcaacaaca aatacgccgcagcagctacctgagcctgaccc cgagcagtggaagtcccacagatcctacagctgcc aggtcacaacgagggcagcaccgtggaaaaga ccgtggcccccaccgagtgcagc |
| | Heavy chain (DNA, IgG1) | SEQ ID NO: 52 | caggtgcagctggtggaatctggcggcggactcgt gaagcctggcggctctctgagactgagctgtgccg ccagcggcttcaccttcaacacctacgccatgaact |

TABLE 5-continued

Amino acid and nucleic acid sequence identifiers of the heavy and light chain variable regions and CDRs of selected CD3 specific humanized antibodies of the invention.

| Antibody# | SEQ ID NO: | [aa]/[nt] |
|---|---|---|
| | | ggatccggcaggcccctggcaagggcctggaatg<br>ggtgtcccggatcagaagcaagtacaacaattacg<br>ccacctactacgccgacagcgtgaaggaccggttc<br>accatcagccgggacaacgccaagaacagcctg<br>tacctgcagatgaactccctgcgggccgaggacac<br>cgccgtgtactattgtgtgcggcacggcaacttcgg<br>caacagctatgtgtcttggtttgcctactggggccag<br>ggcaccctcgtgacagtctcgagcgcgtcgaccaa<br>aggcccagcgtgttccctctggcccccagcagca<br>agagcacctctggcggaacagccgccctgggctg<br>cctggtcaaggactacttccccgagcccgtgaccgt<br>gtcctggaactctggcgccctgaccagcggcgtgc<br>acacctttccagccgtgctccagagcagcggcctgt<br>acagcctgagcagcgtcgtgaccgtgcccagcag<br>cagcctgggcacccagacctacatctgcaacgtga<br>accacaagcccagcaacacaaaggtggacaag<br>cgggtggaacccaagagctgcgacaagacccac<br>acctgtcccccctgccctgccctgaactgctggga<br>ggcccctccgtgttcctgttcccccccaaagcctaag<br>gacaccctgatgatcagccggacccccgaagtga<br>cctgcgtggtggtggacgtgtcccacgaggaccct<br>gaagtgaagtttaattggtacgtggacggcgtggaa<br>gtgcacaacgccaagaccaagcccagagagga<br>acagtacaacagcacctaccgggtggtgtccgtgc<br>tgaccgtgctgcaccaggactggctgaacggcaa<br>agagtacaagtgcaaggtgtccaacaaggccctg<br>cctgcccccatcgagaaaaccatcagcaaggcca<br>aaggccagccccgcgagcccaggtgtacacact<br>gcccctagccgggaagagatgaccaagaacca<br>ggtgtccctgacctgcctcgtgaagggcttctaccc<br>agcgacattgccgtggaatgggagagcaacggcc<br>agcccgagaacaactacaagaccaccccccctgt<br>gctggacagcgacggctcattcttcctgtacagcaa<br>gctgaccgtggacaagagccggtggcagcaggg<br>caacgtgttcagctgctccgtgatgcacgaggccct<br>gcacaaccactacacccagaagtccctgagcctg<br>agccccggcaagtga |
| | scFv (VL-linker-VH) SEQ ID NO: 53<br>(aa) | ASPAAPAPSAELVVTQEPSLTVSPGG<br>TVTLTCRSSTGAVTTSNYANWVQQK<br>PGQAPRGLIGGTNKRAPGTPARFSG<br>SLLGGKAALTLSGVQPEDEAEYYCAL<br>WYSNLWVFGGGTKLTVLGQASPAAP<br>APASPAAPAPASGSQVQLVESGGGL<br>VKPGGSLRLSCAASGFTFNTYAMNW<br>IRQAPGKGLEWVSRIRSKYNNYATYY<br>ADSVKDRFTISRDNAKNSLYLQMNSL<br>RAEDTAVYYCVRHGNFGNSYVSWFA<br>YWGQGTLVTVSS |
| | scFv (VL-linker-VH) SEQ ID NO: 54<br>(DNA) | gcttctcctgctgctcctgctcctagcgctgagctggt<br>ggtcacacaagagcccagcctgacagtttctcctgg<br>cggcacagtgaccctgacctgcagatcttctacagg<br>cgccgtgaccacctccaactacgccaattgggtgc<br>agcagaagcctggacaggctcccagaggactgat<br>cggcggcacaaacaaaagagcccctggcacacc<br>agccagattcagcggatcactgctcggaggaaag<br>gccgctctgacactgtctggtgtccagcctgaagat<br>gaggccgagtactactgcgccctgtggtacagcaa<br>tctgtgggtgttcggcggaggtaccaagctgaccgt<br>gctgggccaggcctctcctgctgctcctgctccagct<br>tctccagccgctccagctcctgctagcggatctcag<br>gtgcagctggtggaatctggcggcggactcgtgaa<br>gcctggcggctctctgagactgagctgtgccgccag<br>cggcttcaccttcaacacctacgccatgaactggat<br>ccggcaggcccctggcaagggcctggaatgggtg<br>tcccggatcagaagcaagtacaacaattacgcca<br>cctactacgccgacagcgtgaaggaccggttcacc<br>atcagccgggacaacgccaagaacagcctgtac<br>ctgcagatgaactccctgcgggccgaggacaccg<br>ccgtgtactattgtgtgcggcacggcaacttcggca<br>acagctatgtgtcttggtttgcctactggggccaggg<br>caccctcgtgacagtctcgagc |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| Freiburg | HCDR1 (Kabat) | SEQ ID NO: 23 | TYAMN |
| | HCDR2 (Kabat) | SEQ ID NO: 24 | RIRSKYNNYATYYADSVKD |
| | HCDR3 (Kabat) | SEQ ID NO: 25 | HGNFGNSYVSWFAY |
| | LCDR1 (Kabat) | SEQ ID NO: 26 | RSSTGAVTTSNYAN |
| | LCDR2 (Kabat) | SEQ ID NO: 27 | GTNKRAP |
| | LCDR3 (Kabat) | SEQ ID NO: 28 | ALWYSNLWV |
| | VL | SEQ ID NO: 55 | QTVVTQEPSLTVSPGGTVTLTCRSST |
| | | SEQ ID NO: 15 | GAVTTSNYANWVQQKPGQAPRGLIG |
| | | | GTNKRAPGTPARFSGSLLGGKAALTL |
| | | | LGAQPEDEAEYYCALWYSNLWVFG |
| | | | GGTKLTVLGQ |
| | VH | SEQ ID NO: 56 | EVQLVESGGGLVKPGGSLRLSCAAS |
| | | SEQ ID NO: 7 | GFTFNTYAMNWVRQAPGKGLEWVG |
| | | | RIRSKYNNYATYYADSVKDRFTISRD |
| | | | DSKNTLYLQMNSLKTEDTAVYYCTTH |
| | | | GNFGNSYVSWFAYWGQGTLVTVSS |
| | VL (DNA) | SEQ ID NO: 57 | cagaccgtggtcacacaagagcccagcctgaca |
| | | SEQ ID NO: 18 | gtttctcctggcggcacagtgaccctgacctgcagat |
| | | | cttctacaggcgccgtgaccaccagcaactacgcc |
| | | | aattgggtgcagcagaagcctggacaggctccca |
| | | | gaggactgatcggcggcacaaacaaaagagccc |
| | | | ctggcacaccagccagattcagcggatcactgctc |
| | | | ggaggaaaggccgctctgacactgcttggagcac |
| | | | agcctgaagatgaggccgagtactactgcgccctg |
| | | | tggtacagcaatctgtgggtgttcggcggaggtacc |
| | | | aagctgaccgtgctgggccag |
| | VH (DNA) | SEQ ID NO: 58 | gaagtgcagctggtggaatctggcggcggactcgt |
| | | SEQ ID NO: 8 | gaagcctggcggctctctgagactgagctgtgccg |
| | | | ccagcggcttcaccttcaacacctacgccatgaact |
| | | | gggtgcgccaggcccctggcaaaggcctggaatg |
| | | | ggtgggacggatcagaagcaagtacaacaattac |
| | | | gccacctactacgccgacagcgtgaaggaccggtt |
| | | | caccatcagccgggacgacagcaagaacaccct |
| | | | gtacctgcagatgaacagcctgaaaaccgaggac |
| | | | accgccgtgtactactgcaccacccacggcaactt |
| | | | cggcaacagctatgtgtcttggtttgcctactggggc |
| | | | cagggcaccctcgtgacagtctcgagc |
| | HCDR1 (Kabat) (DNA) | SEQ ID NO: 33 | acctacgccatg |
| | HCDR2 (Kabat) (DNA) | SEQ ID NO: 34 | cggatcagaagcaagtacaacaattacgccacct actacgccgacagcgtgaaggac |
| | HCDR3 (Kabat) (DNA) | SEQ ID NO: 35 | cacggcaacttcggcaacagctatgtgtcttggtttg cctac |
| | LCDR1 (Kabat) (DNA) | SEQ ID NO: 36 | agatcttctacaggcgccgtgaccaccagcaacta cgccaat |
| | LCDR2 (Kabat) (DNA) | SEQ ID NO: 37 | ggcacaaacaaaagagcccct |
| | LCDR3 (Kabat) (DNA) | SEQ ID NO: 38 | gccctgtggtacagcaatctgtgggtg |
| | Light chain (IgG) | SEQ ID NO: 59 | QTVVTQEPSLTVSPGGTVTLTCRSST |
| | | | GAVTTSNYANWVQQKPGQAPRGLIG |
| | | | GTNKRAPGTPARFSGSLLGGKAALTL |
| | | | LGAQPEDEAEYYCALWYSNLWVFG |
| | | | GGTKLTVLGQPKAAPSVTLFPPSSEE |
| | | | LQANKATLVCLISDFYPGAVTVAWKA |
| | | | DSSPVKAGVETTTPSKQSNNKYAAS |
| | | | SYLSLTPEQWKSHRSYSCQVTHEGS |
| | | | TVEKTVAPTECS |
| | Heavy chain (IgG1) | SEQ ID NO: 60 | EVQLVESGGGLVKPGGSLRLSCAAS |
| | | | GFTFNTYAMNWVRQAPGKGLEWVG |
| | | | RIRSKYNNYATYYADSVKDRFTISRD |
| | | | DSKNTLYLQMNSLKTEDTAVYYCTTH |
| | | | GNFGNSYVSWFAYWGQGTLVTVSS |
| | | | ASTKGPSVFPLAPSSKSTSGGTAALG |
| | | | CLVKDYFPEPVTVSWNSGALTSGVH |
| | | | TFPAVLQSSGLYSLSSVVTVPSSSLG |
| | | | TQTYICNVNHKPSNTKVDKRVEPKSC |
| | | | DKTHTCPPCPAPELLGGPSVFLFPPK |
| | | | PKDTLMISRTPEVTCVVVDVSHEDPE |
| | | | VKFNWYVDGVEVHNAKTKPREEQYN |
| | | | STYRVVSVLTVLHQDWLNGKEYKCK |
| | | | VSNKALPAPIEKTISKAKGQPREPQV |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | YTLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGK |
| | Light chain (DNA) | SEQ ID NO: 61 | cagaccgtggtcacacaagagcccagcctgaca gtttctcctggcggcacagtgaccctgacctgcagat cttctacaggcgccgtgaccaccagcaactacgcc aattgggtgcagcagaagcctggacaggctcca gaggactgatcggcggcacaaacaaaagagccc ctggcacaccagccagattcagcggatcactgctc ggaggaaaggccgctctgacactgcttggagcac agcctgaagatgaggccgagtactactgcgccctg tggtacagcaatctgtgggtgttcggcggaggtacc aagctgaccgtgctgggccagcccaaagccgccc ctagcgtgaccctgttccccccctcgagtgaggaac tccaggccaacaaggccaccctcgtgtgcctgatc agcgacttctaccctggcgccgtgaccgtggcctgg aaggccgatagcagccctgtgaaggccggcgtgg aaaccaccaccccagcaagcagagcaacaac aaatacgccgccagcagctacctgagcctgaccc ccgagcagtggaagtcccacagatcctacagctgc caggtcacacacgagggcagcaccgtggaaaag accgtggcccccaccgagtgcagc |
| | Heavy chain (DNA, IgG1) | SEQ ID NO: 62 | gaagtgcagctggtggaatctggcggcggactcgt gaagcctggcggctctctgagactgagctgtgccg ccagcggcttcaccttcaacacctacgccatgaact gggtgcgccaggcccctggcaaaggcctggaatg ggtgggacggatcagaagcaagtacaacaattac gccacctactacgccgacagcgtgaaggaccggtt caccatcagccgggacgacagcaagaacaccct gtacctgcagatgaacagcctgaaaaccgaggac accgccgtgtactactgcaccacccacggcaactt cggcaacagctatgtgtcttggtttgcctactgggc cagggcaccctcgtgacagtctcgagcgcgtcgac caaaggccccagcgtgttccctctggcccccagca gcaagagcacctctggcggaacagccgccctgg gctgcctggtcaaggactacttccccgagcccgtga ccgtgtcctggaactctggcgcccctgaccagcggc gtgcacacctttccagccgtgctccagagcagcgg cctgtacagcctgagcagcgtcgtgaccgtgccca gcagcagcctgggcacccagacctacatctgcaa cgtgaaccacaagcccagcaacacaaaggtgga caagcgggtggaacccaagagctgcgacaagac ccacacctgtcccccctgccctgcccctgaactgct gggaggcccctccgtgttcctgttcccccccaaagcc taaggacaccctgatgatcagccggacccccgaa gtgacctgcgtggtggtggacgtgtcccacgagga ccctgaagtgaagtttaattggtacgtggacggcgt ggaagtgcacaacgccaagaccaagcccagag aggaacagtacaacagcacctaccgggtggtgtc cgtgctgaccgtgctgcaccaggactggctgaacg gcaaagagtacaagtgcaaggtgtccaacaagg ccctgcctgcccccatcgagaaaaccatcagcaa ggccaaaggccagccccgcgagcccaggtgta cacactgcccccctagccgggaagagatgaccaa gaaccaggtgtccctgacctgcctcgtgaagggctt ctaccccagcgacattgccgtggaatgggagagc aacggccagcccgagaacaactacaagaccacc cccctgtgctggacagcgacggctcattcttcctgt acagcaagctgaccgtggacaagagccggtggc agcagggcaacgtgttcagctgctccgtgatgcac gaggccctgcacaaccactacacccagaagtccc tgagcctgagcccggcaag |
| | scFv (VL-linker-VH) | SEQ ID NO: 63 | ASPAAPAPSAQTVVTQEPSLTVSPG GTVTLTCRSSTGAVTTSNYANWVQQ KPGQAPRGLIGGTNKRAPGTPARFS GSLLGGKAALTLLGAQPEDEAEYYCA LWYSNLWVFGGGTKLTVLGQASPAA PAPASPAAPAPASGSEVQLVESGGG LVKPGGSLRLSCAASGFTFNTYAMN WVRQAPGKGLEWVGRIRSKYNNYAT YYADSVKDRFTISRDDSKNTLYLQMN |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | SLKTEDTAVYYCTTHGNFGNSYVSW FAYWGQGTLVTVSS |
| | scFv (VL-linker-VH) (DNA) | SEQ ID NO: 64 | gcttctcctgctgctcctgctcctagcgctcagaccgt ggtcacacaagagcccagcctgacagtttctcctgg cggcacagtgaccctgacctgcagatcttctacagg cgccgtgaccaccagcaactacgccaattgggtgc agcagaagcctggacaggctcccagaggactgat cggcggcacaaacaaaagagcccctggcacacc agccagattctcggatcactgctcggaggaaag gccgctctgacactgcttggagcacagcctgaaga tgaggccgagtactactgcgccctgtggtacagca atctgtgggtgttcggcggaggtaccaagctgaccg tgctgggccaggcctctcctgctgctcctgctccagc ttctccagccgctccagctcctgctagcggatctgaa gtgcagctggtggaatctggcggcggactcgtgaa gcctggcggctctctgagactgagctgtgccgccag cggcttcaccttcaacacctacgccatgaactgggt gcgccaggcccctggcaaaggcctggaatggtg ggacggatcagaagcaagtacaacaattacgcca cctactacgccgacagcgtgaaggaccggttcacc atcagccgggacgacagcaagaacacccctgtac ctgcagatgaacagcctgaaaaccgaggacacc gccgtgtactactgcaccacccacggcaacttcgg caacagctatgtgtcttggtttgcctactggggccag ggcaccctcgtgacagtctcgagc |
| München | HCDR1 (Kabat) | SEQ ID NO: 23 | TYAMN |
| | HCDR2 (Kabat) | SEQ ID NO: 24 | RIRSKYNNYATYYADSVKD |
| | HCDR3 (Kabat) | SEQ ID NO: 25 | HGNFGNSYVSWFAY |
| | LCDR1 (Kabat) | SEQ ID NO: 26 | RSSTGAVTTSNYAN |
| | LCDR2 (Kabat) | SEQ ID NO: 65 | GTKFLAP |
| | LCDR3 (Kabat) | SEQ ID NO: 28 | ALWYSNLWV |
| | VL | SEQ ID NO: 67 SEQ ID NO: 17 | QTVVTQEPSLTVSPGGTVTLTCRSST GAVTTSNYANWVQQKPGQAPRGLIG GTKFLAPGTPARFSGSLLGGKAALTL LGAQPEDEAEYYCALWYSNLWVFG GGTKLTVLGQ |
| | VH | SEQ ID NO: 68 SEQ ID NO: 7 | EVQLVESGGGLVKPGGSLRLSCAAS GFTFNTYAMNWVRQAPGKGLEWVG RIRSKYNNYATYYADSVKDRFTISRD DSKNTLYLQMNSLKTEDTAVYYCTTH GNFGNSYVSWFAYWGQGTLVTVSS |
| | VL (DNA) | SEQ ID NO: 69 SEQ ID NO: 18 | cagaccgtggtcacacaagagcccagcctgaca gttctcctggcggcacagtgaccctgacctgcagat cttctacaggcgccgtgaccaccagcaactacgcc aattgggtgcagcagaagcctggacaggctccca gaggactgatcggcggcacaaaatttctggcccct ggcacaccagccagattctctggatctctgctcggc ggaaaggccgctctgacactgcttggagcacagc ctgaagatgaggccgagtactactgcgccctgtggt acagcaatctgtgggtgttcggcggaggtaccaag ctgaccgtgctgggccag |
| | VH (DNA) | SEQ ID NO: 70 SEQ ID NO: 8 | gaagtgcagctggtggaatctggcggcggactcgt gaagcctggcggctctctgagactgagctgtgccg ccagcggcttcaccttcaacacctacgccatgaact gggtgcgccaggcccctggcaaaggcctggaatg ggtgggacggatcagaagcaagtacaacaattac gccacctactacgccgacagcgtgaaggaccggtt caccatcagccgggacgacagcaagaacacccct gtacctgcagatgaacagcctgaaaaccgaggac accgccgtgtactactgcaccacccacggcaactt cggcaacagctatgtgtcttggtttgcctactggggc cagggcaccctcgtgacagtctcgagc |
| | HCDR1 (Kabat) (DNA) | SEQ ID NO: 33 | acctacgccatg |
| | HCDR2 (Kabat) (DNA) | SEQ ID NO: 34 | cggatcagaagcaagtacaacaattacgccacct actacgccgacagcgtgaaggac |
| | HCDR3 (Kabat) (DNA) | SEQ ID NO: 35 | cacggcaacttcggcaacagctatgtgtcttggtttg cctac |
| | LCDR1 (Kabat) (DNA) | SEQ ID NO: 36 | agatcttctacaggcgccgtgaccaccagcaacta cgccaat |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | LCDR2 (Kabat) (DNA) | SEQ ID NO: 66 | ggcacaaaatttctggcccct |
| | LCDR3 (Kabat) (DNA) | SEQ ID NO: 38 | gccctgtggtacagcaatctgtgggtg |
| | Light chain (IgG) | SEQ ID NO: 71 | QTVVTQEPSLTVSPGGTVTLTCRSST GAVTTSNYANWVQQKPGQAPRGLIG GTKFLAPGTPARFSGSLLGGKAALTL LGAQPEDEAEYYCALWYSNLWVFG GGTKLTVLGQPKAAPSVTLFPPSSEE LQANKATLVCLISDFYPGAVTVAWKA DSSPVKAGVETTTPSKQSNNKYAAS SYLSLTPEQWKSHRSYSCQVTHEGS TVEKTVAPTECS |
| | Heavy chain (IgG1) | SEQ ID NO: 72 | EVQLVESGGGLVKPGGSLRLSCAAS GFTFNTYAMNWVRQAPGKGLEWVG RIRSKYNNYATYYADSVKDRFTISRD DSKNTLYLQMNSLKTEDTAVYYCTTH GNFGNSYVSWFAYWGQGTLVTVSS ASTKGPSVFPLAPSSKSTSGGTAALG CLVKDYFPEPVTVSWNSGALTSGVH TFPAVLQSSGLYSLSSVVTVPSSSLG TQTYICNVNHKPSNTKVDKRVEPKSC DKTHTCPPCPAPELLGGPSVFLFPPK PKDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQV YTLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGK |
| | Light chain (DNA) | SEQ ID NO: 73 | cagaccgtggtcacacaagagcccagcctgaca gtttctcctggcggcacagtgaccctgacctgcagat cttctacaggcgccgtgaccaccagcaactacgcc aattgggtgcagcagaagcctggacaggctccca gaggactgatcggcggcacaaaatttctggcccct ggcacaccagccagattctctggatctctgctcggc ggaaaggccgctctgacactgcttggagcacagc ctgaagatgaggccgagtactactgcgccctgtggt acagcaatctgtgggtgttcggcggaggtaccaag ctgaccgtgctgggccagcccaaagccgcccta gcgtgaccctgttccccccctcgagtgaggaactcc aggccaacaaggccaccctcgtgtgcctgatcagc gacttctaccctggcgccgtgaccgtggcctggaag gccgatagcagccctgtgaaggccggcgtggaaa ccaccaccccagcaagcagagcaacaacaaat acgccgccagcagctacctgagcctgacccccga gcagtggaagtcccacagatcctacagctgccag gtcacacacgagggcagcaccgtggaaaagacc gtggccccaccgagtgcagc |
| | Heavy chain (DNA, IgG1) | SEQ ID NO: 74 | gaagtgcagctggtggaatctggcggcggactcgt gaagcctggcggctctctgagactgagctgtgccg ccagcggcttcaccttcaacacctacgccatgaact gggtgcgccaggcccctggcaaaggcctggaatg ggtgggacggatcagaagcaagtacaacaattac gccacctactacgccgacagcgtgaaggaccggtt caccatcagccgggacgacagcaagaacaccct gtacctgcagatgaacagcctgaaaaccgaggac accgccgtgtactactgcaccacccacggcaactt cggcaacagctatgtgtcttggtttgcctactgggc cagggcaccctcgtgacagtctcgagcgcgtcgac caaaggcccccagcgtgttccctctggccccagca gcaagagcacctctggcggaacagccgccctgg gctgcctggtcaaggactacttccccgagcccgtga ccgtgtcctggaactctggcgcccctgaccagcggc gtgcacacctttccagccgtgctccagagcagcgg cctgtacagcctgagcagcgtcgtgaccgtgccca gcagcagcctgggcacccagacctacatctgcaa cgtgaaccacaagcccagcaacacaaaggtgga caagcgggtggaacccaagagctgcgacaagac ccacacctgtccccctgccctgccctgaactgct gggaggccctccgtgttcctgttcccccaaagcc |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | taaggacaccctgatgatcagccggaccccgaa<br>gtgacctgcgtggtggtggacgtgtcccacgagga<br>ccctgaagtgaagtttaattggtacgtggacggcgt<br>ggaagtgcacaacgccaagaccaagcccagag<br>aggaacagtacaacagcacctaccgggtggtgtc<br>cgtgctgaccgtgctgcaccaggactggctgaacg<br>gcaaagagtacaagtgcaaggtgtccaacaagg<br>ccctgcctgcccccatcgagaaaaccatcagcaa<br>ggccaaaggccagccccgcgagccccaggtgta<br>cacactgcccccctagccgggaagagatgaccaa<br>gaaccaggtgtccctgacctgcctcgtgaagggctt<br>ctaccccagcgacattgccgtggaatgggagagc<br>aacggccagcccgagaacaactacaagaccacc<br>cccctgtgctggacagcgacggctcattcttcctgt<br>acagcaagctgaccgtggacaagagccggtggc<br>agcagggcaacgtgttcagctgctccgtgatgcac<br>gaggccctgcacaaccactacacccagaagtccc<br>tgagcctgagccccggcaag |
| | scFv (VL-linker-VH) (aa) | SEQ ID NO: 75 | ASPAAPAPSAQTVVTQEPSLTVSPG<br>GTVTLICRSSTGAVTTSNYANWVQQ<br>KPGQAPRGLIGGTKFLAPGTPARFSG<br>SLLGGKAALTLLGAQPEDEAEYYCAL<br>WYSNLWVFGGGTKLTVLGQASPAAP<br>APASPAAPAPASGSEVQLVESGGGL<br>VKPGGSLRLSCAASGFTFNTYAMNW<br>VRQAPGKGLEWVGRIRSKYNNYATY<br>YADSVKDRFTISRDDSKNTLYLQMNS<br>LKTEDTAVYYCTTHGNFGNSYVSWF<br>AYWGQGTLVTVSS |
| | scFv (VL-linker-VH) (DNA) | SEQ ID NO: 76 | gcttctcctgctgctcctgctcctagcgctcagaccgt<br>ggtcacacaagagcccagcctgacagtttctcctgg<br>cggcacagtgaccctgacctgcagatcttctacagg<br>cgccgtgaccaccagcaactacgccaattgggtgc<br>agcagaagcctggacaggctcccagaggactgat<br>cggcggcacaaaattctggcccctggcacaccag<br>ccagattctctggatctctgctcggcggaaaggccg<br>ctctgacactgcttggagcacagcctgaagatgag<br>gccgagtactactgcgccctgtggtacagcaatctg<br>tgggtgttcggcggaggtaccaagctgaccgtgctg<br>ggccaggcctctcctgctgctcctgctccagcttctcc<br>agccgctccagctcctgctagcggatctgaagtgca<br>gctggtggaatctggcggcggactcgtgaagcctg<br>gcggctctctgagactgagctgtgccgccagcggct<br>tcaccttcaacacctacgccatgaactgggtgcgcc<br>aggcccctggcaaaggcctggaatgggtgggacg<br>gatcagaagcaagtacaacaattacgccacctact<br>acgccgacagcgtgaaggaccggttcaccatcag<br>ccgggacgacagcaagaacaccctgtacctgca<br>gatgaacagcctgaaaaccgaggacaccgccgt<br>gtactactgcaccacccacggcaacttcggcaaca<br>gctatgtgtcttggtttgcctactggggccagggcac<br>cctcgtgacagtctcgagc |
| Bremen | HCDR1 (Kabat) | SEQ ID NO: 23 | TYAMN |
| | HCDR2 (Kabat) | SEQ ID NO: 24 | RIRSKYNNYATYYADSVKD |
| | HCDR3 (Kabat) | SEQ ID NO: 25 | HGNFGNSYVSWFAY |
| | LCDR1 (Kabat) | SEQ ID NO: 26 | RSSTGAVTTSNYAN |
| | LCDR2 (Kabat) | SEQ ID NO: 65 | GTKFLAP |
| | LCDR3 (Kabat) | SEQ ID NO: 28 | ALWYSNLWV |
| | VL | SEQ ID NO: 77<br>SEQ ID NO: 19 | QTVVTQEPSLTVSPGGTVTLTCRSST<br>GAVTTSNYANWVQQKPGQAPRGLIG<br>GTKFLAPGTPARFSGSLLGGKAALTL<br>SGVQPEDEAEYYCALWYSNLWVFG<br>GGTKLTVLGQ |
| | VH | SEQ ID NO: 78<br>SEQ ID NO: 7 | EVQLVESGGGLVKPGGSLRLSCAAS<br>GFTFNTYAMNWVRQAPGKGLEWVG<br>RIRSKYNNYATYYADSVKDRFTISRD<br>DSKNTLYLQMNSLKTEDTAVYYCTTH<br>GNFGNSYVSWFAYWGQGTLVTVSS |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | VL (DNA) | SEQ ID NO: 79 SEQ ID NO: 20 | cagaccgtggtcacacaagagcccagcctgaca gtttctcctggcggcacagtgaccctgacctgcagat cttctacaggcgccgtgaccaccagcaactacgcc aattgggtgcagcagaagcctggacaggctccca gaggactgatcggcggcacaaaatttctggcccct ggcacaccagccagattctctggatctctgctcggc ggaaaggccgctctgacactgtctggtgttcagcct gaggacgaggccgagtactattgcgccctgtggta cagcaacctgtgggtgttcggcggaggtaccaagc tgaccgtgctgggccag |
| | VH (DNA) | SEQ ID NO: 80 SEQ ID NO: 8 | gaagtgcagctggtggaatctggcggcggactcgt gaagcctggcggctctctgagactgagctgtgccg ccagcggcttcaccttcaacacctacgccatgaact gggtgcgccaggcccctggcaaaggcctggaatg gtgggacggatcagaagcaagtacaacaattac gccacctactacgccgacagcgtgaaggaccggtt caccatcagccgggacgacagcaagaacaccct gtacctgcagatgaacagcctgaaaaccgaggac accgccgtgtactactgcaccacccacggcaactt cggcaacagctatgtgtcttggtttgcctactgggc cagggcaccctcgtgacagtctcgagc |
| | HCDR1 (Kabat) (DNA) | SEQ ID NO: 33 | acctacgccatg |
| | HCDR2 (Kabat) (DNA) | SEQ ID NO: 34 | cggatcagaagcaagtacaacaattacgccacct actacgccgacagcgtgaaggac |
| | HCDR3 (Kabat) (DNA) | SEQ ID NO: 35 | cacggcaacttcggcaacagctatgtgtcttggtttg cctac |
| | LCDR1 (Kabat (DNA) | SEQ ID NO: 36 | agatcttctacaggcgccgtgaccaccagcaacta cgccaat |
| | LCDR2 (Kabat) (DNA) | SEQ ID NO: 66 | ggcacaaaatttctggcccct |
| | LCDR3 (Kabat) (DNA) | SEQ ID NO: 38 | gccctgtggtacagcaatctgtgggtg |
| | Light chain (IgG) | SEQ ID NO: 81 | QTVVTQEPSLTVSPGGTVTLTCRSST GAVTTSNYANWVQQKPGQAPRGLIG GTKFLAPGTPARFSGSLLGGKAALTL SGVQPEDEAEYYCALWYSNLWVFG GGTKLTVLGQPKAAPSVTLFPPSSEE LQANKATLVCLISDFYPGAVTVAWKA DSSPVKAGVETTTPSKQSNNKYAAS SYLSLTPEQWKSHRSYSCQVTHEGS TVEKTVAPTECS |
| | Heavy chain (IgG1) | SEQ ID NO: 82 | EVQLVESGGGLVKPGGSLRLSCAAS GFTFNTYAMNWVRQAPGKGLEWVG RIRSKYNNYATYYADSVKDRFTISRD DSKNTLYLQMNSLKTEDTAVYYCTTH GNFGNSYVSWFAYWGQGTLVTVSS ASTKGPSVFPLAPSSKSTSGGTAALG CLVKDYFPEPVTVSWNSGALTSGVH TFPAVLQSSGLYSLSSVVTVPSSSLG TQTYICNVNHKPSNTKVDKRVEPKSC DKTHTCPPCPAPELLGGPSVFLFPPK PKDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQV YTLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGK |
| | Light chain (DNA, IgG1) | SEQ ID NO: 83 | cagaccgtggtcacacaagagcccagcctgaca gtttctcctggcggcacagtgaccctgacctgcagat cttctacaggcgccgtgaccaccagcaactacgcc aattgggtgcagcagaagcctggacaggctccca gaggactgatcggcggcacaaaatttctggcccct ggcacaccagccagattctctggatctctgctcggc ggaaaggccgctctgacactgtctggtgttcagcct gaggacgaggccgagtactattgcgccctgtggta cagcaacctgtgggtgttcggcggaggtaccaagc tgaccgtgctgggccagcccaaagccgcccctag cgtgaccctgttcccccctcgagtgaggaactcca ggccaacaaggccaccctcgtgtgcctgatcagcg |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | acttctaccctggcgccgtgaccgtggcctggaagg<br>ccgatagcagccctgtgaaggccggcgtggaaac<br>caccaccccagcaagcagagcaacaacaaata<br>cgccgccagcagctacctgagcctgacccccgag<br>cagtggaagtcccacagatcctacagctgccaggt<br>cacacacgagggcagcaccgtggaaaagaccgt<br>ggcccccaccgagtgcagc |
| | Heavy chain (DNA, IgG1) | SEQ ID NO: 84 | gaagtgcagctggtggaatctgcggcggactcgt<br>gaagcctggcggctctctgagactgagcgtgccg<br>ccagcggcttcaccttcaacacctacgccatgaact<br>gggtgcgccaggcccctggcaaaggcctggaatg<br>ggtgggacggatcagaagcaagtacaacaattac<br>gccacctactacgccgacagcgtgaaggaccggtt<br>caccatcagccgggacgacagcaagaacaccct<br>gtacctgcagatgaacagcctgaaaaccgaggac<br>accgccgtgtactactgcaccacccacggcaactt<br>cggcaacagctatgtgtcttggtttgcctactggggc<br>cagggcaccctcgtgacagtctcgagcgcgtcgac<br>caaaggcccagcgtgttccctctggcccccagca<br>gcaagagcacctctggcggaacagccgccctgg<br>gctgcctggtcaaggactacttccccgagcccgtga<br>ccgtgtcctggaactctggcgccctgaccagcggc<br>gtgcacacctttccagccgtgctccagagcagcgg<br>cctgtacagcctgagcagcgtcgtgaccgtgccca<br>gcagcagcctgggcacccagacctacatctgcaa<br>cgtgaaccacaagcccagcaacacaaaggtgga<br>caagcgggtggaacccaagagctgcgacaagac<br>ccacacctgtcccccctgccctgccctgaactgct<br>gggaggcccctcgtgttcctgttcccccaaagcc<br>taaggacacctgatgatcagccggacccccgaa<br>gtgacctgcgtggtggtggacgtgtcccacgagga<br>ccctgaagtgaagtttaattggtacgtggacggcgt<br>ggaagtgcacaacgccaagaccaagcccagag<br>aggaacagtacaacagcacctaccgggtggtgtc<br>cgtgctgaccgtgctgcaccaggactggctgaacg<br>gcaaagagtacaagtgcaaggtgtccaacaagg<br>ccctgcctgcccccatcgagaaaaccatcagcaa<br>ggccaaaggccagccccgcgagccccaggtgta<br>cacactgcccccctagccgggaagagatgaccaa<br>gaaccaggtgtccctgacctgcctcgtgaagggctt<br>ctaccccagcgacattgccgtggaatgggagagc<br>aacggccagcccgagaacaactacaagaccacc<br>cccctgtgctggacagcgacggctcattcttcctgt<br>acagcaagctgaccgtggacaagagccggtggc<br>agcagggcaacgtgttcagctgctccgtgatgcac<br>gaggccctgcacaaccactacacccagaagtccc<br>tgagcctgagcccccggcaag |
| | scFv (VL-linker-VH) | SEQ ID NO: 156 | ASPAAPAPSAQTVVTQEPSLTVSPG<br>GTVTLTCRSSTGAVTTSNYANWVQQ<br>KPGQAPRGLIGGTKFLAPGTPARFSG<br>SLLGGKAALTLSGVQPEDEAEYYCAL<br>WYSNLWVFGGGTKLTVLGQASPAAP<br>APASPAAPAPASGSEVQLVESGGGL<br>VKPGGSLRLSCAASGFTFNTYAMNW<br>VRQAPGKGLEWVGRIRSKYNNYATY<br>YADSVKDRFTISRDDSKNTLYLQMNS<br>LKTEDTAVYYCTTHGNFGNSYVSWF<br>AYWGQGTLVTVSS |
| | scFv (VL-linker-VH) DNA | SEQ ID NO: 157 | gcttctcctgctgctcctgctcctagcgctcagaccgt<br>ggtcacacaagagcccagcctgacagtttctcctgg<br>cggcacagtgaccctgacctgcagatcttctacagg<br>cgccgtgaccaccagcaactacgccaattgggtgc<br>agcagaagcctggacaggctcccagaggactgat<br>cggcggcacaaaattctggcccctggcacaccag<br>ccagattctctggatctctgctcggcggaaaggccg<br>ctctgacactgtctggtgttcagcctgaggacgagg<br>ccgagtactattgcgccctgtggtacagcaacctgt<br>gggtgttcggcggaggtaccaagctgaccgtgctg<br>ggccaggcctctcctgctgctcctgctccagcttctcc<br>agccgctccagctcctgctagcggatctgaagtgca<br>gctggtggaatctggcggcggactcgtgaagcctg<br>gcggctctctgagactgagctgtgccgccagcggct |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | tcaccttcaacacctacgccatgaactgggtgcgcc |
| | | | aggcccctggcaaaggcctggaatgggtgggacg |
| | | | gatcagaagcaagtacaacaattacgccacctact |
| | | | acgccgacagcgtgaaggaccggttcaccatcag |
| | | | ccgggacaacagcaagaacaccctgtacctgca |
| | | | gatgaacagcctgaaaaccgaggacaccgccgt |
| | | | gtactactgcaccacccacggcaacttcggcaaca |
| | | | gctatgtgtcttggtttgcctactggggccagggcac |
| | | | cctcgtgacagtctcgagc |
| Gladbach | HCDR1 (Kabat) | SEQ ID NO: 23 | TYAMN |
| | HCDR2 (Kabat) | SEQ ID NO: 24 | RIRSKYNNYATYYADSVKD |
| | HCDR3 (Kabat) | SEQ ID NO: 25 | HGNFGNSYVSWFAY |
| | LCDR1 (Kabat) | SEQ ID NO: 26 | RSSTGAVTTSNYAN |
| | LCDR2 (Kabat) | SEQ ID NO: 65 | GTKFLAP |
| | LCDR3 (Kabat) | SEQ ID NO: 28 | ALWYSNLWV |
| | VL | SEQ ID NO: 85 | QTVVTQEPSLTVSPGGTVTLTCRSST |
| | | SEQ ID NO: 19 | GAVTTSNYANWVQQKPGQAPRGLIG |
| | | | GTKFLAPGTPARFSGSLLGGKAALTL |
| | | | SGVQPEDEAEYYCALWYSNLWVFG |
| | | | GGTKLTVLGQ |
| | VH | SEQ ID NO: 86 | QVQLVESGGGLVKPGGSLRLSCAAS |
| | | SEQ ID NO: 9 | GFTFNTYAMNWIRQAPGKGLEWVSR |
| | | | IRSKYNNYATYYADSVKDRFTISRDN |
| | | | AKNSLYLQMNSLRAEDTAVYYCVRH |
| | | | GNFGNSYVSWFAYWGQGTLVTVSS |
| | VL (DNA) | SEQ ID NO: 87 | cagaccgtggtcacacaagagcccagcctgaca |
| | | SEQ ID NO: 20 | gtttctcctggcggcacagtgaccctgacctgcagat |
| | | | cttctacaggcgccgtgaccaccagcaactacgcc |
| | | | aattgggtgcagcagaagcctggacaggctccca |
| | | | gaggactgatcggcggcacaaaatttctggcccct |
| | | | ggcacaccagccagattctctggatctctgctcggc |
| | | | ggaaaggccgctctgacactgtctggtgttcagcct |
| | | | gaggacgaggccgagtactattgcgccctgtggta |
| | | | cagcaacctgtgggtgttcggcggaggtaccaagc |
| | | | tgaccgtgctgggccag |
| | VH (DNA) | SEQ ID NO: 88 | caggtgcagctggtggaatctggcggcggactcgt |
| | | SEQ ID NO: 10 | gaagcctggcggctctctgagactgagctgtgccg |
| | | | ccagcggcttcaccttcaacacctacgccatgaact |
| | | | ggatccggcaggcccctggcaagggcctggaatg |
| | | | ggtgtcccggatcagaagcaagtacaacaattacg |
| | | | ccacctactacgccgacagcgtgaaggaccggttc |
| | | | accatcagccgggacaacgccaagaacagcctg |
| | | | tacctgcagatgaactccctgcgggccgaggacac |
| | | | cgccgtgtactattgtgtgcggcacggcaacttcgg |
| | | | caacagctatgtgtcttggtttgcctactggggccag |
| | | | ggcaccctcgtgacagtctcgagc |
| | HCDR1 (Kabat) | SEQ ID NO: 33 | acctacgccatg |
| | HCDR2 (Kabat) | SEQ ID NO: 34 | cggatcagaagcaagtacaacaattacgccacct |
| | | | actacgccgacagcgtgaaggac |
| | HCDR3 (Kabat) | SEQ ID NO: 35 | cacggcaacttcggcaacagctatgtgtcttggtttg |
| | | | cctac |
| | LCDR1 (Kabat) | SEQ ID NO: 36 | agatcttctacaggcgccgtgaccaccagcaacta |
| | | | cgccaat |
| | LCDR2 (Kabat) | SEQ ID NO: 66 | ggcacaaaatttctggcccct |
| | LCDR3 (Kabat) | SEQ ID NO: 38 | gccctgtggtacagcaatctgtgggtg |
| | Light chain (IgG) | SEQ ID NO: 89 | QTVVTQEPSLTVSPGGTVTLTCRSST |
| | | | GAVTTSNYANWVQQKPGQAPRGLIG |
| | | | GTKFLAPGTPARFSGSLLGGKAALTL |
| | | | SGVQPEDEAEYYCALWYSNLWVFG |
| | | | GGTKLTVLGQPKAAPSVTLFPPSSEE |
| | | | LQANKATLVCLISDFYPGAVTVAWKA |
| | | | DSSPVKAGVETTTPSKQSNNKYAAS |
| | | | SYLSLTPEQWKSHRSYSCQVTHEGS |
| | | | TVEKTVAPTECS |
| | Heavy chain (IgG1) | SEQ ID NO: 90 | QVQLVESGGGLVKPGGSLRLSCAAS |
| | | | GFTFNTYAMNWIRQAPGKGLEWVSR |
| | | | IRSKYNNYATYYADSVKDRFTISRDN |
| | | | AKNSLYLQMNSLRAEDTAVYYCVRH |
| | | | GNFGNSYVSWFAYWGQGTLVTVSS |
| | | | ASTKGPSVFPLAPSSKSTSGGTAALG |
| | | | CLVKDYFPEPVTVSWNSGALTSGVH |

TABLE 5-continued

Amino acid and nucleic acid sequence identifiers of the heavy and light chain variable regions and CDRs of selected CD3 specific humanized antibodies of the invention.

| Antibody# | SEQ ID NO: | [aa]/[nt] |
|---|---|---|
| | | TFPAVLQSSGLYSLSSVVTVPSSSLG<br>TQTYICNVNHKPSNTKVDKRVEPKSC<br>DKTHTCPPCPAPELLGGPSVFLFPPK<br>PKDTLMISRTPEVTCVVVDVSHEDPE<br>VKFNWYVDGVEVHNAKTKPREEQYN<br>STYRVVSVLTVLHQDWLNGKEYKCK<br>VSNKALPAPIEKTISKAKGQPREPQV<br>YTLPPSREEMTKNQVSLTCLVKGFYP<br>SDIAVEWESNGQPENNYKTTPPVLD<br>SDGSFFLYSKLTVDKSRWQQGNVFS<br>CSVMHEALHNHYTQKSLSLSPGK |
| Light chain (DNA) | SEQ ID NO: 91 | cagaccgtggtcacacaagagcccagcctgaca<br>gtttctcctggcggcacagtgacctgacctgcagat<br>cttctacaggcgccgtgaccaccagcaactacgcc<br>aattgggtgcagcagaagcctggacaggctcca<br>gaggactgatcggcggcacaaaatttctggcccct<br>ggcacaccagccagattctctggatctctgctcggc<br>ggaaaggccgctctgacactgtctggtgttcagcct<br>gaggacgaggccgagtactattgcgccctgtggta<br>cagcaacctgtgggtgttcggcggaggtaccaagc<br>tgaccgtgctgggccagcccaaagccgcccctag<br>cgtgaccctgttccccccctcgagtgaggaactcca<br>ggccaacaaggccaccctcgtgtgcctgatcagcg<br>acttctaccctggcgccgtgaccgtggcctggaagg<br>ccgatagcagccctgtgaaggccggcgtggaaac<br>caccaccccagcaagcagagcaacaacaaata<br>cgccgccagcagctacctgagcctgacccccgag<br>cagtggaagtcccacagatcctacagctgccaggt<br>cacacacgagggcagcaccgtggaaaagaccgt<br>ggcccccaccgagtgcagc |
| Heavy chain (DNA, IgG1) | SEQ ID NO: 92 | caggtgcagctggtggaatctggcggcggactcgt<br>gaagcctggcggctctctgagactgagctgtgccg<br>ccagcggcttcaccttcaacacctacgccatgaact<br>ggatccggcaggcccctggcaagggcctggaatg<br>ggtgtcccggatcagaagcaagtacaacaattacg<br>ccacctactacgccgacagcgtgaaggaccggttc<br>accatcagccgggacaacgccaagaacagcctg<br>tacctgcagatgaactccctgcgggccgaggacac<br>cgccgtgtactattgtgtgcggcacggcaacttcgg<br>caacagctatgtgtcttggtttgcctactggggccag<br>ggcaccctcgtgacagtctcgagcgcgtcgaccaa<br>aggccccagcgtgttccctctgcccccagcagca<br>agagcacctctggcggaacagccgccctgggctg<br>cctggtcaaggactacttccccgagcccgtgaccgt<br>gtcctggaactctggcgccctgaccagcggcgtgc<br>acacctttccagccgtgctccagagcagcggcctgt<br>acagcctgagcagcgtcgtgaccgtgcccagcag<br>cagcctgggcacccagacctacatctgcaacgtga<br>accacaagcccagcaacacaaaggtggacaag<br>cgggtggaacccaagagctgcgacaagacccac<br>acctgtcccccctgccctgccctgaactgctggga<br>ggcccctcgtgttcctgttccccccaaagcctaag<br>gacaccctgatgatcagccggacccccgaagtga<br>cctgcgtggtggtggacgtgtcccacgaggaccct<br>gaagtgaagtttaattggtacgtggacggcgtggaa<br>gtgcacaacgccaagaccaagcccagagagga<br>acagtacaacagcacctaccgggtggtgtccgtgc<br>tgaccgtgctgcaccaggactggctgaacggcaa<br>agagtacaagtgcaaggtgtccaacaaggccctg<br>cctgcccccatcgagaaaaccatcagcaaggcca<br>aaggccagccccgcgagccccaggtgtacacact<br>gccccctagccgggaagagatgaccaagaacca<br>ggtgtccctgacctgcctcgtgaagggcttctacccc<br>agcgacattgccgtggaatgggagagcaacggcc<br>agcccgagaacaactacaagaccaccccccctgt<br>gctggacagcgacggctcattcttcctgtacagcaa<br>gctgaccgtggacaagagccggtggcagcaggg<br>caacgtgttcagctgctccgtgatgcacgaggccct<br>gcacaaccactacacccagaagtccctgagcctg<br>agccccggcaagtga |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | scFv (VL-linker-VH) | SEQ ID NO: 93 | ASPAAPAPSAQTVVTQEPSLTVSPG GTVTLTCRSSTGAVTTSNYANWVQQ KPGQAPRGLIGGTKFLAPGTPARFSG SLLGGKAALTLSGVQPEDEAEYYCAL WYSNLWVFGGGTKLTVLGQASPAAP APASPAAPAPASGSQVQLVESGGGL VKPGGSLRLSCAASGFTFNTYAMNW IRQAPGKGLEWVSRIRSKYNNYATYY ADSVKDRFTISRDNAKNSLYLQMNSL RAEDTAVYYCVRHGNFGNSYVSWFA YWGQGTLVTVSS |
| | scFv (VL-linker-VH) (DNA) | SEQ ID NO: 94 | gcttctcctgctgctcctgctcctagcgctcagaccgt ggtcacacaagagcccagcctgacagtttctcctgg cggcacagtgaccctgacctgcagatcttctacagg cgccgtgaccaccagcaactacgccaattgggtgc agcagaagcctggacaggctcccagaggactgat cggcggcacaaaatttctggcccctggcacaccag ccagattctctggatctctgctcggcggaaaggccg ctctgacactgtctggtgttcagcctgaggacgagg ccgagtactattgcgccctgtggtacagcaacctgt gggtgttcggcggaggtaccaagctgaccgtgctg ggccaggcctctcctgctgctcctgctccagcttctcc agccgctccagctcctgctagcggatctcaggtgca gctggtggaatctggcggcggactcgtgaagcctg gcggctctctgagactgagctgtgccgccagcggct tcaccttcaacacctacgccatgaactggatccggc aggcccctggcaagggcctggaatgggtgtcccg gatcagaagcaagtacaacaattacgccacctact acgccgacagcgtgaaggaccggttcaccatcag ccgggacaacgccaagaacagcctgtacctgca gatgaactccctgcgggccgaggacaccgccgtgt actattgtgtgcggcacggcaacttcggcaacagct atgtgtcttggtttgcctactggggccagggcaccct cgtgacagtctcgagc |
| Nürnberg | HCDR1 (Kabat) | SEQ ID NO: 23 | TYAMN |
| | HCDR2 (Kabat) | SEQ ID NO: 24 | RIRSKYNNYATYYADSVKD |
| | HCDR3 (Kabat) | SEQ ID NO: 25 | HGNFGNSYVSWFAY |
| | LCDR1 (Kabat) | SEQ ID NO: 26 | RSSTGAVTTSNYAN |
| | LCDR2 (Kabat) | SEQ ID NO: 27 | GTNKRAP |
| | LCDR3 (Kabat) | SEQ ID NO: 28 | ALWYSNLWV |
| | VL | SEQ ID NO: 95 SEQ ID NO: 21 | QTVVTQEPSLTVSPGGTVTLTCRSST GAVTTSNYANWVQQKPGQAPRGLIG GTNKRAPGTPARFSGSLLGGKAALTL SGVQPEDEAEYYCALWYSNLWVFG GGTKLTVLGQ |
| | VH | SEQ ID NO: 96 SEQ ID NO: 9 | QVQLVESGGGLVKPGGSLRLSCAAS GFTFNTYAMNWIRQAPGKGLEWVSR IRSKYNNYATYYADSVKDRFTISRDN AKNSLYLQMNSLRAEDTAVYYCVRH GNFGNSYVSWFAYWGQGTLVTVSS |
| | VL (DNA) | SEQ ID NO: 97 SEQ ID NO: 22 | cagaccgtggtcacacaagagcccagcctgaca gtttctcctggcggcacagtgaccctgacctgcagat cttctacaggcgccgtgaccaccagcaactacgcc aattgggtgcagcagaagcctggacaggctccca gaggactgatcggcggcacaaacaaaagagccc ctggcacaccagccagattcagcggatcactgctc ggaggaaaggccgctctgacactgtctggtgtcca gcctgaagatgaggccgagtactactgcgccctgt ggtacagcaatctgtgggtgttcggcggaggtacc aagctgaccgtgctgggccag |
| | VH (DNA) | SEQ ID NO: 98 SEQ ID NO: 10 | caggtgcagctggtggaatctggcggcggactcgt gaagcctggcggctctctgagactgagctgtgccg ccagcggcttcaccttcaacacctacgccatgaact ggatccggcaggcccctggcaagggcctggaatg ggtgtcccggatcagaagcaagtacaacaattacg ccacctactacgccgacagcgtgaaggaccggttc accatcagccgggacaacgccaagaacagcctg tacctgcagatgaactccctgcgggccgaggacac cgccgtgtactattgtgtgcggcacggcaacttcgg caacagctatgtgtcttggtttgcctactggggccag ggcaccctcgtgacagtctcgagc |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | HCDR1 (Kabat) | SEQ ID NO: 33 | acctacgccatg |
| | HCDR2 (Kabat) | SEQ ID NO: 34 | cggatcagaagcaagtacaacaattacgccacct actacgccgacagcgtgaaggac |
| | HCDR3 (Kabat) | SEQ ID NO: 35 | cacggcaacttcggcaacagctatgtgtcttggtttg cctac |
| | LCDR1 (Kabat) | SEQ ID NO: 36 | agatcttctacaggcgccgtgaccaccagcaacta cgccaat |
| | LCDR2 (Kabat) | SEQ ID NO: 37 | ggcacaaacaaaagagcccct |
| | LCDR3 (Kabat) | SEQ ID NO: 38 | gccctgtggtacagcaatctgtgggtg |
| | Light chain (IgG) | SEQ ID NO: 99 | QTVVTQEPSLTVSPGGTVTLTCRSST GAVTTSNYANWVQQKPGQAPRGLIG GTNKRAPGTPARFSGSLLGGKAALTL SGVQPEDEAEYYCALWYSNLWVFG GGTKLTVLGQPKAAPSVTLFPPSSEE LQANKATLVCLISDFYPGAVTVAWKA DSSPVKAGVETTTPSKQSNNKYAAS SYLSLTPEQWKSHRSYSCQVTHEGS TVEKTVAPTECS |
| | Heavy chain (IgG1) | SEQ ID NO: 100 | QVQLVESGGGLVKPGGSLRLSCAAS GFTFNTYAMNWIRQAPGKGLEWVSR IRSKYNNYATYYADSVKDRFTISRDN AKNSLYLQMNSLRAEDTAVYYCVRH GNFGNSYVSWFAYWGQGTLVTVSS ASTKGPSVFPLAPSSKSTSGGTAALG CLVKDYFPEPVTVSWNSGALTSGVH TFPAVLQSSGLYSLSSVVTVPSSSLG TQTYICNVNHKPSNTKVDKRVEPKSC DKTHTCPPCPAPELLGGPSVFLFPPK PKIDTLMISRTPEVTCVVVDVSHEDPE VKFNWYVDGVEVHNAKTKPREEQYN STYRVVSVLTVLHQDWLNGKEYKCK VSNKALPAPIEKTISKAKGQPREPQV YTLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGK |
| | Light chain (DNA) | SEQ ID NO: 101 | cagaccgtggtcacacaagagcccagcctgaca gtttctcctggcggcacagtgaccctgacctgcagat cttctacaggcgccgtgaccaccagcaactacgcc aattgggtgcagcagaagcctggacaggctccca gaggactgatcggcggcacaaacaaaagagccc ctggcacaccagccagattcagcggatcactgctc ggaggaaaggccgctctgacactgtctggtgtcca gcctgaagatgaggccgagtactactgcgccctgt ggtacagcaatctgtgggtgttcggcggaggtacc aagctgaccgtgctgggccagcccaaagccgcc ctagcgtgaccctgttccccccctcgagtgaggaac tccaggccaacaaggccaccctcgtgtgcctgatc agcgacttctaccctggcgccgtgaccgtggcctgg aaggccgatagcagccctgtgaaggccggcgtgg aaaccaccacccccagcaagcagagcaacaac aaatacgccgccagcagctacctgagcctgaccc ccgagcagtggaagtcccacagatcctacagctgc caggtcacacacgagggcagcaccgtggaaaag accgtggcccccaccgagtgcagc |
| | Heavy chain (DNA, IgG1) | SEQ ID NO: 102 | caggtgcagctggtggaatctggcggcggactcgt gaagcctggcggctctctgagactgagctgtgccg ccagcggcttcaccttcaacacctacgccatgaact ggatccggcaggcccctggcaagggcctggaatg ggtgtcccggatcagaagcaagtacaacaattacg ccacctactacgccgacagcgtgaaggaccggttc accatcagccgggacaacgccaagaacagcctg tacctgcagatgaactccctgcgggccgaggacac cgccgtgtactattgtgtgcggcacggcaacttcgg caacagctatgtgtcttggtttgcctactggggccag ggcaccctcgtgacagtctcgagcgcgtcgaccaa aggcccagcgtgttccctctggcccccagcagca gagcacctctggcggaacagccgccctgggctg cctggtcaaggactactttcccgagcccgtgaccgt gtcctggaactctggcgccctgaccagcggcgtgc acacctttccagccgtgctccagagcagcggcctgt acagcctgagcagcgtcgtgaccgtgcccagcag |

TABLE 5-continued

Amino acid and nucleic acid sequence identifiers of the heavy and light chain variable regions and CDRs of selected CD3 specific humanized antibodies of the invention.

| Antibody# | | SEQ ID NO: | [aa]/[nt] |
|---|---|---|---|
| | | | cagcctgggcacccagacctacatctgcaacgtga<br>accacaagcccagcaacacaaaggtggacaag<br>cgggtggaacccaagagctgcgacaagacccac<br>acctgtccccctgccctgcccctgaactgctggga<br>ggcccctccgtgttcctgttccccccaaagcctaag<br>gacaccctgatgatcagccggaccccccgaagtga<br>cctgcgtggtggtggacgtgtcccacgaggaccct<br>gaagtgaagtttaattggtacgtggacggcgtggaa<br>gtgcacaacgccaagaccaagcccagagagga<br>acagtacaacagcacctaccgggtggtgtccgtgc<br>tgaccgtgctgcaccaggactggctgaacggcaa<br>agagtacaagtgcaaggtgtccaacaaggccctg<br>cctgcccccatcgagaaaaccatcagcaaggcca<br>aaggccagccccgcgagccccaggtgtacacact<br>gcccccctagccgggaagagatgaccaagaacca<br>ggtgtccctgacctgcctcgtgaagggcttctacccc<br>agcgacattgccgtggaatgggagagcaacggcc<br>agcccgagaacaactacaagaccacccccctgt<br>gctggacagcgacggctcattcttcctgtacagcaa<br>gctgaccgtggacaagagccggtggcagcaggg<br>caacgtgttcagctgctccgtgatgcacgaggccct<br>gcacaaccactacacccagaagtccctgagcctg<br>agccccggcaagtga |
| scFv (VL-linker-VH) | | SEQ ID NO: 103 | ASPAAPAPSAQTVVTQEPSLTVSPG<br>GTVTLTCRSSTGAVTTSNYANWVQQ<br>KPGQAPRGLIGGTNKRAPGTPARFS<br>GSLLGGKAALTLSGVQPEDEAEYYC<br>ALWYSNLWVFGGGTKLTVLGQASPA<br>APAPASPAAPAPASGSQVQLVESGG<br>GLVKPGGSLRLSCAASGFTFNTYAM<br>NWIRQAPGKGLEWVSRIRSKYNNYA<br>TYYADSVKDRFTISRDNAKNSLYLQM<br>NSLRAEDTAVYYCVRHGNFGNSYVS<br>WFAYWGQGTLVTVSS |
| scFv (VL-linker-VH)<br>(DNA) | | SEQ ID NO: 104 | gcttctcctgctgctcctgctcctagcgctcagaccgt<br>ggtcacacaagagcccagcctgacagtttctcctgg<br>cggcacagtgaccctgacctgcagatcttctacagg<br>cgccgtgaccaccagcaactacgccaattgggtgc<br>agcagaagcctggacaggctcccagaggactgat<br>cggcggcacaaacaaaagagcccctggcacacc<br>agccagattcagcggatcactgctcggaggaaag<br>gccgctctgacactgtctggtgtccagcctgaagat<br>gaggccgagtactactgcgccctgtggtacagcaa<br>tctgtgggtgttcggcggaggtaccaagctgaccgt<br>gctgggccaggcctctcctgctgctcctgctccagct<br>tctccagccgctccagctcctgctagcggatctcag<br>gtgcagctggtggaatctggcggcggactcgtgaa<br>gcctggcggctctctgagactgagctgtgccgccag<br>cggcttcaccttcaacacctacgccatgaactggat<br>ccggcaggcccctggcaagggcctggaatgggtg<br>tcccggatcagaagcaagtacaacaattacgcca<br>cctactacgccgacagcgtgaaggaccggttcacc<br>atcagccgggacaacgccaagaacagcctgtac<br>ctgcagatgaactccctgcgggccgaggacaccg<br>ccgtgtactattgtgtgcggcacggcaacttcggca<br>acagctatgtgtcttggtttgcctactggggccaggg<br>caccctcgtgacagtctcgagc |

TABLE 6

Bispecific antibody sequences. Each of the listed antibodies shares the same IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| BsAb#Mainz | RefmAb#2 (IgG1-AEASS_HC) x mAb#Mainz (scFv) | SEQ ID NO: 105 | QVQLVESGGGLVQPGGSLRLSCAASG FNIKDTYIHWVRQAPGKGLEWVARIYP TNGYTRYADSVKGRFTISADTSKNTAY LQMNSLRAEDTAVYYCSRWGGDGFY AMDYWGQGTLVTVSSASTKGPSVFPL APSSKSTSGGTAALGCLVKDYFPEPVT VSWNSGALTSGVHTFPAVLQSSGLYS LSSVVTVPSSSLGTQTYICNVNHKPSN TKVDKRVEPKSCDKTHTCPPCPAPEA EGAPSVFLFPPKPKDTLMISRTPEVTC VVVDVSHEDPEVKFNWYVDGVEVHNA KTKPREEQYNSTYRVVSVLTVLHQDW LNGKEYKCKVSNKALPSSIEKTISKAKG QPREPQVYTLPPSREEMTKNQVSLTC LVKGFYPSDIAVEWESNGQPENNYKT TPPVLDSDGSFFLYSKLTVDKSRWQQ GNVFSCSVMHEALHNHYTQKSLSLSP GKASPAAPAPSAQAVVTQEPSLTVSP GGTVTLTCRSSTGAVTTSNYANWVQQ KPGQAPRGLIGGTNKRAPWTPARFSG SLLGGKAALTITGAQAEDEADYYCALW YSNLWVFGGGTKLTVLGQASPAAPAP ASPAAPAPASGSQVQLVESGGGLVKP GGSLRLSCAASGFTFNTYAMNWIRQA PGKGLEWVSRIRSKYNNYATYYADSV KDRFTISRDNAKNSLYLQMNSLRAEDT AVYYCVRHGNFGNSYVSWFAYWGQG TLVTVSS |
| | RefmAb#2 (IgG1-AEASS_HC) x mAb#Mainz (scFv) (DNA) | SEQ ID NO: 106 | caggtgcaattggtggagtctggcggaggactggtgc agcctggggggcagcctgagactgagctgcgccgcc agcggcttcaacatcaaggacacctacatccactgg gtgcgccaggctccaggcaagggactggaatgggt ggcccggatctacccaccaacggctacaccagata cgccgacagcgtgaagggccggttcaccatcagcg ccgacaccagcaagaacaccgcctacctgcagatg aacagcctgcgggccgaggacaccgccgtgtacta ctgcagcagatggggcggagatggcttctacgccatg gactactggggccagggcaccctggtgaccgtctcg agcgcgtcgaccaaaggcccagcgtgttccctctgg ccccagcagcaagagcacctctggcggaacagcc gccctgggctgcctggtcaaggactacttccccgagc ccgtgaccgtgtcctggaactctggcgccctgaccag cggcgtgcacacctttccagccgtgctccagagcagc ggcctgtacagcctgagcagcgtcgtgaccgtgccc agcagcagcctgggcacccagacctacatctgcaac gtgaaccacaagcccagcaacacaaaggtggaca gcggggtggaacccaagagctgcgacaagaccca cacctgtcccccctgccctgccccctgaagcggaggg agcccctccgtgttcctgttcccccccaaagcctaagg acaccctgatgatcagccggaccccgaagtgacct gcgtggtggtggacgtgtcccacgaggaccctgaagt gaagtttaattggtacgtggacggcgtggaagtgcac aacgccaagaccaagcccagagaggaacagtaca acagcacctacccgggtggtgtccgtgctgaccgtgct gcaccaggactggctgaacggcaaagagtacaagt gcaaggtgtccaacaaggccctgccttcctccatcga gaaaaccatcagcaaggccaaaggccagccccgc gagccccaggtgtacacactgcccctagccgggaa gagatgaccaagaaccaggtgtccctgacctgcctc gtgaagggcttctaccccagcgacattgccgtggaat gggagagcaacggccagcccgagaacaactacaa gaccacccccctgtgctggacagcgacggctcattc ttcctgtacagcaagctgaccgtggacaagagccgt ggcagcagggcaacgtgttcagctgctccgtgatgca cgaggccctgcacaaccactacacccagaagtccct gagcctgagcccggcaaggcttcctctgctgctcctg ctcctagcgctcaggccgtggttacacaagagccca gcctgacagttagccctggcggaacagtgaccctga cctgcagatcttctacaggcgccgtgaccaccagcaa ctacgccaattgggtgcagcagaagcctggacaggc tcccagaggactgatcggcggcacaaacaaaagag cccttggacacccgccagattcagcggatcactgct cggaggaaaggccgcactgacaatcacaggtgccc |

TABLE 6-continued

Bispecific antibody sequences. Each of the listed antibodies shares the same IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | aggccgaagatgaggccgattactattgcgccctgtg<br>gtacagcaacctgtgggtgttcggcggaggtaccaa<br>gctgaccgtgctgggccaggcctctcctgctgctcctg<br>ctccagcttctccagccgctccagctcctgctagcgga<br>tctcaggtgcagctggtggaatctggcggcggactcgt<br>gaagcctggcggctctctgagactgagctgtgccgcc<br>agcggcttcaccttcaacacctacgccatgaactgga<br>tccggcaggcccctggcaagggcctggaatgggtgt<br>cccggatcagaagcaagtacaacaattacgccacct<br>actacgccgacagcgtgaaggaccggttcaccatca<br>gccgggacaacgccaagaacagcctgtacctgcag<br>atgaactccctgcgggccgaggacaccgccgtgtac<br>tattgtgtgcggcacggcaacttcggcaacagctatgt<br>gtcttggtttgcctactggggccagggcaccctcgtga<br>cagtctcgagc |
| BsAb#Köln | RefmAb#2<br>(IgG1f_AEASS_<br>HC) x mAb#Köln<br>(scFv) | SEQ ID NO: 107 | QVQLVESGGGLVQPGGSLRLSCAASG<br>FNIKDTYIHWVRQAPGKGLEWVARIYP<br>TNGYTRYADSVKGRFTISADTSKNTAY<br>LQMNSLRAEDTAVYYCSRWGGDGFY<br>AMDYWGQGTLVTVSSASTKGPSVFPL<br>APSSKSTSGGTAALGCLVKDYFPEPVT<br>VSWNSGALTSGVHTFPAVLQSSGLYS<br>LSSVVTVPSSSLGTQTYICNVNHKPSN<br>TKVDKRVEPKSCDKTHTCPPCPAPEA<br>EGAPSVFLFPPKPKDTLMISRTPEVTC<br>VVVDVSHEDPEVKFNWYVDGVEVHNA<br>KTKPREEQYNSTYRVVSVLTVLHQDW<br>LNGKEYKCKVSNKALPSSIEKTISKAKG<br>QPREPQVYTLPPSREEMTKNQVSLTC<br>LVKGFYPSDIAVEWESNGQPENNYKT<br>TPPVLDSDGSFFLYSKLTVDKSRWQQ<br>GNVFSCSVMHEALHNHYTQKSLSLSP<br>GKASPAAPAPSAELVVTQEPSLTVSPG<br>GTVTLTCRSSTGAVTTSNYANWVQQK<br>PGQAPRGLIGGTNKRAPGTPARFSGS<br>LLGGKAALTLSGVQPEDEAEYYCALW<br>YSNLWVFGGGTKLTVLGQASPAAPAP<br>ASPAAPAPASGSQVQLVESGGGLVKP<br>GGSLRLSCAASGFTFNTYAMNWIRQA<br>PGKGLEWVSRIRSKYNNYATYYADSV<br>KDRFTISRDNAKNSLYLQMNSLRAEDT<br>AVYYCVRHGNFGNSYVSWFAYWGQG<br>TLVTVSS |
| | RefmAb#2<br>(IgG1f_AEASS_<br>HC) x mAb#Köln<br>(scFv)<br>(DNA) | SEQ ID NO: 108 | caggtgcaattggtggagtctggcggaggactggtgc<br>agcctgggggcagcctgagactgagctgcgccgcc<br>agcggcttcaacatcaaggacacctacatccactgg<br>gtgcgccaggctccaggcaagggactggaatgggt<br>ggcccggatctaccccaccaacggctacaccagata<br>cgccgacagcgtgaagggccggttcaccatcagcg<br>ccgacaccagcaagaacaccgcctacctgcagatg<br>aacagcctgcgggccgaggacaccgccgtgtacta<br>ctgcagcagatggggcggagatggcttctacgccatg<br>gactactggggccagggcaccctggtgaccgtctcg<br>agcgcgtcgaccaaaggcccagcgtgttccctctgg<br>ccccagcagcaagagcacctctggcggaacagcc<br>gccctgggctgcctggtcaaggactacttccccgagc<br>ccgtgaccgtgtcctggaactctggcgccctgaccag<br>cggcgtgcacacctctcagccgtgctccagagcagc<br>ggcctgtacagcctgagcagcgtcgtgaccgtgccc<br>agcagcagcctgggcacccagacctacatctgcaac<br>gtgaaccacaagcccagcaacacaaaggtggaca<br>agcgggtggaacccaagagctgcgacaagaccca<br>cacctgtccccctgccctgcccctgaagcggagggg<br>agcccctccgtgttcctgttcccccaaagcctaagg<br>acaccctgatgatcagccggacccccgaagtgacct<br>gcgtggtggtggacgtgtcccacgaggaccctgaagt<br>gaagtttaattggtacgtggacggcgtggaagtgcac<br>aacgccaagaccaagcccagaggaacagtaca<br>acagcacctacccgggtggtgtccgtgctgaccgtgct<br>gcaccaggactggctgaacggcaaagagtacaagt<br>gcaaggtgtccaacaaggccctgccttcctccatcga<br>gaaaaccatcagcaaggccaaaggccagccccgc |

TABLE 6-continued

Bispecific antibody sequences. Each of the listed antibodies shares the same IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | gagccccaggtgtacacactgcccccctagccgggaa<br>gagatgaccaagaaccaggtgtccctgacctgcctc<br>gtgaagggcttctacccccagcgacattgccgtggaat<br>gggagagcaacggccagcccgagaacaactacaa<br>gaccacccccctgtgctggacagcgacggctcattc<br>ttcctgtacagcaagctgaccgtggacaagagccggt<br>ggcagcagggcaacgtgttcagctgctccgtgatgca<br>cgaggccctgcacaaccactacacccagaagtccct<br>gagcctgagccccggcaaggcttctcctgctgctcctg<br>ctcctagcgctgagctggtggtcacacaagagccca<br>gcctgacagtttctcctggcggcacagtgaccctgacc<br>tgcagatcttctacaggcgccgtgacccctccaacta<br>cgccaattgggtgcagcagaagcctggacaggctcc<br>cagaggactgatcggcggcacaaacaaaagagcc<br>cctggcacaccagccagattcagcggatcactgctcg<br>gaggaaaggccgctctgacactgtctggtgtccagcc<br>tgaagatgaggccgagtactactgcgccctgtggtac<br>agcaatctgtgggtgttcggcggaggtaccaagctga<br>ccgtgctgggccaggcctctcctgctgctcctgctcca<br>gcttctccagccgctccagctcctgctagcggatctca<br>ggtgcagctggtggaatctggcggcggactcgtgaa<br>gcctggcggctctctgagactgagctgtgccgccagc<br>ggcttcaccttcaacacctacgccatgaactggatccg<br>gcaggcccctggcaagggcctggaatgggtgtcccg<br>gatcagaagcaagtacaacaattacgccacctacta<br>cgccgacagcgtgaaggaccggttcaccatcagcc<br>gggacaacgccaagaacagcctgtacctgcagatg<br>aactccctgcgggccgaggacaccgccgtgtactatt<br>gtgtgcggcacggcaacttcggcaacagctatgtgtct<br>tggtttgcctactggggccagggcaccctcgtgacagt<br>ctcgagc |
| BsAb# Freiburg | RefmAb#2 (IgG1f_AEASS_HC) x mAb#Freiburg (scFv) | SEQ ID NO: 109 | QVQLVESGGGLVQPGGSLRLSCAASG<br>FNIKDTYIHWVRQAPGKGLEWVARIYP<br>TNGYTRYADSVKGRFTISADTSKNTAY<br>LQMNSLRAEDTAVYYCSRWGGDGFY<br>AMDYWGQGTLVTVSSASTKGPSVFPL<br>APSSKSTSGGTAALGCLVKDYFPEPVT<br>VSWNSGALTSGVHTFPAVLQSSGLYS<br>LSSVVTVPSSSLGTQTYICNVNHKPSN<br>TKVDKRVEPKSCDKTHTCPPCPAPEA<br>EGAPSVFLFPPKPKDTLMISRTPEVTC<br>VVVDVSHEDPEVKFNWYVDGVEVHNA<br>KTKPREEQYNSTYRVVSVLTVLHQDW<br>LNGKEYKCKVSNKALPSSIEKTISKAKG<br>QPREPQVYTLPPSREEMTKNQVSLTC<br>LVKGFYPSDIAVEWESNGQPENNYKT<br>TPPVLDSDGSFFLYSKLTVDKSRWQQ<br>GNVFSCSVMHEALHNHYTQKSLSLSP<br>GKASPAAPAPSAQTVVTQEPSLTVSP<br>GGTVTLTCRSSTGAVTTSNYANWVQQ<br>KPGQAPRGLIGGTNKRAPGTPARFSG<br>SLLGGKAALTLLGAQPEDEAEYYCALW<br>YSNLWVFGGGTKLTVLGQASPAAPAP<br>ASPAAPAPASGSEVQLVESGGGLVKP<br>GGSLRLSCAASGFTFNTYAMNWVRQA<br>PGKGLEWVGRIRSKYNNYATYYADSV<br>KDRFTISRDDSKNTLYLQMNSLKTEDT<br>AVYYCTTHGNFGNSYVSWFAYWGQG<br>TLVTVSS |
| | RefmAb#2 (IgG1f_AEASS_HC) x mAb#Freiburg (scFv) (DNA) | SEQ ID NO: 110 | caggtgcaattggtggagtctggcggaggactggtgc<br>agcctggggggcagcctgagactgagctgcgccgcc<br>agcggcttcaacatcaaggacacctacatccactgg<br>gtgcgccaggctccaggcaagggactggaatgggt<br>ggcccggatctacccaccaacggctacaccagata<br>cgccgacagcgtgaagggccggttcaccatcagcg<br>ccgacaccagcaagaacaccgcctacctgcagatg<br>aacagcctgcgggccgaggacaccgccgtgtacta<br>ctgcagcagatgggcggagatggcttctacgccatg<br>gactactggggccagggcaccctggtgaccgtctcg<br>agcgcgtcgaccaaaggcccagcgtgttccctctgg<br>ccccagcagcaagagcacctctggcggaacagcc<br>gccctgggctgcctggtcaaggactacttccccgagc |

TABLE 6-continued

Bispecific antibody sequences. Each of the listed antibodies shares the same
IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | ccgtgaccgtgtcctggaactctggcgccctgaccag<br>cggcgtgcacacctttccagccgtgctccagagcagc<br>ggcctgtacagcctgagcagcgtcgtgaccgtgccc<br>agcagcagcctgggcacccagacctacatctgcaac<br>gtgaaccacaagcccagcaacacaaaggtggaca<br>agcgggtggaacccaagagctgcgacaagaccca<br>cacctgtcccccctgccctgccctgaagcggaggg<br>agccccctccgtgttcctgttccccccaaagcctaagg<br>acaccctgatgatcagccggaccccgaagtgacct<br>gcgtggtggtggacgtgtcccacgaggaccctgaagt<br>gaagtttaattggtacgtggacggcgtggaagtgcac<br>aacgccaagaccaagcccagagaggaacagtaca<br>acagcacctaccgggtggtgtccgtgctgaccgtgct<br>gcaccaggactggctgaacggcaaagagtacaagt<br>gcaaggtgtccaacaaggccctgccttcctccatcga<br>gaaaaccatcagcaaggccaaaggccagccccgc<br>gagccccaggtgtacacactgcccctagccgggaa<br>gagatgaccaagaaccaggtgtccctgacctgcctc<br>gtgaagggcttctaccccagcgacattgccgtggaat<br>gggagagcaacggccagcccgagaacaactacaa<br>gaccacccccctgtgctggacagcgacggctcattc<br>ttcctgtacagcaagctgaccgtggacaagagccggt<br>ggcagcagggcaacgtgttcagctgctccgtgatgca<br>cgaggccctgcacaaccactacacccagaagtccct<br>gagcctgagccccggcaaggcttctcctgctgctcctg<br>ctcctagcgctcagaccgtggtcacacaagagccca<br>gcctgacagtttctcctggcggcacagtgaccctgacc<br>tgcagatcttctacaggcgccgtgaccaccagcaact<br>acgccaattgggtgcagcagaagcctggacaggctc<br>ccagaggactgatcggcggcacaaacaaaagagc<br>ccctggcacaccagccagattcagcggatcactgctc<br>ggaggaaaggccgctctgacactgcttggagcacag<br>cctgaagatgaggccgagtactactgcgccctgtggt<br>acagcaatctgtgggtgttcggcggaggtaccaagct<br>gaccgtgctgggccaggcctctcctgctgctcctgctc<br>cagcttctccagccgctccagctcctgctagcggatct<br>gaagtgcagctggtggaatctggcggcggactcgtg<br>aagcctggcggctctctgagactgagctgtgccgcca<br>gcggcttcaccttcaacacctacgccatgaactgggtg<br>cgccaggcccctggcaaaggcctggaatgggtgg<br>gacggatcagaagcaagtacaacaattacgccacct<br>actacgccgacagcgtgaaggaccggttcaccatca<br>gccgggacgacagcaagaacaccctgtacctgcag<br>atgaacagcctgaaaaccgaggacaccgccgtgta<br>ctactgcaccaccccacggcaacttcggcaacagctat<br>gtgtcttggtttgcctactggggccagggcaccctcgtg<br>acagtctcgagc |
| BsAb# München | RefmAb#2 (IgG1f_AEASS_HC) x mAb#München (scFv) | SEQ ID NO: 111 | QVQLVESGGGLVQPGGSLRLSCAASG<br>FNIKDTYIHWVRQAPGKGLEWVARIYP<br>TNGYTRYADSVKGRFTISADTSKNTAY<br>LQMNSLRAEDTAVYYCSRWGGDGFY<br>AMDYWGQGTLVTVSSASTKGPSVFPL<br>APSSKSTSGGTAALGCLVKDYFPEPVT<br>VSWNSGALTSGVHTFPAVLQSSGLYS<br>LSSVVTVPSSSLGTQTYICNVNHKPSN<br>TKVDKRVEPKSCDKTHTCPPCPAPEA<br>EGAPSVFLFPPKPKDTLMISRTPEVTC<br>VVVDVSHEDPEVKFNWYVDGVEVHNA<br>KTKPREEQYNSTYRVVSVLTVLHQDW<br>LNGKEYKCKVSNKALPSSIEKTISKAKG<br>QPREPQVYTLPPSREEMTKNQVSLTC<br>LVKGFYPSDIAVEWESNGQPENNYKT<br>TPPVLDSDGSFFLYSKLTVDKSRWQQ<br>GNVFSCSVMHEALHNHYTQKSLSLSP<br>GKASPAAPAPSAQTVVTQEPSLTVSP<br>GGTVTLTCRSSTGAVTTSNYANWVQQ<br>KPGQAPRGLIGGTKFLAPGTPARFSGS<br>LLGGKAALTLLGAQPEDEAEYYCALWY<br>SNLWVFGGGTKLTVLGQASPAAPAPA<br>SPAAPAPASGSEVQLVESGGGLVKPG<br>GSLRLSCAASGFTFNTYAMNWVRQAP<br>GKGLEWVGRIRSKYNNYATYYADSVK |

TABLE 6-continued

Bispecific antibody sequences. Each of the listed antibodies shares the same
IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | DRFTISRDDSKNTLYLQMNSLKTEDTA VYYCTTHGNFGNSYVSWFAYWGQGT LVTVSS |
| | RefmAb#2 (IgG1f_AEASS_ HC) x mAb#München (scFv) (DNA) | SEQ ID NO: 112 | caggtgcaattggtggagtctggcggaggactggtgc agcctgggggcagcctgagactgagctgcgccgcc agcggcttcaacatcaaggacacctacatccactgg gtgcgccaggctccaggcaagggactggaatgggt ggcccggatctacccccaccaacggctacaccagata cgccgacagcgtgaagggccggttcaccatcagcg ccgacaccagcaagaacaccgcctacctgcagatg aacagcctgcgggccgaggacaccgccgtgtacta ctgcagcagatggggcggagatggcttctacgccatg gactactgggccagggcaccctggtgaccgtctcg agcgcgtcgaccaaaggccccagcgtgttccctctgg ccccagcagcaagagcacctctggcggaacagcc gccctgggctgcctggtcaaggactacttccccgagc ccgtgaccgtgtcctggaactctggcgccctgaccag cggcgtgcacacctttccagccgtgctccagagcagc ggcctgtacagcctgagcagcgtcgtgaccgtgccc agcagcagcctgggcacccagacctacatctgcaac gtgaaccacaagcccagcaacacaaaggtggaca agcgggtggaacccaagagctgcgacaagaccca cacctgtcccccctgcccctgcccctgaagcggaggg agccccctcgtgttcctgttccccccaaagcctaagg acacccctgatgatcagccggaccccgaagtgacct gcgtggtggtggacgtgtcccacgaggaccctgaagt gaagtttaattggtacgtggacggcgtggaagtgcac aacgccaagaccaagcccagagaggaacagtaca acagcacctaccgggtggtgtccgtgctgaccgtgct gcaccaggactggctgaacggcaaagagtacaagt gcaaggtgtccaacaaggccctgcccttcctccatcga gaaaaccatcagcaaggccaaaggccagccccgc gagccccaggtgtacacactgccccctagccgggaa gagatgaccaagaaccaggtgtccctgacctgcctc gtgaagggcttctaccccagcgacattgccgtggaat gggagagcaacggccagcccgagaacaactacaa gaccacccccctgtgctggacagcgacggctcattc ttcctgtacagcaagctgaccgtggacaagagccggt ggcagcagggcaacgtgttcagctgctccgtgatgca cgaggccctgcacaaccactacacccagaagtccct gagcctgagccccggcaaggcttctcctgctgctcctg ctcctagcgctcagaccgtggtcacacaagagccca gcctgacagttttctcctggcggcacagtgaccctgacc tgcagatcttctacaggcgccgtgaccaccagcaact acgccaattgggtgcagcagaagcctggacaggctc ccagaggactgatcggcggcacaaaatttctggccc ctggcacaccagccagattctctggatctctgctcggc ggaaaggccgctctgacactgcttggagcacagcct gaagatgaggccgagtactactgcgccctgtggtaca gcaatctgtgggtgttcggcggaggtaccaagctgac cgtgctggccaggcctctcctgctgctcctgctccag cttctccagccgctccagctcctgctagcggatctgaa gtgcagctggtggaatctggcggcggactcgtgaag cctggcggctctctgagactgagctgtgccgccagcg gcttcaccttcaacacctacgccatgaactgggtgcgc caggcccctggcaaaggcctggaatgggtgggacg gatcagaagcaagtacaacaattacgccacctacta cgccgacagcgtgaaggaccggttcaccatcagcc gggacgacagcaagaacaccctgtacctgcagatg aacagcctgaaaaccgaggacaccgccgtgtacta ctgcaccacccacggcaacttcggcaacagctatgtg tcttggtttgcctactggggccagggcaccctcgtgac agtctcgagc |
| BsAb# Bremen | RefmAb#2 (IgG1f_AEASS_ HC) x mAb#Bremen (scFv) | SEQ ID NO: 113 | QVQLVESGGGLVQPGGSLRLSCAASG FNIKDTYIHWVRQAPGKGLEWVARIYP TNGYTRYADSVKGRFTISADTSKNTAY LQMNSLRAEDTAVYYCSRWGGDGFY AMDYWGQGTLVTVSSASTKGPSVFPL APSSKSTSGGTAALGCLVKDYFPEPVT VSWNSGALTSGVHTFPAVLQSSGLYS LSSVVTVPSSSLGTQTYICNVNHKPSN TKVDKRVEPKSCDKTHTCPPCPAPEA |

TABLE 6-continued

Bispecific antibody sequences. Each of the listed antibodies shares the same
IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | EGAPSVFLFPPKPKDTLMISRTPEVTC VVVDVSHEDPEVKFNWYVDGVEVHNA KTKPREEQYNSTYRVVSVLTVLHQDW LNGKEYKCKVSNKALPSSIEKTISKAKG QPREPQVYTLPPSREEMTKNQVSLTC LVKGFYPSDIAVEWESNGQPENNYKT TPPVLDSDGSFFLYSKLTVDKSRWQQ GNVFSCSVMHEALHNHYTQKSLSLSP GKASPAAPAPSAQTVVTQEPSLTVSP GGTVTLTCRSSTGAVTTSNYANWVQQ KPGQAPRGLIGGTKFLAPGTPARFSGS LLGGKAALTLSGVQPEDEAEYYCALW YSNLWVFGGGTKLTVLGQASPAAPAP ASPAAPAPASGSEVQLVESGGGLVKP GGSLRLSCAASGFTFNTYAMNWVRQA PGKGLEWVGRIRSKYNNYATYYADSV KDRFTISRDDSKNTLYLQMNSLKTEDT AVYYCTTHGNFGNSYVSWFAYWGQG TLVTVSS |
| | RefmAb#2 (IgG1f_AEASS_HC) x mAb#Bremen (scFv) (DNA) | SEQ ID NO: 114 | caggtgcaattggtggagtctggcggaggactggtgc agcctgggggcagcctgagactgagctgcgccgcc agcggcttcaacatcaaggacacctacatccactgg gtgcgccaggctccaggcaagggactggaatgggt ggcccggatctaccccaccaacggctacaccagata cgccgacagcgtgaagggccggttcaccatcagcg ccgacaccagcaagaacaccgcctacctgcagatg aacagcctgcgggccgaggacaccgccgtgtacta ctgcagcagatggggcggagatggcttctacgccat gactactggggccagggcaccctggtgaccgtctcg agcgcgtcgaccaaaggcccagcgtgttcctctgg cccccagcagcaagagcacctctggcggaacagcc gccctgggctgcctggtcaaggactacttccccgagc ccgtgaccgtgtcctggaactctggcgccctgaccag cggcgtgcacaccttccagccgtgctccagagcagc ggcctgtacagcctgagcagcgtcgtgaccgtgcc agcagcagcctgggcacccagacctacatctgcaac gtgaaccacaagcccagcaacacaaaggtggaca agcgggtggaacccaagagctgcgacaagaccca cacctgtcccccctgccctgcccctgaagcggaggg agcccctccgtgttcctgttccccccaaagcctaagg acaccctgatgatcagccggacccccgaagtgacct gcgtggtggtggacgtgtcccacgaggaccctgaagt gaagtttaattggtacgtggacggcgtggaagtgcac aacgccaagaccaagcccagagaggaacagtaca acagcacctaccgggtggtgtccgtgctgaccgtgct gcaccaggactggctgaacggcaaagagtacaagt gcaaggtgtccaacaaggccctgccttcctccatcga gaaaaccatcagcaaggccaaaggccagccccgc gagccccaggtgtacacactgcccctagccgggaa gagatgaccaagaaccaggtgtccctgacctgcctc gtgaagggcttctaccccagcgacattgccgtggaat gggagagcaacggccagcccgagaacaactacaa gaccacccccctgtgctggacagcgacggctcattc ttcctgtacagcaagctgaccgtggacaagagccggt ggcagcagggcaacgtgttcagctgctccgtgatgca cgaggccctgcacaaccactacacccagaagtccct gagcctgagccccggcaaggcttctcctgctgctcctg ctcctagcgctcagaccgtggtcacacaagagccca gcctgacagtttctcctggcggcacagtgaccctgacc tgcagatcttctacaggcgccgtgaccaccagcaact acgccaattgggtgcagcagaagcctggacaggctc ccagaggactgatcggcggcacaaaatttctggccc ctggcacaccagccagattctctggatctctgctcggc ggaaaggccgctctgacactgtctggtgttcagcctga ggacgaggccgagtactattgcgccctgtggtacagc aacctgtgggtgttcggcggaggtaccaagctgaccg tgctgggccaggctctcctgctgctcctgctccagctt ctccagccgctccagctcctgctagcggatctgaagtg cagctggtggaatctggcggcggactcgtgaagcctg gcggctctctgagactgagctgtgccgccagcggctt caccttcaacacctacgccatgaactgggtgcgccag gcccctggcaaaggcctggaatgggtgggacggatc agaagcaagtacaacaattacgccacctactacgcc |

TABLE 6-continued

Bispecific antibody sequences. Each of the listed antibodies shares the same IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | gacagcgtgaaggaccggttcaccatcagccggga cgacagcaagaacaccctgtacctgcagatgaaca gcctgaaaaccgaggacaccgccgtgtactactgca ccacccacggcaacttcggcaacagctatgtgtcttg gtttgcctactggggccagggcaccctcgtgacagtct cgagc |
| BsAb# Gladbach | RefmAb#2 (IgG1f_AEASS_ HC) x mAb#Gladbach (scFv) | SEQ ID NO: 115 | QVQLVESGGGLVQPGGSLRLSCAASG FNIKDTYIHWVRQAPGKGLEWVARIYP TNGYTRYADSVKGRFTISADTSKNTAY LQMNSLRAEDTAVYYCSRWGGDGFY AMDYWGQGTLVTVSSASTKGPSVFPL APSSKSTSGGTAALGCLVKDYFPEPVT VSWNSGALTSGVHTFPAVLQSSGLYS LSSVVTVPSSSLGTQTYICNVNHKPSN TKVDKRVEPKSCDKTHTCPPCPAPEA EGAPSVFLFPPKPKDTLMISRTPEVTC VVVDVSHEDPEVKFNWYVDGVEVHNA KTKPREEQYNSTYRVVSVLTVLHQDW LNGKEYKCKVSNKALPSSIEKTISKAKG QPREPQVYTLPPSREEMTKNQVSLTC LVKGFYPSDIAVEWESNGQPENNYKT TPPVLDSDGSFFLYSKLTVDKSRWQQ GNVFSCSVMHEALHNHYTQKSLSLSP GKASPAAPAPSAQTVVTQEPSLTVSP GGTVTLTCRSSTGAVTTSNYANWVQQ KPGQAPRGLIGGTKFLAPGTPARFSGS LLGGKAALTLSGVQPEDEAEYYCALW YSNLWVFGGGTKLTVLGQASPAAPAP ASPAAPAPASGSQVQLVESGGGLVKP GGSLRLSCAASGFTFNTYAMNWIRQA PGKGLEWVSRIRSKYNNYATYYADSV KDRFTISRDNAKNSLYLQMNSLRAEDT AVYYCVRHGNFGNSYVSWFAYWGQG TLVTVSS |
| | RefmAb#2 (IgG1f_AEASS_ HC) x mAb#Gladbach (scFv) (DNA) | SEQ ID NO: 116 | caggtgcaattggtggagtctggcggaggactggtgc agcctgggggcagcctgagactgagctgcgccgcc agcggcttcaacatcaaggacacctacatccactgg gtgcgccaggctccaggcaagggactggaatgggt ggcccggatctaccccaccaacggctacaccagata cgccgacagcgtgaagggccggttcaccatcagcg ccgacaccagcaagaacaccgcctacctgcagatg aacagcctgcgggccgaggacaccgccgtgtacta ctgcagcagatggggcggagatggcttctacgccatg gactactggggccagggcaccctggtgaccgtctcg agcgcgtcgaccaaaggcccagcgtgttccctctgg cccccagcagcaagagcacctctggcggaacagcc gccctgggctgcctggtcaaggactacttccccgagc ccgtgaccgtgtcctggaactctggcgccctgaccag cggcgtgcacacctttccagccgtgctccagagcagc ggcctgtacagcctgagcagcgtcgtgaccgtgccc agcagcagcctgggcacccagacctacatctgcaac gtgaaccacaagcccagcaacacaaaggtggaca agcgggtggaacccaagagctgcgacaagaccca cacctgtccccctgccctgccctgaagcggaggg agccccctccgtgttcctgttccccccaaagcctaagg acaccctgatgatcagccggacccccgaagtgacct gcgtggtggtggacgtgtcccacgaggaccctgaagt gaagtttaattggtacgtggacggcgtggaagtgcac aacgccaagaccaagcccagagaggaacagtaca acagcacctacccgggtggtgtccgtgctgaccgtgct gcaccaggactggctgaacggcaaagagtacaagt gcaaggtgtccaacaaggccctgccttcctccatcga gaaaaccatcagcaaggccaaaggccagccccgc gagccccaggtgtacacactgcccccctagccgggaa gagatgaccaagaaccaggtgtccctgacctgcctc gtgaagggcttctaccccagcgacattgccgtggaat gggagagcaacggccagcccgagaacaactacaa gaccacccccctgtgctggacagcgacggctcattc ttcctgtacagcaagctgaccgtggacaagagccggt ggcagcagggcaacgtgttcagctgctccgtgatgca cgaggccctgcacaaccactacacccagaagtccct gagcctgagccccggcaaggcttctcctgctgctcctg |

TABLE 6-continued

Bispecific antibody sequences. Each of the listed antibodies shares the same IgG light chain of RefmAb#2_h_Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | ctcctagcgctcagaccgtggtcacacaagagccca gcctgacagtttctcctggcgggcacagtgaccctgacc tgcagatcttctacaggcgccgtgaccaccagcaact acgccaattgggtgcagcagaagcctggacaggctc ccagaggactgatcggcggcacaaaattctggccc ctggcacaccagccagattctctggatctctgctcggc ggaaaggccgctctgacactgtctggtgttcagcctga ggacgaggccgagtactattgcgccctgtggtacagc aacctgtgggtgttcggcggaggtaccaagctgaccg tgctgggccaggcctctcctgctgctcctgctccagctt ctccagccgctccagctcctgctagcggatctcaggtg cagctggtggaatctggcggcggactcgtgaagcctg gcggctctctgagactgagctgtgccgccagcggctt caccttcaacacctacgccatgaactggatccggcag gcccctggcaagggcctggaatgggtgtcccggatc agaagcaagtacaacaattacgccacctactacgcc gacagcgtgaaggaccggttcaccatcagccggga caacgccaagaacagcctgtacctgcagatgaactc cctgcgggccgaggacaccgccgtgtactattgtgtg cggcacggcaacttcggcaacagctatgtgtcttggttt gcctactggggccagggcaccctcgtgacagtctcg agc |
| BsAb# Nürnberg | RefmAb#2 (IgG1f_AEASS_HC) x mAb#Nürnberg (scFv) | SEQ ID NO: 117 | QVQLVESGGGLVQPGGSLRLSCAASG FNIKDTYIHWVRQAPGKGLEWVARIYP TNGYTRYADSVKGRFTISADTSKNTAY LQMNSLRAEDTAVYYCSRWGGDGFY AMDYVVGQGTLVTVSSASTKGPSVFPL APSSKSTSGGTAALGCLVKDYFPEPVT VSWNSGALTSGVHTFPAVLQSSGLYS LSSVVTVPSSSLGTQTYICNVNHKPSN TKVDKRVEPKSCDKTHTCPPCPAPEA EGAPSVFLFPPKPKDTLMISRTPEVTC VVVDVSHEDPEVKFNWYVDGVEVHNA KTKPREEQYNSTYRVVSVLTVLHQDW LNGKEYKCKVSNKALPSSIEKTISKAKG QPREPQVYTLPPSREEMTKNQVSLTC LVKGFYPSDIAVEWESNGQPENNYKT TPPVLDSDGSFFLYSKLTVDKSRWQQ GNVFSCSVMHEALHNHYTQKSLSLSP GKASPAAPAPSAQTVVTQEPSLTVSP GGTVTLTCRSSTGAVTTSNYANWVQQ KPGQAPRGLIGGTNKRAPGTPARFSG SLLGGKAALTLSGVQPEDEAEYYCAL WYSNLWVFGGGTKLTVLGQASPAAPA PASPAAPAPASGSQVQLVESGGGLVK PGGSLRLSCAASGFTFNTYAMNWIRQ APGKGLEWVSRIRSKYNNYATYYADS VKDRFTISRDNAKNSLYLQMNSLRAED TAVYYCVRHGNFGNSYVSWFAYWGQ GTLVTVSS |
| | RefmAb#2 (IgG1f_AEASS_HC) x mAb#Nürnberg (scFv) (DNA) | SEQ ID NO: 118 | caggtgcaattggtggagtctggcggaggactggtgc agcctgggggcagcctgagactgagctgcgccgcc agcggcttcaacatcaaggacacctacatccactgg gtgcgccaggctccaggcaagggactggaatgggt ggcccggatctaccccaccaacggctacaccagata cgccgacagcgtgaagggccggttcaccatcagcg ccgacaccagcaagaacaccgcctacctgcagatg aacagcctgcgggccgaggacaccgccgtgtacta ctgcagcagatggggcggagatggcttctacgccatg gactactggggccagggcaccctggtgaccgtctcg agcgcgtcgaccaaaggcccagcgtgttccctctgg cccccagcagcaagagcacctctggcggaacagcc gcccctgggctgcctggtcaaggactacttcccgagc ccgtgaccgtgtcctggaactctggcgccctgaccag cggcgtgcacaccttccagccgtgctccagagcagc ggcctgtacagcctgagcagcgtcgtgaccgtgccc agcagcagcctgggcacccagacctacatctgcaac gtgaaccacaagcccagcaacacaaaggtggaca gcggtggaacccaagagctgcgacaagaccca cacctgtcccctgccctgccctgaagcggaggg agcccctcgtgttcctgttccccccaaagcctaagg acaccctgatgatcagccggaccccgaagtgacct |

TABLE 6-continued

Bispecific antibody sequences. Each of the listed antibodies shares the same
IgG light chain of RefmAb#2 h Igkappa (SEQ ID NO: 119/120)

| Antibody | anti-Her2 [IgG1-AEASS] x anti-CD3 [scFv] | SEQ ID NO: | [aa]/DNA |
|---|---|---|---|
| | | | gcgtggtggtggacgtgtcccacgaggaccctgaagt<br>gaagtttaattggtacgtggacggcgtggaagtgcac<br>aacgccaagaccaagcccagagaggaacagtaca<br>acagcacctaccgggtggtgtccgtgctgaccgtgct<br>gcaccaggactggctgaacggcaaagagtacaagt<br>gcaaggtgtccaacaaggccctgccttcctccatcga<br>gaaaaccatcagcaaggccaaaggccagccccgc<br>gagccccaggtgtacacactgcccctagccgggaa<br>gagatgaccaagaaccaggtgtccctgacctgcctc<br>gtgaagggcttctaccccagcgacattgccgtggaat<br>gggagagcaacggccagcccgagaacaactacaa<br>gaccaccccctgtgctggacagcgacggctcattc<br>ttcctgtacagcaagctgaccgtggacaagagccggt<br>ggcagcagggcaacgtgttcagctgctccgtgatgca<br>cgaggccctgcacaaccactacacccagaagtccct<br>gagcctgagcccggcaaggcttctcctgctgctcctg<br>ctcctagcgctcagaccgtggtcacacaagagccca<br>gcctgacagtttctcctggcggcacagtgaccctgacc<br>tgcagatcttctacaggcgccgtgaccaccagcaact<br>acgccaattgggtgcagcagaagcctggacaggctc<br>ccagaggactgatcggcggcacaaacaaaagagc<br>ccctggcacaccagccagattcagcggatcactgctc<br>ggaggaaaggccgctctgacactgtctggtgtccagc<br>ctgaagatgaggccgagtactactgcgccctgtggta<br>cagcaatctgtgggtgttcggcggaggtaccaagctg<br>accgtgctgggccaggcctctcctgctgctcctgctcc<br>agcttctccagccgctccagctcctgctagcggatctc<br>aggtgcagctggtggaatctggcggcggactcgtga<br>agcctggcggctctctgagactgagctgtgccgccag<br>cggcttcaccttcaacacctacgccatgaactggatcc<br>ggcaggcccctggcaagggcctggaatgggtgtccc<br>ggatcagaagcaagtacaacaattacgccacctact<br>acgccgacagcgtgaaggaccggttcaccatcagc<br>cgggacaacgccaagaacagcctgtacctgcagat<br>gaactccctgcgggccgaggacaccgccgtgtacta<br>ttgtgtgcggcacggcaacttcggcaacagctatgtgt<br>cttggttcgcctactggggccagggcaccctcgtgaca<br>gtctcgagc |
| IgG light chain | RefmAb#2_h_Igkappa | SEQ ID NO: 119 | DIQMTQSPSSLSASVGDRVTITCRASQ<br>DVNTAVAWYQQKPGKAPKLLIYSASFL<br>YSGVPSRFSGSRSGTDFTLTISSLQPE<br>DFATYYCQQHYTTPPTFGQGTKVEIKR<br>TVAAPSVFIFPPSDEQLKSGTASVVCLL<br>NNFYPREAKVQWKVDNALQSGNSQE<br>SVTEQDSKDSTYSLSSTLTLSKADYEK<br>HKVYACEVTHQGLSSPVTKSFNRGEC |
| | RefmAb#2_h_Igkappa (DNA) | SEQ ID NO: 120 | gatatccagatgacccagagcccagcagcctgag<br>cgccagcgtgggcgacagagtgaccatcacctgcc<br>gggccagccaggacgtgaacaccgccgtggcctgg<br>tatcagcagaagcccggcaaggcccccaagctgct<br>gatctacagcgccagcttcctgtacagcggcgtgccc<br>agccggttcagcggcagcagaagcggcaccgactt<br>caccctgaccatcagctccctgcagcccgaggacttc<br>gccacctactactgccagcagcactacaccaccccc<br>cccaccttcggccagggtaccaaagtggaaatcaag<br>cggaccgtggccgctcctccgtgttcatcttcccaccc<br>agcgacgagcagctgaagtccggcacagccagcgt<br>cgtgtgcctgctgaacaacttctaccccgcgaggcc<br>aaagtgcagtggaaggtggacaacgccctccagag<br>cggcaacagccaggaaagcgtcaccgagcaggac<br>agcaaggactccacctacagcctgagcagcaccctg<br>accctgagcaaggccgactacgagaagcacaaggt<br>gtacgcctgcgaagtgacccaccagggcctgtccag<br>ccccgtgaccaagagcttcaaccggggcgagtgt |

TABLE 7

Bispecific antibody sequences

| Antibody# | anti-CD3 [IgG1f-AEASS_HC] x anti-HER2 [scFv] | SEQ ID NO: | [aa]/DNA |
|---|---|---|---|
| BsAb# München_2 | mAb# München_2 (IgG1f_AEASS_HC) x RefmAb#2 (scFv) | SEQ ID NO: 121 | EVQLVESGGGLVKPGGSLRLSCAASG FTFNTYAMNWVRQAPGKGLEWVGRIR SKYNNYATYYADSVKDRFTISRDDSKN TLYLQMNSLKTEDTAVYYCTTHGNFG NSYVSWFAYWGQGTLVTVSSASTKGP SVFPLAPSSKSTSGGTAALGCLVKDYF PEPVTVSWNSGALTSGVHTFPAVLQS SGLYSLSSVVTVPSSSLGTQTYICNVN HKPSNTKVDKRVEPKSCDKTHTCPPC PAPEAEGAPSVFLFPPKPKDTLMISRT PEVTCVVVDVSHEDPEVKFNWYVDGV EVHNAKTKPREEQYNSTYRVVSVLTVL HQDWLNGKEYKCKVSNKALPSSIEKTI SKAKGQPREPQVYTLPPSREEMTKNQ VSLTCLVKGFYPSDIAVEWESNGQPEN NYKTTPPVLDSDGSFFLYSKLTVDKSR WQQGNVFSCSVMHEALHNHYTQKSL SLSPGKASPAAPAPSADIQMTQSPSSL SASVGDRVTITCRASQDVNTAVAWYQ QKPGKAPKLLIYSASFLYSGVPSRFSG SRSGTDFTLTISSLQPEDFATYYCQQH YTTPPTFGQGTKVEIKRTASPAAPAPA SPAAPAPASGSQVQLVESGGGLVQPG GSLRLSCAASGFNIKDTYIHWVRQAPG KGLEWVARIYPTNGYTRYADSVKGRF TISADTSKNTAYLQMNSLRAEDTAVYY CSRWGGDGFYAMDYWGQGTLVTVSS |
| | mAb# München_2 (IgG1f_AEASS_HC) x RefmAb#2 (scFv) (DNA) | SEQ ID NO: 122 | gaagtgcagctggtggaatctggcggcggactcgtg aagcctggcggctctctgagactgagctgtgccgcca gcggcttcaccttcaacacctacgccatgaactgggt gcgccaggcccctggcaaaggcctggaatgggtgg gacggatcagaagcaagtacaacaattacgccacct actacgccgacagcgtgaaggaccggttcaccatca gccgggacgacagcaagaacacccgtacctgcag atgaacagcctgaaaaccgaggacaccgccgtgta ctactgcaccacccacggcaacttcggcaacagctat gtgtcttggttttgcctactggggccagggcaccctcgtg acagtctcgagcgcgtcgaccaaaggcccccagcgt gttccctctggcccccagcagcaagagcacctctggc ggaacagccgccctgggctgcctggtcaaggactac ttcccccgagcccgtgaccgtgtcctggaactctggcgc cctgaccagcggcgtgcacacctttccagccgtgctc cagagcagcggcctgtacagcctgagcagcgtcgtg accgtgcccagcagcagcctgggcacccagaccta catctgcaacgtgaaccacaagcccagcaacacaa aggtggacaagcgggtggaacccaagagctgcga caagacccacacctgtcccccctgccctgccctgaa gcggaggggagccccctccgtgttcctgttcccccaa agcctaaggacaccctgatgatcagccggacccccg aagtgacctgcgtggtggtggacgtgtcccacgagg accctgaagtgaagtttaattggtacgtggacggcgtg gaagtgcacaacgccaagaccaagcccagagagg aacagtacaacagcacctaccgggtggtgtccgtgct gaccgtgctgcaccaggactggctgaacggcaaag agtacaagtgcaaggtgtccaacaaggccctgccttc ctccatcgagaaaaccatcagcaaggccaaaggcc agccccgcgagccccaggtgtacacactgcccccta gccgggaagagatgaccaagaaccaggtgtccctg acctgcctcgtgaagggcttctaccccagcgacattgc cgtggaatgggagagcaacggccagcccgagaac aactacaagaccacccccccctgtgctggacagcgac ggctcattcttcctgtacagcaagctgaccgtggacaa gagccggtggcagcagggcaacgtgttcagctgctc cgtgatgcacgaggccctgcacaaccactacaccca gaagtccctgagcctgagccccggcaaggcttctcct gctgctcctgctcctagcgctgacatccagatgaccca gagccctagcagcctgagcgccagcgtgggcgaca gagtgaccatcacctgtagagccagccaggacgtga acaccgccgtggcctgtatcagcagaagcctggca aggccccccaagctgctgatctacagcgccagcttcct gtacagcggcgtgcccagcagattcagcggcagca gatccggcaccgacttcacccctgaccatcagcagcct gcagccgaggacttcgccacctactactgccagca gcactacaccaccccccccacatttggccagggcac |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | caaggtggaaatcaagcggacagcctctcctgccgc<br>ccctgctcctgcttctcctgctgctccagctccagccag<br>cggatctcaggtgcagctggtggaatctggcggcgg<br>actggtgcagcctggcggatctctgagactgagctgtg<br>ccgccagcggcttcaacatcaaggacacctacatcc<br>actgggtgcgccaggcccctggaaagggactggaat<br>gggtggcagaatctaccccaccaacggctacacca<br>gatacgccgacagcgtgaagggccggttcaccatca<br>gcgccgacaccagcaagaataccgcctacctgcag<br>atgaacagcctgagagccgaggataccgccgtgtac<br>tactgctccagatggggaggcgacggcttctacgcca<br>tggactattggggccagggaaccctcgtgaccgtgtc<br>ctct |
| | mAb#<br>München<br>(h_Iglambda) | SEQ ID NO:<br>123 | QTVVTQEPSLTVSPGGTVTLTCRSSTG<br>AVTTSNYANWVQQKPGQAPRGLIGGT<br>KFLAPGTPARFSGSLLGGKAALTLLGA<br>QPEDEAEYYCALWYSNLWVFGGGTKL<br>TVLGQPKAAPSVTLFPPSSEELQANKA<br>TLVCLISDFYPGAVTVAWKADSSPVKA<br>GVETTTPSKQSNNKYAASSYLSLTPEQ<br>WKSHRSYSCQVTHEGSTVEKTVAPTE<br>CS |
| | mAb#<br>München<br>(h_Iglambda)<br>(DNA) | SEQ ID NO:<br>124 | cagaccgtggtcacacaagagcccagcctgacagtt<br>tctcctggcggcacagtgaccctgacctgcagatcttct<br>acaggcgccgtgaccaccagcaactacgccaattg<br>ggtgcagcagaagcctggacaggctcccagaggac<br>tgatcggcggcacaaaatttctggccccctggcacacc<br>agccagattctctggatctctgctcggcggaaaggcc<br>gctctgacactgcttggagcacagcctgaagatgagg<br>ccgagtactactgcgccctgtggtacagcaatctgtgg<br>gtgttcggcggaggtaccaagctgaccgtgctgggcc<br>agcccaaagccgcccctagcgtgaccctgttccccc<br>ctcgagtgaggaactccaggccaacaaggccaccc<br>tcgtgtgcctgatcagcgacttctaccctggcgccgtg<br>accgtggcctggaaggccgatagcagccctgtgaag<br>gccggcgtggaaaccaccaccccccagcaagaga<br>gcaacaacaaatacgccgccagcagctacctgagc<br>ctgaccccgagcagtggaagtcccacagatcctac<br>agctgccaggtcacacacgagggcagcaccgtgga<br>aaagaccgtggccccaccgagtgcagc |
| BsAb#<br>Bremen_2 | mAb#Bremen<br>(IgG1f_AEASS_<br>HC) x<br>RefmAb#2<br>(scFv) | SEQ ID NO:<br>125 | EVQLVESGGGLVKPGGSLRLSCAASG<br>FTFNTYAMNWVRQAPGKGLEWVGRIR<br>SKYNNYATYYADSVKDRFTISRDDSKN<br>TLYLQMNSLKTEDTAVYYCTTHGNFG<br>NSYVSWFAYWGQGTLVTVSSASTKGP<br>SVFPLAPSSKSTSGGTAALGCLVKDYF<br>PEPVTVSWNSGALTSGVHTFPAVLQS<br>SGLYSLSSVVTVPSSSLGTQTYICNVN<br>HKPSNTKVDKRVEPKSCDKTHTCPPC<br>PAPEAEGAPSVFLFPPKPKDTLMISRT<br>PEVTCVVVDVSHEDPEVKFNWYVDGV<br>EVHNAKTKPREEQYNSTYRVVSVLTVL<br>HQDWLNGKEYKCKVSNKALPSSIEKTI<br>SKAKGQPREPQVYTLPPSREEMTKNQ<br>VSLTCLVKGFYPSDIAVEWESNGQPEN<br>NYKTTPPVLDSDGSFFLYSKLTVDKSR<br>WQQGNVFSCSVMHEALHNHYTQKSL<br>SLSPGKASPAAPAPSADIQMTQSPSSL<br>SASVGDRVTITCRASQDVNTAVAWYQ<br>QKPGKAPKLLIYSASFLYSGVPSRFSG<br>SRSGTDFTLTISSLQPEDFATYYCQQH<br>YTTPPTFGQGTKVEIKRTASPAAPAPA<br>SPAAPAPASGSQVQLVESGGGLVQPG<br>GSLRLSCAASGFNIKDTYIHWVRQAPG<br>KGLEWVARIYPINGYTRYADSVKGRF<br>TISADTSKNTAYLQMNSLRAEDTAVYY<br>CSRWGGDGFYAMDYWGQGTLVTVSS |
| | mAb#Bremen<br>(IgG1f_AEASS_<br>HC) x<br>RefmAb#2<br>(scFv) | SEQ ID NO:<br>126 | gaagtgcagctggtggaatctggcggcggactcgtg<br>aagcctggcggctctctgagactgagctgtgccgcca<br>gcggcttcaccttcaacacctacgccatgaactgggt<br>gcgccaggcccctggcaaaggcctggaatgggtgg<br>gacggatcagaagcaagtacaacaattacgccacct<br>actacgccgacagcgtgaaggaccggttcaccatca |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | gccgggacgacagcaagaacaccctgtacctgcag<br>atgaacagcctgaaaaccgaggacaccgccgtgta<br>ctactgcaccacccacggcaacttcggcaacagctat<br>gtgtcttggttttgcctactggggccagggcaccctcgtg<br>acagtctcgagcgcgtcgaccaaaggcccccagcgt<br>gttccctctggccccccagcagcaagagcacctctggc<br>ggaacagccgccctgggctgcctggtcaaggactac<br>ttccccgagcccgtgaccgtgtcctggaactctggcgc<br>cctgaccagcggcgtgcacaccttccagccgtgctc<br>cagagcagcggcctgtacagcctgagcagcgtcgtg<br>accgtgcccagcagcagcctgggcacccagaccta<br>catctgcaacgtgaaccacaagcccagcaacacaa<br>aggtggacaagcgggtggaacccaagagctgcga<br>caagacccacacctgtcccccctgccctgccctgaa<br>gcggagggagcccctccgtgttcctgttccccccaa<br>agcctaaggacaccctgatgatcagccggacccccg<br>aagtgacctgcgtggtggtggacgtgtcccacgagg<br>accctgaagtgaagtttaattggtacgtggacggcgtg<br>gaagtgcacaacgccaagaccaagcccagagagg<br>aacagtacaacagcacctaccgggtggtgtccgtgct<br>gaccgtgctgcaccaggactggctgaacggcaaag<br>agtacaagtgcaaggtgtccaacaaggccctgccttc<br>ctccatcgagaaaaccatcagcaaggccaaaggcc<br>agccccgcgagcccaggtgtacacactgccccta<br>gcggggaagagatgaccaagaaccaggtgtccctg<br>acctgcctcgtgaagggcttctaccccagcgacattgc<br>cgtggaatgggagagcaacggccagcccgagaac<br>aactacaagaccaccccccctgtgctggacagcgac<br>ggctcattcttcctgtacagcaagctgaccgtggacaa<br>gagccggtggcagcagggcaacgtgttcagctgctc<br>cgtgatgcacgaggccctgcacaaccactacaccca<br>gaagtccctgagcctgagccccggcaaggcttctcct<br>gctgctcctgctcctagcgctgacatccagatgaccca<br>gagccctagcagcctgagcgccagcgtgggcgaca<br>gagtgaccatcacctgtagagccagccaggacgtga<br>acaccgccgtggcctggtatcagcagaagcctggca<br>aggcccccaagctgctgatctacagcgccagcttcct<br>gtacagcggcgtgcccagcagattcagcggcagca<br>gatccggcaccgacttcaccctgaccatcagcagcct<br>gcagcccgaggacttcgccacctactactgccagca<br>gcactacaccacccccccacatttggccagggcac<br>caaggtggaaatcaagcggacagcctctcctgccgc<br>ccctgctcctgcttctcctgctgctccagctccagccag<br>cggatctcaggtgcagctggtggaatctggcggcgg<br>actggtgcagcctggcggatctctgagactgagctgtg<br>ccgccagcggcttcaacatcaaggacacctacatcc<br>actgggtgcgccaggcccctggaaagggactggaat<br>gggtggccagaatctaccccaccaacggctacacca<br>gatacgccgacagcgtgaagggccggttcaccatca<br>gcgccgacaccagcaagaataccgcctacctgcag<br>atgaacagcctgagagccgaggataccgccgtgtac<br>tactgctccagatgggggaggcgacggcttctacgcca<br>tggactattggggccagggaaccctcgtgaccgtgtc<br>ctct |
| | mAb#Bremen<br>(h_Iglambda) | SEQ ID NO: 127 | QTVVTQEPSLTVSPGGTVTLTCRSSTG<br>AVTTSNYANWVQQKPGQAPRGLIGGT<br>KFLAPGTPARFSGSLLGGKAALTLSGV<br>QPEDEAEYYCALWYSNLWVFGGGTKL<br>TVLGQPKAAPSVTLFPPSSEELQANKA<br>TLVCLISDFYPGAVTVAWKADSSPVKA<br>GVETTTPSKQSNNKYAASSYLSLTPEQ<br>WKSHRSYSCQVTHEGSTVEKTVAPTE<br>CS |
| | mAb#Bremen<br>(h_Iglambda) | SEQ ID NO: 128 | cagaccgtggtcacacaagagcccagcctgacagtt<br>tctcctggcggcacagtgaccctgacctgcagatcttct<br>acaggcgccgtgaccaccagcaactacgccaattg<br>ggtgcagcagaagcctggacaggctcccagaggac<br>tgatcggcggcacaaaatttctggccctggcacacc<br>agccagattctctggatctctgctcggcggaaaggcc<br>gctctgacactgtctggtgttcagcctgaggacgaggc<br>cgagtactattgcgccctgtggtacagcaacctgtggg<br>tgttcggcggaggtaccaagctgaccgtgctgggcca<br>gcccaaagccgcccctagcgtgaccctgttccccccc<br>tcgagtgaggaactccaggccaacaaggccaccct |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | cgtgtgcctgatcagcgacttctaccctggcgccgtga<br>ccgtggcctggaaggccgatagcagccctgtgaagg<br>ccggcgtggaaaccaccaccccccagcaagcagag<br>caacaacaaatacgccgccagcagctacctgagcct<br>gaccccccgagcagtggaagtcccacagatcctaca<br>gctgccaggtcacacacgagggcagcaccgtggaa<br>aagaccgtggccccccaccgagtgcagc |
| BsAb#<br>Mainz_2 | mAb#Mainz<br>(IgG1f_AEASS_<br>HC) x<br>RefmAb#2<br>(scFv) | SEQ ID NO:<br>129 | QVQLVESGGGLVKPGGSLRLSCAASG<br>FTFNTYAMNWIRQAPGKGLEWVSRIR<br>SKYNNYATYYADSVKDRFTISRDNAKN<br>SLYLQMNSLRAEDTAVYYCVRHGNFG<br>NSYVSWFAYWGQGTLVTVSSASTKGP<br>SVFPLAPSSKSTSGGTAALGCLVKDYF<br>PEPVTVSWNSGALTSGVHTFPAVLQS<br>SGLYSLSSVVTVPSSSLGTQTYICNVN<br>HKPSNTKVDKRVEPKSCDKTHTCPPC<br>PAPEAEGAPSVFLFPPKPKDTLMISRT<br>PEVTCVVVDVSHEDPEVKFNWYVDGV<br>EVHNAKTKPREEQYNSTYRVVSVLTVL<br>HQDWLNGKEYKCKVSNKALPSSIEKTI<br>SKAKGQPREPQVYTLPPSREEMTKNQ<br>VSLTCLVKGFYPSDIAVEWESNGQPEN<br>NYKTTPPVLDSDGSFFLYSKLTVDKSR<br>WQQGNVFSCSVMHEALHNHYTQKSL<br>SLSPGKASPAAPAPSADIQMTQSPSSL<br>SASVGDRVTITCRASQDVNTAVAWYQ<br>QKPGKAPKLLIYSASFLYSGVPSRFSG<br>SRSGTDFTLTISSLQPEDFATYYCQQH<br>YTTPPTFGQGTKVEIKRTASPAAPAPA<br>SPAAPAPASGSQVQLVESGGGLVQPG<br>GSLRLSCAASGFNIKDTYIHWVRQAPG<br>KGLEWVARIYPTNGYTRYADSVKGRF<br>TISADTSKNTAYLQMNSLRAEDTAVYY<br>CSRWGGDGFYAMDYWGQGTLVTVSS |
| | mAb#Mainz<br>(IgG1f_AEASS_<br>HC) x<br>RefmAb#2<br>(scFv) (DNA) | SEQ ID NO:<br>130 | caggtgcagctggtggaatctggcggcggactcgtg<br>aagcctggcggctctctgagactgagctgtgccgcca<br>gcggcttcaccttcaacacctacgccatgaactggatc<br>cggcaggcccctggcaagggcctggaatgggtgtcc<br>cggatcagaagcaagtacaacaattacgccacctac<br>tacgccgacagcgtgaaggaccggttcaccatcagc<br>cgggacaacgccaagaacagcctgtacctgcagat<br>gaactccctgcgggccgaggacaccgccgtgtacta<br>ttgtgtgcggcacggcaacttcggcaacagctatgtgt<br>cttggtttgcctactggggccagggcaccctcgtgaca<br>gtctcgagcgcgtcgaccaaaggcccagcgtgttcc<br>ctctggcccccagcagcaagagcacctctggcggaa<br>cagccgccctgggctgcctggtcaaggactacttccc<br>cgagcccgtgaccgtgtcctggaactctggcgccctg<br>accagcggcgtgcacacctttccagccgtgctccaga<br>gcagcggcctgtacagcctgagcagcgtcgtgaccg<br>tgcccagcagcagcctgggcacccagacctacatct<br>gcaacgtgaaccacaagcccagcaacacaaaggt<br>ggacaagcgggtggaacccaagagctgcgacaag<br>acccacacctgtccccctgccctgcccctgaagcgg<br>agggagccccctccgtgttcctgttccccccaaagcct<br>aaggacaccctgatgatcagccggacccccgaagt<br>gacctgcgtggtggtggacgtgtcccacgaggaccct<br>gaagtgaagtttaattggtacgtggacggcgtggaag<br>tgcacaacgccaagaccaagcccagagaggaaca<br>gtacaacagcacctacggggtggtgtccgtgctgacc<br>gtgctgcaccaggactggctgaacggcaaagagtac<br>aagtgcaaggtgtccaacaaggccctgccttcctcca<br>tcgagaaaaccatcagcaaggccaaaggccagcc<br>ccgcgagccccaggtgtacacactgcccccctagccg<br>ggaagagatgaccaagaaccaggtgtccctgacctg<br>cctcgtgaagggcttctaccccagcgacattgccgtg<br>gaatgggagagcaacggccagcccgagaacaact<br>acaagaccacccccccctgtgctggacagcgacggct<br>cattcttcctgtacagcaagctgaccgtggacaagag<br>ccggtggcagcagggcaacgtgttcagctgctccgtg<br>atgcacgaggccctgcacaaccactacacccagaa<br>gtccctgagcctgagccccggcaaggcttctcctgctg<br>ctcctgctcctagcgctgacatccagatgacccagag |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | ccctagcagcctgagcgccagcgtgggcgacagag<br>tgaccatcacctgtagagccagccaggacgtgaaca<br>ccgccgtggcctggtatcagcagaagcctggcaagg<br>cccccaagctgctgatctacagcgccagcttcctgtac<br>agcggcgtgcccagcagattcagcggcagcagatc<br>cggcaccgacttcaccctgaccatcagcagcctgca<br>gcccgaggacttcgccacctactactgccagcagca<br>ctacaccacccccccacatttggccagggcaccaa<br>ggtggaaatcaagcggacagcctctcctgccgcccct<br>gctcctgcttctcctgctgctccagctccagccagcgg<br>atctcaggtgcagctggtggaatctggcggcggactg<br>gtgcagcctggcggatctctgagactgagctgtgccg<br>ccagcggcttcaacatcaaggacacctacatccactg<br>ggtgcgccaggcccctggaaagggactggaatggg<br>tggcagaatctaccccaccaacggctacaccagat<br>acgccgacagcgtgaagggccggttcaccatcagc<br>cgcgacaccagcaagaataccgcctacctgcagat<br>gaacagcctgagagccgaggataccgccgtgtacta<br>ctgctccagatggggaggcgacggcttctacgccatg<br>gactattggggccagggaaccctcgtgaccgtgtcct<br>ct |
| | mAb#Mainz (h_Iglambda_LC) | SEQ ID NO: 131 | QAVVTQEPSLTVSPGGTVTLTCRSSTG<br>AVTTSNYANWVQQKPGQAPRGLIGGT<br>NKRAPWTPARFSGSLLGGKAALTITGA<br>QAEDEADYYCALWYSNLWVFGGGTKL<br>TVLGQPKAAPSVTLFPPSSEELQANKA<br>TLVCLISDFYPGAVTVAWKADSSPVKA<br>GVETTTPSKQSNNKYAASSYLSLTPEQ<br>WKSHRSYSCQVTHEGSTVEKTVAPTE<br>CS |
| | mAb#Mainz (h_Iglambda_LC) | SEQ ID NO: 132 | caggccgtggttacacaagagcccagcctgacagtt<br>agccctggcggaacagtgaccctgacctgcagatctt<br>ctacaggcgccgtgaccaccagcaactacgccaatt<br>gggtgcagcagaagcctggacaggctcccagagga<br>ctgatcggcggcacaaacaaaagagccccttggac<br>acccgccagattcagcggatcactgctcggaggaaa<br>ggccgcactgacaatcacaggtgcccaggccgaag<br>atgaggccgattactattgcgccctgtggtacagcaac<br>ctgtgggtgttcggcggaggtaccaagctgaccgtgct<br>gggccagcccaaagccgcccctagcgtgaccctgtt<br>ccccccctcgagtgaggaactccaggccaacaagg<br>ccaccctcgtgtgcctgatcagcgacttctaccctggc<br>gccgtgaccgtggcctggaaggccgatagcagccct<br>gtgaaggccggcgtggaaaccaccaccccccagca<br>agcagagcaacaacaaatacgccgccagcagcta<br>cctgagcctgaccccgagcagtggaagtcccacag<br>atcctacagctgccaggtcacacacgagggcagca<br>ccgtggaaaagaccgtggcccccaccgagtgcagc |
| BsAb# Köln_2 | mAb#Köln (IgG1f_AEASS_HC) x RefmAb#2 (scFv) | SEQ ID NO: 133 | QVQLVESGGGLVKPGGSLRLSCAASG<br>FTFNTYAMNWIRQAPGKGLEWVSRIR<br>SKYNNYATYYADSVKDRFTISRDNAKN<br>SLYLQMNSLRAEDTAVYYCVRHGNFG<br>NSYVSWFAYWGQGTLVTVSSASTKGP<br>SVFPLAPSSKSTSGGTAALGCLVKDYF<br>PEPVTVSWNSGALTSGVHTFPAVLQS<br>SGLYSLSSVVTVPSSSLGTQTYICNVN<br>HKPSNTKVDKRVEPKSCDKTHTCPPC<br>PAPEAEGAPSVFLFPPKPKDTLMISRT<br>PEVTCVVVDVSHEDPEVKFNWYVDGV<br>EVHNAKTKPREEQYNSTYRVVSVLTVL<br>HQDWLNGKEYKCKVSNKALPSSIEKTI<br>SKAKGQPREPQVYTLPPSREEMTKNQ<br>VSLTCLVKGFYPSDIAVEWESNGQPEN<br>NYKTTPPVLDSDGSFFLYSKLTVDKSR<br>WQQGNVFSCSVMHEALHNHYTQKSL<br>SLSPGKASPAAPAPSADIQMTQSPSSL<br>SASVGDRVTITCRASQDVNTAVAWYQ<br>QKPGKAPKLLIYSASFLYSGVPSRFSG<br>SRSGTDFTLTISSLQPEDFATYYCQQH<br>YTTPPTFGQGTKVEIKRTASPAAPAPA<br>SPAAPAPASGSQVQLVESGGGLVQPG<br>GSLRLSCAASGFNIKDTYIHWVRQAPG<br>KGLEWVARIYPTNGYTRYADSVKGRF |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | mAb#Köln (IgG1f_AEASS_HC) x RefmAb#2 (scFv) (DNA) | SEQ ID NO: 134 | TISADTSKNTAYLQMNSLRAEDTAVYY CSRWGGDGFYAMDYWGQGTLVTVSS caggtgcagctggtggaatctggcggcggactcgtg aagcctggcggctctctgagactgagctgtgccgcca gcggcttcaccttcaacacctacgccatgaactggatc cggcaggcccctggcaagggcctggaatgggtgtcc cggatcagaagcaagtacaacaattacgccaccctac tacgccgacagcgtgaaggaccggttcaccatcagc cgggacaacgccaagaacagcctgtacctgcagat gaactccctgcgggccgaggacaccgccgtgtacta ttgtgtgcggcacggcaacttcggcaacagctatgtgt cttggtttgcctactggggccagggcaccctcgtgaca gtctcgagcgcgtcgaccaaaggcccagcgtgttcc ctctggcccccagcagcaagagcacctctggcgga a cagccgccctgggctgcctggtcaaggactacttccc cgagcccgtgaccgtgtcctggaactctggcgccctg accagcggcgtgcacacctttccagccgtgctccaga gcagcggcctgtacagcctgagcagcgtcgtgaccg tgcccagcagcagcctgggcacccagacctacatct gcaacgtgaaccacaagcccagcaacacaaaggt ggacaagcgggtggaacccaagagctgcgacaag acccacacctgtcccccctgccctgcccctgaagcgg agggagccccctccgtgttcctgttccccccaaagcct aaggacacccctgatgatcagccggacccccgaagt gacctgcgtggtggtggacgtgtcccacgaggaccct gaagtgaagtttaattggtacgtggacggcgtggaag tgcacaacgccaagaccaagcccagagaggaaca gtacaacagcaccctacccgggtggtgtccgtgctgacc gtgctgcaccaggactggctgaacggcaaagagtac aagtgcaaggtgtccaacaaggccctgccttcctcca tcgagaaaaccatcagcaaggccaaaggccagcc ccgcgagccccaggtgtacacactgcccccctagccg ggaagagatgaccaagaaccaggtgtccctgacctg cctcgtgaagggcttctacccagccacattgccgtg aatgggagagcaacggccagcccgagaacaact acaagaccacccccccctgtgctggacagcgacggct cattcttcctgtacagcaagctgaccgtggacaagag ccggtggcagcagggcaacgtgttcagctgctccgtg atgcacgaggcccctgcacaaccactacacccagaa gtccctgagcctgagccccggcaaggcttctcctgctg ctcctgctcctagcgctgacatccagatgacccagag ccctagcagcctgagcgccagcgtgggcgacagag tgaccatcacctgtagagccagccaggacgtgaaca ccgccgtggcctggtatcagcagaagcctggcaagg cccccaagctgctgatctacagcgccagcttcctgtac agcggcgtgcccagcagattcagcggcagcagatc cggcaccgacttcaccctgaccatcagcagcctgca gcccgaggacttcgccacctactactgccagcagca ctacaccacccccccacatttggccagggcaccaa ggtggaaatcaagcggacagcctctcctgccgcccct gctcctgcttctcctgctgctccagctccagccagcgg atctcaggtgcagctggtggaatctggcggcggactg gtgcagcctggcggatctctgagactgagctgtgcc c cagcggcttcaacatcaaggacacctacatccactg ggtgcgccaggcccctggaaagggactggaatggg tggccagaatctacccccaccaacggctacaccagat acgccgacagcgtgaagggccggttcaccatcagc gccgacaccagcaagaataccgcctacctgcagat gaacagcctgagagccgaggataccgccgtgtacta ctgctccagatggggaggcgacggcttctacgccatg gactattggggccagggaaccctcgtgaccgtgtcct ct |
| | mAb#Köln (h_Iglambda_LC) | SEQ ID NO: 135 | ELVVTQEPSLTVSPGGTVTLTCRSSTG AVTTSNYANWVQQKPGQAPRGLIGGT NKRAPGTPARFSGSLLGGKAALTLSGV QPEDEAEYYCALWYSNLWVFGGGTKL TVLGQPKAAPSVTLFPPSSEELQANKA TLVCLISDFYPGAVTVAWKADSSPVKA GVETTTPSKQSNNKYAASSYLSLTPEQ WKSHRSYSCQVTHEGSTVEKTVAPTE CS |
| | mAb#Köln (h_Iglambda_LC) (DNA) | SEQ ID NO: 136 | gagctggtggtcacacaagagcccagcctgacagttt ctcctggcggcacagtgaccctgacctgcagatcttct acaggcgccgtgaccacctccaactacgccaattgg |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | gtgcagcagaagcctggacaggctcccagaggact<br>gatcggcggcacaaacaaaagagcccctggcaca<br>ccagccagattcagcggatcactgctcggaggaaag<br>gccgctctgacactgtctggtgtccagcctgaagatga<br>ggccgagtactactgcgccctgtggtacagcaatctgt<br>gggtgttcggcggaggtaccaagctgaccgtgctgg<br>gccagcccaaagccgcccctagcgtgaccctgttcc<br>cccctcgagtgaggaactccaggccaacaaggcc<br>accctcgtgtgcctgatcagcgacttctaccctggcgc<br>cgtgaccgtggcctggaaggccgatagcagccctgt<br>gaaggccggcgtggaaaccaccaccccccagcaag<br>cagagcaacaacaaatacgccgccagcagctacct<br>gagcctgacccccgagcagtggaagtcccacagat<br>cctacagctgccaggtcacacacgagggcagcacc<br>gtggaaaagaccgtggccccaccgagtgcagc |
| BsAb# Gladbach_2 | mAb#Gladbach (IgG1f_AEASS_HC) x RefmAb#2 (scFv) | SEQ ID NO: 137 | QVQLVESGGGLVKPGGSLRLSCAASG<br>FTFNTYAMNWIRQAPGKGLEWVSRIR<br>SKYNNYATYYADSVKDRFTISRDNAKN<br>SLYLQMNSLRAEDTAVYYCVRHGNFG<br>NSYVSWFAYWGQGTLVTVSSASTKGP<br>SVFPLAPSSKSTSGGTAALGCLVKDYF<br>PEPVTVSWNSGALTSGVHTFPAVLQS<br>SGLYSLSSVVTVPSSSLGTQTYICNVN<br>HKPSNTKVDKRVEPKSCDKTHTCPPC<br>PAPEAEGAPSVFLFPPKPKDTLMISRT<br>PEVTCVVVDVSHEDPEVKFNWYVDGV<br>EVHNAKTKPREEQYNSTYRVVSVLTVL<br>HQDWLNGKEYKCKVSNKALPSSIEKTI<br>SKAKGQPREPQVYTLPPSREEMTKNQ<br>VSLTCLVKGFYPSDIAVEWESNGQPEN<br>NYKTTPPVLDSDGSFFLYSKLTVDKSR<br>WQQGNVFSCSVMHEALHNHYTQKSL<br>SLSPGKASPAAPAPSADIQMTQSPSSL<br>SASVGDRVTITCRASQDVNTAVAWYQ<br>QKPGKAPKLLIYSASFLYSGVPSRFSG<br>SRSGTDFTLTISSLQPEDFATYYCQQH<br>YTTPPTFGQGTKVEIKRTASPAAPAPA<br>SPAAPAPASGSQVQLVESGGGLVQPG<br>GSLRLSCAASGFNIKDTYIHWVRQAPG<br>KGLEWVARIYPTNGYTRYADSVKGRF<br>TISADTSKNTAYLQMNSLRAEDTAVYY<br>CSRWGGDGFYAMDYWGQGTLVTVSS |
| | mAb#Gladbach (IgG1f_AEASS_HC) x RefmAb#2 (scFv) | SEQ ID NO: 138 | caggtgcagctggtggaatctggcggcggactcgtg<br>aagcctggcggctctctgagactgagctgtgccgcca<br>gcggcttcaccttcaacacctacgccatgaactggatc<br>cggcaggcccctggcaagggcctggaatgggtgtcc<br>cggatcagaagcaagtacaacaattacgccacctac<br>tacgccgacagcgtgaaggaccggttcaccatcagc<br>cgggacaacgccaagaacagcctgtacctgcagat<br>gaactccctgcgggccgaggacaccgccgtgtacta<br>ttgtgtgcggcacggcaacttcggcaacagctatgtgt<br>cttggtttgcctactggggccagggcaccctcgtgaca<br>gtctcgagcgcgtcgaccaaaggcccagcgtgttcc<br>ctctggccccagcagcaagagcacctctggcggaa<br>cagccgccctgggctgcctggtcaaggactacttccc<br>cgagcccgtgaccgtgtcctggaactctggcgccctg<br>accagcggcgtgcacacctttccagccgtgctccaga<br>gcagcggcctatacagcctgagcagcgtcgtgaccg<br>tgcccagcagcagcctgggcacccagacctacatct<br>gcaacgtgaaccacaagcccagcaacacaaaggt<br>ggacaagcgggtggaacccaagagctgcgacaag<br>acccacacctgtcccccctgccctgcccctgaagcgg<br>agggagccccctccgtgttcctgttccccccaaagcct<br>aaggacaccctgatgatcagccggaccccccgaagt<br>gacctgcgtggtggtggacgtgtcccacgaggaccct<br>gaagtgaagtttaattggtacgtggacggcgtggaag<br>tgcacaacgccaagaccaagcccagagaggaaca<br>gtacaacagcacctaccgggtggtgtccgtgctgacc<br>gtgctgcaccaggactggctgaacggcaaagagtac<br>aagtgcaaggtgtccaacaaggccctgccttcctcca<br>tcgagaaaaccatcagcaaggccaaaggccagcc<br>ccgcgagccccaggtgtacacactgcccctagccg<br>ggaagagatgaccaagaaccaggtgtccctgacctg |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | cctcgtgaagggcttctaccccagcgacattgccgtg gaatgggagagcaacggccagcccgagaacaact acaagaccaccccccctgtgctggacagcgacggct cattcttcctgtacagcaagctgaccgtggacaagag ccggtggcagcagggcaacgtgttcagctgctccgtg atgcacgaggccctgcacaaccactacacccagaa gtccctgagcctgagccccggcaaggcttctcctgctg ctcctgctcctagcgctgacatccagatgacccagag ccctagcagcctgagcgccagcgtgggcgacagag tgaccatcacctgtagagccagccaggacgtgaaca ccgccgtggcctggtatcagcagaagcctggcaagg cccccaagctgctgatctacagcgccagcttcctgtac agcggcgtgcccagcagattcagcggcagcagatc cggcaccgacttcaccctgaccatcagcagcctgca gcccgaggacttcgccacctactactgccagcagca ctacaccaccccccccacatttggccagggcaccaa ggtggaaatcaagcggacagcctctcctgccgcccct gctcctgcttctcctgctgctccagctccagccagcgg atctcaggtgcagctggtggaatctggcggcggactg gtgcagcctggcggatctctgagactgagcgtgcg ccagcggcttcaacatcaaggacacctacatccactg ggtgcgccaggcccctggaaagggactggaatggg tggcagaatctaccccaccaacggctacaccagat acgccgacagcgtgaagggccggttcaccatcagc gccgacaccagcaagaataccgcctacctgcagat gaacagcctgagagccgaggataccgccgtgtacta ctgctccagatggggaggcgacggcttctacgccatg gactattggggccagggaaccctcgtgaccgtgtcct ct |
| | mAb# Gladbach (h_Iglambda_LC) | SEQ ID NO: 139 | QTVVTQEPSLTVSPGGTVTLICRSSTG AVTTSNYANWVQQKPGQAPRGLIGGT KFLAPGTPARFSGSLLGGKAALTLSGV QPEDEAEYYCALWYSNLWVFGGGTKL TVLGQPKAAPSVTLFPPSSEELQANKA TLVCLISDFYPGAVTVAWKADSSPVKA GVETTTPSKQSNNKYAASSYLSLTPEQ WKSHRSYSCQVTHEGSTVEKTVAPTE CS |
| | mAb# Gladbach (h_Iglambda_LC) | SEQ ID NO: 140 | cagaccgtggtcacacaagagcccagcctgacagtt tctcctggcggcacagtgaccctgacctgcagatcttct acaggcgccgtgaccaccagcaactacgccaattg ggtgcagcagaagcctggacaggctcccagaggac tgatcggcggcacaaaatttctggcccctggcacacc agccagattctctggatctctgctcggcggaaaggcc gctctgacactgtctggtgttcagcctgaggacgaggc cgagtactattgcgccctgtggtacagcaacctgtggg tgttcggcggaggtaccaagctgaccgtgctgggcca gcccaaagccgccccagcgtgaccctgttccccc tcgagtgaggaactccaggccaacaaggccaccct cgtgtgcctgatcagcgacttctaccctggcgccgtga ccgtggcctggaaggccgatagcagccctgtgaagg ccggcgtggaaaccaccccccagcaagcagag caacaacaaatacgccgccagcagctacctgagcct gacccccgagcagtggaagtcccacagatcctaca gctgccaggtcacacgagggcagcaccgtggaa aagaccgtggccccaccgagtgcagc |
| BsAb# Nürnberg_2 | mAb# Nürnberg (IgG1f_AEASS_HC) x RefmAb#2 (scFv) | SEQ ID NO: 141 | QVQLVESGGGLVKPGGSLRLSCAASG FTFNTYAMNWIRQAPGKGLEWVSRIR SKYNNYATYYADSVKDRFTISRDNAKN SLYLQMNSLRAEDTAVYYCVRHGNFG NSYVSWFAYWGQGTLVTVSSASTKGP SVFPLAPSSKSTSGGTAALGCLVKDYF PEPVTVSWNSGALTSGVHTFPAVLQS SGLYSLSSVVTVPSSSLGTQTYICNVN HKPSNTKVDKRVEPKSCDKTHTCPPC PAPEAEGAPSVFLFPPKPKDTLMISRT PEVTCVVVDVSHEDPEVKFNWYVDGV EVHNAKTKPREEQYNSTYRVVSVLTVL HQDWLNGKEYKCKVSNKALPSSIEKTI SKAKGQPREPQVYTLPPSREEMTKNQ VSLTCLVKGFYPSDIAVEWESNGQPEN NYKTTPPVLDSDGSFFLYSKLTVDKSR WQQGNVFSCSVMHEALHNHYTQKSL |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | SLSPGKASPAAPAPSADIQMTQSPSSL<br>SASVGDRVTITCRASQDVNTAVAWYQ<br>QKPGKAPKLLIYSASFLYSGVPSRFSG<br>SRSGTDFTLTISSLQPEDFATYYCQQH<br>YTTPPTFGQGTKVEIKRTASPAAPAPA<br>SPAAPAPASGSQVQLVESGGGLVQPG<br>GSLRLSCAASGFNIKDTYIHWVRQAPG<br>KGLEWVARIYPTNGYTRYADSVKGRF<br>TISADTSKNTAYLQMNSLRAEDTAVYY<br>CSRWGGDGFYAMDYWGQGTLVTVSS |
| | mAb#<br>Nürnberg<br>(IgG1f_AEASS_<br>HC) x<br>RefmAb#2<br>(scFv) | SEQ ID NO:<br>142 | caggtgcagctggtggaatctggcggcggactcgtg<br>aagcctggcggctctctgagactgagctgtgccgcca<br>gcggcttcaccttcaacacctacgccatgaactggatc<br>cggcaggcccctggcaagggcctggaatgggtgtcc<br>cggatcagaagcaagtacaacaattacgccaccctac<br>tacgccgacagcgtgaaggaccggttcaccatcagc<br>cgggacaacgccaagaacagcctgtacctgcagat<br>gaactccctgcgggccgaggacaccgccgtgtacta<br>ttgtgtgcggcacggcaacttcggcaacagctatgtgt<br>cttggtttgcctactggggccagggcaccctcgtgaca<br>gtctcgagcgcgtcgaccaaaggcccagcgtgttcc<br>ctctggccccagcagcaagagcacctctggcggaa<br>cagccgcctgggctgcctggtcaaggactacttccc<br>cgagcccgtgaccgtgtcctggaactctggcgccctg<br>accagcggcgtgcacacctttccagccgtgctccaga<br>gcagcggcctgtacagcctgagcagcgtcgtgaccg<br>tgcccagcagcagcctgggcacccagacctacatct<br>gcaacgtgaaccacaagcccagcaacacaaaggt<br>ggacaagcgggtggaacccaagagctgcgacaag<br>acccacacctgtcccccctgccctgccctgaagcgg<br>agggagcccctccgtgttcctgttcccccaaagcct<br>aaggacaccctgatgatcagccggacccccgaagt<br>gacctgcgtggtggtggacgtgtcccacgaggaccct<br>gaagtgaagtttaattggtacgtggacggcgtggaag<br>tgcacaacgccaagaccaagcccagagaggaaca<br>gtacaacagcacctaccgggtggtgtccgtgctgacc<br>gtgctgcaccaggactggctgaacggcaaagagtac<br>aagtgcaaggtgtccaacaaggccctgccttcctcca<br>tcgagaaaaccatcagcaaggccaaaggccagcc<br>ccgcgagccccaggtgtacacactgcccctagccg<br>ggaagagatgaccaagaaccaggtgtccctgacctg<br>cctcgtgaagggcttctaccccagcgacattgccgtg<br>gaatgggagagcaacggccagcccgagaacaact<br>acaagaccacccccccgtgctggacagcgacggct<br>cattcttcctgtacagcaagctgaccgtggacaagag<br>ccggtggcagcagggcaacgtgttcagctgctccgtg<br>atgcacgaggcccgcacaaccactacacccagaa<br>gtccctgagcctgagccccggcaaggcttctcctgctg<br>ctcctgctcctagcgctgacatccagatgacccagag<br>ccctagcagcctgagcgccagcgtgggcgacagag<br>tgaccatcacctgtagagccagccaggacgtgaaca<br>ccgccgtggcctggtatcagcagaagcctggcaagg<br>cccccaagctgctgatctacagcgccagcttcctgtac<br>agcggcgtgcccagcagattcagcggcagcagatc<br>cggcaccgacttcaccctgaccatcagcagcctgca<br>gcccgaggacttcgccacctactactgccagcagca<br>ctacaccacccccccacatttggccagggcaccaa<br>ggtggaaatcaagcggacagcctctcctgccgccct<br>gctcctgcttctcctgctgctccagctccagccagcgg<br>atctcaggtgcagctggtggaatctggcggcggactg<br>gtgcagcctggcggatctctgagactgagctgtgccg<br>ccagcggcttcaacatcaaggacacctacatccactg<br>ggtgcgccaggcccctggaaagggactggaatggg<br>tggccagaatctaccccaccaacggctacaccagat<br>acgccgacagcgtgaagggccggttcaccatcagc<br>gccgacaccagcaagaataccgcctacctgcagat<br>gaacagcctgagagccgaggataccgccgtgtacta<br>ctgctccagatggggaggcgacggcttctacgccatg<br>gactattggggccagggaaccctcgtgaccgtgtcct<br>ct |
| | mAb#<br>Nürnberg<br>(h_Iglambda_<br>LC) | SEQ ID NO:<br>143 | QTVVTQEPSLTVSPGGTVTLTCRSSTG<br>AVTTSNYANWVQQKPGQAPRGLIGGT<br>NKRAPGTPARFSGSLLGGKAALTLSGV<br>QPEDEAEYYCALWYSNLWVFGGGTKL |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | TVLGQPKAAPSVTLFPPSSEELQANKA TLVCLISDFYPGAVTVAWKADSSPVKA GVETTTPSKQSNNKYAASSYLSLTPEQ WKSHRSYSCQVTHEGSTVEKTVAPTE CS |
| | | SEQ ID NO: 144 | cagaccgtggtcacacaagagcccagcctgacagtt tctcctggcggcacagtgacccctgacctgcagatcttct acaggcgccgtgaccaccagcaactacgccaattg ggtgcagcagaagcctggacaggctcccagaggac tgatcggcggcacaaacaaaagagcccctggcaca ccagccagattcagcggatcactgctcggaggaaag gccgctctgacactgtctggtgtccagcctgaagatga ggccgagtactactgcgcccctgtggtacagcaatctgt gggtgttcggcggaggtaccaagctgaccgtgctgg gccagcccaaagccgcccctagcgtgaccctgttcc cccctcgagtgaggaactccaggccaacaaggcc accctcgtgtgcctgatcagcgacttctaccctggcgc cgtgaccgtggcctggaaggccgatagcagccctgt gaaggccggcgtggaaaccaccaccccccagcaag cagagcaacaacaaatacgccgccagcagctacct gagcctgacccccgagcagtggaagtcccacagat cctacagctgccaggtcacacacgagggcagcacc gtggaaaagaccgtggcccccaccgagtgcagc |
| BsAb# Freiburg_2 | mAb# Freiburg (IgG1f_AEASS_HC) x RefmAb#2 (scFv) | SEQ ID NO: 145 | EVQLVESGGGLVKPGGSLRLSCAASG FTFNTYAMNWVRQAPGKGLEWVGRIR SKYNNYATYYADSVKDRFTISRDDSKN TLYLQMNSLKTEDTAVYYCTTHGNFG NSYVSWFAYWGQGTLVTVSSASTKGP SVFPLAPSSKSTSGGTAALGCLVKDYF PEPVTVSWNSGALTSGVHTFPAVLQS SGLYSLSSVVTVPSSSLGTQTYICNVN HKPSNTKVDKRVEPKSCDKTHTCPPC PAPEAEGAPSVFLFPPKPKDTLMISRT PEVTCVVVDVSHEDPEVKFNWYVDGV EVHNAKTKPREEQYNSTYRVVSVLTVL HQDWLNGKEYKCKVSNKALPSSIEKTI SKAKGQPREPQVYTLPPSREEMTKNQ VSLTCLVKGFYPSDIAVEWESNGQPEN NYKTTPPVLDSDGSFFLYSKLTVDKSR WQQGNVFSCSVMHEALHNHYTQKSL SLSPGKASPAAPAPSADIQMTQSPSSL SASVGDRVTITCRASQDVNTAVAWYQ QKPGKAPKLLIYSASFLYSGVPSRFSG SRSGTDFTLTISSLQPEDFATYYCQQH YTTPPTFGQGTKVEIKRTASPAAPAPA SPAAPAPASGSQVQLVESGGGLVQPG GSLRLSCAASGFNIKDTYIHWVRQAPG KGLEWVARIYPTNGYTRYADSVKGRF TISADTSKNTAYLQMNSLRAEDTAVYY CSRWGGDGFYAMDYWGQGTLVTVSS |
| | mAb#Freiburg (IgG1f_AEASS_HC) x RefmAb#2 (scFv) | SEQ ID NO: 146 | gaagtgcagctggtggaatctggcggcggactcgtg aagcctggcggctctctgagactgagctgtgccgcca gcggcttcaccttcaacacctacgccatgaactgggt gcgccaggcccctggcaaaggcctggaatgggtgg gacggatcagaagcaagtacaacaattacgccacct actacgccgacagcgtgaaggaccggttcaccatca gccgggacgacagcaagaacaccctgtacctgcag atgaacagcctgaaaaccgaggacaccgccgtgta ctactgcaccacccacggcaacttcggcaacagctat gtgtcttggtttgcctactggggccagggcaccctcgtg acagtctcgagcgcgtcgaccaaaggcccccagcgt gttccctctggccccagcagcaagagcacctctggc ggaacagccgcccgggctgcctggtcaaggactac ttccccgagcccgtgaccgtgtcctggaactctggcgc cctgaccagcggcgtgcacacctttccagccgtgctc cagagcagcggcctgtacagcctgagcagcgtcgtg accgtgcccagcagcagcctgggcacccagaccta catctgcaacgtgaatcacaagcccagcaacacaa aggtggacaagcgggtggaacccaagagctgcga caagacccacacctgtcccccctgccctgccctgaa gcggagggagcccctccgtgttcctgttccccccaa agcctaaggacaccctgatgatcagccggacccccg aagtgacctgcgtggtggtggacgtgtcccacgagg |

TABLE 7-continued

Bispecific antibody sequences

| Antibody# | anti-CD3 [IgG1f-AEASS_HC] x anti-HER2 [scFv] | SEQ ID NO: | [aa]/DNA |
|---|---|---|---|
| | | | accctgaagtgaagtttaattggtacgtggacggcgtg<br>gaagtgcacaacgccaagaccaagcccagagagg<br>aacagtacaacagcacctaccgggtggtgtccgtgct<br>gaccgtgctgcaccaggactggctgaacggcaaag<br>agtacaagtgcaaggtgtccaacaaggccctgccttc<br>ctccatcgagaaaaccatcagcaaggccaaaggcc<br>agccccgcgagccccaggtgtacacactgcccccta<br>gccgggaagagatgaccaagaaccaggtgtccctg<br>acctgcctcgtgaagggcttctaccccagcgacattgc<br>cgtggaatgggagagcaacggccagcccgagaac<br>aactacaagaccacccccctgtgctggacagcgac<br>ggctcattcttcctgtacagcaagctgaccgtggacaa<br>gagccggtggcagcagggcaacgtgttcagctgctc<br>cgtgatgcacgaggccctgcacaaccactacaccca<br>gaagtccctgagcctgagcccggcaaggcttctcct<br>gctgctcctgctcctagcgctgacatccagatgaccca<br>gagcccagcagcctgagcgccagcgtgggcgaca<br>gagtgaccatcacctgtagagccagccaggacgtga<br>acaccgccgtggcctggtatcagcagaagcctggca<br>aggcccccaagctgctgatctacagcgccagcttcct<br>gtacagcggcgtgcccagcagattcagcggcagca<br>gatccggcaccgacttcaccctgaccatcagcagcct<br>gcagcccgaggacttcgccacctactactgccagca<br>gcactacaccacccccccacatttggccagggcac<br>caaggtggaaatcaagcggacagcctctcctgccgc<br>ccctgctcctgcttctcctgctgctccagctccagccag<br>cggatctcaggtgcagctggtggaatctggcggcgg<br>actggtgcagcctggcggatctctgagactgagctgtg<br>ccgccagcggcttcaacatcaaggacacctacatcc<br>actgggtgcgccaggcccctggaaagggactggaat<br>gggtggccagaatctaccccaccaacggctacacca<br>gatacgccgacagcgtgaagggccggttcaccatca<br>gcgccgacaccagcaagaataccgcctacctgcag<br>atgaacagcctgagagccgaggataccgccgtgtac<br>tactgctccagatggggaggcgacggcttctacgcca<br>tggactattggggccagggaaccctcgtgaccgtgtc<br>ctct |
| | mAb# Freiburg (h_Iglambda_LC) | SEQ ID NO: 147 | QTVVTQEPSLTVSPGGTVTLTCRSSTG<br>AVTTSNYANWVQQKPGQAPRLIGGT<br>NKRAPGTPARFSGSLLGGKAALTLLGA<br>QPEDEAEYYCALWYSNLWVFGGGTKL<br>TVLGQPKAAPSVTLFPPSSEELQANKA<br>TLVCLISDFYPGAVTVAWKADSSPVKA<br>GVETTTPSKQSNNKYAASSYLSLTPEQ<br>WKSHRSYSCQVTHEGSTVEKTVAPTE<br>CS |
| | mAb#Freiburg (h_Iglambda_LC) | SEQ ID NO: 148 | cagaccgtggtcacacaagagcccagcctgacagtt<br>tctcctggcggcacagtgaccctgacctgcagatcttct<br>acaggcgccgtgaccaccagcaactacgccaattg<br>ggtgcagcagaagcctggacaggctcccagaggac<br>tgatcggcggcacaaacaaaagagcccctggcaca<br>ccagccagattcagcggatcactgctcggaggaaag<br>gccgctctgacactgcttggagcacagcctgaagatg<br>aggccgagtactactgcgccctgtggtacagcaatct<br>gtgggtgttcggcggaggtaccaagctgaccgtgctg<br>ggccagcccaaagccgcccctagcgtgaccctgttc<br>ccccctcgagtgaggaactccaggccaacaaggc<br>caccctcgtgtgcctgatcagcgacttctaccctggcg<br>ccgtgaccgtggcctggaaggccgatagcagccctg<br>tgaaggccggcgtggaaaccaccaccccagcaa<br>gcagagcaacaacaaatacgccgccagcagctac<br>ctgagcctgaccccccgagcagtggaagtcccacag<br>atcctacagctgccaggtcacacacgagggcagca<br>ccgtggaaaagaccgtggcccccaccgagtgcagc |

WORKING EXAMPLES

Example 1—Humanization of Murine Antibody SP34

Humanized derivatives of SP34 and variants thereof were prepared.

The amino acid sequence of either the murine variable heavy chain (SEQ ID NO: 3) and the murine variable light chain (SEQ ID NO: 4) of SP34 were aligned to the repertoire of human VL or VH germline sequences (https with the extension ncbi.nlm.nih.gov/igblast of the world wide web) using the Vector NTI DNA analysis software.

On the basis of this analysis, the human germline segments VL7-43 and VL7-46 were chosen as template sequences for the humanized SP34 VL variants. For the human VH, the human germline sequences VH3-15 and VH3-73 were chosen as template sequences.

Selected amino acid residues that differed between the murine VL chain and the human Vlambda segment VL7-43 and VL7-46 or the murine VH chain and the human VH3-15 and VH3-73 chain within the framework regions were mutated on the DNA level towards the human residues. Potentially crucial framework residues of the original murine Vlambda or VH sequence were maintained.

In sum, 4 distinct humanized VL amino acid sequences and 2 distinct humanized VH amino acid sequences were designed, whose CDRs were identical to the CDRs from the murine antibody SP34 VL and VH chain, respectively.

In addition, for two of the designed VL sequences, additional amino acid substitutions at Kabat Positions 52-54 within the LCDR2 were introduced, namely N52K, K53F, R54L.

An in silico T cell epitope screening for the obtained VH and VL sequences was done (Lonza, The Epibase™ In Silico tool). The screening tool allows for the identification of potential T cell epitopes in biotherapeutic protein and antibody targets. The tool uses structural characteristics of the HLA receptor along with experimentally determined binding affinities to predict potential peptide/HLA binding, a condition necessary for T cell activation An exemplary result of the in silico immunogenicity analysis for the VH and VL sequences of the humanized SP34 variant "Munchen" is shown in Table 13. The analysis revealed a significant lower immunogenicity score for the VH and VL of the humanized variant in view of the parental murine antibody SP34.

TABLE 13

| Immunogenic risk scores for Caucasian DRB1 alleles | |
|---|---|
| Sequence | Risk Score (Caucasian) |
| SP34_VL | 621.4 |
| München_VL | 333.0 |
| SP34_VH | 953.0 |
| München_VH | 549.1 |

Figure 1:
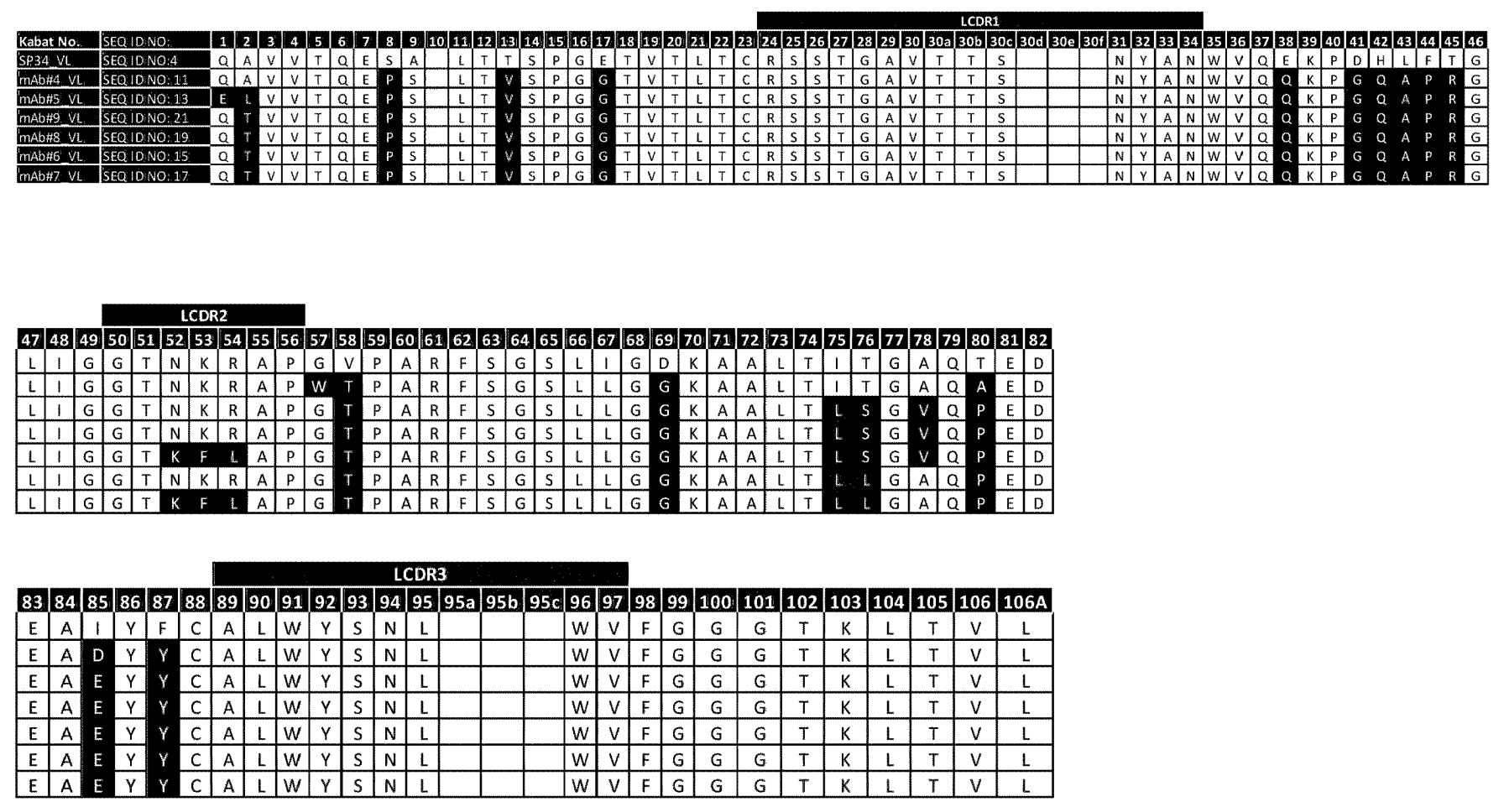

FIG. 1 and FIG. 2 depict the amino acid sequence alignments of the humanized VL and VH amino acid sequences in comparison to the corresponding murine SP34 sequences.

The amino acid sequences and encoding polynucleotide sequences of these humanized derivatives are shown in TABLE 3 and TABLE 4.

Example 2: Gene Synthesis and Cloning of the Humanized VH and VL Region of SP34 into Human IgG Backbones The afore-mentioned humanized VH and VL regions of SP34 were gene synthesized by an external provider (GeneArt® (chemical preparations for laboratory analysis), ThermoFisher Scientific) and in-house cloned into a set of suitable prepared mammalian IgG expression vectors (two vector IgG expression system).

Subsequently, Eukaryotic HKB-11 cells were transfected with the mammalian expression vector DNAs encoding the heavy and light chains of IgG, respectively. Cell culture supernatants were harvested on day 3 or 6 post transfection and subjected to standard Protein A affinity chromatography (MabSelect SURE® (chromatography chemicals)|GE Healthcare). Buffer exchange was performed to 1× Dulbecco's PBS (pH 7.2|Invitrogen) and samples were sterile filtered (0.2 µm pore size).

Protein concentrations were determined by UV-spectrophotometry and purities of IgG were analyzed under denaturing, reducing and non-reducing conditions using CE-SDS (LabChip® (biological chemical diagnostic test kits for scientific or research use, consisting of nucleic acid molecules, DNA molecules, slides and membranes for comparison testing of expression levels of biological samples) GXII|Perkin Elmer PerkinElmer® (full line of scientific, electrical, photographic, optical, weighing, measuring and signalling apparatus)|USA). HP-SEC was performed to analyze IgG preparations in native state.

Example 3—Control Constructs Used in the Following Examples

Various control constructs (CD3 specific IgGs or HER2× CD3 bispecific Abs) were included in the following experiments for comparative purposes:

Nucleotide sequences encoding the VH and VL domains from "Trastuzumab" ((RefmAb #2); an antibody specific for HER2) as described by Baselga et al. 1998, Cancer Res 58(13): 2825-2831).

Nucleotide sequences encoding VH and VL domains from "SP34" a murine monoclonal antibody as described by Yoshino et al. (Exp. Anim. 49(2), 97-110, 2000) as well as RefMAb #1, an antibody disclosed in WO2008119566A2. Both antibodies are reactive against the N-terminus of the epsilon chain of the T3 complex on human T lymphocyte cells.

All nucleotide sequences were gene synthesized as linear DNA fragments with appropriate flanking regions (e.g. suitable restriction enzyme recognition sites, linker sequences) either in-house or by an external provider. All synthesized DNA fragments were cloned into suited mammalian IgG expression vectors using standard molecular biology methods.

The murine monoclonal antibody "OKT-3" (J Pediatr. 1982 April; 100(4):665-8) which also binds to the human epsilon chain of CD3 but to a distinct epitope as RefMab #1 and SP34 is commercially available and was purchased from Thermo Fisher (Catalog Nr. 16-0037-85).

Example 4: Binding of CD3 Specific IgGs to Recombinant CD3Epsilon Antigens 7 humanized CD3 epsilon specific IgGs according to the present disclosure and two CD3 specific reference antibodies were tested for their ability to bind to recombinant human and cynomolgus CD3 epsilon in ELISA.

5 nM of recombinant human CD3e (22-49)-Fc2 (K105-K330) (SEQ ID NO: 149) or 1 nM of recombinant cynomolgus CD3e (22-49)-Fc2 (K105-K330) (SEQ ID NO: 150) were coated on Maxisorp plates (Nunc, #460518). Coated plates were blocked with 5% skim milk in PBS. Antibodies were serially diluted in PBS containing 0.5% skim milk and 0.5% Tween®-20 (biocompatible surfactants used in food, biotechnical, and pharmaceutical applications). Bound antibodies were detected using an alkaline phosphatase-conjugated detection antibody directed against human F(ab')2 fragment (Jackson Immuno Research, #109-055-097). $EC_{50}$ values were calculated using 4-parameter non-linear regression analysis in Prism software (GrapPad Software Inc., version 5.04).

The results of the experiment are summarized in TABLE 8 and FIG. 3A and FIG. 3B, and reveal that the humanized variants of the present disclosure exhibited equivalent or weaker binding to human or cynomolgus monkey CD3 epsilon when compared to SP34 or RefMab #1.

TABLE 8

| | ELISA binding | |
|---|---|---|
| | EC50 [nM] | |
| IgGs | hCD3e(22-49)_Fc2(K105-K330) | cyCD3e(22-49)_Fc2(K105-K330) |
| SP-34 (m/h chimeric) | 0.39 | 0.15 |
| RefmAb#1 | 0.38 | 0.12 |
| mAb#Mainz | 1.21 | 1.53 |
| mAb#Köln | 0.31 | 0.20 |
| mAb#Freiburg | 0.91 | 1.26 |
| mAb#München | 0.60 | 1.43 |
| mAb#Bremen | 1.10 | 0.80 |
| mAb#Gladbach | 0.38 | 0.21 |
| mAb#Nürnberg | 0.34 | 0.21 |

Example 5: Binding of CD3 Specific IgGs to CD3 Expressing Cell Lines 7 humanized CD3 epsilon specific IgGs of the present disclosure were tested for their ability to bind to Jurkat cells (a CD3 positive human T-cell line) and to the corresponding CD3 negative cell line J.RT3-T3.5., a derivative mutant of the parental Jurkat leukemia cell.

Jurkat and J.RT3-T3.5. cells were resuspended and counted in Superblock® (chemical preparations for use in connection with analytical procedures in research and diagnostic applications and in the chemical and biotechnological industries; ThermoScientific, #37515) and blocked for 1 h on ice. Blocked cells were resuspended in anti-CD3 antibodies serially diluted in Superblock® and incubated for 1 h on ice. Cells were washed 2 times in D-PBS (Gibco) containing 3% fetal bovine serum (Sigma, #F7524). Bound antibodies were detected using R-Phycoerythrin-conjugated detection antibody directed against human F(ab)$_2$ fragment (Jackson Immuno Research, #109-116-097). Antibody staining was measured using FACS Array FACSArray® (Flow Cytometer; Beckton Dickinson) or IntelliCyt iQue® flow cytometer and analyzed in FlowJo® (Computer software for data analysis; version 7.6.5) or ForeCyt (version 4.1.5379, IntelliCyt) softwares, respectively. $EC_{50}$ values were calculated using 4-parameter non-linear regression analysis in Prism software (GraphPad Software Inc., version 5.04).

The results of the experiment are shown in TABLE 9 and FIG. 4A, and reveal that the humanized variants exhibited equivalent or weaker binding to Jurkat cells when compared to SP34 (m/h chimeric) or RefmAb #01. Furthermore, no or only very weak binding to the CD3 negative cell line J.RT3-T3.5. was observable (data no shown).

TABLE 9

| Cell binding | |
|---|---|
| IgG | Jurkat $EC_{50}$ [nM] |
| SP34 (m/h chimeric) | 1.4 |
| RefmAb#01 | 1.1 |
| mAb#Mainz | 9.4 |
| mAb#Köln | 1.8 |
| mAb#Freiburg | 10.7 |
| mAb#München | 6.6 |
| mAb#Bremen | 6.3 |
| mAb#Gladbach | 1.4 |
| mAb#Nürnberg | 1.0 |

Example 6: $K_D$ Determination Using SPR in Antibody Capture Setup

High-capacity capture surfaces were prepared by covalently immobilizing MabSelect SuRe® ligand (GE Healthcare, 28-4018-60) onto all flowcells of a CM5 chip (GE Healthcare, BR-100530) using EDC/NHS chemistry.

Each cycle of the kinetic experiment consisted of capture steps (of different antibody ligands on the specific flow cells 2, 3 and 4), followed by an analyte injection (on all flow cells, including reference, or flow cell 1). At the end of each cycle, the sensor surface was regenerated by 2 consecutive injections of 10 mM Glycine/HCl pH1.5 (GE Healthcare, BR-100354) to remove captured antibody/antigen complexes, while maintaining the integrity of the capture surface. A blank injection of running buffer was used for referencing, i.e. correcting for dissociation of captured antibody. Association was recorded for 180 s and dissociation for 300 s at a flow rate of 30 μL/min. HBS-EP+ (GE Healthcare, BR-100669; 10 fold stock diluted to 1× with $H_2O$) was used as running buffer.

Capture levels of antibodies were adjusted to approx. 75-185 RU to achieve saturation levels Rmax of approx. 20-60 RU by the hCD3e analyte. Six different analyte concentrations were used for analysis during kinetic experiments (pMAX_hCD3e(1-118)_F-chLys_avi; applied molarities 4.1-999 nM, in a 3 fold serial dilution series).

Sensorgrams were evaluated with Biacore® T200 Evaluation Software 3.0 (Biacore®, GE Healthcare). All sensorgrams were fitted to a 1:1 binding model to determine $k_{on}$ and $k_{off}$ rate constants, which were used to calculate the $K_D$ value. For kinetic profiles deviating from the expected 1:1 binding, the sensorgrams were evaluated using a best approximation to the monovalent kinetics, and results marked with comment "heterogeneous binding". These results are considered less precise than kinetic profiles completely following the expected monovalent binding kinetics, but are assumed to be good approximations for $K_D$.

The results of this experiment are shown in TABLE 10 and reveal that SP34 and the humanized CD3 variants of the present disclosure exhibited equivalent or lower affinity binding to recombinant human CD3 epsilon.

TABLE 10

$K_D$ values of IgGs as determined on CD3 antigen pMAX_hCD3e(22-118)_F-chLys_avi

| IgG | $k_{on}$ [1/Ms] | $k_{off}$ [1/s] | $K_D$ [nM] | Comment | KD restriction (yes/no) |
|---|---|---|---|---|---|
| SP34 (m/h chimeric) | 4.87E+05 | 8.35E−04 | 1.7 | | no |
| RefmAb#1 | 3.74E+05 | 4.91E−04 | 1.3 | | no |
| mAb#Mainz | 1.42E+04 | 8.47E−03 | 600 | weak binding signals, only 333 nM & 999 nM evaluated | yes |
| mAb#Köln | 7.62E+04 | 3.86E−03 | 51 | slightly heterogeneous binding | no |
| mAb#Freiburg | 3.52E+04 | 4.67E−03 | 130 | heterogeneous binding | yes |
| mAb#München | 8.40E+04 | 6.58E−03 | 78 | slightly heterogeneous binding | no |
| mAb#Bremen | 6.50E+04 | 4.79E−03 | 74 | heterogeneous binding | yes |
| mAb#Gladbach | 7.18E+04 | 3.85E−03 | 54 | slightly heterogeneous binding | no |
| mAb#Nürnberg | 8.00E+04 | 3.87E−03 | 48 | only conc. 37-333 nM used for evaluation | yes |

Example 7: Generation of Bispecific Antibodies (bsAbs) that Specifically Bind to CD3 Epsilon and HER2

Bispecific antibodies according to the present disclosure were designed using an IgG-scFv format comprising an aglycosylated monoclonal IgG1 binding moiety and a scFv binding moiety, with the N-terminus of each scFv VL domain fused to the C-terminal end of each IgG heavy chain via a peptide linker. Both Fabs arms of the IgG bind to HER2 while the scFv is specific for CD3 (both scFv are identical and display the same specificity for CD3). Alternatively, bispecific antibodies were generated, wherein the two scFv molecules were specific for HER2 and the Fab arms of the IgG1 portion were specific for CD3.

All constructs were generated using standard molecular methodologies as described in Example 3.

A summary of the components of the antigen-binding domains of the various bispecific antibodies and of the bispecific antibodies made in accordance with this example is set forth in TABLE 5, 6 and 7.

Subsequently, Eukaryotic HKB-11 cells were transfected with mammalian expression vectors with DNA encoding all component of the various bispecific antibodies. Cell culture supernatants were harvested on day 3 or 6 post transfection and subjected to standard Protein A affinity chromatography (MabSelect SURE®|GE Healthcare). Buffer exchange was performed to 1× Dulbcecco's PBS (pH 7.2|Invitrogen) and samples were sterile filtered (0.2 µm pore size).

Protein concentrations were determined by UV-spectrophotometry and purities of IgG were analyzed under denaturing, reducing and non-reducing conditions using CE-SDS (LabChip® GXII|Perkin Elmer PerkinElmer®|USA). HP-SEC was performed to analyze IgG preparations in native state.

Example 8: Isolation of Human and Cynomolgus PBMCs

Human whole blood from healthy donors (in house) and whole blood from cynomolgus monkey (retrieved from LPT Laboratory of Pharmacology and Toxicology, Hamburg, Germany) was collected in Li-Heparin containing S-Monovette® (scientific laboratory instruments, apparatus and equipment for clinical use) containers (Sarstedt). Blood was transferred to 50 ml conical tubes and mixed with an equal volume of PBS containing 2% fetal bovine serum (Sigma, #F7524) and 2 mM EDTA. Diluted blood was transferred to SepMate® (cell separation equipment)-50 tubes (StemCell Technologies® (cell separation equipment), #86450) containing 15 ml Biocoll solution (Biochrom, #L6115) and centrifuged for 10 min at 1200×g. Supernatant was transferred into a 50 ml conical tube, diluted to 45 ml with PBS and centrifuged for 8 min at 300×g. Supernatant was discarded, cell pellet resuspended in 1 ml PBS and cells counted using a Neubauer chamber.

Example 9: Cell Binding of HER2×CD3 bsAbs to CD3 or HER2 Expressing Cell Lines

3 HER2 IgG×CD3 scFv bispecific antibodies of the present disclosure and one control bispecific antibody comprising the variable domains of RefmAb #1 were tested for their ability to bind to Jurkat cells expressing CD3 or to SKBR3 cells expressing high levels of the target antigen HER2. Experiments were done as described in Example 5.

The results of this experiment are summarized in TABLE 11 and reveal that the humanized variants of the present disclosure exhibited equivalent or weaker binding to Jurkat cells when compared to the control bispecific antibody comprising the Fab binding domains of RefMab #2 and the scFv binding domains of RefMab #1. In contrast, binding to SKBR3 cells remained unaffected.

TABLE 11

Cell binding of HER2 × CD3
bsABs to Jurkat and SKBR3 cells

| Bispecific antibody | FACS EC$_{50}$ [nM] | |
|---|---|---|
| | Jurkat | SKBR3 |
| BsAb#RefMab1 | 23 | 21 |
| BsAb#Freiburg | >100 | 15 |
| BsAb#München | 52 | 10 |
| BsAb#Bremen | 34 | 12 |

Example 10: Cell Binding of CD3 Specific IgGs and HER2×CD3 Bispecific Antibodies to Lymphocytes Expressing CD3

3 HER2 IgG×CD3 scFv bispecific antibodies of the present disclosure and a control bispecific antibody comprising the variable domains of RefmAb #1 were tested by FACS for their ability to bind to human and cynomolgus lymphocytes expressing CD3.

In addition, 7 humanized anti-CD3 epsilon specific IgGs of the present disclosure were tested for their ability to bind to human derived (n=3) and cynomolgus derived (n=1) PBMCs.

200,000 purified human or cynomolgus PBMCs were mixed with antibodies serially diluted (final concentration: 0.1 nM-400 nM or 0.01-200 nM) in D-PBS (Gibco) containing 3% fetal bovine serum (Sigma, #F7524) and incubated for 1 h on ice. Bound antibodies were detected using R-Phycoerythrin-conjugated detection antibody directed against human F(ab')2 fragment (Jackson Immuno Research, #109-116-097). Antibody staining was measured using a FACSArray® flow cytometer (Beckton Dickinson) and analyzed using FlowJo® software (version 7.6.5). Lymphocytes were identified by morphological gating of forward and side scatters. EC$_{50}$ values were calculated using 4-parameter non-linear regression analysis in Prism software (GraphPad Software Inc., version 5.04).

The results of the experiments are shown in FIG. 4B, FIG. 5A and FIG. 5B and reveal that the anti-CD3 IgGs and bispecific antibodies comprising the humanized SP34 variants of the present disclosure exhibited significant weaker binding to CD3 expressed on human or cynomolgus lymphocytes when compared to SP34 or to the control antibody comprising the single chain variable domains of RefmAb #1.

Example 11: T Cell Activation by HER2×CD3 bsAbs in the Absence of Target Cancer Cells 3 HER2 IgG×CD3 scFv bispecific antibodies of the present disclosure were tested for their ability to activate human T cells derived from different from human blood samples of different donors in the absence of target cancer cells.

Human PBMCs were purified as described above. Cells were resuspended to a density of 1E+07 cells/mL in RPMI 1640 medium (Gibco, #31870-025) supplemented with GlutaMax® (cell culture supplement for adherent and suspension culture of mammalian cells all for research use or further manufacturing) (Gibco, #35050-038), non-essential amino acids (Gibco, #11140-035), HEPES buffer bolution (Gibco #15630-056), sodium pyruvate (Gibco, #11360-039), β-mercaptoethanol, Penicillin/Streptomycin (Gibco #15140-122) and human serum (Sigma, #H4522) and incubated for 48 h at 37° C. and 5% $CO_2$. Following high-density preincubation, 200,000 PBMCs in medium were mixed with an equal volume of serially diluted antibodies (final concentration: 10 nM, 0.1 nM, 0.001 nM) in medium and incubated for 24 h at 37° C. and 5% $CO_2$.

Activation of T cells was assessed by evaluation of upregulation of CD69 expression on CD4 positive or CD8 positive T cells. For this, PBMCs were stained with antibodies to CD69, CD4 and CD8 conjugated with APC, APC/Cy7 and PE/Cy7, respectively (Biolegend® (reagents for scientific or research use), #310910/#300518/#344712). Antibody staining was measured using NovoCyte® (instrumentation for measuring, detecting or analyzing chemical or biological samples, including biological cells, polymer beads of different sizes such as from nanometer to mm range or scale) 3000 flow cytometer (Acea Biosciences, Inc.) and analyzed using FlowJo® software (version 7.6.5).

Results of the T cell activation experiments are shown in FIG. 6A (CD4 negative/CD8 positive T-cells) and FIG. 6B (CD4 positive/CD8 negative T-cells) at an antibody concentration of 10 nM. The results and reveal a donor-dependent upregulation of CD69 expression on CD4 positive or on CD8 positive T-cells by the positive murine control IgG OKT-3 and the bispecific control construct bsAb_RefMab #1 comprising scFv domains with the variable domains of RefmAb #1.

In contrast, no or very weak activation of T-cells was observable for the 3 HER2 IgG×CD3 scFv bispecific antibodies (BsAb #Freiburg, BsAb #Munchen, BsAb #Bremen) in the absence of HER2 expressing target cells. This finding clearly demonstrating the preferred safety profile of the humanized CD3 specific antibodies of the present disclosure even when bivalently binding to CD3.

Example 12: Cytotoxicity Assay with HER2×CD3 Bispecific Constructs

3 HER2 IgG×CD3 scFv bsAbs of the present disclosure were tested for their ability to mediate T cell dependent killing of HER2 tumor cell lines.

5,000 HER2-expressing SKBR3, A498 cells and HER2-negative MDA-MB468 cells were suspended in culture medium (SKBR3: McCoy's 5A Medium (Gibco, #26600), 10% FCS (Sigma, #F7524); MDA-MB468: DMEM (Gibco, #10938), GlutaMax® (Gibco, #35050), 10% FCS, 1x Sodium Pyruvate (Gibco, #11360-039)), seeded in black 96 well assay plates (Corning, #3340) and incubated over night at 37° C. and 5% $CO_2$. CellToxGreen™ dye (Promega, #G8731), serially diluted bispecific antibody constructs (final concentration: 0.1-100 pM) and 100,000 purified PBMCs, all diluted in assay medium comprising RPMI 1640 w/o Phenol red (Gibco, #32404-014), GlutaMax® and 10% fetal bovine serum, were added to the cells and incubated for 48 h at 37° C. and 5% $CO_2$.

Cytotoxic activity was assessed by measuring incorporated CellToxGreen™ fluorescence at 485 nm excitation and 535 nm emission using a Tecan Infinite F500 device. EC$_{50}$ values were calculated using 4-parameter non-linear regression analysis in Prism software (GraphPad Software Inc., version 5.04).

Further evidence for T cell-mediated target cell killing was assessed by determined by secretion of the pro-inflammatory cytokine IFN-gamma using a commercially available kit (Human IFN-gamma Duo Set ELISA, R&D Systems, DY285).

Results of the experiments for one exemplified doner are shown in FIG. 7A-C and reveal T-cell mediated and antibody dose dependent killing of HER2 high expressing SKBR3 cells by the bispecific antibodies of the present disclosure equivalent to that of the control antibody bsAb_RefMab #1.

However, bispecific constructs of the present disclosure displayed a much weaker antibody dose dependent killing of HER2 low expressing A498 cells compared to that of the control antibody bsAb_RefMab #1. This clearly indicates a favorable safety profile for the antibodies of the present disclosure. The $IC_{50}$ values were higher for the humanized antibodies displaying weaker binding to CD3 as compared to the control antibody bsAb_RefMab #1, most likely because of a decreased activation of CD8+ T cells (FIG. 7B).

FIG. 8 illustrates the antibody dose-dependent IFN-gamma release by T-cells in the presence of SKBR3 cells. The ELISA signals for bsAb #Freiburg and BsAb #refMAb #1 at an antibody concentration of 100 pM exceeded the detection limit. No IFN-gamma release could be observed in the presence of HER2 low expressing A498 cells (data not shown). This finding further supports the favorable safety profile of the humanized CD3 specific antibodies of the present disclosure.

Example 13: Cytotoxicity Assay with CD3×HER2 Bispecific Constructs

7 CD3 IgG×HER2 scFv bispecific antibodies of the present disclosure were tested for their ability to induce T-cell directed target cell killing as described in Example 12.

Results of the experiments are depicted in FIG. 9A and FIG. 9B and reveal that the T-cell-mediated dose dependent killing of HER2 high expressing SKBR3 cells is equivalent to that mediated by the control antibody bsAb_RefMab #1 but significant weaker on HER2 low expressing A498 cells. Again, no IFN-gamma release could be observed in the presence of HER2 low expressing A498 cells (data not shown).

These results clearly demonstrates that the favorable killing and safety properties of the bispecific antibodies of the present disclosure are independent from a particular CD3 format.

Example 14: $K_D$ Determination Using SPR in Antibody Capture Setup

Affinities for 3 HER2 IgG×CD3 scFv bispecific antibodies on recombinant human CD3 epsilon was determined as described in Example 6.

As shown in TABLE 12, the bispecific antibodies comprising humanized CD3 specific binding domains according to the present disclosure bind to human CD3 epsilon with significant weaker affinity when compared to the affinity of control antibody bsAb_RefMab #1.

TABLE 12

KD values of HER2 [IgG] × CD3 [scFv] bispecific antibodies determined on CD3 antigen pMAX_hCD3e(22-118)_F-chLys_avi

| Construct | $k_{on}$ [1/Ms] | $k_{off}$ [1/s] | $K_D$ [nM] | Comment | $K_D$ restriction (yes/no) |
|---|---|---|---|---|---|
| bsAb_RefMab#1 | 3.63E+05 | 3.67E−04 | 1.0 | | no |
| BsAb#Freiburg | 3.13E+04 | 3.36E−03 | 110 | heterogeneous binding | yes |
| BsAb#München | 3.65E+04 | 1.80E−03 | 49 | slightly heterogeneous binding | no |
| BsAb#Bremen | 6.15E+04 | 2.07E−03 | 34 | slightly heterogeneous binding | no |

The invention claimed is:

1. An antibody or antibody fragment specific for cluster of differentiation 3 (CD3), wherein said antibody or antibody fragment specifically binds to human CD3 and to non-human primate CD3, wherein said antibody or antibody fragment comprises a heavy chain variable domain of SEQ ID NO: 7 and a light chain variable domain of SEQ ID NO: 17.

2. The antibody or antibody fragment according to claim 1, wherein said antibody or antibody fragment specifically binds to human CD3 epsilon and cynomolgus monkey CD3 epsilon.

3. The antibody or antibody fragment according to claim 1, wherein said antibody or antibody fragment is a humanized or chimeric antibody or antibody fragment thereof.

4. The antibody or antibody fragment according to claim 1, wherein said antibody or antibody fragment is an isolated antibody or antibody fragment.

5. The antibody or antibody fragment according to claim 1, wherein said antibody or antibody fragment is a recombinant antibody or antibody fragment.

6. The antibody or antibody fragment according to claim 1, wherein the antibody is a full-length IgG.

7. The antibody or antibody fragment according to claim 6, wherein the full-length IgG is of an isotype selected from the group consisting of IgG1, IgG2, IgG3, and IgG4.

8. The antibody or antibody fragment according to claim 6, wherein the full-length IgG comprises an Fc region that has reduced effector function relative to that of a wild type Fc-receptor or an Fc region, wherein in at least 5 amino acids in the positions corresponding to positions L234, L235, D237, N330, P331 in a human IgG1 heavy chain, are mutated to A, E, A, S, and S, respectively.

9. The antibody or antibody fragment according to claim 1, wherein the antibody fragment is a Fab fragment.

10. The antibody or antibody fragment according to claim 1, wherein the antibody is a single chain antibody.

11. A pharmaceutical composition comprising the antibody or antibody fragment according to claim 1 and a pharmaceutically acceptable carrier or excipient.

12. A bispecific antibody comprising a first antigen binding domain of an antibody or antibody fragment according to claim 1, and a second antigen binding domain which binds a different target antigen than said first antigen binding region.

13. The bispecific antibody according claim 12, wherein the second binding region specifically binds a cell surface target antigen.

14. The bispecific antibody according to claim 12, wherein said bispecific antibody comprises an Fc region that has reduced effector function relative to that of a wild type Fc-receptor or an Fc region wherein in at least 5 amino acids in the positions corresponding to positions L234, L235, D237, N330, P331 in a human IgG1 heavy chain, are mutated to A, E, A, S, and S, respectively.

15. A method for treating or delaying progression of cancer in a subject in need thereof, said method comprising administering to the subject a bispecific antibody of claim 12 wherein the second antigen binding domain binds a tumor antigen.

* * * * *